United States Patent
Atkins et al.

(10) Patent No.: US 11,752,283 B2
(45) Date of Patent: *Sep. 12, 2023

(54) VAPORIZATION DEVICE SYSTEMS AND METHODS

(71) Applicant: JUUL Labs, Inc., Washington, DC (US)

(72) Inventors: Ariel Atkins, San Francisco, CA (US); Adam Bowen, San Mateo, CA (US); Steven Christensen, Burlingame, CA (US); Nicholas Jay Hatton, Oakland, CA (US); Christopher Nicholas HibmaCronan, Oakland, CA (US); James Monsees, San Francisco, CA (US); Joshua Morenstein, San Francisco, CA (US)

(73) Assignee: JUUL Labs, Inc., Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/832,719

(22) Filed: Dec. 5, 2017

(65) Prior Publication Data

US 2018/0092405 A1   Apr. 5, 2018

Related U.S. Application Data

(63) Continuation of application No. 14/581,666, filed on Dec. 23, 2014, now Pat. No. 10,058,124.
(Continued)

(51) Int. Cl.
*A24F 40/40* (2020.01)
*A61M 15/06* (2006.01)
(Continued)

(52) U.S. Cl.
CPC .............. *A61M 15/06* (2013.01); *A24F 40/40* (2020.01); *A24F 40/42* (2020.01); *A61M 11/042* (2014.02);
(Continued)

(58) Field of Classification Search
CPC ....................................... A24F 40/00
See application file for complete search history.

(56) References Cited

U.S. PATENT DOCUMENTS

| 374,584 | A | 12/1887 | Cook |
| 576,653 | A | 2/1897 | Bowlby |

(Continued)

FOREIGN PATENT DOCUMENTS

| AT | 507187 A4 | 3/2010 |
| AT | 507188 B1 | 3/2010 |

(Continued)

OTHER PUBLICATIONS

Engadget. *Juul is the e-cig that will finally stop me from smoking (I hope)*, [online], published on Jun. 3, 2015. Available at: https://www.engadget.com/2015/06/03/pax-labs-juul-ecigarette/#/.
(Continued)

*Primary Examiner* — Paul S Hyun
(74) *Attorney, Agent, or Firm* — Mintz, Levin, Cohn, Ferris, Glovsky and Popeo, P.C.; Nicholas P. Mouton, Esq.

(57) ABSTRACT

Provided herein are systems and methods to generate an inhalable vapor in an electronic vaporization device. The vaporization device may generate a vapor with one or more defined characteristics. In some cases, the vapor may have a predetermined aerosol number density and/or a predetermined average aerosol diameter. The vaporization device may generate a vapor from a vaporizable material. In some cases, the vaporizable material may be a liquid material
(Continued)

housed in a cartridge. The vaporization device may comprise a rechargeable power storage device.

21 Claims, 16 Drawing Sheets

Related U.S. Application Data

(60) Provisional application No. 61/937,755, filed on Feb. 10, 2014, provisional application No. 61/936,593, filed on Feb. 6, 2014, provisional application No. 61/920,225, filed on Dec. 23, 2013.

(51) Int. Cl.
    *A61M 11/04*     (2006.01)
    *H02J 7/00*     (2006.01)
    *A24F 40/42*     (2020.01)
    *H05B 1/02*     (2006.01)
    *A61M 16/00*     (2006.01)
    *A61M 15/00*     (2006.01)
    *A24F 40/10*     (2020.01)

(52) U.S. Cl.
    CPC .......... *H02J 7/0034* (2013.01); *H02J 7/0044* (2013.01); *H05B 1/0244* (2013.01); *A24F 40/10* (2020.01); *A61M 15/002* (2014.02); *A61M 15/0015* (2014.02); *A61M 15/0016* (2014.02); *A61M 2016/0021* (2013.01); *A61M 2205/3331* (2013.01); *A61M 2205/3368* (2013.01); *A61M 2205/3606* (2013.01); *A61M 2205/3653* (2013.01); *A61M 2205/8206* (2013.01); *A61M 2205/8237* (2013.01); *H02J 7/00* (2013.01)

(56) References Cited

U.S. PATENT DOCUMENTS

| | | |
|---|---|---|
| 595,070 A | 12/1897 | Oldenbusch |
| 720,007 A | 2/1903 | Dexter |
| 799,844 A | 9/1905 | Fuller |
| 968,160 A | 8/1910 | Johnson |
| 969,076 A | 8/1910 | Pender |
| 1,067,531 A | 7/1913 | MacGregor |
| 1,163,183 A | 12/1915 | Stoll |
| 1,299,162 A | 4/1919 | Fisher |
| 1,505,748 A | 8/1924 | Louis |
| 1,552,877 A | 9/1925 | Phillipps et al. |
| 1,632,335 A | 6/1927 | Hiering |
| 1,706,244 A | 3/1929 | Louis |
| 1,845,340 A | 2/1932 | Ritz |
| 1,972,118 A | 9/1934 | McDill |
| 1,998,683 A | 4/1935 | Montgomery |
| 2,031,363 A | 2/1936 | Elof |
| 2,039,559 A | 5/1936 | Segal |
| 2,104,266 A | 1/1938 | McCormick |
| 2,159,698 A | 5/1939 | Harris et al. |
| 2,177,636 A | 10/1939 | Coffelt et al. |
| 2,195,260 A | 3/1940 | Rasener |
| 2,231,909 A | 2/1941 | Hempal |
| 2,327,120 A | 8/1943 | McCoon |
| D142,178 S | 8/1945 | Becwar |
| 2,460,427 A | 2/1949 | Musselman et al. |
| 2,483,304 A | 9/1949 | Rudolf |
| 2,502,561 A | 4/1950 | Ludwig |
| 2,765,949 A | 10/1956 | Swan |
| 2,830,597 A | 4/1958 | Kummli |
| 2,860,638 A | 11/1958 | Bartolomeo |
| 2,897,958 A | 8/1959 | Tarleton et al. |
| 2,935,987 A | 5/1960 | Ackerbauer |
| 3,085,145 A | 4/1963 | Wray |
| 3,146,937 A | 9/1964 | Joseph |
| 3,258,015 A | 6/1966 | Ellis et al. |
| 3,271,719 A | 9/1966 | Ovshinsky |
| 3,292,634 A | 12/1966 | Beucler |
| D207,887 S | 6/1967 | Parsisson |
| 3,373,915 A | 3/1968 | Anderson et al. |
| 3,420,360 A | 1/1969 | Young |
| 3,443,827 A | 5/1969 | Acker et al. |
| 3,456,645 A | 7/1969 | Brock |
| 3,479,561 A | 11/1969 | Janning |
| 3,567,014 A | 3/1971 | Feigelman |
| 3,675,661 A | 7/1972 | Weaver |
| 3,707,017 A | 12/1972 | Paquette |
| 3,792,704 A | 2/1974 | Parker |
| 3,815,597 A | 6/1974 | Goettelman |
| 3,861,523 A | 1/1975 | Fountain et al. |
| 3,918,451 A | 11/1975 | Steil |
| 3,934,117 A | 1/1976 | Schladitz |
| 3,941,300 A | 3/1976 | Troth |
| 4,020,853 A | 5/1977 | Nuttall |
| 4,049,005 A | 9/1977 | Hernandez et al. |
| 4,066,088 A | 1/1978 | Ensor |
| D250,485 S | 12/1978 | Cuthbertson |
| 4,171,000 A | 10/1979 | Uhle |
| D255,548 S | 6/1980 | Grodin |
| 4,207,976 A | 6/1980 | Herman |
| 4,215,708 A | 8/1980 | Bron |
| 4,219,032 A | 8/1980 | Tabatznik et al. |
| D260,690 S | 9/1981 | Stutzer |
| 4,303,083 A | 12/1981 | Burruss, Jr. |
| 4,312,367 A | 1/1982 | Seeman |
| 4,347,855 A | 9/1982 | Lanzilotti et al. |
| 4,391,285 A | 7/1983 | Burnett et al. |
| D271,255 S | 11/1983 | Rousseau |
| 4,492,480 A | 1/1985 | Wadso et al. |
| 4,506,683 A | 3/1985 | Cantrell et al. |
| 4,519,319 A | 5/1985 | Howlett |
| 4,520,938 A | 6/1985 | Finke |
| D280,494 S | 9/1985 | Abel |
| 4,548,454 A | 10/1985 | Zeller et al. |
| 4,595,024 A | 6/1986 | Greene et al. |
| 4,625,737 A | 12/1986 | Keritsis et al. |
| 4,648,393 A | 3/1987 | Landis et al. |
| 4,708,151 A | 11/1987 | Shelar |
| 4,735,217 A | 4/1988 | Gerth et al. |
| 4,745,705 A | 5/1988 | Yamamoto et al. |
| 4,771,796 A | 9/1988 | Myer |
| 4,793,365 A | 12/1988 | Sensabaugh, Jr. et al. |
| 4,794,323 A | 12/1988 | Zhou et al. |
| 4,798,310 A | 1/1989 | Kasai et al. |
| 4,811,731 A | 3/1989 | Newell et al. |
| 4,813,536 A | 3/1989 | Willis |
| 4,819,665 A | 4/1989 | Roberts et al. |
| 4,830,028 A | 5/1989 | Lawson et al. |
| D301,837 S | 6/1989 | Peterson et al. |
| 4,836,224 A | 6/1989 | Lawson et al. |
| 4,846,199 A | 7/1989 | Rose |
| 4,848,374 A | 7/1989 | Chard et al. |
| 4,848,563 A | 7/1989 | Robbins |
| D302,659 S | 8/1989 | Peterson et al. |
| D303,722 S | 9/1989 | Marlow et al. |
| 4,870,748 A | 10/1989 | Hensgen et al. |
| D304,771 S | 11/1989 | Katayama |
| 4,893,639 A | 1/1990 | White |
| 4,896,683 A | 1/1990 | Cohen et al. |
| 4,907,606 A | 3/1990 | Lilja et al. |
| 4,924,883 A | 5/1990 | Perfetti et al. |
| 4,938,236 A | 7/1990 | Banerjee et al. |
| 4,941,483 A | 7/1990 | Ridings et al. |
| 4,944,317 A | 7/1990 | Thal |
| D310,171 S | 8/1990 | Cusenza |
| 4,945,929 A | 8/1990 | Egilmex |
| 4,947,874 A | 8/1990 | Brooks et al. |
| 4,947,875 A | 8/1990 | Brooks et al. |
| D310,349 S | 9/1990 | Rowen |
| 4,955,397 A | 9/1990 | Johnson et al. |
| 4,974,609 A | 12/1990 | Southwick et al. |
| 4,984,588 A | 1/1991 | Stewart, Jr. |
| D315,032 S | 2/1991 | Hayes |
| 4,993,436 A | 2/1991 | Bloom, Jr. |

(56) References Cited

U.S. PATENT DOCUMENTS

| | | |
|---|---|---|
| 5,005,759 A | 4/1991 | Bouche |
| 5,019,122 A | 5/1991 | Clearman et al. |
| 5,020,548 A | 6/1991 | Farrier et al. |
| 5,027,836 A | 7/1991 | Shannon et al. |
| 5,031,646 A | 7/1991 | Lippiello et al. |
| 5,040,551 A | 8/1991 | Schlatter et al. |
| 5,042,509 A | 8/1991 | Banerjee et al. |
| 5,050,621 A | 9/1991 | Creighton et al. |
| 5,060,671 A | 10/1991 | Counts et al. |
| 5,065,776 A | 11/1991 | Lawson et al. |
| 5,076,297 A | 12/1991 | Farrier et al. |
| 5,101,838 A | 4/1992 | Schwartz et al. |
| 5,105,831 A | 4/1992 | Banerjee et al. |
| 5,105,836 A | 4/1992 | Gentry et al. |
| 5,105,838 A | 4/1992 | White et al. |
| 5,117,482 A | 5/1992 | Hauber |
| 5,123,530 A | 6/1992 | Lee |
| 5,127,511 A | 7/1992 | Keen, Jr. et al. |
| 5,133,368 A | 7/1992 | Neumann et al. |
| 5,141,004 A | 8/1992 | Porenski |
| 5,144,962 A | 9/1992 | Counts et al. |
| 5,148,817 A | 9/1992 | Houminer et al. |
| 5,152,456 A | 10/1992 | Ross et al. |
| 5,183,062 A | 2/1993 | Clearman et al. |
| D336,346 S | 6/1993 | Miller et al. |
| 5,224,498 A | 7/1993 | Deevi et al. |
| 5,228,460 A | 7/1993 | Sprinkel et al. |
| 5,240,012 A | 8/1993 | Ehrman et al. |
| 5,249,586 A | 10/1993 | Morgan et al. |
| 5,259,786 A | 11/1993 | Huang |
| 5,261,424 A | 11/1993 | Sprinkel, Jr. |
| 5,269,237 A | 12/1993 | Baker et al. |
| 5,269,327 A | 12/1993 | Counts et al. |
| H1271 H | 1/1994 | Shouse |
| 5,296,685 A | 3/1994 | Burstein et al. |
| 5,303,720 A | 4/1994 | Banerjee et al. |
| 5,322,075 A | 6/1994 | Deevi et al. |
| 5,324,498 A | 6/1994 | Streusand et al. |
| 5,345,951 A | 9/1994 | Serrano et al. |
| 5,369,723 A | 11/1994 | Counts et al. |
| 5,372,148 A | 12/1994 | McCafferty et al. |
| 5,388,574 A | 2/1995 | Ingebrethsen |
| 5,449,078 A | 9/1995 | Akers |
| 5,456,269 A | 10/1995 | Kollasch |
| 5,472,001 A | 12/1995 | Nicholson |
| 5,479,948 A | 1/1996 | Counts et al. |
| D367,605 S | 3/1996 | Moore |
| 5,497,791 A | 3/1996 | Bowen et al. |
| D368,552 S | 4/1996 | Adams |
| 5,529,078 A | 6/1996 | Rehder et al. |
| D371,633 S | 7/1996 | Chenard |
| 5,545,904 A | 8/1996 | Orbach |
| 5,564,442 A | 10/1996 | MacDonald et al. |
| 5,579,934 A | 12/1996 | Buono |
| 5,591,368 A | 1/1997 | Fleischhauer et al. |
| 5,605,226 A | 2/1997 | Hernlein |
| 5,623,550 A | 4/1997 | Killion |
| D379,810 S | 6/1997 | Giordano et al. |
| 5,641,064 A | 6/1997 | Goserud |
| D380,293 S | 7/1997 | Cudmore |
| 5,649,552 A | 7/1997 | Cho et al. |
| D382,146 S | 8/1997 | Sandy |
| 5,661,329 A | 8/1997 | Hiramoto et al. |
| 5,666,977 A | 9/1997 | Higgins et al. |
| 5,666,978 A | 9/1997 | Counts et al. |
| 5,682,050 A | 10/1997 | Williams |
| 5,708,258 A | 1/1998 | Counts et al. |
| 5,730,118 A | 3/1998 | Hermanson |
| 5,730,158 A | 3/1998 | Collins et al. |
| 5,746,587 A | 5/1998 | Racine et al. |
| D397,504 S | 8/1998 | Zelenik |
| D398,150 S | 9/1998 | Vonarburg |
| 5,810,164 A | 9/1998 | Rennecamp |
| 5,819,756 A | 10/1998 | Mielordt |
| 5,845,649 A | 12/1998 | Saito et al. |
| D405,007 S | 2/1999 | Naas, Sr. |
| 5,865,185 A | 2/1999 | Collins et al. |
| 5,865,186 A | 2/1999 | Volsey, II |
| 5,878,752 A | 3/1999 | Adams et al. |
| 5,881,884 A | 3/1999 | Podosek |
| 5,894,841 A | 4/1999 | Voges |
| D411,332 S | 6/1999 | Zelenik |
| D412,279 S | 7/1999 | Brice |
| 5,931,828 A | 8/1999 | Durkee |
| 5,934,289 A | 8/1999 | Watkins et al. |
| 5,938,018 A | 8/1999 | Keaveney et al. |
| 5,944,025 A | 8/1999 | Cook et al. |
| 5,954,979 A | 9/1999 | Counts et al. |
| D414,893 S | 10/1999 | Moore |
| 5,967,310 A | 10/1999 | Hill |
| 5,975,415 A | 11/1999 | Zehnal |
| 5,979,460 A | 11/1999 | Matsumura |
| 5,994,025 A | 11/1999 | Iwasa et al. |
| 5,996,589 A | 12/1999 | St. Charles |
| 6,024,097 A | 2/2000 | Von Wielligh |
| 6,026,820 A | 2/2000 | Baggett, Jr. et al. |
| 6,040,560 A | 3/2000 | Fleischhauer et al. |
| D422,884 S | 4/2000 | Lafond |
| 6,053,176 A | 4/2000 | Adams et al. |
| D424,236 S | 5/2000 | Reed |
| 6,089,857 A | 7/2000 | Matsuura et al. |
| 6,090,082 A | 7/2000 | King et al. |
| 6,095,153 A | 8/2000 | Kessler et al. |
| 6,102,036 A | 8/2000 | Slutsky et al. |
| 6,119,684 A | 9/2000 | Nohl et al. |
| 6,125,853 A | 10/2000 | Susa et al. |
| D433,532 S | 11/2000 | Higgins et al. |
| 6,155,268 A | 12/2000 | Takeuchi |
| 6,164,287 A | 12/2000 | White |
| D436,686 S | 1/2001 | Fujisawa |
| 6,196,218 B1 | 3/2001 | Voges |
| 6,196,232 B1 | 3/2001 | Chkadua |
| 6,203,339 B1 | 3/2001 | Nieminen |
| 6,216,705 B1 | 4/2001 | Ossepian |
| D442,328 S | 5/2001 | Barmes |
| 6,234,169 B1 | 5/2001 | Bulbrook et al. |
| 6,265,789 B1 | 7/2001 | Honda et al. |
| D447,276 S | 8/2001 | Gustafson |
| 6,269,966 B1 | 8/2001 | Pallo et al. |
| 6,283,610 B1 | 9/2001 | Alajajian |
| D450,313 S | 11/2001 | Koinuma |
| D450,662 S | 11/2001 | Kwok |
| 6,324,261 B1 | 11/2001 | Merte |
| 6,349,728 B1 | 2/2002 | Pham |
| D454,079 S | 3/2002 | Fong |
| 6,381,739 B1 | 4/2002 | Breternitz, Jr. et al. |
| 6,386,371 B1 | 5/2002 | Parsons |
| 6,407,371 B1 | 6/2002 | Toya et al. |
| 6,418,938 B1 | 7/2002 | Fleischhauer et al. |
| 6,431,363 B1 | 8/2002 | Hacker |
| 6,443,146 B1 | 9/2002 | Voges |
| 6,446,793 B1 | 9/2002 | Layshock |
| D465,660 S | 11/2002 | Doeing |
| 6,510,982 B2 | 1/2003 | White et al. |
| 6,516,796 B1 | 2/2003 | Cox et al. |
| D471,104 S | 3/2003 | Hunt |
| 6,532,965 B1 | 3/2003 | Abhulimen et al. |
| 6,536,442 B2 | 3/2003 | St. Charles et al. |
| 6,557,708 B2 | 5/2003 | Polacco |
| 6,598,607 B2 | 7/2003 | Adiga et al. |
| D477,920 S | 8/2003 | McCarty et al. |
| D478,569 S | 8/2003 | Hussain et al. |
| D478,897 S | 8/2003 | Tsuge |
| 6,603,924 B2 | 8/2003 | Brown et al. |
| 6,606,998 B1 | 8/2003 | Gold |
| 6,612,404 B2 | 9/2003 | Sweet et al. |
| 6,615,840 B1 | 9/2003 | Fournier et al. |
| 6,622,867 B2 | 9/2003 | Menceles |
| 6,637,430 B1 | 10/2003 | Voges et al. |
| 6,655,379 B2 | 12/2003 | Clark et al. |
| D485,639 S | 1/2004 | Stronski |
| 6,672,762 B1 | 1/2004 | Faircloth et al. |
| 6,688,313 B2 | 2/2004 | Wrenn et al. |
| 6,707,274 B1 | 3/2004 | Karr |

(56) References Cited

U.S. PATENT DOCUMENTS

| | | |
|---|---|---|
| 6,708,846 B1 | 3/2004 | Fuchs et al. |
| 6,726,006 B1 | 4/2004 | Funderburk et al. |
| 6,743,030 B2 | 6/2004 | Lin et al. |
| 6,747,573 B1 | 6/2004 | Gerlach et al. |
| 6,752,649 B2 | 6/2004 | Arkin et al. |
| D494,315 S | 8/2004 | Cartier |
| 6,769,436 B2 | 8/2004 | Horian |
| 6,772,756 B2 | 8/2004 | Shayan |
| D495,599 S | 9/2004 | Biesecker |
| 6,799,576 B2 | 10/2004 | Farr |
| 6,803,545 B2 | 10/2004 | Blake et al. |
| 6,803,744 B1 | 10/2004 | Sabo |
| 6,805,545 B2 | 10/2004 | Slaboden |
| 6,810,883 B2 | 11/2004 | Felter et al. |
| D500,301 S | 12/2004 | Deguchi |
| D500,302 S | 12/2004 | Deguchi |
| 6,827,573 B2 | 12/2004 | St. Charles et al. |
| 6,854,470 B1 | 2/2005 | Pu |
| 6,874,507 B2 | 4/2005 | Farr |
| D505,922 S | 6/2005 | Mayo et al. |
| D506,447 S | 6/2005 | Mayo et al. |
| D506,731 S | 6/2005 | Mayo et al. |
| 6,909,840 B2 | 6/2005 | Harwig |
| D507,244 S | 7/2005 | Mayo et al. |
| 6,923,890 B2 | 8/2005 | Ricatto et al. |
| 6,954,979 B2 | 10/2005 | Logan |
| 6,994,096 B2 | 2/2006 | Rostami et al. |
| 7,000,775 B2 | 2/2006 | Gelardi et al. |
| 7,015,796 B2 | 3/2006 | Snyder |
| 7,025,066 B2 | 4/2006 | Lawson et al. |
| D523,171 S | 6/2006 | Mitten et al. |
| D525,948 S | 8/2006 | Blair et al. |
| 7,082,825 B2 | 8/2006 | Aoshima et al. |
| D528,992 S | 9/2006 | Hobart et al. |
| D529,044 S | 9/2006 | Andre et al. |
| 7,109,876 B2 | 9/2006 | Smith et al. |
| D530,340 S | 10/2006 | Andre et al. |
| D531,190 S | 10/2006 | Lee et al. |
| 7,117,707 B2 | 10/2006 | Adams et al. |
| D532,927 S | 11/2006 | Sann |
| D534,921 S | 1/2007 | Andre et al. |
| D535,261 S | 1/2007 | Daniels |
| D535,308 S | 1/2007 | Andre et al. |
| 7,173,222 B2 | 2/2007 | Cox et al. |
| 7,185,659 B2 | 3/2007 | Sharpe |
| D539,813 S | 4/2007 | Chen |
| D540,687 S | 4/2007 | Egawa |
| D540,749 S | 4/2007 | Kaule |
| 7,214,075 B2 | 5/2007 | He et al. |
| D544,643 S | 6/2007 | Lin |
| D545,303 S | 6/2007 | Chang |
| D545,490 S | 6/2007 | Tai |
| 7,234,593 B2 | 6/2007 | Fath et al. |
| D545,904 S | 7/2007 | Chen et al. |
| D546,782 S | 7/2007 | Poulet et al. |
| D547,002 S | 7/2007 | Lin |
| D551,548 S | 9/2007 | Didier |
| D551,970 S | 10/2007 | Didier |
| 7,275,866 B2 | 10/2007 | Tseng |
| 7,275,941 B1 | 10/2007 | Bushby |
| D556,154 S | 11/2007 | Poulet et al. |
| 7,290,549 B2 | 11/2007 | Banerjee et al. |
| D557,209 S | 12/2007 | Ahlgren et al. |
| D558,060 S | 12/2007 | Milan |
| 7,311,526 B2 | 12/2007 | Rohrbach et al. |
| 7,318,435 B2 | 1/2008 | Pentafragas |
| D562,151 S | 2/2008 | Larocca et al. |
| D565,496 S | 4/2008 | Disla |
| D566,709 S | 4/2008 | Kim et al. |
| D568,298 S | 5/2008 | Lundgren et al. |
| D569,727 S | 5/2008 | Moretti |
| 7,374,048 B2 | 5/2008 | Mazurek |
| D571,202 S | 6/2008 | Vogt |
| D571,556 S | 6/2008 | Ralie |
| D573,474 S | 7/2008 | Beam et al. |
| 7,415,982 B1 | 8/2008 | Sheridan |
| D576,619 S | 9/2008 | Udagawa et al. |
| D577,019 S | 9/2008 | Udagawa et al. |
| D577,150 S | 9/2008 | Bryman et al. |
| D577,591 S | 9/2008 | Bouroullec et al. |
| 7,428,905 B2 | 9/2008 | Mua |
| 7,434,584 B2 | 10/2008 | Steinberg |
| D580,756 S | 11/2008 | Seebold |
| D585,077 S | 1/2009 | Sheba et al. |
| 7,488,171 B2 | 2/2009 | St. Charles et al. |
| D589,941 S | 4/2009 | Maier et al. |
| D590,988 S | 4/2009 | Hon |
| D590,989 S | 4/2009 | Hon |
| D590,990 S | 4/2009 | Hon |
| D590,991 S | 4/2009 | Hon |
| D591,758 S | 5/2009 | Lee |
| 7,530,352 B2 | 5/2009 | Childers et al. |
| 7,546,703 B2 | 6/2009 | Johnske et al. |
| D599,670 S | 9/2009 | Qin |
| 7,581,540 B2 | 9/2009 | Hale et al. |
| 7,621,403 B2 | 11/2009 | Althoff et al. |
| D605,509 S | 12/2009 | Leonardis |
| D606,505 S | 12/2009 | Seflic et al. |
| 7,633,270 B2 | 12/2009 | Wong et al. |
| 7,644,823 B2 | 1/2010 | Gelardi et al. |
| 7,646,613 B2 | 1/2010 | Ligtenberg et al. |
| D610,588 S | 2/2010 | Chen |
| D611,409 S | 3/2010 | Green et al. |
| D616,753 S | 6/2010 | Beam et al. |
| 7,726,320 B2 | 6/2010 | Robinson et al. |
| 7,753,055 B2 | 7/2010 | Bryman |
| D621,357 S | 8/2010 | Dong |
| 7,767,698 B2 | 8/2010 | Warchol et al. |
| D624,238 S | 9/2010 | Turner |
| 7,793,860 B2 | 9/2010 | Bankers et al. |
| 7,793,861 B2 * | 9/2010 | Bankers ............ A01M 1/2044 239/102.1 |
| 7,801,573 B2 | 9/2010 | Yazdi et al. |
| 7,802,569 B2 | 9/2010 | Yeates et al. |
| D624,880 S | 10/2010 | Felegy, Jr. et al. |
| 7,813,832 B2 | 10/2010 | Sundar |
| 7,815,332 B1 | 10/2010 | Smith |
| D627,962 S | 11/2010 | Mudrick |
| 7,832,397 B2 | 11/2010 | Lipowicz |
| 7,832,410 B2 | 11/2010 | Hon |
| 7,845,359 B2 | 12/2010 | Montaser |
| D631,055 S | 1/2011 | Gilbert et al. |
| D631,458 S | 1/2011 | Liao et al. |
| 7,886,507 B2 | 2/2011 | McGuinness, Jr. |
| 7,891,666 B2 | 2/2011 | Kuenzler et al. |
| D634,735 S | 3/2011 | Maier |
| 7,905,236 B2 | 3/2011 | Bryman et al. |
| 7,913,686 B2 | 3/2011 | Hughes et al. |
| 7,913,688 B2 | 3/2011 | Cross et al. |
| D639,303 S | 6/2011 | Ni et al. |
| D639,782 S | 6/2011 | Kim |
| D641,718 S | 7/2011 | Sakai |
| D642,330 S | 7/2011 | Turner |
| D644,375 S | 8/2011 | Zhou |
| 7,987,846 B2 | 8/2011 | Hale et al. |
| 7,988,034 B2 | 8/2011 | Pezzoli |
| 8,003,080 B2 | 8/2011 | Rabinowitz et al. |
| D645,817 S | 9/2011 | Sasada et al. |
| D647,247 S | 10/2011 | Jones |
| 8,042,550 B2 | 10/2011 | Urtsev et al. |
| D649,708 S | 11/2011 | Oneil |
| D649,932 S | 12/2011 | Symons |
| 8,079,371 B2 | 12/2011 | Robinson et al. |
| 8,080,975 B2 | 12/2011 | Bessa et al. |
| 8,091,558 B2 | 1/2012 | Martzel |
| D653,803 S | 2/2012 | Timmermans |
| D656,496 S | 3/2012 | Andre et al. |
| 8,141,701 B2 | 3/2012 | Hodges |
| 8,156,944 B2 | 4/2012 | Han |
| 8,157,918 B2 | 4/2012 | Becker et al. |
| 8,170,623 B2 | 5/2012 | Dorogusker et al. |
| D661,889 S | 6/2012 | Wu |
| D661,991 S | 6/2012 | Brummelhuis et al. |
| 8,205,622 B2 | 6/2012 | Pan |

(56) References Cited

U.S. PATENT DOCUMENTS

| | | |
|---|---|---|
| D664,146 S | 7/2012 | Hoehn et al. |
| D664,636 S | 7/2012 | Robinson et al. |
| 8,251,060 B2 | 8/2012 | White et al. |
| 8,282,995 B2 | 10/2012 | Calzia et al. |
| D670,272 S | 11/2012 | Suzuki |
| D670,659 S | 11/2012 | Ishikawa et al. |
| 8,308,624 B2 | 11/2012 | Travers et al. |
| 8,314,235 B2 | 11/2012 | Dixit et al. |
| D672,715 S | 12/2012 | Brunner et al. |
| 8,322,350 B2 | 12/2012 | Lipowicz |
| D674,182 S | 1/2013 | Copeland et al. |
| D674,748 S | 1/2013 | Ferber et al. |
| 8,344,693 B2 | 1/2013 | Budziszek et al. |
| D676,741 S | 2/2013 | van Landsveld et al. |
| 8,371,310 B2 | 2/2013 | Brenneise |
| 8,375,957 B2 | 2/2013 | Hon |
| 8,381,739 B2 | 2/2013 | Gonda |
| 8,387,612 B2 | 3/2013 | Damani et al. |
| 8,393,331 B2 | 3/2013 | Hon |
| 8,402,978 B2 | 3/2013 | Karles et al. |
| 8,424,539 B2 | 4/2013 | Braunshteyn et al. |
| D681,445 S | 5/2013 | van Landsveld et al. |
| D682,090 S | 5/2013 | Scatterday |
| D682,698 S | 5/2013 | Young |
| D682,841 S | 5/2013 | Suetake et al. |
| 8,443,534 B2 | 5/2013 | Goodfellow et al. |
| D684,683 S | 6/2013 | Curti et al. |
| 8,464,867 B2 | 6/2013 | Holloway et al. |
| D686,336 S | 7/2013 | Horian |
| D686,987 S | 7/2013 | Vanstone et al. |
| D687,042 S | 7/2013 | Yoneta et al. |
| 8,479,747 B2 | 7/2013 | O'Connell |
| 8,485,099 B2 | 7/2013 | Skidmore et al. |
| 8,485,180 B2 | 7/2013 | Smutney et al. |
| 8,490,629 B1 | 7/2013 | Shenassa et al. |
| 8,495,998 B2 | 7/2013 | Schennum |
| 8,499,766 B1 | 8/2013 | Newton |
| 8,511,318 B2 | 8/2013 | Hon |
| D690,461 S | 9/2013 | Chen |
| 8,522,776 B2 | 9/2013 | Wright et al. |
| 8,539,959 B1 | 9/2013 | Scatterday |
| 8,541,401 B2 | 9/2013 | Mishra et al. |
| D691,324 S | 10/2013 | Saliman |
| D692,615 S | 10/2013 | Verleur |
| 8,550,069 B2 | 10/2013 | Alelov |
| 8,552,691 B2 | 10/2013 | Wu |
| D693,054 S | 11/2013 | Verleur |
| 8,578,942 B2 | 11/2013 | Schennum |
| 8,578,943 B2 | 11/2013 | Luan et al. |
| D695,450 S | 12/2013 | Benassayag et al. |
| D696,051 S | 12/2013 | Scatterday |
| 8,596,460 B2 | 12/2013 | Scatterday |
| 8,646,462 B2 | 2/2014 | Yamada et al. |
| D700,572 S | 3/2014 | Esses |
| 8,671,952 B2 | 3/2014 | Winterson et al. |
| 8,678,012 B2 | 3/2014 | Li et al. |
| 8,689,789 B2 | 4/2014 | Andrus et al. |
| 8,689,805 B2 | 4/2014 | Hon |
| 8,695,794 B2 | 4/2014 | Scatterday |
| 8,707,965 B2 | 4/2014 | Newton |
| D704,629 S | 5/2014 | Liu |
| D704,634 S | 5/2014 | Eidelman et al. |
| D705,918 S | 5/2014 | Robinson et al. |
| 8,714,150 B2 | 5/2014 | Alelov |
| 8,714,161 B2 | 5/2014 | Liu |
| 8,733,345 B2 | 5/2014 | Siller |
| 8,733,346 B2 | 5/2014 | Rinker |
| D707,389 S | 6/2014 | Liu |
| D707,627 S | 6/2014 | Brunner et al. |
| 8,739,788 B2 | 6/2014 | Yomtov |
| 8,741,348 B2 | 6/2014 | Hansson et al. |
| 8,752,545 B2 | 6/2014 | Buchberger |
| 8,752,557 B2 | 6/2014 | Lipowicz |
| 8,757,169 B2 | 6/2014 | Gysland |
| D708,727 S | 7/2014 | Postma |
| 8,770,187 B2 | 7/2014 | Murphy |
| 8,781,307 B2 | 7/2014 | Buzzetti |
| 8,790,556 B2 | 7/2014 | Bundren et al. |
| 8,794,231 B2 | 8/2014 | Thorens et al. |
| 8,794,244 B2 | 8/2014 | Hammel et al. |
| 8,794,245 B1 | 8/2014 | Scatterday |
| 8,794,434 B2 | 8/2014 | Scatterday et al. |
| 8,807,140 B1 | 8/2014 | Scatterday |
| 8,809,261 B2 | 8/2014 | Elsohly et al. |
| 8,813,747 B2 | 8/2014 | Gibson et al. |
| 8,813,759 B1 | 8/2014 | Horian |
| 8,820,330 B2 | 9/2014 | Bellinger et al. |
| 8,829,395 B2 | 9/2014 | Bao |
| 8,833,364 B2 | 9/2014 | Buchberger |
| 8,851,068 B2 | 10/2014 | Cohen et al. |
| 8,851,081 B2 | 10/2014 | Fernando et al. |
| 8,851,083 B2 | 10/2014 | Oglesby et al. |
| 8,857,446 B2 | 10/2014 | Wu |
| 8,863,752 B2 | 10/2014 | Hon |
| 8,869,792 B1 | 10/2014 | Lee |
| 8,881,737 B2 | 11/2014 | Collett et al. |
| 8,881,738 B2 | 11/2014 | Bryman |
| 8,893,726 B2 | 11/2014 | Hon |
| 8,897,628 B2 | 11/2014 | Conley et al. |
| D718,621 S | 12/2014 | Mitchell et al. |
| D718,723 S | 12/2014 | Clymer et al. |
| D718,933 S | 12/2014 | Brown, Jr. |
| D719,701 S | 12/2014 | Scatterday |
| D720,095 S | 12/2014 | Alima |
| D720,496 S | 12/2014 | Alima |
| D720,497 S | 12/2014 | Alima |
| 8,899,238 B2 | 12/2014 | Robinson et al. |
| 8,899,240 B2 | 12/2014 | Mass |
| 8,905,040 B2 | 12/2014 | Scatterday et al. |
| 8,910,630 B2 | 12/2014 | Todd |
| 8,910,639 B2 | 12/2014 | Chang et al. |
| 8,910,640 B2 | 12/2014 | Sears et al. |
| 8,910,641 B2 | 12/2014 | Hon |
| 8,910,783 B2 | 12/2014 | Liu |
| 8,915,254 B2 | 12/2014 | Monsees et al. |
| 8,919,561 B2 | 12/2014 | Boisseau |
| D721,202 S | 1/2015 | Liu |
| D721,577 S | 1/2015 | Scatterday |
| 8,925,555 B2 | 1/2015 | Monsees et al. |
| 8,928,277 B2 | 1/2015 | Xiang et al. |
| 8,931,492 B2 | 1/2015 | Scatterday |
| D721,972 S | 2/2015 | Brewer et al. |
| D722,023 S | 2/2015 | Brunner et al. |
| 8,948,578 B2 | 2/2015 | Buchberger |
| 8,950,395 B2 | 2/2015 | Schennum |
| 8,955,522 B1 | 2/2015 | Bowen et al. |
| 8,960,199 B2 | 2/2015 | Zhuang et al. |
| 8,961,492 B2 | 2/2015 | Imran et al. |
| 8,963,725 B2 | 2/2015 | Xiang |
| D723,735 S | 3/2015 | Liu |
| D723,736 S | 3/2015 | Liu |
| D724,037 S | 3/2015 | Yoshioka |
| D725,310 S | 3/2015 | Eksouzian |
| D725,821 S | 3/2015 | Levin et al. |
| D725,823 S | 3/2015 | Scatterday et al. |
| 8,967,382 B2 | 3/2015 | Liu |
| 8,973,587 B2 | 3/2015 | Liu |
| 8,975,764 B1 | 3/2015 | Abehasera |
| 8,978,663 B2 | 3/2015 | Newton |
| 8,991,402 B2 | 3/2015 | Bowen et al. |
| 8,993,836 B2 | 3/2015 | Tissier et al. |
| D726,727 S | 4/2015 | Holz et al. |
| 9,004,073 B2 | 4/2015 | Tucker et al. |
| 9,010,335 B1 | 4/2015 | Scatterday |
| 9,016,274 B1 | 4/2015 | White |
| 9,018,899 B2 | 4/2015 | Xiang |
| D728,855 S | 5/2015 | Liu |
| D729,030 S | 5/2015 | Novick et al. |
| D729,277 S | 5/2015 | Uchida |
| D729,366 S | 5/2015 | Kauss et al. |
| D729,439 S | 5/2015 | Scatterday |
| D729,444 S | 5/2015 | Leidel |
| D729,445 S | 5/2015 | Leidel |
| D730,571 S | 5/2015 | Chen |

(56) References Cited

U.S. PATENT DOCUMENTS

| | | |
|---|---|---|
| D730,572 S | 5/2015 | Leidel |
| 9,022,026 B2 | 5/2015 | Fang |
| 9,022,039 B2 | 5/2015 | Hearn |
| 9,025,291 B2 | 5/2015 | Xiang |
| 9,028,808 B2 | 5/2015 | Huland |
| 9,032,968 B2 | 5/2015 | Glasberg et al. |
| 9,038,626 B2 | 5/2015 | Yamada et al. |
| 9,038,642 B2 | 5/2015 | Liu |
| D731,114 S | 6/2015 | Leidel |
| D732,733 S | 6/2015 | Spagnolo et al. |
| D733,142 S | 6/2015 | Solomon et al. |
| D733,356 S | 6/2015 | Leidel |
| 9,046,278 B2 | 6/2015 | Koller |
| 9,050,431 B2 | 6/2015 | Turner et al. |
| 9,055,617 B2 | 6/2015 | Thorens et al. |
| 9,055,770 B2 | 6/2015 | Liu |
| 9,060,388 B2 | 6/2015 | Liu |
| 9,060,548 B2 | 6/2015 | Zheng et al. |
| 9,066,543 B2 | 6/2015 | Cameron |
| 9,072,321 B2 | 7/2015 | Liu |
| 9,072,322 B2 | 7/2015 | Liu |
| 9,078,472 B2 | 7/2015 | Liu |
| 9,078,474 B2 | 7/2015 | Thompson |
| 9,078,475 B2 | 7/2015 | Li et al. |
| 9,089,166 B1 | 7/2015 | Scatterday |
| 9,089,168 B2 | 7/2015 | Liu |
| 9,090,173 B2 | 7/2015 | Oishi |
| D736,706 S | 8/2015 | Huang et al. |
| D736,995 S | 8/2015 | Redo |
| D737,508 S | 8/2015 | Liu |
| 9,095,174 B2 | 8/2015 | Capuano |
| 9,095,175 B2 | 8/2015 | Terry et al. |
| 9,099,873 B2 | 8/2015 | Xiang |
| 9,101,729 B2 | 8/2015 | Liu |
| 9,113,659 B2 | 8/2015 | Liu |
| D737,566 S | 9/2015 | Gaddis |
| D738,038 S | 9/2015 | Smith |
| D739,973 S | 9/2015 | Chao |
| 9,131,733 B2 | 9/2015 | Liu |
| 9,132,248 B2 | 9/2015 | Qiu |
| D741,001 S | 10/2015 | Alarcon et al. |
| D741,002 S | 10/2015 | Liu |
| D741,541 S | 10/2015 | Liu |
| D742,063 S | 10/2015 | Redo |
| D742,064 S | 10/2015 | Leidel |
| 9,155,336 B2 | 10/2015 | Liu |
| 9,166,424 B2 | 10/2015 | Oakley, Jr. |
| 9,167,849 B2 | 10/2015 | Adamic |
| 9,167,850 B2 | 10/2015 | Liu |
| 9,167,852 B2 | 10/2015 | Xiu |
| 9,167,853 B2 | 10/2015 | Xiang |
| D742,492 S | 11/2015 | Robinson et al. |
| D742,624 S | 11/2015 | Meyers |
| D743,099 S | 11/2015 | Oglesby |
| D744,159 S | 11/2015 | Lukas |
| 9,185,937 B2 | 11/2015 | Liu |
| 9,197,726 B2 | 11/2015 | Stanimirovic et al. |
| D744,342 S | 12/2015 | Blasko et al. |
| D744,419 S | 12/2015 | Bowen et al. |
| D744,696 S | 12/2015 | Malhi |
| D745,004 S | 12/2015 | Kim |
| D745,388 S | 12/2015 | Taylor |
| D746,291 S | 12/2015 | Solomon et al. |
| 9,198,463 B2 | 12/2015 | Liu |
| 9,198,464 B2 | 12/2015 | Liu |
| 9,198,466 B2 | 12/2015 | Liu |
| 9,204,670 B2 | 12/2015 | Liu |
| 9,215,895 B2 | 12/2015 | Bowen et al. |
| 9,220,302 B2 | 12/2015 | DePiano et al. |
| 9,220,303 B2 | 12/2015 | Li et al. |
| D747,035 S | 1/2016 | Moradian |
| D747,265 S | 1/2016 | Marini |
| D747,546 S | 1/2016 | Liu |
| D747,603 S | 1/2016 | Gaddis |
| D747,722 S | 1/2016 | Webb |
| D747,852 S | 1/2016 | Meyers |
| D748,329 S | 1/2016 | Bagai et al. |
| 9,226,525 B2 | 1/2016 | Liu |
| 9,226,526 B2 | 1/2016 | Liu |
| 9,233,217 B2 | 1/2016 | Jones |
| 9,240,695 B2 | 1/2016 | Xiang |
| 9,240,697 B2 | 1/2016 | Xiang |
| D748,852 S | 2/2016 | Wu |
| D748,853 S | 2/2016 | Seibel et al. |
| D749,260 S | 2/2016 | Wu |
| D749,261 S | 2/2016 | Chen |
| D749,505 S | 2/2016 | Verleur et al. |
| D749,510 S | 2/2016 | Liu |
| D749,781 S | 2/2016 | Lane |
| D750,320 S | 2/2016 | Verleur et al. |
| D750,321 S | 2/2016 | Chen |
| 9,247,773 B2 | 2/2016 | Memari et al. |
| 9,254,002 B2 | 2/2016 | Chong et al. |
| 9,254,005 B2 | 2/2016 | Liu |
| 9,255,277 B2 | 2/2016 | Bakker et al. |
| D750,835 S | 3/2016 | Wei |
| D751,250 S | 3/2016 | Vuong |
| D751,527 S | 3/2016 | Hinokio et al. |
| D751,755 S | 3/2016 | Van Riper |
| D751,757 S | 3/2016 | Stern |
| D752,277 S | 3/2016 | Liu |
| D752,278 S | 3/2016 | Verleur et al. |
| D752,279 S | 3/2016 | Liu |
| D752,280 S | 3/2016 | Verleur et al. |
| D752,282 S | 3/2016 | Doster |
| D752,283 S | 3/2016 | Doster |
| D752,284 S | 3/2016 | Doster |
| D752,285 S | 3/2016 | Doster |
| D752,286 S | 3/2016 | Doster |
| D752,808 S | 3/2016 | Hearn |
| 9,271,525 B2 | 3/2016 | Liu |
| 9,271,526 B2 | 3/2016 | Liu |
| 9,271,529 B2 | 3/2016 | Alima |
| 9,272,103 B2 | 3/2016 | Storz |
| 9,277,768 B2 | 3/2016 | Xiu |
| 9,277,769 B2 | 3/2016 | Liu |
| 9,281,705 B2 | 3/2016 | Xiang |
| 9,282,772 B2 | 3/2016 | Tucker et al. |
| 9,282,773 B2 | 3/2016 | Greim et al. |
| 9,289,014 B2 | 3/2016 | Tucker et al. |
| 9,295,286 B2 | 3/2016 | Shin |
| D753,090 S | 4/2016 | Langhammer et al. |
| D753,338 S | 4/2016 | Chen |
| D753,873 S | 4/2016 | Schuessler |
| D753,874 S | 4/2016 | Moreno Medina et al. |
| D754,919 S | 4/2016 | Alarcon et al. |
| 9,301,545 B2 | 4/2016 | Li et al. |
| 9,301,549 B2 | 4/2016 | Liu |
| 9,302,800 B2 | 4/2016 | Holmes et al. |
| 9,302,825 B2 | 4/2016 | Liu |
| 9,308,336 B2 | 4/2016 | Newton |
| 9,312,687 B2 | 4/2016 | Xiang |
| 9,315,890 B1 | 4/2016 | Frick et al. |
| 9,320,300 B2 | 4/2016 | Hon |
| D755,057 S | 5/2016 | Mutter |
| D755,506 S | 5/2016 | Neely, III et al. |
| D755,733 S | 5/2016 | Ikegaya et al. |
| D755,735 S | 5/2016 | Kashimoto |
| D756,030 S | 5/2016 | Chen |
| D756,031 S | 5/2016 | Wu |
| D756,559 S | 5/2016 | Li |
| D757,352 S | 5/2016 | Bagai |
| D757,353 S | 5/2016 | Nunnelly et al. |
| D757,690 S | 5/2016 | Lee et al. |
| D757,994 S | 5/2016 | Moradian |
| D757,995 S | 5/2016 | Liu |
| 9,326,547 B2 | 5/2016 | Tucker et al. |
| 9,326,549 B2 | 5/2016 | Hon |
| 9,332,787 B2 | 5/2016 | Liu |
| 9,345,269 B2 | 5/2016 | Liu |
| 9,345,541 B2 | 5/2016 | Greeley et al. |
| 9,350,102 B2 | 5/2016 | Wu |
| 9,350,178 B2 | 5/2016 | Xiang |
| 9,350,181 B2 | 5/2016 | Xiang |

(56) References Cited

U.S. PATENT DOCUMENTS

| | | |
|---|---|---|
| 9,351,522 B2 | 5/2016 | Safari |
| D758,647 S | 6/2016 | Liu |
| D758,649 S | 6/2016 | Liu |
| D758,650 S | 6/2016 | Wu |
| D759,031 S | 6/2016 | Ozolins et al. |
| D759,297 S | 6/2016 | Liu |
| D759,303 S | 6/2016 | Afridi |
| D760,431 S | 6/2016 | Liu |
| 9,357,802 B2 | 6/2016 | Liu |
| 9,360,379 B2 | 6/2016 | Liu |
| 9,364,025 B2 | 6/2016 | Liu |
| 9,364,026 B2 | 6/2016 | Liu |
| 9,364,027 B2 | 6/2016 | Hon |
| 9,364,800 B2 | 6/2016 | Dubief |
| 9,379,364 B2 | 6/2016 | Alima |
| D760,952 S | 7/2016 | Mayor |
| D761,488 S | 7/2016 | Alarcon et al. |
| D761,999 S | 7/2016 | Liu |
| D762,000 S | 7/2016 | Liu |
| D762,001 S | 7/2016 | Liu |
| D762,003 S | 7/2016 | Lomeli |
| D762,326 S | 7/2016 | Liu |
| 9,380,810 B2 | 7/2016 | Rose et al. |
| 9,380,812 B2 | 7/2016 | Chung |
| 9,383,053 B2 | 7/2016 | Liu |
| 9,385,554 B2 | 7/2016 | Xiang |
| 9,386,803 B2 | 7/2016 | Burke et al. |
| 9,386,805 B2 | 7/2016 | Liu |
| D763,203 S | 8/2016 | Ikegaya et al. |
| D763,204 S | 8/2016 | Ikegaya et al. |
| D763,502 S | 8/2016 | Verleur et al. |
| D764,098 S | 8/2016 | Liu |
| D764,703 S | 8/2016 | Liu |
| D765,307 S | 8/2016 | Liu |
| D765,308 S | 8/2016 | Liu |
| D765,309 S | 8/2016 | Liu |
| 9,408,416 B2 | 8/2016 | Monsees et al. |
| 9,413,180 B2 | 8/2016 | Liu |
| 9,414,627 B2 | 8/2016 | Liu |
| 9,414,628 B2 | 8/2016 | Liu |
| 9,414,629 B2 | 8/2016 | Egoyants et al. |
| 9,415,929 B2 | 8/2016 | Liu |
| 9,417,107 B2 | 8/2016 | Xiang |
| 9,420,829 B2 | 8/2016 | Thorens et al. |
| 9,420,831 B2 | 8/2016 | Liu |
| 9,423,152 B2 | 8/2016 | Ampolini et al. |
| 9,427,022 B2 | 8/2016 | Levin et al. |
| 9,427,023 B2 | 8/2016 | Liu |
| 9,427,024 B2 | 8/2016 | Liu |
| 9,427,025 B2 | 8/2016 | Liu |
| 9,427,026 B2 | 8/2016 | Wu |
| D765,907 S | 9/2016 | Liu |
| D766,503 S | 9/2016 | Liu |
| D766,873 S | 9/2016 | Washio |
| D767,200 S | 9/2016 | Liu |
| D767,201 S | 9/2016 | Starr |
| D767,820 S | 9/2016 | Jordan et al. |
| D767,822 S | 9/2016 | Jordan et al. |
| 9,433,242 B1 | 9/2016 | Buffone |
| 9,438,049 B2 | 9/2016 | Xiang |
| 9,438,051 B2 | 9/2016 | Firman, II et al. |
| 9,439,455 B2 | 9/2016 | Alarcon et al. |
| 9,439,456 B2 | 9/2016 | Liu |
| 9,440,035 B2 | 9/2016 | Chung |
| 9,451,790 B2 | 9/2016 | Liu |
| 9,451,793 B2 | 9/2016 | Zhou |
| 9,455,579 B2 | 9/2016 | Xiang |
| D768,331 S | 10/2016 | Chen |
| D768,920 S | 10/2016 | Jones et al. |
| D768,980 S | 10/2016 | Alexander |
| D769,518 S | 10/2016 | Liu |
| D769,519 S | 10/2016 | Chen |
| D769,520 S | 10/2016 | Hua |
| D769,830 S | 10/2016 | Clymer et al. |
| D770,088 S | 10/2016 | Abadi et al. |
| 9,456,632 B2 | 10/2016 | Hon |
| 9,456,633 B2 | 10/2016 | Liu |
| 9,456,634 B2 | 10/2016 | Wang et al. |
| 9,459,021 B2 | 10/2016 | Greim et al. |
| 9,462,832 B2 | 10/2016 | Lord |
| 9,465,081 B2 | 10/2016 | Xiang |
| 9,474,305 B2 | 10/2016 | Liu |
| D770,395 S | 11/2016 | Clymer et al. |
| D770,676 S | 11/2016 | Bennett et al. |
| D770,678 S | 11/2016 | Shin |
| D770,679 S | 11/2016 | Weigensberg |
| D771,219 S | 11/2016 | Gilbarte |
| D771,307 S | 11/2016 | Wu |
| D771,308 S | 11/2016 | Saydar et al. |
| D772,477 S | 11/2016 | Shin |
| D772,478 S | 11/2016 | Liu |
| D772,479 S | 11/2016 | Stowers et al. |
| D772,480 S | 11/2016 | Hua |
| D772,879 S | 11/2016 | Eliyahu |
| D773,114 S | 11/2016 | Leidel et al. |
| D773,115 S | 11/2016 | Liu |
| D773,116 S | 11/2016 | Liu et al. |
| 9,480,285 B2 | 11/2016 | Liu |
| 9,480,286 B2 | 11/2016 | Liu |
| 9,497,993 B2 | 11/2016 | Vallar |
| 9,497,994 B2 | 11/2016 | Liu |
| 9,497,995 B2 | 11/2016 | Liu |
| 9,497,997 B2 | 11/2016 | Wu |
| 9,497,998 B2 | 11/2016 | Chen |
| 9,497,999 B2 | 11/2016 | Lord |
| 9,498,001 B2 | 11/2016 | Wu |
| 9,498,002 B1 | 11/2016 | Soreide |
| 9,498,588 B2 | 11/2016 | Benassayag et al. |
| 9,502,917 B2 | 11/2016 | Xiang |
| 9,504,278 B2 | 11/2016 | Liu |
| 9,504,279 B2 | 11/2016 | Chen et al. |
| D773,391 S | 12/2016 | Haarburger et al. |
| D773,727 S | 12/2016 | Eksouzian |
| D773,729 S | 12/2016 | Jordan et al. |
| D774,247 S | 12/2016 | Chen |
| D774,248 S | 12/2016 | Jordan et al. |
| D774,514 S | 12/2016 | Turksu et al. |
| D774,693 S | 12/2016 | Liu |
| D774,892 S | 12/2016 | Liu |
| D775,412 S | 12/2016 | Di Bari |
| D775,413 S | 12/2016 | Liu |
| 9,510,623 B2 | 12/2016 | Tucker et al. |
| 9,510,624 B2 | 12/2016 | Li et al. |
| 9,516,898 B2 | 12/2016 | Liu |
| 9,516,899 B2 | 12/2016 | Plojoux et al. |
| 9,521,867 B2 | 12/2016 | Xiang |
| 9,526,272 B2 | 12/2016 | Liu |
| 9,526,273 B2 | 12/2016 | Liu |
| 9,531,183 B2 | 12/2016 | Xiang |
| D776,051 S | 1/2017 | Wang |
| D776,162 S | 1/2017 | Beck et al. |
| D776,270 S | 1/2017 | Wilcox et al. |
| D776,338 S | 1/2017 | Lomeli |
| D776,340 S | 1/2017 | Seibel et al. |
| D776,659 S | 1/2017 | Hou |
| D777,372 S | 1/2017 | Liu |
| D777,976 S | 1/2017 | Mahlmeister |
| 9,532,598 B2 | 1/2017 | Liu |
| 9,532,599 B2 | 1/2017 | Liu |
| 9,532,601 B2 | 1/2017 | Liu |
| 9,532,602 B2 | 1/2017 | Liu |
| 9,532,604 B2 | 1/2017 | Conley et al. |
| 9,532,605 B2 | 1/2017 | Yamada et al. |
| 9,538,781 B2 | 1/2017 | Zheng |
| 9,538,783 B2 | 1/2017 | Xiang |
| 9,538,787 B2 | 1/2017 | Liu |
| 9,538,789 B2 | 1/2017 | Liu |
| 9,545,489 B2 | 1/2017 | Turner et al. |
| 9,549,572 B2 | 1/2017 | Dincer et al. |
| 9,549,573 B2 | 1/2017 | Monsees et al. |
| 9,554,596 B2 | 1/2017 | Liu |
| 9,554,597 B2 | 1/2017 | Liu |
| 9,555,203 B2 | 1/2017 | Terry et al. |
| D778,493 S | 2/2017 | Scott |

(56) References Cited

U.S. PATENT DOCUMENTS

| | | |
|---|---|---|
| D778,831 S | 2/2017 | Chen |
| D779,677 S | 2/2017 | Chen |
| D779,719 S | 2/2017 | Qiu |
| D780,179 S | 2/2017 | Bae et al. |
| D780,372 S | 2/2017 | Liu |
| 9,560,882 B2 | 2/2017 | Xiang |
| 9,565,873 B2 | 2/2017 | Zheng |
| 9,565,876 B2 | 2/2017 | Tsai |
| 9,572,372 B2 | 2/2017 | Liu |
| 9,572,373 B2 | 2/2017 | Chen |
| 9,572,374 B2 | 2/2017 | Gabbay |
| 9,573,751 B2 | 2/2017 | Liu |
| 9,578,002 B2 | 2/2017 | Wu |
| 9,578,898 B2 | 2/2017 | Liu |
| D780,990 S | 3/2017 | Liu |
| D780,991 S | 3/2017 | Liu |
| D782,108 S | 3/2017 | Jordan et al. |
| D782,728 S | 3/2017 | Pinder |
| D782,729 S | 3/2017 | Wright et al. |
| 9,591,876 B2 | 3/2017 | Alima |
| 9,596,881 B2 | 3/2017 | Chiolini et al. |
| 9,596,884 B2 | 3/2017 | Liu |
| 9,596,885 B2 | 3/2017 | Liu |
| 9,596,886 B2 | 3/2017 | Liu |
| 9,596,887 B2 | 3/2017 | Newton |
| 9,602,646 B2 | 3/2017 | Stanimirovic et al. |
| 9,603,198 B2 | 3/2017 | Liu |
| 9,603,386 B2 | 3/2017 | Xiang |
| 9,603,387 B2 | 3/2017 | Liu |
| 9,603,389 B2 | 3/2017 | Chen |
| 9,603,390 B2 | 3/2017 | Li et al. |
| D784,609 S | 4/2017 | Liu |
| D785,234 S | 4/2017 | Liu |
| D785,237 S | 4/2017 | Wu |
| 9,609,893 B2 | 4/2017 | Novak, III et al. |
| 9,615,605 B2 | 4/2017 | Liu |
| 9,615,606 B2 | 4/2017 | Liu |
| 9,615,607 B2 | 4/2017 | Liu |
| 9,620,958 B2 | 4/2017 | Liu |
| 9,622,511 B2 | 4/2017 | Zhu |
| 9,623,592 B2 | 4/2017 | Liu |
| 9,627,661 B2 | 4/2017 | Liu |
| 9,629,391 B2 | 4/2017 | Dube et al. |
| 9,629,394 B2 | 4/2017 | Aronie et al. |
| D785,859 S | 5/2017 | Pang |
| D785,862 S | 5/2017 | Wu |
| D786,789 S | 5/2017 | Jordan et al. |
| D787,114 S | 5/2017 | Scott |
| D788,362 S | 5/2017 | Qiu |
| 9,635,886 B2 | 5/2017 | Tu |
| 9,641,208 B2 | 5/2017 | Sela et al. |
| 9,642,396 B2 | 5/2017 | Liu |
| 9,642,397 B2 | 5/2017 | Dai et al. |
| 9,645,134 B1 | 5/2017 | Farmen et al. |
| 9,648,905 B2 | 5/2017 | Levitz et al. |
| 9,648,908 B1 | 5/2017 | Rinehart et al. |
| 9,648,909 B2 | 5/2017 | Zhou et al. |
| 9,655,383 B2 | 5/2017 | Holzherr et al. |
| 9,655,890 B2 | 5/2017 | Hearn et al. |
| 9,661,878 B2 | 5/2017 | Liu |
| 9,663,266 B2 | 5/2017 | Schwester |
| D788,697 S | 6/2017 | Verleur et al. |
| D790,122 S | 6/2017 | Hawes et al. |
| D790,126 S | 6/2017 | Bennett et al. |
| D790,129 S | 6/2017 | Bennett et al. |
| D790,766 S | 6/2017 | Li |
| 9,668,517 B2 | 6/2017 | Liu |
| 9,668,518 B2 | 6/2017 | Esses |
| 9,668,519 B2 | 6/2017 | Mishra et al. |
| 9,668,520 B2 | 6/2017 | Boldrini |
| 9,668,521 B2 | 6/2017 | Kuczaj |
| 9,668,522 B2 | 6/2017 | Memari et al. |
| 9,668,523 B2 | 6/2017 | Tucker et al. |
| 9,675,108 B2 | 6/2017 | Liu |
| 9,675,109 B2 | 6/2017 | Monsees et al. |
| 9,675,113 B2 | 6/2017 | Liu |
| 9,675,114 B2 | 6/2017 | Timmermans |
| 9,675,115 B2 | 6/2017 | Liu |
| 9,675,116 B2 | 6/2017 | Liu |
| 9,675,117 B2 | 6/2017 | Li et al. |
| 9,675,118 B2 | 6/2017 | Chen |
| 9,681,687 B2 | 6/2017 | Liu |
| 9,681,688 B1 | 6/2017 | Rinehart et al. |
| 9,682,203 B2 | 6/2017 | Dahne et al. |
| 9,682,204 B2 | 6/2017 | Matsumoto et al. |
| 9,682,800 B2 | 6/2017 | Xiang |
| 9,687,025 B2 | 6/2017 | Cyphert et al. |
| 9,687,027 B2 | 6/2017 | Poston et al. |
| 9,687,028 B2 | 6/2017 | Park |
| 9,687,029 B2 | 6/2017 | Liu |
| D792,021 S | 7/2017 | Beer et al. |
| D792,022 S | 7/2017 | Li |
| D792,644 S | 7/2017 | Jordan et al. |
| D793,004 S | 7/2017 | Liu |
| 9,693,584 B2 | 7/2017 | Hearn et al. |
| 9,693,586 B2 | 7/2017 | Liu |
| 9,693,587 B2 | 7/2017 | Plojoux et al. |
| 9,693,588 B2 | 7/2017 | Zhu |
| 9,695,033 B1 | 7/2017 | Alshouse et al. |
| 9,700,074 B2 | 7/2017 | Liu |
| 9,700,075 B2 | 7/2017 | Liu |
| 9,700,076 B2 | 7/2017 | Xiang |
| 9,713,345 B2 | 7/2017 | Farine et al. |
| 9,713,346 B2 | 7/2017 | Hon |
| 9,714,878 B2 | 7/2017 | Powers et al. |
| D793,620 S | 8/2017 | Bennett et al. |
| 9,717,274 B2 | 8/2017 | Daehne et al. |
| 9,717,275 B2 | 8/2017 | Liu |
| 9,717,276 B2 | 8/2017 | Brammer et al. |
| 9,717,277 B2 | 8/2017 | Mironov |
| 9,717,278 B2 | 8/2017 | Hon |
| 9,717,279 B2 | 8/2017 | Hon |
| 9,723,872 B2 | 8/2017 | Liu |
| 9,723,873 B2 | 8/2017 | Liu |
| 9,723,874 B2 | 8/2017 | Liu |
| 9,723,875 B2 | 8/2017 | Liu |
| 9,723,876 B2 | 8/2017 | Cadieux et al. |
| 9,723,877 B2 | 8/2017 | Wong et al. |
| 9,730,471 B2 | 8/2017 | Li et al. |
| 9,738,622 B2 | 8/2017 | Dull et al. |
| 9,763,478 B2 | 9/2017 | Cameron et al. |
| 9,770,055 B2 | 9/2017 | Cameron et al. |
| 9,772,245 B2 | 9/2017 | Besling et al. |
| D799,746 S | 10/2017 | Leidel et al. |
| 9,775,380 B2 | 10/2017 | Fernando et al. |
| 9,781,953 B2 | 10/2017 | Verleur et al. |
| 9,795,168 B2 | 10/2017 | Zhu |
| 9,801,413 B2 | 10/2017 | Zhu |
| 9,802,011 B2 | 10/2017 | Davidson et al. |
| 9,806,549 B2 | 10/2017 | Libert et al. |
| D802,206 S | 11/2017 | Huang et al. |
| 9,809,567 B2 | 11/2017 | Willis et al. |
| 9,814,263 B2 | 11/2017 | Cochand et al. |
| 9,814,265 B2 | 11/2017 | Rinker et al. |
| 9,814,272 B2 | 11/2017 | Li et al. |
| 9,820,508 B2 | 11/2017 | Arnel et al. |
| D806,311 S | 12/2017 | Smith |
| 9,844,234 B2 | 12/2017 | Thorens et al. |
| 9,861,135 B2 | 1/2018 | Chen |
| 9,974,743 B2 | 5/2018 | Rose et al. |
| 10,039,321 B2 | 8/2018 | Verleur et al. |
| 10,045,568 B2 | 8/2018 | Monsees et al. |
| 10,058,122 B2 | 8/2018 | Steingraber et al. |
| 10,058,124 B2 | 8/2018 | Monsees et al. |
| 10,058,129 B2 | 8/2018 | Monsees et al. |
| 10,085,481 B2 | 10/2018 | Verleur et al. |
| 10,092,713 B2 | 10/2018 | Terry et al. |
| 10,104,915 B2 | 10/2018 | Bowen et al. |
| 10,111,470 B2 | 10/2018 | Monsees et al. |
| 10,117,465 B2 | 11/2018 | Monsees et al. |
| 10,117,466 B2 | 11/2018 | Monsees et al. |
| 10,130,123 B2 | 11/2018 | Hatton et al. |
| 10,143,233 B2 | 12/2018 | Dubief et al. |
| 10,195,345 B2 | 2/2019 | Senior et al. |

(56) References Cited

U.S. PATENT DOCUMENTS

| | | |
|---|---|---|
| 10,195,370 B2 | 2/2019 | Chen |
| 10,264,823 B2 | 4/2019 | Monsees et al. |
| 2001/0015209 A1 | 8/2001 | Zielke |
| 2001/0032643 A1 | 10/2001 | Hochrainer et al. |
| 2001/0032795 A1 | 10/2001 | Weinstein et al. |
| 2001/0052480 A1 | 12/2001 | Kawaguchi et al. |
| 2002/0029779 A1 | 3/2002 | Schmidt et al. |
| 2002/0043262 A1 | 4/2002 | Langford et al. |
| 2002/0043554 A1 | 4/2002 | White et al. |
| 2002/0078951 A1 | 6/2002 | Nichols et al. |
| 2002/0088469 A1 | 7/2002 | Rennecamp |
| 2002/0142291 A1 | 10/2002 | Bauer et al. |
| 2002/0175164 A1 | 11/2002 | Dees et al. |
| 2003/0004426 A1 | 1/2003 | Melker et al. |
| 2003/0005926 A1 | 1/2003 | Jones et al. |
| 2003/0033055 A1 | 2/2003 | McRae et al. |
| 2003/0089377 A1 | 5/2003 | Hajaligol et al. |
| 2003/0096542 A1 | 5/2003 | Kojima |
| 2003/0149372 A1 | 8/2003 | Smith et al. |
| 2003/0150451 A1 | 8/2003 | Shayan |
| 2003/0154991 A1 | 8/2003 | Fournier et al. |
| 2003/0226837 A1 | 12/2003 | Blake et al. |
| 2004/0031495 A1 | 2/2004 | Steinberg |
| 2004/0050382 A1 | 3/2004 | Goodchild |
| 2004/0099266 A1 | 5/2004 | Cross et al. |
| 2004/0129280 A1 | 7/2004 | Woodson et al. |
| 2004/0149296 A1 | 8/2004 | Rostami et al. |
| 2004/0149624 A1 | 8/2004 | Wischusen et al. |
| 2004/0173224 A1 | 9/2004 | Burgard et al. |
| 2004/0173229 A1 | 9/2004 | Crooks et al. |
| 2004/0182403 A1 | 9/2004 | Andersson et al. |
| 2004/0191322 A1 | 9/2004 | Hansson |
| 2004/0221857 A1 | 11/2004 | Dominguez |
| 2004/0226569 A1 | 11/2004 | Yang et al. |
| 2004/0237974 A1 | 12/2004 | Min |
| 2005/0016549 A1 | 1/2005 | Banerjee et al. |
| 2005/0016550 A1 | 1/2005 | Katase |
| 2005/0029137 A1 | 2/2005 | Wang |
| 2005/0034723 A1 | 2/2005 | Bennett et al. |
| 2005/0061759 A1 | 3/2005 | Doucette |
| 2005/0069831 A1 | 3/2005 | St. Charles et al. |
| 2005/0081601 A1 | 4/2005 | Lawson |
| 2005/0090798 A1 | 4/2005 | Clark et al. |
| 2005/0118545 A1 | 6/2005 | Wong |
| 2005/0134215 A1 | 6/2005 | Bozzone et al. |
| 2005/0145533 A1 | 7/2005 | Seligson |
| 2005/0172976 A1 | 8/2005 | Newman et al. |
| 2005/0225292 A1 | 10/2005 | Damlamian et al. |
| 2005/0229918 A1 | 10/2005 | Shim |
| 2005/0235991 A1 | 10/2005 | Nichols et al. |
| 2005/0236006 A1 | 10/2005 | Cowan |
| 2005/0244521 A1 | 11/2005 | Strickland et al. |
| 2005/0252511 A1 | 11/2005 | Pentafragas |
| 2005/0268911 A1 | 12/2005 | Cross et al. |
| 2006/0016453 A1 | 1/2006 | Kim |
| 2006/0018840 A1 | 1/2006 | Lechuga-Ballesteros et al. |
| 2006/0047368 A1 | 3/2006 | Maharajh et al. |
| 2006/0054676 A1 | 3/2006 | Wischusen |
| 2006/0102175 A1 | 5/2006 | Nelson |
| 2006/0141344 A1 | 6/2006 | Chen et al. |
| 2006/0150991 A1 | 7/2006 | Lee |
| 2006/0185687 A1 | 8/2006 | Hearn et al. |
| 2006/0191546 A1 | 8/2006 | Takano et al. |
| 2006/0191548 A1 | 8/2006 | Strickland et al. |
| 2006/0191594 A1 | 8/2006 | Py |
| 2006/0196518 A1 | 9/2006 | Hon |
| 2006/0207466 A1 | 9/2006 | McNulty et al. |
| 2006/0254948 A1 | 11/2006 | Herbert et al. |
| 2006/0255105 A1 | 11/2006 | Sweet |
| 2007/0006889 A1 | 1/2007 | Kobal et al. |
| 2007/0045288 A1 | 3/2007 | Nelson |
| 2007/0062548 A1 | 3/2007 | Horstmann et al. |
| 2007/0072443 A1 | 3/2007 | Rohrbach et al. |
| 2007/0074734 A1 | 4/2007 | Braunshteyn et al. |
| 2007/0089757 A1 | 4/2007 | Bryman |
| 2007/0098148 A1 | 5/2007 | Sherman |
| 2007/0102013 A1 | 5/2007 | Adams et al. |
| 2007/0119450 A1 | 5/2007 | Wharton et al. |
| 2007/0125765 A1 | 6/2007 | Nelson |
| 2007/0144514 A1 | 6/2007 | Yeates et al. |
| 2007/0163610 A1 | 7/2007 | Lindell et al. |
| 2007/0191756 A1 | 8/2007 | Tapper |
| 2007/0215164 A1 | 9/2007 | Mehio |
| 2007/0215168 A1 | 9/2007 | Banerjee et al. |
| 2007/0235046 A1 | 10/2007 | Gedevanishvili |
| 2007/0267033 A1 | 11/2007 | Mishra et al. |
| 2007/0277816 A1 | 12/2007 | Morrison et al. |
| 2007/0280652 A1 | 12/2007 | Williams |
| 2007/0283972 A1 | 12/2007 | Monsees et al. |
| 2007/0295347 A1 | 12/2007 | Paine et al. |
| 2008/0000763 A1 | 1/2008 | Cove |
| 2008/0023003 A1 | 1/2008 | Rosenthal |
| 2008/0029095 A1 | 2/2008 | Esser |
| 2008/0068602 A1 | 3/2008 | Delaage et al. |
| 2008/0092912 A1 | 4/2008 | Robinson et al. |
| 2008/0138423 A1 | 6/2008 | Gonda |
| 2008/0149118 A1 | 6/2008 | Oglesby et al. |
| 2008/0207276 A1 | 8/2008 | Burrell |
| 2008/0216828 A1 | 9/2008 | Wensley et al. |
| 2008/0241255 A1 | 10/2008 | Rose et al. |
| 2008/0245363 A1 | 10/2008 | Korevaar et al. |
| 2008/0257367 A1 | 10/2008 | Paterno et al. |
| 2008/0276947 A1 | 11/2008 | Martzel |
| 2008/0286340 A1 | 11/2008 | Andersson et al. |
| 2008/0302374 A1 | 12/2008 | Wengert et al. |
| 2008/0302375 A1 | 12/2008 | Andersson et al. |
| 2009/0004249 A1 | 1/2009 | Gonda |
| 2009/0068602 A1 | 3/2009 | Smith |
| 2009/0095287 A1 | 4/2009 | Emarlou |
| 2009/0095311 A1 | 4/2009 | Han |
| 2009/0111287 A1 | 4/2009 | Lindberg et al. |
| 2009/0126745 A1 | 5/2009 | Hon |
| 2009/0133691 A1 | 5/2009 | Yamada et al. |
| 2009/0133703 A1 | 5/2009 | Strickland et al. |
| 2009/0133704 A1 | 5/2009 | Strickland et al. |
| 2009/0151717 A1 | 6/2009 | Bowen et al. |
| 2009/0188490 A1 | 7/2009 | Han |
| 2009/0230117 A1 | 9/2009 | Fernando et al. |
| 2009/0255534 A1 | 10/2009 | Paterno |
| 2009/0260641 A1 | 10/2009 | Monsees et al. |
| 2009/0260642 A1 | 10/2009 | Monsees et al. |
| 2009/0267252 A1 | 10/2009 | Ikeyama |
| 2009/0272379 A1 | 11/2009 | Thorens et al. |
| 2009/0283103 A1 | 11/2009 | Nielsen et al. |
| 2009/0288668 A1 | 11/2009 | Inagaki |
| 2009/0288669 A1 | 11/2009 | Hutchens |
| 2009/0293892 A1 | 12/2009 | Williams et al. |
| 2009/0293895 A1 | 12/2009 | Axelsson et al. |
| 2010/0000672 A1 | 1/2010 | Fogle |
| 2010/0006092 A1 | 1/2010 | Hale et al. |
| 2010/0024834 A1 | 2/2010 | Oglesby et al. |
| 2010/0031968 A1 | 2/2010 | Sheikh et al. |
| 2010/0059073 A1 | 3/2010 | Hoffmann et al. |
| 2010/0156193 A1 | 6/2010 | Rhodes et al. |
| 2010/0163063 A1 | 7/2010 | Fernando et al. |
| 2010/0163065 A1 | 7/2010 | Chang |
| 2010/0186757 A1 | 7/2010 | Crooks et al. |
| 2010/0192949 A1 | 8/2010 | Wright et al. |
| 2010/0194337 A1 | 8/2010 | Opolka |
| 2010/0200006 A1 | 8/2010 | Robinson et al. |
| 2010/0200008 A1 | 8/2010 | Taieb |
| 2010/0236562 A1 | 9/2010 | Hearn et al. |
| 2010/0242974 A1 | 9/2010 | Pan |
| 2010/0242976 A1 | 9/2010 | Katayama et al. |
| 2010/0275938 A1 | 11/2010 | Roth et al. |
| 2010/0276333 A1 | 11/2010 | Couture |
| 2010/0307116 A1 | 12/2010 | Fisher |
| 2010/0307518 A1 | 12/2010 | Wang |
| 2010/0313901 A1 | 12/2010 | Fernando et al. |
| 2011/0005535 A1 | 1/2011 | Xiu |
| 2011/0011396 A1 | 1/2011 | Fang |
| 2011/0030706 A1 | 2/2011 | Gibson et al. |
| 2011/0036346 A1 | 2/2011 | Cohen et al. |
| 2011/0036363 A1 | 2/2011 | Urtsev et al. |

(56) References Cited

U.S. PATENT DOCUMENTS

| | | |
|---|---|---|
| 2011/0041861 A1 | 2/2011 | Sebastian et al. |
| 2011/0049226 A1 | 3/2011 | Moreau et al. |
| 2011/0083684 A1 | 4/2011 | Luan et al. |
| 2011/0094523 A1 | 4/2011 | Thorens et al. |
| 2011/0097060 A1 | 4/2011 | Michael Buzzetti |
| 2011/0108023 A1 | 5/2011 | McKinney et al. |
| 2011/0120482 A1 | 5/2011 | Brenneise |
| 2011/0125146 A1 | 5/2011 | Greeley et al. |
| 2011/0126831 A1 | 6/2011 | Pernia |
| 2011/0155151 A1 | 6/2011 | Newman et al. |
| 2011/0155153 A1 | 6/2011 | Thorens et al. |
| 2011/0162667 A1 | 7/2011 | Burke et al. |
| 2011/0168194 A1 | 7/2011 | Hon |
| 2011/0180433 A1 | 7/2011 | Rennecamp |
| 2011/0192397 A1 | 8/2011 | Saskar et al. |
| 2011/0226236 A1 | 9/2011 | Buchberger |
| 2011/0226266 A1 | 9/2011 | Tao |
| 2011/0232654 A1 | 9/2011 | Mass |
| 2011/0232655 A1 | 9/2011 | Chan et al. |
| 2011/0236002 A1 | 9/2011 | Oglesby et al. |
| 2011/0240047 A1 | 10/2011 | Adamic |
| 2011/0263947 A1 | 10/2011 | Utley et al. |
| 2011/0265806 A1 | 11/2011 | Alarcon et al. |
| 2011/0268809 A1 | 11/2011 | Brinkley et al. |
| 2011/0277756 A1 | 11/2011 | Terry et al. |
| 2011/0277757 A1 | 11/2011 | Terry et al. |
| 2011/0277780 A1 | 11/2011 | Terry et al. |
| 2011/0278189 A1 | 11/2011 | Terry et al. |
| 2011/0290248 A1 | 12/2011 | Schennum |
| 2011/0290269 A1 | 12/2011 | Shimizu |
| 2011/0293535 A1 | 12/2011 | Kosik et al. |
| 2011/0303231 A1 | 12/2011 | Li |
| 2011/0308521 A1 | 12/2011 | Kofford |
| 2011/0315152 A1 | 12/2011 | Hearn et al. |
| 2011/0315701 A1 | 12/2011 | Everson |
| 2012/0006342 A1 | 1/2012 | Rose et al. |
| 2012/0018529 A1 | 1/2012 | Gammon et al. |
| 2012/0048266 A1 | 3/2012 | Alelov |
| 2012/0060853 A1 | 3/2012 | Robinson et al. |
| 2012/0077849 A1 | 3/2012 | Howson et al. |
| 2012/0086391 A1 | 4/2012 | Smith |
| 2012/0111346 A1 | 5/2012 | Rinker et al. |
| 2012/0111347 A1 | 5/2012 | Hon |
| 2012/0118301 A1 | 5/2012 | Montaser |
| 2012/0118307 A1 | 5/2012 | Tu |
| 2012/0125353 A1 | 5/2012 | Wollin |
| 2012/0138052 A1 | 6/2012 | Hearn et al. |
| 2012/0174914 A1 | 7/2012 | Pirshafiey et al. |
| 2012/0186594 A1 | 7/2012 | Liu |
| 2012/0188687 A1 | 7/2012 | Yamamoto |
| 2012/0199146 A1 | 8/2012 | Marangos |
| 2012/0199663 A1 | 8/2012 | Qiu |
| 2012/0204889 A1 | 8/2012 | Xiu |
| 2012/0211015 A1 | 8/2012 | Li et al. |
| 2012/0223673 A1 | 9/2012 | Chen et al. |
| 2012/0227753 A1 | 9/2012 | Newton |
| 2012/0234315 A1 | 9/2012 | Li et al. |
| 2012/0234821 A1 | 9/2012 | Shimizu |
| 2012/0247494 A1 | 10/2012 | Oglesby et al. |
| 2012/0255567 A1 | 10/2012 | Rose et al. |
| 2012/0260926 A1 | 10/2012 | Tu et al. |
| 2012/0260927 A1 | 10/2012 | Liu |
| 2012/0261286 A1 | 10/2012 | Holloway et al. |
| 2012/0267383 A1 | 10/2012 | Van Rooyen |
| 2012/0279512 A1 | 11/2012 | Hon |
| 2012/0285475 A1 | 11/2012 | Liu |
| 2012/0291791 A1 | 11/2012 | Pradeep |
| 2012/0298676 A1 | 11/2012 | Cooks |
| 2012/0312313 A1 | 12/2012 | Frija |
| 2012/0318882 A1 | 12/2012 | Abehasera |
| 2012/0325227 A1 | 12/2012 | Robinson et al. |
| 2012/0325228 A1 | 12/2012 | Williams |
| 2013/0008457 A1 | 1/2013 | Zheng et al. |
| 2013/0014755 A1 | 1/2013 | Kumar et al. |
| 2013/0014772 A1 | 1/2013 | Liu |
| 2013/0019887 A1 | 1/2013 | Liu |
| 2013/0023850 A1 | 1/2013 | Imran et al. |
| 2013/0025609 A1 | 1/2013 | Liu |
| 2013/0037041 A1 | 2/2013 | Worm et al. |
| 2013/0042865 A1 | 2/2013 | Monsees et al. |
| 2013/0047984 A1 | 2/2013 | Dahne et al. |
| 2013/0056012 A1 | 3/2013 | Hearn et al. |
| 2013/0056013 A1 | 3/2013 | Terry et al. |
| 2013/0068239 A1 | 3/2013 | Youn |
| 2013/0074857 A1 | 3/2013 | Buchberger |
| 2013/0081642 A1 | 4/2013 | Safari |
| 2013/0087160 A1 | 4/2013 | Gherghe |
| 2013/0099725 A1 | 4/2013 | Burrell et al. |
| 2013/0115821 A1 | 5/2013 | Golko et al. |
| 2013/0140200 A1 | 6/2013 | Scatterday |
| 2013/0146489 A1 | 6/2013 | Scatterday |
| 2013/0152922 A1 | 6/2013 | Benassayag et al. |
| 2013/0152954 A1 | 6/2013 | Youn |
| 2013/0167854 A1 | 7/2013 | Shin |
| 2013/0168880 A1 | 7/2013 | Duke |
| 2013/0169230 A1 | 7/2013 | Li et al. |
| 2013/0182421 A1 | 7/2013 | Popper et al. |
| 2013/0186416 A1 | 7/2013 | Gao et al. |
| 2013/0192615 A1 | 8/2013 | Tucker et al. |
| 2013/0192618 A1 | 8/2013 | Li et al. |
| 2013/0192619 A1 | 8/2013 | Tucker |
| 2013/0192623 A1 | 8/2013 | Tucker et al. |
| 2013/0199528 A1 | 8/2013 | Goodman et al. |
| 2013/0213417 A1 | 8/2013 | Chong et al. |
| 2013/0213418 A1 | 8/2013 | Tucker et al. |
| 2013/0213419 A1 | 8/2013 | Tucker et al. |
| 2013/0220314 A1 | 8/2013 | Bottom |
| 2013/0220315 A1 | 8/2013 | Conley et al. |
| 2013/0220316 A1 | 8/2013 | Oglesby et al. |
| 2013/0220847 A1 | 8/2013 | Fisher et al. |
| 2013/0228190 A1 | 9/2013 | Weiss et al. |
| 2013/0228191 A1 | 9/2013 | Newton |
| 2013/0233086 A1 | 9/2013 | Besling et al. |
| 2013/0247924 A1 | 9/2013 | Scatterday et al. |
| 2013/0248385 A1 | 9/2013 | Scatterday et al. |
| 2013/0253433 A1 | 9/2013 | Senior et al. |
| 2013/0255675 A1 | 10/2013 | Liu |
| 2013/0255702 A1 | 10/2013 | Griffith, Jr. et al. |
| 2013/0263869 A1 | 10/2013 | Zhu |
| 2013/0276802 A1 | 10/2013 | Scatterday |
| 2013/0284190 A1 | 10/2013 | Scatterday et al. |
| 2013/0284191 A1 | 10/2013 | Scatterday et al. |
| 2013/0284192 A1 | 10/2013 | Peleg et al. |
| 2013/0298905 A1 | 11/2013 | Levin et al. |
| 2013/0306065 A1 | 11/2013 | Thorens et al. |
| 2013/0306084 A1 | 11/2013 | Flick |
| 2013/0312742 A1 | 11/2013 | Monsees et al. |
| 2013/0319407 A1 | 12/2013 | Liu |
| 2013/0319431 A1 | 12/2013 | Cyphert et al. |
| 2013/0319435 A1 | 12/2013 | Flick |
| 2013/0319436 A1 | 12/2013 | Liu |
| 2013/0319437 A1 | 12/2013 | Liu |
| 2013/0319438 A1 | 12/2013 | Liu |
| 2013/0319439 A1 | 12/2013 | Gorelick et al. |
| 2013/0319440 A1 | 12/2013 | Capuano |
| 2013/0323941 A1 | 12/2013 | Zeliff et al. |
| 2013/0333700 A1 | 12/2013 | Buchberger |
| 2013/0333711 A1 | 12/2013 | Liu |
| 2013/0336358 A1 | 12/2013 | Liu |
| 2013/0340775 A1 | 12/2013 | Juster et al. |
| 2013/0342157 A1 | 12/2013 | Liu |
| 2014/0000638 A1 | 1/2014 | Sebastian et al. |
| 2014/0007891 A1 | 1/2014 | Liu |
| 2014/0007892 A1 | 1/2014 | Liu |
| 2014/0014124 A1 | 1/2014 | Glasberg et al. |
| 2014/0014126 A1 | 1/2014 | Peleg et al. |
| 2014/0020697 A1 | 1/2014 | Liu |
| 2014/0034071 A1 | 2/2014 | Levitz et al. |
| 2014/0035391 A1 | 2/2014 | Kitani |
| 2014/0041655 A1 | 2/2014 | Barron et al. |
| 2014/0041658 A1 | 2/2014 | Goodman et al. |
| 2014/0048086 A1 | 2/2014 | Zhanghua |
| 2014/0053856 A1 | 2/2014 | Liu |
| 2014/0053857 A1 | 2/2014 | Liu |

(56) References Cited

U.S. PATENT DOCUMENTS

| | | |
|---|---|---|
| 2014/0053858 A1 | 2/2014 | Liu |
| 2014/0060528 A1 | 3/2014 | Liu |
| 2014/0060529 A1 | 3/2014 | Zhang |
| 2014/0060552 A1 | 3/2014 | Cohen |
| 2014/0060554 A1 | 3/2014 | Collett et al. |
| 2014/0060556 A1 | 3/2014 | Liu |
| 2014/0062417 A1 | 3/2014 | Li et al. |
| 2014/0069424 A1 | 3/2014 | Poston et al. |
| 2014/0069425 A1 | 3/2014 | Zhang |
| 2014/0072230 A1 | 3/2014 | Xiang et al. |
| 2014/0083442 A1 | 3/2014 | Scatterday |
| 2014/0096782 A1 | 4/2014 | Ampolini et al. |
| 2014/0107815 A1 | 4/2014 | LaMothe |
| 2014/0109898 A1 | 4/2014 | Li et al. |
| 2014/0109921 A1 | 4/2014 | Chen |
| 2014/0116426 A1 | 5/2014 | Mullinger et al. |
| 2014/0116455 A1 | 5/2014 | Youn |
| 2014/0123989 A1 | 5/2014 | LaMothe |
| 2014/0123990 A1 | 5/2014 | Timmermans |
| 2014/0130796 A1 | 5/2014 | Liu |
| 2014/0130797 A1 | 5/2014 | Liu |
| 2014/0130816 A1 | 5/2014 | Liu |
| 2014/0130817 A1 | 5/2014 | Li et al. |
| 2014/0144429 A1 | 5/2014 | Wensley et al. |
| 2014/0144453 A1 | 5/2014 | Capuano et al. |
| 2014/0150784 A1 | 6/2014 | Liu |
| 2014/0150785 A1 | 6/2014 | Malik et al. |
| 2014/0150810 A1 | 6/2014 | Hon |
| 2014/0161301 A1 | 6/2014 | Merenda |
| 2014/0166028 A1 | 6/2014 | Fuisz et al. |
| 2014/0166029 A1 | 6/2014 | Weigensberg et al. |
| 2014/0166030 A1 | 6/2014 | Li et al. |
| 2014/0166032 A1 | 6/2014 | Gindrat |
| 2014/0174458 A1 | 6/2014 | Katz |
| 2014/0174459 A1 | 6/2014 | Burstyn |
| 2014/0175081 A1 | 6/2014 | Hwa |
| 2014/0178461 A1 | 6/2014 | Rigas |
| 2014/0182609 A1 | 7/2014 | Liu |
| 2014/0182610 A1 | 7/2014 | Liu |
| 2014/0182611 A1 | 7/2014 | Liu |
| 2014/0182612 A1 | 7/2014 | Chen |
| 2014/0190477 A1 | 7/2014 | Qiu |
| 2014/0190478 A1 | 7/2014 | Liu |
| 2014/0190496 A1 | 7/2014 | Wensley et al. |
| 2014/0190501 A1 | 7/2014 | Liu |
| 2014/0190502 A1 | 7/2014 | Liu |
| 2014/0190503 A1 | 7/2014 | Li et al. |
| 2014/0196716 A1 | 7/2014 | Liu |
| 2014/0196718 A1 | 7/2014 | Li et al. |
| 2014/0196731 A1 | 7/2014 | Scatterday |
| 2014/0196733 A1 | 7/2014 | Liu |
| 2014/0196734 A1 | 7/2014 | Liu |
| 2014/0196735 A1 | 7/2014 | Liu |
| 2014/0202454 A1 | 7/2014 | Buchberger |
| 2014/0202474 A1 | 7/2014 | Peleg et al. |
| 2014/0202475 A1 | 7/2014 | Liu |
| 2014/0202477 A1 | 7/2014 | Qi et al. |
| 2014/0209096 A1 | 7/2014 | Cheyene |
| 2014/0209106 A1 | 7/2014 | Liu |
| 2014/0209107 A1 | 7/2014 | Liu |
| 2014/0209108 A1 | 7/2014 | Li et al. |
| 2014/0209109 A1 | 7/2014 | Larson |
| 2014/0216450 A1 | 8/2014 | Liu |
| 2014/0216483 A1 | 8/2014 | Alima |
| 2014/0216484 A1 | 8/2014 | Liu |
| 2014/0224244 A1 | 8/2014 | Liu |
| 2014/0224267 A1 | 8/2014 | Levitz et al. |
| 2014/0230835 A1 | 8/2014 | Saliman |
| 2014/0238421 A1 | 8/2014 | Shapiro |
| 2014/0238422 A1 | 8/2014 | Plunkett et al. |
| 2014/0238423 A1 | 8/2014 | Tucker et al. |
| 2014/0238424 A1 | 8/2014 | Macko et al. |
| 2014/0246031 A1 | 9/2014 | Liu |
| 2014/0246033 A1 | 9/2014 | Daehne et al. |
| 2014/0251324 A1 | 9/2014 | Xiang |
| 2014/0251325 A1 | 9/2014 | Liu |
| 2014/0251356 A1 | 9/2014 | Xiang |
| 2014/0253144 A1 | 9/2014 | Novak, III et al. |
| 2014/0254055 A1 | 9/2014 | Xiang |
| 2014/0259026 A1 | 9/2014 | Xiang |
| 2014/0261408 A1 | 9/2014 | Depiano et al. |
| 2014/0261474 A1 | 9/2014 | Gonda |
| 2014/0261479 A1 | 9/2014 | Xu et al. |
| 2014/0261483 A1 | 9/2014 | Hopps |
| 2014/0261486 A1 | 9/2014 | Potter et al. |
| 2014/0261487 A1 | 9/2014 | Chapman et al. |
| 2014/0261488 A1 | 9/2014 | Tucker |
| 2014/0261489 A1 | 9/2014 | Cadieux et al. |
| 2014/0261490 A1 | 9/2014 | Kane |
| 2014/0261491 A1 | 9/2014 | Hawes |
| 2014/0261492 A1 | 9/2014 | Kane et al. |
| 2014/0261493 A1 | 9/2014 | Smith et al. |
| 2014/0261494 A1 | 9/2014 | Scatterday |
| 2014/0261495 A1 | 9/2014 | Novak, III et al. |
| 2014/0261497 A1 | 9/2014 | Liu |
| 2014/0261498 A1 | 9/2014 | Liu |
| 2014/0261500 A1 | 9/2014 | Park |
| 2014/0270727 A1 | 9/2014 | Ampolini et al. |
| 2014/0270729 A1 | 9/2014 | Depiano et al. |
| 2014/0270730 A1 | 9/2014 | Depiano et al. |
| 2014/0271946 A1 | 9/2014 | Kobal et al. |
| 2014/0274940 A1 | 9/2014 | Mishra et al. |
| 2014/0276536 A1 | 9/2014 | Estes |
| 2014/0278250 A1 | 9/2014 | Smith et al. |
| 2014/0278258 A1 | 9/2014 | Shafer |
| 2014/0283823 A1 | 9/2014 | Liu |
| 2014/0283855 A1 | 9/2014 | Hawes et al. |
| 2014/0283856 A1 | 9/2014 | Xiang |
| 2014/0283857 A1 | 9/2014 | Liu |
| 2014/0283858 A1 | 9/2014 | Liu |
| 2014/0290673 A1 | 10/2014 | Liu |
| 2014/0290676 A1 | 10/2014 | Liu |
| 2014/0290677 A1 | 10/2014 | Liu |
| 2014/0299125 A1 | 10/2014 | Buchberger |
| 2014/0299137 A1 | 10/2014 | Kieckbusch et al. |
| 2014/0299138 A1 | 10/2014 | Xiang |
| 2014/0299139 A1 | 10/2014 | Liu |
| 2014/0299140 A1 | 10/2014 | Liu |
| 2014/0299141 A1 | 10/2014 | Flick |
| 2014/0301721 A1 | 10/2014 | Ruscio et al. |
| 2014/0305450 A1 | 10/2014 | Xiang |
| 2014/0305451 A1 | 10/2014 | Liu |
| 2014/0305452 A1 | 10/2014 | Liu |
| 2014/0305454 A1 | 10/2014 | Rinker et al. |
| 2014/0311503 A1 | 10/2014 | Liu |
| 2014/0311504 A1 | 10/2014 | Liu |
| 2014/0311505 A1 | 10/2014 | Liu |
| 2014/0332016 A1 | 11/2014 | Bellinger et al. |
| 2014/0332017 A1 | 11/2014 | Liu |
| 2014/0332018 A1 | 11/2014 | Liu |
| 2014/0332019 A1 | 11/2014 | Liu |
| 2014/0332020 A1 | 11/2014 | Li et al. |
| 2014/0332022 A1 | 11/2014 | Li et al. |
| 2014/0334803 A1 | 11/2014 | Li et al. |
| 2014/0334804 A1 | 11/2014 | Choi |
| 2014/0338680 A1 | 11/2014 | Abramov et al. |
| 2014/0338681 A1 | 11/2014 | Liu |
| 2014/0338682 A1 | 11/2014 | Liu |
| 2014/0338683 A1 | 11/2014 | Liu |
| 2014/0338684 A1 | 11/2014 | Liu |
| 2014/0338685 A1 | 11/2014 | Amir |
| 2014/0345631 A1 | 11/2014 | Bowen et al. |
| 2014/0345632 A1 | 11/2014 | Scatterday |
| 2014/0345633 A1 | 11/2014 | Talon et al. |
| 2014/0345635 A1 | 11/2014 | Rabinowitz et al. |
| 2014/0352177 A1 | 12/2014 | Rehkemper |
| 2014/0352705 A1 | 12/2014 | Liu |
| 2014/0352707 A1 | 12/2014 | Liu |
| 2014/0353856 A1 | 12/2014 | Dubief |
| 2014/0353867 A1 | 12/2014 | Liu |
| 2014/0354215 A1 | 12/2014 | Xiang |
| 2014/0355969 A1 | 12/2014 | Stern |
| 2014/0356607 A1 | 12/2014 | Woodcock |
| 2014/0360512 A1 | 12/2014 | Xiang |

(56) References Cited

U.S. PATENT DOCUMENTS

| | | |
|---|---|---|
| 2014/0360516 A1 | 12/2014 | Liu |
| 2014/0363145 A1 | 12/2014 | Plojoux et al. |
| 2014/0366894 A1 | 12/2014 | Liu |
| 2014/0366895 A1 | 12/2014 | Li et al. |
| 2014/0366896 A1 | 12/2014 | Li et al. |
| 2014/0366897 A1 | 12/2014 | Liu |
| 2014/0366898 A1 | 12/2014 | Monsees et al. |
| 2014/0366902 A1 | 12/2014 | Chiolini et al. |
| 2014/0373833 A1 | 12/2014 | Liu |
| 2014/0373855 A1 | 12/2014 | Zheng |
| 2014/0373857 A1 | 12/2014 | Steinberg |
| 2014/0373858 A1 | 12/2014 | Liu |
| 2014/0376895 A1 | 12/2014 | Han |
| 2014/0378790 A1 | 12/2014 | Cohen |
| 2015/0000682 A1 | 1/2015 | Liu |
| 2015/0000683 A1 | 1/2015 | Liu |
| 2015/0007834 A1 | 1/2015 | Liu |
| 2015/0007835 A1 | 1/2015 | Liu |
| 2015/0007836 A1 | 1/2015 | Li et al. |
| 2015/0013692 A1 | 1/2015 | Liu |
| 2015/0013693 A1 | 1/2015 | Fuisz et al. |
| 2015/0013696 A1 | 1/2015 | Plojoux et al. |
| 2015/0013700 A1 | 1/2015 | Liu |
| 2015/0013701 A1 | 1/2015 | Liu |
| 2015/0013702 A1 | 1/2015 | Liu |
| 2015/0015187 A1 | 1/2015 | Xiang |
| 2015/0020822 A1 | 1/2015 | Janardhan et al. |
| 2015/0020823 A1 | 1/2015 | Lipowicz et al. |
| 2015/0020824 A1 | 1/2015 | Bowen et al. |
| 2015/0020825 A1 | 1/2015 | Galloway et al. |
| 2015/0020826 A1 | 1/2015 | Liu |
| 2015/0020827 A1 | 1/2015 | Liu |
| 2015/0020828 A1 | 1/2015 | Liu |
| 2015/0020829 A1 | 1/2015 | Li |
| 2015/0020830 A1 | 1/2015 | Koller |
| 2015/0020831 A1 | 1/2015 | Weigensberg et al. |
| 2015/0020833 A1 | 1/2015 | Conley et al. |
| 2015/0027454 A1 | 1/2015 | Li et al. |
| 2015/0027455 A1 | 1/2015 | Peleg et al. |
| 2015/0027456 A1 | 1/2015 | Janardhan et al. |
| 2015/0027457 A1 | 1/2015 | Janardhan et al. |
| 2015/0027460 A1 | 1/2015 | Liu |
| 2015/0027461 A1 | 1/2015 | Liu |
| 2015/0027462 A1 | 1/2015 | Liu |
| 2015/0027463 A1 | 1/2015 | Liu |
| 2015/0027464 A1 | 1/2015 | Liu |
| 2015/0027465 A1 | 1/2015 | Liu |
| 2015/0027466 A1 | 1/2015 | Xiang |
| 2015/0027467 A1 | 1/2015 | Liu |
| 2015/0027468 A1 | 1/2015 | Li et al. |
| 2015/0027469 A1 | 1/2015 | Tucker et al. |
| 2015/0027470 A1 | 1/2015 | Kane et al. |
| 2015/0027471 A1 | 1/2015 | Feldman et al. |
| 2015/0027472 A1 | 1/2015 | Amir |
| 2015/0027473 A1 | 1/2015 | Graf |
| 2015/0034102 A1 | 2/2015 | Faramarzian |
| 2015/0034103 A1 | 2/2015 | Hon |
| 2015/0034104 A1 | 2/2015 | Zhou et al. |
| 2015/0034105 A1 | 2/2015 | Liu |
| 2015/0034106 A1 | 2/2015 | Liu |
| 2015/0034107 A1 | 2/2015 | Liu |
| 2015/0034507 A1 | 2/2015 | Liu |
| 2015/0035540 A1 | 2/2015 | Xiang |
| 2015/0038567 A1 | 2/2015 | Herkenroth et al. |
| 2015/0040927 A1 | 2/2015 | Li et al. |
| 2015/0040928 A1 | 2/2015 | Saydar et al. |
| 2015/0040929 A1 | 2/2015 | Hon |
| 2015/0041482 A1 | 2/2015 | Liu |
| 2015/0047658 A1 | 2/2015 | Cyphert et al. |
| 2015/0047659 A1 | 2/2015 | Liu |
| 2015/0047660 A1 | 2/2015 | Liu |
| 2015/0047661 A1 | 2/2015 | Blackley et al. |
| 2015/0047663 A1 | 2/2015 | Liu |
| 2015/0053214 A1 | 2/2015 | Alarcon et al. |
| 2015/0053215 A1 | 2/2015 | Liu |
| 2015/0053216 A1 | 2/2015 | Liu |
| 2015/0053217 A1 | 2/2015 | Steingraber et al. |
| 2015/0053220 A1 | 2/2015 | Levy et al. |
| 2015/0057341 A1 | 2/2015 | Perry |
| 2015/0059779 A1 | 3/2015 | Alarcon et al. |
| 2015/0059780 A1 | 3/2015 | Davis et al. |
| 2015/0059782 A1 | 3/2015 | Liu |
| 2015/0059783 A1 | 3/2015 | Liu |
| 2015/0059784 A1 | 3/2015 | Liu |
| 2015/0059785 A1 | 3/2015 | Liu |
| 2015/0059787 A1 | 3/2015 | Qiu |
| 2015/0068523 A1 | 3/2015 | Powers et al. |
| 2015/0068543 A1 | 3/2015 | Liu |
| 2015/0068545 A1 | 3/2015 | Moldoveanu et al. |
| 2015/0070832 A1 | 3/2015 | Schneider et al. |
| 2015/0075545 A1 | 3/2015 | Xiang |
| 2015/0075546 A1 | 3/2015 | Kueny, Sr. et al. |
| 2015/0078735 A1 | 3/2015 | Cormack |
| 2015/0080265 A1 | 3/2015 | Elzinga et al. |
| 2015/0082859 A1 | 3/2015 | Xiang |
| 2015/0083144 A1 | 3/2015 | Xiang |
| 2015/0083145 A1 | 3/2015 | Li et al. |
| 2015/0083146 A1 | 3/2015 | Goldman et al. |
| 2015/0083147 A1 | 3/2015 | Schiff et al. |
| 2015/0090256 A1 | 4/2015 | Chung |
| 2015/0090277 A1 | 4/2015 | Xiang |
| 2015/0090278 A1 | 4/2015 | Schiff et al. |
| 2015/0090279 A1 | 4/2015 | Chen |
| 2015/0090280 A1 | 4/2015 | Chen |
| 2015/0090281 A1 | 4/2015 | Chen |
| 2015/0100441 A1 | 4/2015 | Alarcon et al. |
| 2015/0101606 A1 | 4/2015 | White |
| 2015/0101622 A1 | 4/2015 | Liu |
| 2015/0101623 A1 | 4/2015 | Liu |
| 2015/0101625 A1 | 4/2015 | Newton et al. |
| 2015/0101626 A1 | 4/2015 | Li et al. |
| 2015/0101945 A1 | 4/2015 | Scatterday |
| 2015/0102777 A1 | 4/2015 | Cooper |
| 2015/0105455 A1 | 4/2015 | Bjorncrantz |
| 2015/0107609 A1 | 4/2015 | Liu |
| 2015/0107610 A1 | 4/2015 | Metrangolo et al. |
| 2015/0107611 A1 | 4/2015 | Metrangolo et al. |
| 2015/0107612 A1 | 4/2015 | Liu |
| 2015/0108019 A1 | 4/2015 | Liu |
| 2015/0114407 A1 | 4/2015 | Duncan et al. |
| 2015/0114409 A1 | 4/2015 | Brammer et al. |
| 2015/0117842 A1 | 4/2015 | Brammer et al. |
| 2015/0118895 A1 | 4/2015 | Zheng et al. |
| 2015/0122252 A1 | 5/2015 | Frija |
| 2015/0122274 A1 | 5/2015 | Cohen et al. |
| 2015/0122278 A1 | 5/2015 | Hardgrove et al. |
| 2015/0128965 A1 | 5/2015 | Lord |
| 2015/0128966 A1 | 5/2015 | Lord |
| 2015/0128967 A1 | 5/2015 | Robinson et al. |
| 2015/0128969 A1 | 5/2015 | Chapman et al. |
| 2015/0128970 A1 | 5/2015 | Liu |
| 2015/0128971 A1 | 5/2015 | Verleur et al. |
| 2015/0128972 A1 | 5/2015 | Verleur et al. |
| 2015/0128973 A1 | 5/2015 | Li et al. |
| 2015/0128976 A1 | 5/2015 | Verleur et al. |
| 2015/0128977 A1 | 5/2015 | Li et al. |
| 2015/0136153 A1 | 5/2015 | Lord |
| 2015/0136155 A1 | 5/2015 | Verleur et al. |
| 2015/0136156 A1 | 5/2015 | Liu |
| 2015/0136157 A1 | 5/2015 | Liu |
| 2015/0136158 A1 | 5/2015 | Stevens et al. |
| 2015/0142387 A1 | 5/2015 | Alarcon et al. |
| 2015/0144145 A1 | 5/2015 | Chang et al. |
| 2015/0144147 A1 | 5/2015 | Li et al. |
| 2015/0144148 A1 | 5/2015 | Chen |
| 2015/0150302 A1 | 6/2015 | Metrangolo et al. |
| 2015/0150303 A1 | 6/2015 | Jensen |
| 2015/0150305 A1 | 6/2015 | Shenkal |
| 2015/0150306 A1 | 6/2015 | Chen |
| 2015/0150307 A1 | 6/2015 | Liu |
| 2015/0150308 A1 | 6/2015 | Monsees et al. |
| 2015/0157053 A1 | 6/2015 | Mayor |
| 2015/0157054 A1 | 6/2015 | Liu |
| 2015/0157055 A1 | 6/2015 | Lord |

(56) References Cited

U.S. PATENT DOCUMENTS

| | | |
|---|---|---|
| 2015/0157056 A1 | 6/2015 | Bowen et al. |
| 2015/0163859 A1 | 6/2015 | Schneider et al. |
| 2015/0164138 A1 | 6/2015 | Liu |
| 2015/0164141 A1 | 6/2015 | Newton |
| 2015/0164142 A1 | 6/2015 | Li et al. |
| 2015/0164143 A1 | 6/2015 | Maas |
| 2015/0164144 A1 | 6/2015 | Liu |
| 2015/0164145 A1 | 6/2015 | Zhou |
| 2015/0164146 A1 | 6/2015 | Li et al. |
| 2015/0164147 A1 | 6/2015 | Verleur et al. |
| 2015/0167976 A1 | 6/2015 | Recio |
| 2015/0173124 A1 | 6/2015 | Qiu |
| 2015/0173417 A1 | 6/2015 | Gennrich et al. |
| 2015/0173419 A1 | 6/2015 | Tu |
| 2015/0173421 A1 | 6/2015 | Hsieh |
| 2015/0173422 A1 | 6/2015 | Liu |
| 2015/0181928 A1 | 7/2015 | Liu |
| 2015/0181937 A1 | 7/2015 | Dubief et al. |
| 2015/0181939 A1 | 7/2015 | Liu |
| 2015/0181940 A1 | 7/2015 | Liu |
| 2015/0181941 A1 | 7/2015 | Liu |
| 2015/0181943 A1 | 7/2015 | Li et al. |
| 2015/0181944 A1 | 7/2015 | Li et al. |
| 2015/0184846 A1 | 7/2015 | Liu |
| 2015/0186837 A1 | 7/2015 | Bianco et al. |
| 2015/0189695 A1 | 7/2015 | Xiang |
| 2015/0189915 A1 | 7/2015 | Liu |
| 2015/0189918 A1 | 7/2015 | Liu |
| 2015/0189919 A1 | 7/2015 | Liu |
| 2015/0189920 A1 | 7/2015 | Liu |
| 2015/0196055 A1 | 7/2015 | Liu |
| 2015/0196056 A1 | 7/2015 | Liu |
| 2015/0196057 A1 | 7/2015 | Wu |
| 2015/0196058 A1 | 7/2015 | Lord |
| 2015/0196059 A1 | 7/2015 | Liu |
| 2015/0196060 A1 | 7/2015 | Wensley et al. |
| 2015/0196062 A1 | 7/2015 | Li et al. |
| 2015/0200385 A1 | 7/2015 | Liu |
| 2015/0201674 A1 | 7/2015 | Dooly et al. |
| 2015/0201675 A1 | 7/2015 | Lord |
| 2015/0201676 A1 | 7/2015 | Shin |
| 2015/0208724 A1 | 7/2015 | Wu |
| 2015/0208725 A1 | 7/2015 | Tsai |
| 2015/0208726 A1 | 7/2015 | Liu |
| 2015/0208728 A1 | 7/2015 | Lord |
| 2015/0208729 A1 | 7/2015 | Monsees et al. |
| 2015/0208730 A1 | 7/2015 | Li et al. |
| 2015/0208731 A1 | 7/2015 | Malamud et al. |
| 2015/0216232 A1 | 8/2015 | Bless et al. |
| 2015/0216233 A1 | 8/2015 | Sears et al. |
| 2015/0216234 A1 | 8/2015 | Chung |
| 2015/0216235 A1 | 8/2015 | Liu |
| 2015/0216237 A1 | 8/2015 | Wensley et al. |
| 2015/0217067 A1 | 8/2015 | Hearn et al. |
| 2015/0217068 A1 | 8/2015 | Wakalopulos |
| 2015/0223520 A1 | 8/2015 | Phillips et al. |
| 2015/0223521 A1 | 8/2015 | Menting et al. |
| 2015/0223522 A1 | 8/2015 | Ampolini et al. |
| 2015/0223523 A1 | 8/2015 | McCullough |
| 2015/0224268 A1 | 8/2015 | Henry et al. |
| 2015/0227471 A1 | 8/2015 | Stafford et al. |
| 2015/0237914 A1 | 8/2015 | Han |
| 2015/0237916 A1 | 8/2015 | Farine et al. |
| 2015/0237917 A1 | 8/2015 | Lord |
| 2015/0237918 A1 | 8/2015 | Liu |
| 2015/0238723 A1 | 8/2015 | Knudsen |
| 2015/0245654 A1 | 9/2015 | Memari et al. |
| 2015/0245655 A1 | 9/2015 | Memari et al. |
| 2015/0245657 A1 | 9/2015 | Memari et al. |
| 2015/0245658 A1 | 9/2015 | Worm et al. |
| 2015/0245659 A1 | 9/2015 | DePiano et al. |
| 2015/0245660 A1 | 9/2015 | Lord |
| 2015/0245661 A1 | 9/2015 | Milin |
| 2015/0245665 A1 | 9/2015 | Memari et al. |
| 2015/0245666 A1 | 9/2015 | Memari et al. |
| 2015/0245667 A1 | 9/2015 | Memari et al. |
| 2015/0245668 A1 | 9/2015 | Memari et al. |
| 2015/0245669 A1 | 9/2015 | Cadieux et al. |
| 2015/0257441 A1 | 9/2015 | Gerkin |
| 2015/0257444 A1 | 9/2015 | Chung |
| 2015/0257445 A1 | 9/2015 | Henry, Jr. et al. |
| 2015/0257446 A1 | 9/2015 | Chung |
| 2015/0257447 A1 | 9/2015 | Sullivan |
| 2015/0257449 A1 | 9/2015 | Gabbay |
| 2015/0257451 A1 | 9/2015 | Brannon et al. |
| 2015/0258289 A1 | 9/2015 | Henry, Jr. et al. |
| 2015/0272211 A1 | 10/2015 | Chung |
| 2015/0272215 A1 | 10/2015 | Esses |
| 2015/0272217 A1 | 10/2015 | Chen |
| 2015/0272218 A1 | 10/2015 | Chen |
| 2015/0272220 A1 | 10/2015 | Spinka et al. |
| 2015/0272221 A1 | 10/2015 | Liu |
| 2015/0272222 A1 | 10/2015 | Spinka et al. |
| 2015/0272223 A1 | 10/2015 | Weigensberg et al. |
| 2015/0276262 A1 | 10/2015 | Dai et al. |
| 2015/0280273 A1 | 10/2015 | Liu |
| 2015/0282524 A1 | 10/2015 | Elhalwani |
| 2015/0282525 A1 | 10/2015 | Plojoux et al. |
| 2015/0282526 A1 | 10/2015 | Wu |
| 2015/0282527 A1 | 10/2015 | Henry, Jr. |
| 2015/0282529 A1 | 10/2015 | Li et al. |
| 2015/0282530 A1 | 10/2015 | Johnson et al. |
| 2015/0288468 A1 | 10/2015 | Xiang |
| 2015/0289565 A1 | 10/2015 | Cadieux et al. |
| 2015/0289567 A1 | 10/2015 | Liu |
| 2015/0295921 A1 | 10/2015 | Cao |
| 2015/0296883 A1 | 10/2015 | Wu |
| 2015/0296885 A1 | 10/2015 | Liu |
| 2015/0296886 A1 | 10/2015 | Li et al. |
| 2015/0296887 A1 | 10/2015 | Zhu |
| 2015/0296888 A1 | 10/2015 | Liu |
| 2015/0296889 A1 | 10/2015 | Liu |
| 2015/0304401 A1 | 10/2015 | Liu |
| 2015/0304402 A1 | 10/2015 | Liu |
| 2015/0305403 A1 | 10/2015 | Coelho Belo Fernandes De Carvalho |
| 2015/0305404 A1 | 10/2015 | Rosales |
| 2015/0305406 A1 | 10/2015 | Li et al. |
| 2015/0305407 A1 | 10/2015 | Li et al. |
| 2015/0305408 A1 | 10/2015 | Liu |
| 2015/0305409 A1 | 10/2015 | Verleur et al. |
| 2015/0305464 A1 | 10/2015 | Nelson, Jr. et al. |
| 2015/0313275 A1 | 11/2015 | Anderson et al. |
| 2015/0313282 A1 | 11/2015 | Ademe et al. |
| 2015/0313283 A1 | 11/2015 | Collett et al. |
| 2015/0313284 A1 | 11/2015 | Liu |
| 2015/0313285 A1 | 11/2015 | Waller et al. |
| 2015/0313287 A1 | 11/2015 | Verleur et al. |
| 2015/0313288 A1 | 11/2015 | Liu |
| 2015/0313868 A1 | 11/2015 | Morgan |
| 2015/0320114 A1 | 11/2015 | Wu |
| 2015/0320116 A1 | 11/2015 | Bleloch et al. |
| 2015/0322451 A1 | 11/2015 | Kudithipudi et al. |
| 2015/0327595 A1 | 11/2015 | Scatterday |
| 2015/0327596 A1 | 11/2015 | Alarcon et al. |
| 2015/0327597 A1 | 11/2015 | Li et al. |
| 2015/0327598 A1 | 11/2015 | Xiang |
| 2015/0328415 A1 | 11/2015 | Minskoff et al. |
| 2015/0332379 A1 | 11/2015 | Alarcon |
| 2015/0333542 A1 | 11/2015 | Alarcon et al. |
| 2015/0333552 A1 | 11/2015 | Alarcon |
| 2015/0333561 A1 | 11/2015 | Alarcon |
| 2015/0335071 A1 | 11/2015 | Brinkley et al. |
| 2015/0335072 A1 | 11/2015 | Giller |
| 2015/0335074 A1 | 11/2015 | Leung |
| 2015/0335075 A1 | 11/2015 | Minskoff et al. |
| 2015/0342254 A1 | 12/2015 | Mironov et al. |
| 2015/0342255 A1 | 12/2015 | Wu |
| 2015/0342256 A1 | 12/2015 | Chen |
| 2015/0342257 A1 | 12/2015 | Chen |
| 2015/0342258 A1 | 12/2015 | Chen |
| 2015/0342259 A1 | 12/2015 | Baker et al. |
| 2015/0351449 A1 | 12/2015 | Righetti |
| 2015/0351454 A1 | 12/2015 | Huang |

(56) References Cited

U.S. PATENT DOCUMENTS

| | | |
|---|---|---|
| 2015/0351455 A1 | 12/2015 | Liu |
| 2015/0351456 A1 | 12/2015 | Johnson et al. |
| 2015/0351457 A1 | 12/2015 | Liu |
| 2015/0357608 A1 | 12/2015 | Huang |
| 2015/0357839 A1 | 12/2015 | Cai et al. |
| 2015/0359258 A1 | 12/2015 | Mishra et al. |
| 2015/0359261 A1 | 12/2015 | Li et al. |
| 2015/0359262 A1 | 12/2015 | Liu et al. |
| 2015/0359263 A1 | 12/2015 | Bellinger |
| 2015/0359264 A1 | 12/2015 | Fernando et al. |
| 2015/0359265 A1 | 12/2015 | Liu |
| 2015/0366250 A1 | 12/2015 | Landau |
| 2015/0366265 A1 | 12/2015 | Lansing |
| 2015/0366266 A1 | 12/2015 | Chen |
| 2015/0366267 A1 | 12/2015 | Liu |
| 2015/0366268 A1 | 12/2015 | Shabat |
| 2015/0374035 A1 | 12/2015 | Sanchez et al. |
| 2015/0374039 A1 | 12/2015 | Zhu |
| 2015/0374040 A1 | 12/2015 | Chen |
| 2016/0000147 A1 | 1/2016 | Li et al. |
| 2016/0000148 A1 | 1/2016 | Liu |
| 2016/0000149 A1 | 1/2016 | Scatterday |
| 2016/0002649 A1 | 1/2016 | Kudithipudi et al. |
| 2016/0007650 A1 | 1/2016 | Duncan et al. |
| 2016/0007651 A1 | 1/2016 | Ampolini et al. |
| 2016/0007653 A1 | 1/2016 | Tu |
| 2016/0007654 A1 | 1/2016 | Zhu |
| 2016/0007655 A1 | 1/2016 | Li et al. |
| 2016/0010103 A1 | 1/2016 | Kudithipudi et al. |
| 2016/0015082 A1 | 1/2016 | Liu |
| 2016/0020048 A1 | 1/2016 | Ware |
| 2016/0021771 A1 | 1/2016 | Zhang et al. |
| 2016/0021930 A1 | 1/2016 | Minskoff et al. |
| 2016/0021931 A1 | 1/2016 | Hawes et al. |
| 2016/0021932 A1 | 1/2016 | Silvestrini et al. |
| 2016/0021933 A1 | 1/2016 | Thorens et al. |
| 2016/0021934 A1 | 1/2016 | Cadieux et al. |
| 2016/0029225 A1 | 1/2016 | Hu |
| 2016/0029694 A1 | 2/2016 | Clements et al. |
| 2016/0029697 A1 | 2/2016 | Shafer |
| 2016/0029698 A1 | 2/2016 | Xiang |
| 2016/0029699 A1 | 2/2016 | Li et al. |
| 2016/0029700 A1 | 2/2016 | Li et al. |
| 2016/0037826 A1 | 2/2016 | Hearn et al. |
| 2016/0044961 A1 | 2/2016 | Liu |
| 2016/0044962 A1 | 2/2016 | Thorens et al. |
| 2016/0044964 A1 | 2/2016 | Liu |
| 2016/0044965 A1 | 2/2016 | Liu |
| 2016/0044966 A1 | 2/2016 | Li et al. |
| 2016/0044967 A1 | 2/2016 | Bowen et al. |
| 2016/0044968 A1 | 2/2016 | Bowen et al. |
| 2016/0049682 A1 | 2/2016 | Won et al. |
| 2016/0051716 A1 | 2/2016 | Wheelock |
| 2016/0053988 A1 | 2/2016 | Quintana |
| 2016/0057811 A1 | 2/2016 | Alarcon et al. |
| 2016/0058066 A1 | 3/2016 | Banks et al. |
| 2016/0058071 A1 | 3/2016 | Hearn |
| 2016/0058072 A1 | 3/2016 | Liu |
| 2016/0058073 A1 | 3/2016 | Chen |
| 2016/0058074 A1 | 3/2016 | Liu |
| 2016/0073677 A1 | 3/2016 | Kappel et al. |
| 2016/0073678 A1 | 3/2016 | Fujisawa et al. |
| 2016/0073690 A1 | 3/2016 | Liu |
| 2016/0073691 A1 | 3/2016 | Liu |
| 2016/0073692 A1 | 3/2016 | Alarcon et al. |
| 2016/0073693 A1 | 3/2016 | Reevell |
| 2016/0073694 A1 | 3/2016 | Liu |
| 2016/0080469 A1 | 3/2016 | Liu |
| 2016/0081393 A1 | 3/2016 | Black |
| 2016/0081394 A1 | 3/2016 | Alarcon et al. |
| 2016/0081395 A1 | 3/2016 | Thorens et al. |
| 2016/0088874 A1 | 3/2016 | Lipowicz |
| 2016/0089508 A1 | 3/2016 | Smith et al. |
| 2016/0091194 A1 | 3/2016 | Liu |
| 2016/0095352 A1 | 4/2016 | Liu |
| 2016/0095353 A1 | 4/2016 | Liu |
| 2016/0095354 A1 | 4/2016 | Wu |
| 2016/0095355 A1 | 4/2016 | Hearn |
| 2016/0095356 A1 | 4/2016 | Chan |
| 2016/0095357 A1 | 4/2016 | Burton |
| 2016/0099592 A1 | 4/2016 | Gatta et al. |
| 2016/0100456 A1 | 4/2016 | Tsai |
| 2016/0100632 A1 | 4/2016 | Debono et al. |
| 2016/0101909 A1 | 4/2016 | Schennum et al. |
| 2016/0106144 A1 | 4/2016 | Muehlbauer et al. |
| 2016/0106151 A1 | 4/2016 | Swepston et al. |
| 2016/0106152 A1 | 4/2016 | Liu |
| 2016/0106153 A1 | 4/2016 | Zhu |
| 2016/0106154 A1 | 4/2016 | Lord |
| 2016/0106155 A1 | 4/2016 | Reevell |
| 2016/0106156 A1 | 4/2016 | Qiu |
| 2016/0106936 A1 | 4/2016 | Kimmel |
| 2016/0109115 A1 | 4/2016 | Lipowicz |
| 2016/0113323 A1 | 4/2016 | Liu |
| 2016/0113325 A1 | 4/2016 | Liu |
| 2016/0113326 A1 | 4/2016 | Li et al. |
| 2016/0113327 A1 | 4/2016 | Wu |
| 2016/0120218 A1 | 5/2016 | Schennum et al. |
| 2016/0120220 A1 | 5/2016 | Malgat et al. |
| 2016/0120222 A1* | 5/2016 | Bagai .................... A24F 40/42 206/242 |
| 2016/0120223 A1 | 5/2016 | Keen et al. |
| 2016/0120224 A1 | 5/2016 | Mishra et al. |
| 2016/0120225 A1 | 5/2016 | Mishra et al. |
| 2016/0120226 A1 | 5/2016 | Rado |
| 2016/0120227 A1 | 5/2016 | Levitz et al. |
| 2016/0120228 A1 | 5/2016 | Rostami et al. |
| 2016/0121058 A1 | 5/2016 | Chen |
| 2016/0128384 A1 | 5/2016 | Luciani et al. |
| 2016/0128385 A1 | 5/2016 | Lin |
| 2016/0128387 A1 | 5/2016 | Chen |
| 2016/0128388 A1 | 5/2016 | Liu |
| 2016/0128389 A1 | 5/2016 | Lamb et al. |
| 2016/0128390 A1 | 5/2016 | Liu |
| 2016/0129205 A1 | 5/2016 | Shahaf et al. |
| 2016/0131629 A1 | 5/2016 | Cadieux, Jr. et al. |
| 2016/0132898 A1 | 5/2016 | Cadieux et al. |
| 2016/0134143 A1 | 5/2016 | Liu |
| 2016/0135494 A1 | 5/2016 | Liu et al. |
| 2016/0135500 A1 | 5/2016 | Hearn et al. |
| 2016/0135501 A1 | 5/2016 | Liu |
| 2016/0135503 A1 | 5/2016 | Liu |
| 2016/0135504 A1 | 5/2016 | Li et al. |
| 2016/0135505 A1 | 5/2016 | Li et al. |
| 2016/0135506 A1 | 5/2016 | Sanchez et al. |
| 2016/0135507 A1 | 5/2016 | Thorens et al. |
| 2016/0136153 A1 | 5/2016 | Jenkins |
| 2016/0136213 A1 | 5/2016 | Paul |
| 2016/0138795 A1 | 5/2016 | Meinhart et al. |
| 2016/0143354 A1 | 5/2016 | Liu |
| 2016/0143357 A1 | 5/2016 | Liu |
| 2016/0143358 A1 | 5/2016 | Zhu |
| 2016/0143359 A1 | 5/2016 | Xiang |
| 2016/0143360 A1 | 5/2016 | Sanchez et al. |
| 2016/0143361 A1 | 5/2016 | Juster et al. |
| 2016/0143362 A1 | 5/2016 | Boldrini |
| 2016/0143363 A1 | 5/2016 | Boldrini |
| 2016/0143365 A1 | 5/2016 | Liu |
| 2016/0144458 A1 | 5/2016 | Boldrini |
| 2016/0150820 A1 | 6/2016 | Liu |
| 2016/0150821 A1 | 6/2016 | Liu |
| 2016/0150823 A1 | 6/2016 | Liu |
| 2016/0150824 A1 | 6/2016 | Memari et al. |
| 2016/0150826 A1 | 6/2016 | Liu |
| 2016/0150827 A1 | 6/2016 | Liu |
| 2016/0150828 A1 | 6/2016 | Goldstein et al. |
| 2016/0150872 A1 | 6/2016 | Zayat |
| 2016/0157523 A1 | 6/2016 | Liu |
| 2016/0157524 A1 | 6/2016 | Bowen et al. |
| 2016/0157525 A1 | 6/2016 | Tucker et al. |
| 2016/0158782 A1 | 6/2016 | Henry, Jr. et al. |
| 2016/0165952 A1 | 6/2016 | Liu |
| 2016/0165955 A1 | 6/2016 | Horne |
| 2016/0166564 A1 | 6/2016 | Myers et al. |

(56) References Cited

U.S. PATENT DOCUMENTS

| | | |
|---|---|---|
| 2016/0167846 A1 | 6/2016 | Zahr et al. |
| 2016/0174076 A1 | 6/2016 | Wu |
| 2016/0174609 A1 | 6/2016 | Mironov |
| 2016/0174611 A1 | 6/2016 | Monsees et al. |
| 2016/0174613 A1 | 6/2016 | Zuber et al. |
| 2016/0176564 A1 | 6/2016 | Garthaffner |
| 2016/0177285 A1 | 6/2016 | Voerman et al. |
| 2016/0183592 A1 | 6/2016 | Liu |
| 2016/0183593 A1 | 6/2016 | Liu |
| 2016/0183594 A1 | 6/2016 | Liu |
| 2016/0183595 A1 | 6/2016 | Grimandi et al. |
| 2016/0183597 A1 | 6/2016 | Li et al. |
| 2016/0189216 A1 | 6/2016 | Liu |
| 2016/0192705 A1 | 7/2016 | Borkovec et al. |
| 2016/0192706 A1 | 7/2016 | Kananen |
| 2016/0192707 A1 | 7/2016 | Li et al. |
| 2016/0192708 A1 | 7/2016 | Dermitt et al. |
| 2016/0192709 A1 | 7/2016 | Liu |
| 2016/0192710 A1 | 7/2016 | Liu |
| 2016/0198759 A1 | 7/2016 | Kuntawala et al. |
| 2016/0198763 A1 | 7/2016 | Adkins et al. |
| 2016/0198765 A1 | 7/2016 | Liu |
| 2016/0198766 A1 | 7/2016 | Liu |
| 2016/0198767 A1 | 7/2016 | Verleur |
| 2016/0198768 A1 | 7/2016 | Liu |
| 2016/0198769 A1 | 7/2016 | Liu |
| 2016/0198770 A1 | 7/2016 | Alarcon |
| 2016/0200463 A1 | 7/2016 | Hodges et al. |
| 2016/0201224 A1 | 7/2016 | Xiang |
| 2016/0204637 A1 | 7/2016 | Alarcon et al. |
| 2016/0205998 A1 | 7/2016 | Matsumoto et al. |
| 2016/0205999 A1 | 7/2016 | Liu |
| 2016/0206000 A1 | 7/2016 | Lord et al. |
| 2016/0206002 A1 | 7/2016 | Borkovec et al. |
| 2016/0206005 A1 | 7/2016 | Yamada et al. |
| 2016/0206006 A1 | 7/2016 | Li et al. |
| 2016/0211693 A1 | 7/2016 | Stevens et al. |
| 2016/0212520 A1 | 7/2016 | Merenda |
| 2016/0213060 A1 | 7/2016 | Thaler |
| 2016/0213061 A1 | 7/2016 | Liu |
| 2016/0213062 A1 | 7/2016 | Doyle |
| 2016/0213065 A1 | 7/2016 | Wensley et al. |
| 2016/0213066 A1 | 7/2016 | Zitzke et al. |
| 2016/0213067 A1 | 7/2016 | Hon |
| 2016/0213866 A1 | 7/2016 | Tan |
| 2016/0219932 A1 | 8/2016 | Glaser |
| 2016/0219933 A1 | 8/2016 | Henry, Jr. et al. |
| 2016/0219934 A1 | 8/2016 | Li et al. |
| 2016/0219936 A1 | 8/2016 | Alarcon |
| 2016/0219937 A1 | 8/2016 | Rado |
| 2016/0219938 A1 | 8/2016 | Mamoun et al. |
| 2016/0221707 A1 | 8/2016 | Xu et al. |
| 2016/0226286 A1 | 8/2016 | Xiang |
| 2016/0227837 A1 | 8/2016 | Hammel et al. |
| 2016/0227838 A1 | 8/2016 | Johnson et al. |
| 2016/0227839 A1 | 8/2016 | Zuber et al. |
| 2016/0227840 A1 | 8/2016 | Xiang |
| 2016/0227841 A1 | 8/2016 | Li et al. |
| 2016/0227842 A1 | 8/2016 | Xiang |
| 2016/0233705 A1 | 8/2016 | Liu |
| 2016/0233708 A1 | 8/2016 | Liu |
| 2016/0235119 A1 | 8/2016 | Liu |
| 2016/0235120 A1 | 8/2016 | Liu |
| 2016/0235121 A1 | 8/2016 | Rogan et al. |
| 2016/0235124 A1 | 8/2016 | Krietzman |
| 2016/0235125 A1 | 8/2016 | Safari |
| 2016/0242463 A1 | 8/2016 | Liu |
| 2016/0242464 A1 | 8/2016 | Liu |
| 2016/0242465 A1 | 8/2016 | Zheng et al. |
| 2016/0242466 A1 | 8/2016 | Lord et al. |
| 2016/0242467 A1 | 8/2016 | Vaughn |
| 2016/0242468 A1 | 8/2016 | Liu |
| 2016/0249680 A1 | 9/2016 | Liu |
| 2016/0249682 A1 | 9/2016 | Leadley et al. |
| 2016/0249683 A1 | 9/2016 | Li et al. |
| 2016/0249684 A1 | 9/2016 | Liu |
| 2016/0255876 A1 | 9/2016 | Rostami |
| 2016/0255878 A1 | 9/2016 | Huang et al. |
| 2016/0260156 A1 | 9/2016 | Liu |
| 2016/0261021 A1 | 9/2016 | Marion et al. |
| 2016/0262443 A1 | 9/2016 | Piccirilli et al. |
| 2016/0262445 A1 | 9/2016 | Benjak et al. |
| 2016/0262449 A1 | 9/2016 | Liu |
| 2016/0262450 A1 | 9/2016 | Liu |
| 2016/0262451 A1 | 9/2016 | Liu |
| 2016/0262452 A1 | 9/2016 | Zhu |
| 2016/0262453 A1 | 9/2016 | Ampolini et al. |
| 2016/0262454 A1 | 9/2016 | Sears et al. |
| 2016/0262455 A1 | 9/2016 | Chen |
| 2016/0262456 A1 | 9/2016 | Borkovec et al. |
| 2016/0262457 A1 | 9/2016 | Borkovec et al. |
| 2016/0262459 A1 | 9/2016 | Monsees et al. |
| 2016/0262526 A1 | 9/2016 | Gonzalez |
| 2016/0268824 A1 | 9/2016 | Liu |
| 2016/0270441 A1 | 9/2016 | Lewis et al. |
| 2016/0270442 A1 | 9/2016 | Liu |
| 2016/0270443 A1 | 9/2016 | Liu |
| 2016/0270444 A1 | 9/2016 | Lin |
| 2016/0270445 A1 | 9/2016 | Liu |
| 2016/0270446 A1 | 9/2016 | Shenkal et al. |
| 2016/0270447 A1 | 9/2016 | Borkovec |
| 2016/0271347 A1 | 9/2016 | Raichman |
| 2016/0278163 A1 | 9/2016 | Chen |
| 2016/0278431 A1 | 9/2016 | Liu |
| 2016/0278432 A1 | 9/2016 | Liu |
| 2016/0278433 A1 | 9/2016 | Xiang |
| 2016/0278434 A1 | 9/2016 | Liu |
| 2016/0278435 A1 | 9/2016 | Choukroun et al. |
| 2016/0278436 A1 | 9/2016 | Verleur et al. |
| 2016/0280450 A1 | 9/2016 | Hearn et al. |
| 2016/0284197 A1 | 9/2016 | Liu |
| 2016/0285983 A1 | 9/2016 | Liu |
| 2016/0286856 A1 | 10/2016 | Liu |
| 2016/0286858 A1 | 10/2016 | Liu |
| 2016/0286859 A1 | 10/2016 | Liu |
| 2016/0286860 A1 | 10/2016 | Flayler |
| 2016/0286862 A1 | 10/2016 | Silvetrini |
| 2016/0286863 A1 | 10/2016 | Lin |
| 2016/0286864 A1 | 10/2016 | Lin |
| 2016/0286865 A1 | 10/2016 | King et al. |
| 2016/0295913 A1 | 10/2016 | Guo et al. |
| 2016/0295915 A1 | 10/2016 | Jochnowitz et al. |
| 2016/0295916 A1 | 10/2016 | Malgat et al. |
| 2016/0295917 A1 | 10/2016 | Malgat et al. |
| 2016/0295918 A1 | 10/2016 | Liu |
| 2016/0295920 A1 | 10/2016 | Liu |
| 2016/0295922 A1 | 10/2016 | John et al. |
| 2016/0295923 A1 | 10/2016 | Lin |
| 2016/0295924 A1 | 10/2016 | Liu |
| 2016/0295925 A1 | 10/2016 | Chen |
| 2016/0295926 A1 | 10/2016 | Zuber |
| 2016/0297341 A1 | 10/2016 | Wallace et al. |
| 2016/0302471 A1 | 10/2016 | Bowen et al. |
| 2016/0302483 A1 | 10/2016 | Liu |
| 2016/0302484 A1 | 10/2016 | Gupta et al. |
| 2016/0302485 A1 | 10/2016 | Alima |
| 2016/0302486 A1 | 10/2016 | Eroch |
| 2016/0302487 A1 | 10/2016 | Chen |
| 2016/0302488 A1 | 10/2016 | Fernando et al. |
| 2016/0309775 A1 | 10/2016 | Parker |
| 2016/0309779 A1 | 10/2016 | Liu |
| 2016/0309780 A1 | 10/2016 | Chen et al. |
| 2016/0309781 A1 | 10/2016 | Malgat et al. |
| 2016/0309783 A1 | 10/2016 | Hopps et al. |
| 2016/0309784 A1 | 10/2016 | Silvestrini et al. |
| 2016/0309785 A1 | 10/2016 | Holtz |
| 2016/0309786 A1 | 10/2016 | Holtz et al. |
| 2016/0309789 A1 | 10/2016 | Thomas, Jr. |
| 2016/0315488 A1 | 10/2016 | Moon |
| 2016/0316818 A1 | 11/2016 | Liu |
| 2016/0316820 A1 | 11/2016 | Liu |
| 2016/0316821 A1 | 11/2016 | Liu |
| 2016/0316822 A1 | 11/2016 | Liu |
| 2016/0321879 A1 | 11/2016 | Oh et al. |

(56) References Cited

U.S. PATENT DOCUMENTS

| | | |
|---|---|---|
| 2016/0323404 A1 | 11/2016 | Liu |
| 2016/0324211 A1 | 11/2016 | Yankelevich |
| 2016/0324213 A1 | 11/2016 | Liu |
| 2016/0324215 A1 | 11/2016 | Mironov et al. |
| 2016/0324217 A1 | 11/2016 | Cameron |
| 2016/0324218 A1 | 11/2016 | Wang et al. |
| 2016/0324219 A1 | 11/2016 | Li et al. |
| 2016/0325055 A1 | 11/2016 | Cameron |
| 2016/0325858 A1 | 11/2016 | Ampolini et al. |
| 2016/0331022 A1 | 11/2016 | Cameron |
| 2016/0331023 A1 | 11/2016 | Cameron |
| 2016/0331024 A1 | 11/2016 | Cameron |
| 2016/0331025 A1 | 11/2016 | Cameron |
| 2016/0331026 A1 | 11/2016 | Cameron |
| 2016/0331027 A1 | 11/2016 | Cameron |
| 2016/0331028 A1 | 11/2016 | Xu |
| 2016/0331029 A1 | 11/2016 | Contreras |
| 2016/0331030 A1 | 11/2016 | Ampolini et al. |
| 2016/0331032 A1 | 11/2016 | Malgat et al. |
| 2016/0331033 A1 | 11/2016 | Hopps et al. |
| 2016/0331034 A1 | 11/2016 | Cameron |
| 2016/0331035 A1 | 11/2016 | Cameron |
| 2016/0331037 A1 | 11/2016 | Cameron |
| 2016/0331038 A1 | 11/2016 | Farine et al. |
| 2016/0331039 A1 | 11/2016 | Thorens et al. |
| 2016/0331040 A1 | 11/2016 | Nakano et al. |
| 2016/0332754 A1 | 11/2016 | Brown et al. |
| 2016/0334847 A1 | 11/2016 | Cameron |
| 2016/0337141 A1 | 11/2016 | Cameron |
| 2016/0337362 A1 | 11/2016 | Cameron |
| 2016/0337444 A1 | 11/2016 | Cameron |
| 2016/0338402 A1 | 11/2016 | Buehler et al. |
| 2016/0338405 A1 | 11/2016 | Liu |
| 2016/0338406 A1 | 11/2016 | Liu |
| 2016/0338407 A1 | 11/2016 | Kerdemelidis |
| 2016/0338408 A1 | 11/2016 | Guenther, Jr. et al. |
| 2016/0338409 A1 | 11/2016 | Varone |
| 2016/0338410 A1 | 11/2016 | Batista et al. |
| 2016/0338411 A1 | 11/2016 | Liu |
| 2016/0338412 A1 | 11/2016 | Monsees et al. |
| 2016/0338413 A1 | 11/2016 | Li et al. |
| 2016/0338945 A1 | 11/2016 | Knight |
| 2016/0345621 A1 | 12/2016 | Li et al. |
| 2016/0345625 A1 | 12/2016 | Liu |
| 2016/0345626 A1 | 12/2016 | Wong et al. |
| 2016/0345627 A1 | 12/2016 | Liu |
| 2016/0345628 A1 | 12/2016 | Sabet |
| 2016/0345630 A1 | 12/2016 | Mironov et al. |
| 2016/0345631 A1 | 12/2016 | Monsees et al. |
| 2016/0345632 A1 | 12/2016 | Lipowicz |
| 2016/0345633 A1 | 12/2016 | DePiano et al. |
| 2016/0345634 A1 | 12/2016 | Fernando et al. |
| 2016/0345636 A1 | 12/2016 | Liu |
| 2016/0351044 A1 | 12/2016 | Liu |
| 2016/0353798 A1 | 12/2016 | Liu |
| 2016/0353800 A1 | 12/2016 | Di Carlo |
| 2016/0353805 A1 | 12/2016 | Hawes et al. |
| 2016/0356751 A1 | 12/2016 | Blackley |
| 2016/0360784 A1 | 12/2016 | Liu |
| 2016/0360785 A1 | 12/2016 | Bless et al. |
| 2016/0360786 A1 | 12/2016 | Bellinger et al. |
| 2016/0360787 A1 | 12/2016 | Bailey |
| 2016/0360788 A1 | 12/2016 | Wang |
| 2016/0360789 A1 | 12/2016 | Hawes et al. |
| 2016/0360790 A1 | 12/2016 | Calfee et al. |
| 2016/0360792 A1 | 12/2016 | Liu |
| 2016/0360793 A1 | 12/2016 | Liu |
| 2016/0363570 A1 | 12/2016 | Blackley |
| 2016/0363917 A1 | 12/2016 | Blackley |
| 2016/0366725 A1 | 12/2016 | Tucker et al. |
| 2016/0366927 A1 | 12/2016 | Liu |
| 2016/0366928 A1 | 12/2016 | Liu |
| 2016/0366933 A1 | 12/2016 | Liu |
| 2016/0366935 A1 | 12/2016 | Liu |
| 2016/0366936 A1 | 12/2016 | Liu |
| 2016/0366937 A1 | 12/2016 | Liu |
| 2016/0366938 A1 | 12/2016 | Wu |
| 2016/0366939 A1 | 12/2016 | Alarcon et al. |
| 2016/0366940 A1 | 12/2016 | Liu |
| 2016/0366941 A1 | 12/2016 | Lin |
| 2016/0366942 A1 | 12/2016 | Liu |
| 2016/0366943 A1 | 12/2016 | Li et al. |
| 2016/0366945 A1 | 12/2016 | Rado |
| 2016/0366947 A1 | 12/2016 | Monsees et al. |
| 2016/0367925 A1 | 12/2016 | Blackley |
| 2016/0368670 A1 | 12/2016 | Beardsall |
| 2016/0368677 A1 | 12/2016 | Parsons et al. |
| 2016/0370335 A1 | 12/2016 | Blackley |
| 2016/0371437 A1 | 12/2016 | Alarcon et al. |
| 2016/0371464 A1 | 12/2016 | Bricker |
| 2016/0374390 A1 | 12/2016 | Liu |
| 2016/0374391 A1 | 12/2016 | Liu |
| 2016/0374392 A1 | 12/2016 | Liu |
| 2016/0374393 A1 | 12/2016 | Chen |
| 2016/0374394 A1 | 12/2016 | Hawes et al. |
| 2016/0374395 A1 | 12/2016 | Jordan et al. |
| 2016/0374396 A1 | 12/2016 | Jordan et al. |
| 2016/0374397 A1 | 12/2016 | Jordan et al. |
| 2016/0374398 A1 | 12/2016 | Amir |
| 2016/0374399 A1 | 12/2016 | Monsees et al. |
| 2016/0374400 A1 | 12/2016 | Monsees et al. |
| 2016/0374401 A1 | 12/2016 | Liu |
| 2017/0000190 A1 | 1/2017 | Wu |
| 2017/0000192 A1 | 1/2017 | Li |
| 2017/0006915 A1 | 1/2017 | Li et al. |
| 2017/0006916 A1 | 1/2017 | Liu |
| 2017/0006917 A1 | 1/2017 | Alvarez |
| 2017/0006918 A1 | 1/2017 | Chen et al. |
| 2017/0006919 A1 | 1/2017 | Liu |
| 2017/0006920 A1 | 1/2017 | Liu |
| 2017/0006921 A1 | 1/2017 | Lemay et al. |
| 2017/0006922 A1 | 1/2017 | Wang et al. |
| 2017/0013875 A1 | 1/2017 | Schennum et al. |
| 2017/0013876 A1 | 1/2017 | Schennum et al. |
| 2017/0013878 A1 | 1/2017 | Schuler et al. |
| 2017/0013880 A1 | 1/2017 | O'Brien et al. |
| 2017/0013881 A1 | 1/2017 | Liu |
| 2017/0013882 A1 | 1/2017 | Liu |
| 2017/0013883 A1 | 1/2017 | Han et al. |
| 2017/0013885 A1 | 1/2017 | Qiu |
| 2017/0014582 A1 | 1/2017 | Skoda |
| 2017/0018000 A1 | 1/2017 | Cameron |
| 2017/0019951 A1 | 1/2017 | Louveau et al. |
| 2017/0020188 A1 | 1/2017 | Cameron |
| 2017/0020191 A1 | 1/2017 | Lamb et al. |
| 2017/0020193 A1 | 1/2017 | Davis et al. |
| 2017/0020194 A1 | 1/2017 | Rehders |
| 2017/0020195 A1 | 1/2017 | Cameron |
| 2017/0020196 A1 | 1/2017 | Cameron |
| 2017/0020197 A1 | 1/2017 | Cameron |
| 2017/0020198 A1 | 1/2017 | Naqwi et al. |
| 2017/0020201 A1 | 1/2017 | Xiang |
| 2017/0020791 A1 | 1/2017 | Moszner et al. |
| 2017/0021969 A1 | 1/2017 | Smith et al. |
| 2017/0023952 A1 | 1/2017 | Henry, Jr. et al. |
| 2017/0027221 A1 | 2/2017 | Liu |
| 2017/0027223 A1 | 2/2017 | Eksouzian |
| 2017/0027224 A1 | 2/2017 | Volodarsky |
| 2017/0027227 A1 | 2/2017 | Lipowicz |
| 2017/0027228 A1 | 2/2017 | Rastogi |
| 2017/0027229 A1 | 2/2017 | Cameron |
| 2017/0027230 A1 | 2/2017 | Fornarelli |
| 2017/0027231 A1 | 2/2017 | Xiang |
| 2017/0027232 A1 | 2/2017 | Scheck et al. |
| 2017/0027233 A1 | 2/2017 | Mironov |
| 2017/0027234 A1 | 2/2017 | Farine et al. |
| 2017/0033568 A1 | 2/2017 | Holzherr |
| 2017/0033836 A1 | 2/2017 | Bernauer et al. |
| 2017/0035101 A1 | 2/2017 | Balder |
| 2017/0035109 A1 | 2/2017 | Liu |
| 2017/0035110 A1 | 2/2017 | Keen |
| 2017/0035111 A1 | 2/2017 | Slurink et al. |
| 2017/0035112 A1 | 2/2017 | Thorens |
| 2017/0035113 A1 | 2/2017 | Thorens |

(56) References Cited

U.S. PATENT DOCUMENTS

| | | |
|---|---|---|
| 2017/0035114 A1 | 2/2017 | Lord |
| 2017/0035115 A1 | 2/2017 | Monsees et al. |
| 2017/0035117 A1 | 2/2017 | Lin |
| 2017/0035118 A1 | 2/2017 | Liu |
| 2017/0035119 A1 | 2/2017 | Otto |
| 2017/0041646 A1 | 2/2017 | Pizzurro et al. |
| 2017/0042225 A1 | 2/2017 | Liu |
| 2017/0042227 A1 | 2/2017 | Gavrielov et al. |
| 2017/0042228 A1 | 2/2017 | Liu |
| 2017/0042229 A1 | 2/2017 | Liu |
| 2017/0042230 A1 | 2/2017 | Cameron |
| 2017/0042231 A1 | 2/2017 | Cameron |
| 2017/0042242 A1 | 2/2017 | Hon |
| 2017/0042243 A1 | 2/2017 | Plojoux et al. |
| 2017/0042245 A1 | 2/2017 | Buchberger et al. |
| 2017/0042246 A1 | 2/2017 | Lau et al. |
| 2017/0042247 A1 | 2/2017 | Xiang |
| 2017/0042248 A1 | 2/2017 | Xiang |
| 2017/0042250 A1 | 2/2017 | Takeuchi et al. |
| 2017/0046357 A1 | 2/2017 | Cameron |
| 2017/0046722 A1 | 2/2017 | Ertugrul |
| 2017/0046738 A1 | 2/2017 | Cameron |
| 2017/0047756 A1 | 2/2017 | Xiang |
| 2017/0048691 A1 | 2/2017 | Liu |
| 2017/0049149 A1 | 2/2017 | Carty |
| 2017/0049150 A1 | 2/2017 | Xue et al. |
| 2017/0049151 A1 | 2/2017 | Xue et al. |
| 2017/0049152 A1 | 2/2017 | Liu |
| 2017/0049153 A1 | 2/2017 | Guo et al. |
| 2017/0049154 A1 | 2/2017 | Batista |
| 2017/0049155 A1 | 2/2017 | Liu |
| 2017/0049156 A1 | 2/2017 | Wang et al. |
| 2017/0050798 A1 | 2/2017 | Ludewig et al. |
| 2017/0055577 A1 | 3/2017 | Batista |
| 2017/0055579 A1 | 3/2017 | Kuna et al. |
| 2017/0055586 A1 | 3/2017 | Liu |
| 2017/0055588 A1 | 3/2017 | Cameron |
| 2017/0055589 A1 | 3/2017 | Fernando et al. |
| 2017/0064994 A1 | 3/2017 | Xu et al. |
| 2017/0064999 A1 | 3/2017 | Perez et al. |
| 2017/0065000 A1 | 3/2017 | Sears et al. |
| 2017/0065001 A1 | 3/2017 | Li et al. |
| 2017/0066556 A1 | 3/2017 | Liu |
| 2017/0071249 A1 | 3/2017 | Ampolini et al. |
| 2017/0071251 A1 | 3/2017 | Goch |
| 2017/0071252 A1 | 3/2017 | Liu |
| 2017/0071256 A1 | 3/2017 | Verleur et al. |
| 2017/0071257 A1 | 3/2017 | Lin |
| 2017/0071258 A1 | 3/2017 | Li et al. |
| 2017/0071260 A1 | 3/2017 | Li et al. |
| 2017/0071262 A1 | 3/2017 | Liu |
| 2017/0079110 A1 | 3/2017 | Plattner |
| 2017/0079319 A1 | 3/2017 | Muhammed et al. |
| 2017/0079321 A1 | 3/2017 | Golz |
| 2017/0079322 A1 | 3/2017 | Li et al. |
| 2017/0079323 A1 | 3/2017 | Wang |
| 2017/0079324 A1 | 3/2017 | Eksouzian |
| 2017/0079327 A1 | 3/2017 | Wu et al. |
| 2017/0079328 A1 | 3/2017 | Wu |
| 2017/0079329 A1 | 3/2017 | Zitzke |
| 2017/0079330 A1 | 3/2017 | Mironov et al. |
| 2017/0079331 A1 | 3/2017 | Monsees et al. |
| 2017/0079332 A1 | 3/2017 | Li et al. |
| 2017/0086496 A1 | 3/2017 | Cameron |
| 2017/0086497 A1 | 3/2017 | Cameron |
| 2017/0086498 A1 | 3/2017 | Daryani |
| 2017/0086499 A1 | 3/2017 | Mize |
| 2017/0086500 A1 | 3/2017 | Li et al. |
| 2017/0086501 A1 | 3/2017 | Buehler et al. |
| 2017/0086502 A1 | 3/2017 | Hearn et al. |
| 2017/0086503 A1 | 3/2017 | Cameron |
| 2017/0086504 A1 | 3/2017 | Cameron |
| 2017/0086505 A1 | 3/2017 | Cameron |
| 2017/0086506 A1 | 3/2017 | Rado |
| 2017/0086507 A1 | 3/2017 | Rado |
| 2017/0086508 A1 | 3/2017 | Mironov et al. |
| 2017/0091490 A1 | 3/2017 | Cameron |
| 2017/0091853 A1 | 3/2017 | Cameron |
| 2017/0092106 A1 | 3/2017 | Cameron |
| 2017/0092900 A1 | 3/2017 | Yang |
| 2017/0093960 A1 | 3/2017 | Cameron |
| 2017/0093981 A1 | 3/2017 | Cameron |
| 2017/0094998 A1 | 4/2017 | Bernauer et al. |
| 2017/0094999 A1 | 4/2017 | Hearn et al. |
| 2017/0095000 A1 | 4/2017 | Spirito et al. |
| 2017/0095001 A1 | 4/2017 | Liu |
| 2017/0095002 A1 | 4/2017 | Silvestrini |
| 2017/0095003 A1 | 4/2017 | Mironov |
| 2017/0095004 A1 | 4/2017 | Liu |
| 2017/0095005 A1 | 4/2017 | Monsees et al. |
| 2017/0095518 A1 | 4/2017 | Bjorncrantz |
| 2017/0095623 A1 | 4/2017 | Trzecieski |
| 2017/0099877 A1 | 4/2017 | Worm et al. |
| 2017/0099879 A1 | 4/2017 | Heidi |
| 2017/0099880 A1 | 4/2017 | Hawes |
| 2017/0101256 A1 | 4/2017 | Zeitlin et al. |
| 2017/0102013 A1 | 4/2017 | Wallman et al. |
| 2017/0105448 A1 | 4/2017 | Scarpulla |
| 2017/0105449 A1 | 4/2017 | Hearn et al. |
| 2017/0105450 A1 | 4/2017 | Reed et al. |
| 2017/0105451 A1 | 4/2017 | Fornarelli |
| 2017/0105452 A1 | 4/2017 | Mironov et al. |
| 2017/0105453 A1 | 4/2017 | Li et al. |
| 2017/0105454 A1 | 4/2017 | Li et al. |
| 2017/0105455 A1 | 4/2017 | Qiu |
| 2017/0108210 A1 | 4/2017 | Meinhart et al. |
| 2017/0108840 A1 | 4/2017 | Hawes et al. |
| 2017/0109877 A1 | 4/2017 | Peleg et al. |
| 2017/0112182 A1 | 4/2017 | Arnold |
| 2017/0112190 A1 | 4/2017 | Buchberger |
| 2017/0112192 A1 | 4/2017 | Shan |
| 2017/0112193 A1 | 4/2017 | Chen |
| 2017/0112196 A1 | 4/2017 | Sur et al. |
| 2017/0112197 A1 | 4/2017 | Li et al. |
| 2017/0113819 A1 | 4/2017 | Marz |
| 2017/0117654 A1 | 4/2017 | Cruz |
| 2017/0118292 A1 | 4/2017 | Xiang |
| 2017/0118584 A1 | 4/2017 | Xiang |
| 2017/0119040 A1 | 5/2017 | Cameron |
| 2017/0119044 A1 | 5/2017 | Oligschlaeger et al. |
| 2017/0119050 A1 | 5/2017 | Blandino et al. |
| 2017/0119052 A1 | 5/2017 | Williams et al. |
| 2017/0119053 A1 | 5/2017 | Henry, Jr. et al. |
| 2017/0119054 A1 | 5/2017 | Zinovik et al. |
| 2017/0119055 A1 | 5/2017 | Liu |
| 2017/0119057 A1 | 5/2017 | Liu |
| 2017/0119058 A1 | 5/2017 | Cameron |
| 2017/0119060 A1 | 5/2017 | Li et al. |
| 2017/0119061 A1 | 5/2017 | Li et al. |
| 2017/0127722 A1 | 5/2017 | Davis et al. |
| 2017/0127723 A1 | 5/2017 | Wu |
| 2017/0127724 A1 | 5/2017 | Liu |
| 2017/0127725 A1 | 5/2017 | Buchberger et al. |
| 2017/0127726 A1 | 5/2017 | Xiang |
| 2017/0127728 A1 | 5/2017 | Li et al. |
| 2017/0129661 A1 | 5/2017 | Van Tassell, III et al. |
| 2017/0135397 A1 | 5/2017 | Buehler et al. |
| 2017/0135398 A1 | 5/2017 | Scott et al. |
| 2017/0135399 A1 | 5/2017 | Gavrielov et al. |
| 2017/0135400 A1 | 5/2017 | Liu |
| 2017/0135401 A1 | 5/2017 | Dickens |
| 2017/0135402 A1 | 5/2017 | Zitzke |
| 2017/0135403 A1 | 5/2017 | Liu |
| 2017/0135407 A1 | 5/2017 | Cameron |
| 2017/0135408 A1 | 5/2017 | Cameron |
| 2017/0135409 A1 | 5/2017 | Cameron |
| 2017/0135410 A1 | 5/2017 | Cameron |
| 2017/0135411 A1 | 5/2017 | Cameron |
| 2017/0135412 A1 | 5/2017 | Cameron |
| 2017/0136193 A1 | 5/2017 | Cameron |
| 2017/0136194 A1 | 5/2017 | Cameron |
| 2017/0136301 A1 | 5/2017 | Cameron |
| 2017/0143035 A1 | 5/2017 | Pucci |
| 2017/0143037 A9 | 5/2017 | Larson |

(56) References Cited

U.S. PATENT DOCUMENTS

| | | |
|---|---|---|
| 2017/0143038 A1 | 5/2017 | Dickens |
| 2017/0143040 A1 | 5/2017 | Liu |
| 2017/0143043 A1 | 5/2017 | Liu |
| 2017/0143917 A1 | 5/2017 | Cohen et al. |
| 2017/0144827 A1 | 5/2017 | Batista |
| 2017/0146005 A1 | 5/2017 | Edelen |
| 2017/0150753 A1 | 6/2017 | Macko |
| 2017/0150754 A1 | 6/2017 | Lin |
| 2017/0150755 A1 | 6/2017 | Batista |
| 2017/0150756 A1 | 6/2017 | Rexroad et al. |
| 2017/0150758 A1 | 6/2017 | Fernando et al. |
| 2017/0156397 A1 | 6/2017 | Sur et al. |
| 2017/0156398 A1 | 6/2017 | Sur et al. |
| 2017/0156400 A1 | 6/2017 | Liu |
| 2017/0156401 A1 | 6/2017 | Liu |
| 2017/0156402 A1 | 6/2017 | Liu |
| 2017/0156403 A1 | 6/2017 | Gill et al. |
| 2017/0156404 A1 | 6/2017 | Novak, III et al. |
| 2017/0156408 A1 | 6/2017 | Li et al. |
| 2017/0157341 A1 | 6/2017 | Pandya et al. |
| 2017/0158436 A1 | 6/2017 | Slurink |
| 2017/0162523 A1 | 6/2017 | Hu |
| 2017/0162979 A1 | 6/2017 | Liu |
| 2017/0164655 A1 | 6/2017 | Chen |
| 2017/0164656 A1 | 6/2017 | Eusepi et al. |
| 2017/0164657 A1 | 6/2017 | Batista |
| 2017/0164658 A1 | 6/2017 | Lin et al. |
| 2017/0170439 A1 | 6/2017 | Jarvis et al. |
| 2017/0172204 A1 | 6/2017 | Kane et al. |
| 2017/0172205 A1 | 6/2017 | Chang et al. |
| 2017/0172207 A1 | 6/2017 | Liu |
| 2017/0172208 A1 | 6/2017 | Mironov |
| 2017/0172209 A1 | 6/2017 | Saydar et al. |
| 2017/0172213 A1 | 6/2017 | Hon |
| 2017/0172214 A1 | 6/2017 | Li et al. |
| 2017/0172215 A1 | 6/2017 | Li et al. |
| 2017/0181223 A1 | 6/2017 | Sur et al. |
| 2017/0181467 A1 | 6/2017 | Cameron |
| 2017/0181468 A1 | 6/2017 | Bowen et al. |
| 2017/0181470 A1 | 6/2017 | Li |
| 2017/0181471 A1 | 6/2017 | Phillips et al. |
| 2017/0181473 A1 | 6/2017 | Batista et al. |
| 2017/0181474 A1 | 6/2017 | Cameron |
| 2017/0181475 A1 | 6/2017 | Cameron |
| 2017/0181476 A1 | 6/2017 | Li et al. |
| 2017/0181928 A1 | 6/2017 | Collins et al. |
| 2017/0185364 A1 | 6/2017 | Cameron |
| 2017/0186122 A1 | 6/2017 | Levings et al. |
| 2017/0188626 A1 | 7/2017 | Davis et al. |
| 2017/0188627 A1 | 7/2017 | Sur |
| 2017/0188628 A1 | 7/2017 | Montgomery |
| 2017/0188629 A1 | 7/2017 | Dickens et al. |
| 2017/0188631 A1 | 7/2017 | Lin |
| 2017/0188632 A1 | 7/2017 | Hon |
| 2017/0188634 A1 | 7/2017 | Plojoux et al. |
| 2017/0188635 A1 | 7/2017 | Force et al. |
| 2017/0188636 A1 | 7/2017 | Li et al. |
| 2017/0196263 A1 | 7/2017 | Sur |
| 2017/0196264 A1 | 7/2017 | Liu |
| 2017/0196265 A1 | 7/2017 | Liu |
| 2017/0196267 A1 | 7/2017 | Zou et al. |
| 2017/0196268 A1 | 7/2017 | Reevell |
| 2017/0196269 A1 | 7/2017 | Bernauer et al. |
| 2017/0196270 A1 | 7/2017 | Vick et al. |
| 2017/0196271 A1 | 7/2017 | Levitz et al. |
| 2017/0196272 A1 | 7/2017 | Li et al. |
| 2017/0196273 A1 | 7/2017 | Qiu |
| 2017/0202265 A1 | 7/2017 | Hawes et al. |
| 2017/0202266 A1 | 7/2017 | Sur |
| 2017/0202267 A1 | 7/2017 | Liu |
| 2017/0202268 A1 | 7/2017 | Li et al. |
| 2017/0207499 A1 | 7/2017 | Leadley |
| 2017/0208857 A1 | 7/2017 | Branton et al. |
| 2017/0208858 A1 | 7/2017 | Li |
| 2017/0208862 A1 | 7/2017 | Li et al. |
| 2017/0208863 A1 | 7/2017 | Davis et al. |
| 2017/0208864 A1 | 7/2017 | Anderson, Jr. et al. |
| 2017/0208865 A1 | 7/2017 | Nettenstrom et al. |
| 2017/0208866 A1 | 7/2017 | Liu |
| 2017/0208867 A1 | 7/2017 | Li et al. |
| 2017/0208868 A1 | 7/2017 | Li et al. |
| 2017/0208869 A1 | 7/2017 | Li et al. |
| 2017/0208870 A1 | 7/2017 | Liu |
| 2017/0208882 A1 | 7/2017 | Lambertz |
| 2017/0214261 A1 | 7/2017 | Gratton |
| 2017/0215470 A1 | 8/2017 | Piccirilli et al. |
| 2017/0215473 A1 | 8/2017 | Nakano et al. |
| 2017/0215474 A1 | 8/2017 | Li |
| 2017/0215476 A1 | 8/2017 | Dickens et al. |
| 2017/0215477 A1 | 8/2017 | Reevell |
| 2017/0215478 A1 | 8/2017 | Harrison et al. |
| 2017/0215479 A1 | 8/2017 | Kies |
| 2017/0215480 A1 | 8/2017 | Qiu |
| 2017/0215481 A1 | 8/2017 | Li et al. |
| 2017/0215482 A1 | 8/2017 | Levitz et al. |
| 2017/0215483 A1 | 8/2017 | Li et al. |
| 2017/0215484 A1 | 8/2017 | Xiang |
| 2017/0215485 A1 | 8/2017 | Zitzke |
| 2017/0217607 A1 | 8/2017 | Slurink |
| 2017/0219199 A1 | 8/2017 | Lou et al. |
| 2017/0219391 A1 | 8/2017 | Lin et al. |
| 2017/0222468 A1 | 8/2017 | Schennum et al. |
| 2017/0224013 A1 | 8/2017 | Huang |
| 2017/0224014 A1 | 8/2017 | Fraser |
| 2017/0224016 A1 | 8/2017 | Reevell |
| 2017/0224017 A1 | 8/2017 | Li et al. |
| 2017/0224018 A1 | 8/2017 | Li et al. |
| 2017/0224022 A1 | 8/2017 | Liu |
| 2017/0224023 A1 | 8/2017 | Lin et al. |
| 2017/0224024 A1 | 8/2017 | Jochnowitz et al. |
| 2017/0229885 A1 | 8/2017 | Bernauer |
| 2017/0229888 A1 | 8/2017 | Liu |
| 2017/0231266 A1 | 8/2017 | Mishra et al. |
| 2017/0231267 A1 | 8/2017 | Shi et al. |
| 2017/0231269 A1 | 8/2017 | Besso et al. |
| 2017/0231273 A1 | 8/2017 | Xiang |
| 2017/0231275 A1 | 8/2017 | Guenther |
| 2017/0231276 A1 | 8/2017 | Mironov et al. |
| 2017/0231277 A1 | 8/2017 | Mironov et al. |
| 2017/0231278 A1 | 8/2017 | Mironov et al. |
| 2017/0231279 A1 | 8/2017 | Watson |
| 2017/0231280 A1 | 8/2017 | Anton |
| 2017/0231281 A1 | 8/2017 | Hatton et al. |
| 2017/0231282 A1 | 8/2017 | Bowen et al. |
| 2017/0231283 A1 | 8/2017 | Gadas |
| 2017/0231284 A1 | 8/2017 | Newns |
| 2017/0231285 A1 | 8/2017 | Holzherr et al. |
| 2017/0231286 A1 | 8/2017 | Borkovec et al. |
| 2017/0233114 A1 | 8/2017 | Christensen et al. |
| 2017/0238596 A1 | 8/2017 | Matsumoto et al. |
| 2017/0238605 A1 | 8/2017 | Matsumoto et al. |
| 2017/0238606 A1 | 8/2017 | Matsumoto et al. |
| 2017/0238608 A1 | 8/2017 | Matsumoto et al. |
| 2017/0238609 A1 | 8/2017 | Schlipf |
| 2017/0238611 A1 | 8/2017 | Buchberger |
| 2017/0238612 A1 | 8/2017 | Daryani et al. |
| 2017/0238613 A1 | 8/2017 | Suess et al. |
| 2017/0238614 A1 | 8/2017 | Li et al. |
| 2017/0238617 A1 | 8/2017 | Scatterday |
| 2017/0241857 A1 | 8/2017 | Hearn et al. |
| 2017/0245543 A1 | 8/2017 | Karles et al. |
| 2017/0245546 A1 | 8/2017 | Huang |
| 2017/0245547 A1 | 8/2017 | Lipowicz |
| 2017/0245550 A1 | 8/2017 | Freelander |
| 2017/0245551 A1 | 8/2017 | Reevell |
| 2017/0245554 A1 | 8/2017 | Perez et al. |
| 2017/0246399 A1 | 8/2017 | Forlani et al. |
| 2017/0246405 A1 | 8/2017 | Wensley et al. |
| 2017/0246407 A1 | 8/2017 | Matsumoto et al. |
| 2017/0250552 A1 | 8/2017 | Liu |
| 2017/0251714 A1 | 9/2017 | Mishra et al. |
| 2017/0251718 A1 | 9/2017 | Armoush et al. |
| 2017/0251719 A1 | 9/2017 | Cyphert et al. |
| 2017/0251721 A1 | 9/2017 | Rostami et al. |

(56) References Cited

U.S. PATENT DOCUMENTS

| | | |
|---|---|---|
| 2017/0251722 A1 | 9/2017 | Kobal et al. |
| 2017/0251723 A1 | 9/2017 | Kobal et al. |
| 2017/0251724 A1 | 9/2017 | Lamb et al. |
| 2017/0251725 A1 | 9/2017 | Buchberger et al. |
| 2017/0251726 A1 | 9/2017 | Nielsen |
| 2017/0251727 A1 | 9/2017 | Nielsen |
| 2017/0251728 A1 | 9/2017 | Peleg et al. |
| 2017/0251729 A1 | 9/2017 | Li et al. |
| 2017/0258129 A1 | 9/2017 | Haun |
| 2017/0258132 A1 | 9/2017 | Rostami et al. |
| 2017/0258134 A1 | 9/2017 | Kane |
| 2017/0258137 A1 | 9/2017 | Smith et al. |
| 2017/0258138 A1 | 9/2017 | Rostami et al. |
| 2017/0258139 A1 | 9/2017 | Rostami et al. |
| 2017/0258140 A1 | 9/2017 | Rostami et al. |
| 2017/0258142 A1 | 9/2017 | Hatton et al. |
| 2017/0258143 A1 | 9/2017 | Lederer |
| 2017/0259170 A1 | 9/2017 | Bowen et al. |
| 2017/0259954 A1 | 9/2017 | Schwester |
| 2017/0261200 A1 | 9/2017 | Stultz |
| 2017/0265517 A1 | 9/2017 | Swede et al. |
| 2017/0265522 A1 | 9/2017 | Li et al. |
| 2017/0265524 A1 | 9/2017 | Cadieux et al. |
| 2017/0265525 A1 | 9/2017 | Li et al. |
| 2017/0266397 A1 | 9/2017 | Mayle et al. |
| 2017/0273353 A1 | 9/2017 | Gindrat |
| 2017/0273354 A1 | 9/2017 | Tucker et al. |
| 2017/0273355 A1 | 9/2017 | Rogers et al. |
| 2017/0273357 A1 | 9/2017 | Barbuck |
| 2017/0273358 A1 | 9/2017 | Batista et al. |
| 2017/0273359 A1 | 9/2017 | Liu |
| 2017/0273360 A1 | 9/2017 | Brinkley et al. |
| 2017/0273361 A1 | 9/2017 | Li et al. |
| 2017/0273914 A1 | 9/2017 | Knudsen |
| 2017/0280767 A1 | 10/2017 | Li et al. |
| 2017/0280768 A1 | 10/2017 | Lipowicz |
| 2017/0280769 A1 | 10/2017 | Li et al. |
| 2017/0280770 A1 | 10/2017 | Wang et al. |
| 2017/0280771 A1 | 10/2017 | Courbat et al. |
| 2017/0280775 A1 | 10/2017 | Manca et al. |
| 2017/0280776 A1 | 10/2017 | Manca et al. |
| 2017/0280778 A1 | 10/2017 | Force |
| 2017/0281883 A1 | 10/2017 | Li et al. |
| 2017/0283154 A1 | 10/2017 | Karles et al. |
| 2017/0285810 A1 | 10/2017 | Krah |
| 2017/0290368 A1 | 10/2017 | Hearn |
| 2017/0290369 A1 | 10/2017 | Norasak |
| 2017/0290370 A1 | 10/2017 | Garthaffner et al. |
| 2017/0290371 A1 | 10/2017 | Davis et al. |
| 2017/0290373 A1 | 10/2017 | Hon |
| 2017/0290998 A1 | 10/2017 | Poston et al. |
| 2017/0295840 A1 | 10/2017 | Rath et al. |
| 2017/0295843 A1 | 10/2017 | Storch |
| 2017/0295844 A1 | 10/2017 | Thevenaz et al. |
| 2017/0295845 A1 | 10/2017 | Bajpai et al. |
| 2017/0295846 A1 | 10/2017 | Liu |
| 2017/0295847 A1 | 10/2017 | Liu |
| 2017/0295848 A1 | 10/2017 | LaMothe |
| 2017/0295849 A1 | 10/2017 | Cadieux et al. |
| 2017/0297892 A1 | 10/2017 | Li et al. |
| 2017/0301898 A1 | 10/2017 | Lin et al. |
| 2017/0302089 A1 | 10/2017 | Bernauer et al. |
| 2017/0302324 A1 | 10/2017 | Stanimirovic et al. |
| 2017/0303597 A1 | 10/2017 | Tsui |
| 2017/0311648 A1 | 11/2017 | Gill et al. |
| 2017/0318860 A1 | 11/2017 | Adair |
| 2017/0318861 A1 | 11/2017 | Thorens |
| 2017/0325503 A1 | 11/2017 | Liu |
| 2017/0325504 A1 | 11/2017 | Liu |
| 2017/0325506 A1 | 11/2017 | Batista |
| 2017/0332695 A1 | 11/2017 | Zappoli et al. |
| 2017/0333415 A1 | 11/2017 | Williams |
| 2017/0333650 A1 | 11/2017 | Buchberger et al. |
| 2017/0333651 A1 | 11/2017 | Qiu |
| 2017/0334605 A1 | 11/2017 | Murphy et al. |
| 2017/0367406 A1 | 12/2017 | Schuler et al. |
| 2017/0367410 A1 | 12/2017 | Hon |
| 2018/0070644 A1 | 3/2018 | Monsees et al. |
| 2019/0037926 A1 | 2/2019 | Qiu |

FOREIGN PATENT DOCUMENTS

| | | |
|---|---|---|
| AU | 2014206215 A1 | 8/2014 |
| AU | 2014208287 A1 | 8/2014 |
| AU | 2017202891 A1 | 5/2017 |
| CA | 2614869 A1 | 1/2006 |
| CA | 2641869 A1 | 5/2010 |
| CH | 105346 A | 6/1924 |
| CN | 1122213 A | 5/1996 |
| CN | 1138768 A | 12/1996 |
| CN | 2401042 Y | 10/2000 |
| CN | 2420773 Y | 2/2001 |
| CN | 2643529 Y | 9/2004 |
| CN | 1548934 A | 11/2004 |
| CN | 2719043 Y | 8/2005 |
| CN | 1906096 A | 1/2007 |
| CN | 201018481 Y | 2/2008 |
| CN | 201067079 Y | 6/2008 |
| CN | 201104488 Y | 8/2008 |
| CN | 101277622 A | 10/2008 |
| CN | 101277623 A | 10/2008 |
| CN | 201375023 Y | 1/2010 |
| CN | 201408820 Y | 2/2010 |
| CN | 201430916 Y | 3/2010 |
| CN | 101869356 A | 10/2010 |
| CN | 101951796 A | 1/2011 |
| CN | 201767027 U | 3/2011 |
| CN | 301485739 | 3/2011 |
| CN | 102014677 A | 4/2011 |
| CN | 201781984 U | 4/2011 |
| CN | 201789924 U | 4/2011 |
| CN | 201839801 U | 5/2011 |
| CN | 301547686 S | 5/2011 |
| CN | 201878765 U | 6/2011 |
| CN | 102160906 A | 8/2011 |
| CN | 102176941 A | 9/2011 |
| CN | 202004499 U | 10/2011 |
| CN | 102326869 A | 1/2012 |
| CN | 202218034 U | 5/2012 |
| CN | 301970169 S | 6/2012 |
| CN | 202385728 U | 8/2012 |
| CN | 102655773 A | 9/2012 |
| CN | 102754924 A | 10/2012 |
| CN | 202456410 U | 10/2012 |
| CN | 202474905 U | 10/2012 |
| CN | 202603608 U | 12/2012 |
| CN | 202635601 U | 1/2013 |
| CN | 202635602 U | 1/2013 |
| CN | 202663148 U | 1/2013 |
| CN | 102920028 A | 2/2013 |
| CN | 102970885 A | 3/2013 |
| CN | 202890462 U | 4/2013 |
| CN | 302396126 | 4/2013 |
| CN | 302396126 S | 4/2013 |
| CN | 103141944 A | 6/2013 |
| CN | 203040683 U | 7/2013 |
| CN | 203072896 U | 7/2013 |
| CN | 203087525 U | 7/2013 |
| CN | 103237469 A | 8/2013 |
| CN | 103237470 A | 8/2013 |
| CN | 203121009 U | 8/2013 |
| CN | 203152489 U | 8/2013 |
| CN | 203168032 U | 9/2013 |
| CN | 203168033 U | 9/2013 |
| CN | 203182012 U | 9/2013 |
| CN | 203243945 U | 10/2013 |
| CN | 203327953 U | 12/2013 |
| CN | 203353689 U | 12/2013 |
| CN | 203481880 U | 3/2014 |
| CN | 302799554 S | 4/2014 |
| CN | 302810246 S | 4/2014 |
| CN | 104010529 A | 8/2014 |
| CN | 302884434 S | 8/2014 |
| CN | 302926289 S | 8/2014 |

(56) References Cited

FOREIGN PATENT DOCUMENTS

| | | |
|---|---|---|
| CN | 104055223 A | 9/2014 |
| CN | 302950830 | 9/2014 |
| CN | 302950830 S | 9/2014 |
| CN | 204120231 U | 1/2015 |
| CN | 303089422 S | 1/2015 |
| CN | 303091331 S | 1/2015 |
| CN | 204132390 U | 2/2015 |
| CN | 104382237 A | 3/2015 |
| CN | 204217907 U | 3/2015 |
| CN | 303210086 S | 5/2015 |
| CN | 104738816 A | 7/2015 |
| CN | 105011375 A | 11/2015 |
| CN | 303103389 S | 11/2015 |
| CN | 204905326 U | 12/2015 |
| CN | 303568163 S | 1/2016 |
| CN | 303103390 S | 2/2016 |
| CN | 102883631 A | 11/2016 |
| DE | 1093936 B | 12/1960 |
| DE | 19619536 A1 | 10/1997 |
| DE | 19854005 A1 | 5/2000 |
| DE | 19854012 A1 | 5/2000 |
| DE | 69430196 T2 | 10/2002 |
| DE | 102006004484 A1 | 8/2007 |
| DE | 102007011120 A1 | 9/2008 |
| DE | 102008046932 A1 | 5/2009 |
| DE | 102012100831 B3 | 2/2013 |
| EP | 0267847 B1 | 5/1988 |
| EP | 0283672 A2 | 9/1988 |
| EP | 0503767 A1 | 9/1992 |
| EP | 0532194 A1 | 3/1993 |
| EP | 0535695 A2 | 4/1993 |
| EP | 0762258 | 3/1997 |
| EP | 0762258 A2 | 3/1997 |
| EP | 1093936 A1 | 4/2001 |
| EP | 1736065 A1 | 12/2006 |
| EP | 1736177 A1 | 12/2006 |
| EP | 2110034 A1 | 4/2008 |
| EP | 2110033 A1 | 10/2009 |
| EP | 2113178 A1 | 11/2009 |
| EP | 2186507 A2 | 5/2010 |
| EP | 2319334 A1 | 5/2011 |
| EP | 2399636 A1 | 12/2011 |
| EP | 2460424 A1 | 6/2012 |
| EP | 2489391 A1 | 8/2012 |
| EP | 2493341 A1 | 9/2012 |
| EP | 2573900 A1 | 3/2013 |
| EP | 2606756 A1 | 6/2013 |
| EP | 2609821 A1 | 7/2013 |
| EP | 2614731 A1 | 7/2013 |
| EP | 2672847 B1 | 12/2013 |
| EP | 2711006 A1 | 3/2014 |
| EP | 2641669 B1 | 5/2014 |
| EP | 2789248 A1 | 10/2014 |
| EP | 2493342 B1 | 12/2014 |
| EP | 2856893 A1 | 4/2015 |
| EP | 2862454 A1 | 4/2015 |
| EP | 2862457 A1 | 4/2015 |
| EP | 2884861 A1 | 6/2015 |
| EP | 2888964 A1 | 7/2015 |
| EP | 2895390 A1 | 7/2015 |
| EP | 2895930 A2 | 7/2015 |
| EP | 2944206 A1 | 11/2015 |
| EP | 2944207 A1 | 11/2015 |
| EP | 2952110 A1 | 12/2015 |
| EP | 2989912 A1 | 3/2016 |
| EP | 3001918 A1 | 4/2016 |
| EP | 3007305 A1 | 4/2016 |
| EP | 3012213 A1 | 4/2016 |
| EP | 3016233 A1 | 5/2016 |
| EP | 3023016 A1 | 5/2016 |
| EP | 3023351 A1 | 5/2016 |
| EP | 3023947 A1 | 5/2016 |
| EP | 3024343 A2 | 6/2016 |
| EP | 3025598 A1 | 6/2016 |
| EP | 3026779 A1 | 6/2016 |
| EP | 3031338 A1 | 6/2016 |
| EP | 3047742 A1 | 7/2016 |
| EP | 3056099 A1 | 8/2016 |
| EP | 3061358 A1 | 8/2016 |
| EP | 3062646 A1 | 9/2016 |
| EP | 3075270 A1 | 10/2016 |
| EP | 3075271 A1 | 10/2016 |
| EP | 3081102 A1 | 10/2016 |
| EP | 3085638 A1 | 10/2016 |
| EP | 3087853 A1 | 11/2016 |
| EP | 3092909 A1 | 11/2016 |
| EP | 3097803 A1 | 11/2016 |
| EP | 3103355 A1 | 12/2016 |
| EP | 3103356 A1 | 12/2016 |
| EP | 3111787 A1 | 1/2017 |
| EP | 3130238 A1 | 2/2017 |
| EP | 3132843 A1 | 2/2017 |
| EP | 3135139 A1 | 3/2017 |
| EP | 3135603 A1 | 3/2017 |
| EP | 3143882 A3 | 3/2017 |
| EP | 3143884 A3 | 4/2017 |
| EP | 3155908 A1 | 4/2017 |
| EP | 3158880 A1 | 4/2017 |
| EP | 3158881 A1 | 4/2017 |
| EP | 3195738 A2 | 7/2017 |
| EP | 3165102 A3 | 8/2017 |
| EP | 3199043 A1 | 8/2017 |
| EP | 3205220 A1 | 8/2017 |
| EP | 3205597 A1 | 8/2017 |
| EP | 3213649 A1 | 9/2017 |
| EP | 3225118 A1 | 10/2017 |
| EP | 3228198 A1 | 10/2017 |
| EP | 3228345 A1 | 10/2017 |
| EP | 3086671 B1 | 9/2018 |
| ES | 2118034 A1 | 9/1998 |
| FR | 002626416-001 | 4/2015 |
| FR | 002626416-002 | 4/2015 |
| GB | 1025630 A | 4/1966 |
| GB | 1065678 A | 4/1967 |
| GB | 2264237 A | 8/1993 |
| GB | 2266466 A | 11/1993 |
| GB | 2504074 A | 1/2014 |
| GB | 2507104 A1 | 4/2014 |
| GB | 2533174 A | 6/2016 |
| GB | 2560653 A | 9/2018 |
| IE | S20050615 | 9/2005 |
| JP | 62278975 | 12/1987 |
| JP | H06114105 A | 4/1994 |
| JP | 09-075058 | 3/1997 |
| JP | H09075058 A | 3/1997 |
| JP | 11178563 | 6/1999 |
| JP | 2000203639 A | 7/2000 |
| JP | 2000236865 A | 9/2000 |
| JP | 2001161819 A | 6/2001 |
| JP | 2001165437 A | 6/2001 |
| JP | 3325591 B2 | 9/2002 |
| JP | 2006320285 A | 11/2006 |
| JP | 2006320286 A | 11/2006 |
| JP | 2009213428 A | 9/2009 |
| JP | 2010020929 A | 1/2010 |
| JP | 2011024430 A | 2/2011 |
| JP | 2012005412 A | 1/2012 |
| JP | 2013507976 A | 3/2013 |
| JP | 2013516159 A | 5/2013 |
| JP | 2015504669 A | 2/2015 |
| JP | 201712730 A | 1/2017 |
| KR | 100579783 B1 | 5/2006 |
| KR | 10-2012-0016167 A | 2/2012 |
| KR | 20120008751 A | 2/2012 |
| KR | 200460784 Y1 | 6/2012 |
| KR | 20120006582 U | 9/2012 |
| KR | 20120105655 A | 9/2012 |
| KR | 20-2012-0007263 U | 10/2012 |
| KR | 101193644 B1 | 10/2012 |
| KR | 20120113519 A | 10/2012 |
| KR | 1020120132004 | 12/2012 |
| KR | 20130092252 A | 8/2013 |
| KR | 20130106009 A | 9/2013 |
| KR | 20130106741 A | 9/2013 |

(56) References Cited

FOREIGN PATENT DOCUMENTS

| | | |
|---|---|---|
| KR | 20130107658 A | 10/2013 |
| KR | 20130122713 A | 11/2013 |
| KR | 20130127412 A | 11/2013 |
| KR | 20110084387 A | 4/2018 |
| RU | 2528945 C1 | 9/2014 |
| RU | 2606942 C2 | 1/2017 |
| SG | 11201707778 W | 10/2017 |
| TW | 515721 B | 1/2003 |
| TW | I320698 B | 2/2010 |
| TW | 201330787 A | 1/2013 |
| TW | 201436722 A | 10/2014 |
| TW | 201438608 A | 10/2014 |
| TW | 201524383 A | 7/2015 |
| TW | 201540203 A | 11/2015 |
| WO | WO-9712639 A1 | 4/1997 |
| WO | WO-2000005976 A1 | 2/2000 |
| WO | WO-0028842 A1 | 5/2000 |
| WO | WO-03055486 A1 | 7/2003 |
| WO | WO-03056948 A1 | 7/2003 |
| WO | WO-2003061716 A1 | 7/2003 |
| WO | WO-03082031 A1 | 10/2003 |
| WO | WO-03094900 A1 | 11/2003 |
| WO | WO-03101454 A1 | 12/2003 |
| WO | WO-03103387 A2 | 12/2003 |
| WO | WO-2004064548 A1 | 8/2004 |
| WO | WO-2004080216 A1 | 9/2004 |
| WO | WO-2004098324 A2 | 11/2004 |
| WO | WO-2005020726 A1 | 3/2005 |
| WO | WO-2005060366 A2 | 7/2005 |
| WO | WO-2006021153 A1 | 3/2006 |
| WO | WO-2007066374 A1 | 6/2007 |
| WO | WO-2007078273 A1 | 7/2007 |
| WO | WO-2007095109 A2 | 8/2007 |
| WO | WO-2007098337 A2 | 8/2007 |
| WO | WO-2007117675 A2 | 10/2007 |
| WO | WO-2007/141520 A1 | 12/2007 |
| WO | WO-2008077271 A1 | 7/2008 |
| WO | WO-2008083165 A2 | 7/2008 |
| WO | WO-2008138650 A1 | 11/2008 |
| WO | WO-2008151777 A2 | 12/2008 |
| WO | WO-2009003204 A2 | 1/2009 |
| WO | WO-2009079641 A2 | 6/2009 |
| WO | WO-2009132793 A1 | 11/2009 |
| WO | WO-2010003480 A1 | 1/2010 |
| WO | WO-2010020634 A1 | 2/2010 |
| WO | WO-2010118122 A1 | 10/2010 |
| WO | WO-2010118644 A1 | 10/2010 |
| WO | WO-2010140841 A2 | 12/2010 |
| WO | WO-2010145805 A1 | 12/2010 |
| WO | WO-2011010334 A1 | 1/2011 |
| WO | WO-2011050943 A1 | 5/2011 |
| WO | WO-2011050964 A1 | 5/2011 |
| WO | WO-2011079932 A1 | 7/2011 |
| WO | WO-2011107737 A1 | 9/2011 |
| WO | WO-2011125058 A1 | 10/2011 |
| WO | WO-2011137453 A2 | 11/2011 |
| WO | WO-2011146174 A2 | 11/2011 |
| WO | WO-2011147691 A1 | 12/2011 |
| WO | WO-2012014490 A1 | 2/2012 |
| WO | WO-2012019533 A1 | 2/2012 |
| WO | WO-2012043941 A1 | 4/2012 |
| WO | WO-2012059726 A2 | 5/2012 |
| WO | WO-2012062600 A1 | 5/2012 |
| WO | WO2012062600 A1 | 5/2012 |
| WO | WO-2012/085207 A1 | 6/2012 |
| WO | WO-2012085203 A1 | 6/2012 |
| WO | WO-2012088675 A1 | 7/2012 |
| WO | WO-2012091249 A1 | 7/2012 |
| WO | WO-2012100523 A1 | 8/2012 |
| WO | WO-2012/120487 A2 | 9/2012 |
| WO | WO-2012129812 A1 | 10/2012 |
| WO | WO-2012134117 A2 | 10/2012 |
| WO | WO-2012164033 A1 | 12/2012 |
| WO | WO-2012173322 A1 | 12/2012 |
| WO | WO-2012174677 A1 | 12/2012 |
| WO | WO-D079112-0010 | 12/2012 |
| WO | WOD79112-0010 | 12/2012 |
| WO | WO-2013012157 A1 | 1/2013 |
| WO | WO-2013020220 A1 | 2/2013 |
| WO | WO-2013025921 A1 | 2/2013 |
| WO | WO-2013030202 A1 | 3/2013 |
| WO | WO-2013034453 A1 | 3/2013 |
| WO | WO-2013034456 A1 * | 3/2013 ........... A24F 47/008 |
| WO | WO-2013040193 A2 | 3/2013 |
| WO | WO2013044537 | 4/2013 |
| WO | WO2013044537 | 4/2013 |
| WO | WO-2013044537 A1 | 4/2013 |
| WO | WO-2013045582 A2 | 4/2013 |
| WO | WO-2013/060781 A1 | 5/2013 |
| WO | WO-2013060784 A2 | 5/2013 |
| WO | WO-2013068100 A1 | 5/2013 |
| WO | WO-2013075439 A1 | 5/2013 |
| WO | WO-2013076750 A1 | 5/2013 |
| WO | WO-2013/083636 A1 | 6/2013 |
| WO | WO-2013083631 A1 | 6/2013 |
| WO | WO-2013083634 A1 | 6/2013 |
| WO | WO2013083635 | 6/2013 |
| WO | WO-2013083635 A1 | 6/2013 |
| WO | WO-2013086661 A1 | 6/2013 |
| WO | WO-2013089358 A1 | 6/2013 |
| WO | WO-2013089551 A1 | 6/2013 |
| WO | WO-2013093695 A1 | 6/2013 |
| WO | WO-2013098395 A1 | 7/2013 |
| WO | WO-2013110208 A1 | 8/2013 |
| WO | WO-2013110209 A1 | 8/2013 |
| WO | WO-2013110210 A1 | 8/2013 |
| WO | WO-2013113173 A1 | 8/2013 |
| WO | WO-2013113174 A1 | 8/2013 |
| WO | WO-2013113612 A1 | 8/2013 |
| WO | WO-2013116558 A1 | 8/2013 |
| WO | WO-2013116567 A1 | 8/2013 |
| WO | WO-2013116983 A1 | 8/2013 |
| WO | WO-2013131763 A1 | 9/2013 |
| WO | WO-2013142678 A1 | 9/2013 |
| WO | WO-2013147492 A1 | 10/2013 |
| WO | WO-2013150406 A2 | 10/2013 |
| WO | WO-2013152873 A1 | 10/2013 |
| WO | WO-2013155645 A1 | 10/2013 |
| WO | WO-2013155654 A1 | 10/2013 |
| WO | WO-2013156658 A1 | 10/2013 |
| WO | WO-2013159245 A1 | 10/2013 |
| WO | WO-2013165878 A1 | 11/2013 |
| WO | WO-2013171206 A1 | 11/2013 |
| WO | WO-2013174001 A1 | 11/2013 |
| WO | WO-2013190036 A1 | 12/2013 |
| WO | WO-2014012906 A1 | 1/2014 |
| WO | WO-2014020539 A1 | 2/2014 |
| WO | WO-2014020953 A1 | 2/2014 |
| WO | WO-2014023171 A1 | 2/2014 |
| WO | WO-2014/040988 A2 | 3/2014 |
| WO | WO-2014032280 A1 | 3/2014 |
| WO | WO-2014039308 A1 | 3/2014 |
| WO | WO-2014040915 A1 | 3/2014 |
| WO | WO-2014047948 A1 | 4/2014 |
| WO | WO-2014047955 A1 | 4/2014 |
| WO | WO-2014067236 A1 | 5/2014 |
| WO | WO-2014071747 A1 | 5/2014 |
| WO | WO-2014/102091 A1 | 7/2014 |
| WO | WO-2014101119 A1 | 7/2014 |
| WO | WO-2014101401 A1 | 7/2014 |
| WO | WO-2014101734 A1 | 7/2014 |
| WO | WO-2014106323 A1 | 7/2014 |
| WO | WO-2014110761 A1 | 7/2014 |
| WO | WO-2014113949 A1 | 7/2014 |
| WO | WO-2014114328 A1 | 7/2014 |
| WO | WO-2014117382 A1 | 8/2014 |
| WO | WO-2014121509 A1 | 8/2014 |
| WO | WO-2014125340 A1 | 8/2014 |
| WO | WO-2014127446 A1 | 8/2014 |
| WO | WO-2014134781 A1 | 9/2014 |
| WO | WO-2014138244 A1 | 9/2014 |
| WO | WO-2014139609 | 9/2014 |
| WO | WO-2014139610 A1 | 9/2014 |
| WO | WO-2014144678 A2 | 9/2014 |

(56) References Cited

FOREIGN PATENT DOCUMENTS

| | | |
|---|---|---|
| WO | WO-2014146270 A1 | 9/2014 |
| WO | WO-2014147470 A2 | 9/2014 |
| WO | WO-2014150979 A2 | 9/2014 |
| WO | WO-2014151040 A2 | 9/2014 |
| WO | WO-2014/166121 A1 | 10/2014 |
| WO | WO-2014153796 A1 | 10/2014 |
| WO | WO-2014159982 A1 | 10/2014 |
| WO | WO-2014161181 A1 | 10/2014 |
| WO | WO-2014166039 A1 | 10/2014 |
| WO | WO-2014167530 A1 | 10/2014 |
| WO | WO-2014169437 A1 | 10/2014 |
| WO | WO-2014169667 A1 | 10/2014 |
| WO | WO-2014185937 A1 | 11/2014 |
| WO | WO-2014186983 A1 | 11/2014 |
| WO | WO-2014194499 A1 | 12/2014 |
| WO | WO-2014195687 A1 | 12/2014 |
| WO | WO-2014198042 A1 | 12/2014 |
| WO | WO-2014201610 A1 | 12/2014 |
| WO | WO-2014201611 A1 | 12/2014 |
| WO | WO-2014201646 A1 | 12/2014 |
| WO | WO-2014201664 A1 | 12/2014 |
| WO | WO-2014201666 A1 | 12/2014 |
| WO | WO-2014201668 A1 | 12/2014 |
| WO | WO-2014205263 A1 | 12/2014 |
| WO | WO-2014205749 A1 | 12/2014 |
| WO | WO-2014205780 A1 | 12/2014 |
| WO | WO-2014205807 A1 | 12/2014 |
| WO | WO-2014205811 A1 | 12/2014 |
| WO | WO-2014206148 A1 | 12/2014 |
| WO | WO-2015000125 A1 | 1/2015 |
| WO | WO-2015000180 A1 | 1/2015 |
| WO | WO-2015003327 A1 | 1/2015 |
| WO | WO-2015003372 A1 | 1/2015 |
| WO | WO-2015003374 A1 | 1/2015 |
| WO | WO-2015006929 A1 | 1/2015 |
| WO | WO-2015010242 A1 | 1/2015 |
| WO | WO-2015010277 A1 | 1/2015 |
| WO | WO-2015010284 A1 | 1/2015 |
| WO | WO-2015010291 A1 | 1/2015 |
| WO | WO-2015010310 A1 | 1/2015 |
| WO | WO-2015010336 A1 | 1/2015 |
| WO | WO-2015010345 A1 | 1/2015 |
| WO | WO-2015010349 A1 | 1/2015 |
| WO | WO-2015013890 A1 | 2/2015 |
| WO | WO-2015013891 A1 | 2/2015 |
| WO | WO-2015013892 A1 | 2/2015 |
| WO | WO-2015013926 A1 | 2/2015 |
| WO | WO-2015013950 A1 | 2/2015 |
| WO | WO-2015013967 A1 | 2/2015 |
| WO | WO-2015015156 A1 | 2/2015 |
| WO | WO-2015017971 A1 | 2/2015 |
| WO | WO-2015018026 A1 | 2/2015 |
| WO | WO-2015018120 A1 | 2/2015 |
| WO | WO-2015021612 A1 | 2/2015 |
| WO | WO-2015021646 A1 | 2/2015 |
| WO | WO-2015021651 A1 | 2/2015 |
| WO | WO-2015021652 A1 | 2/2015 |
| WO | WO-2015021655 A1 | 2/2015 |
| WO | WO-2015021658 A1 | 2/2015 |
| WO | WO-2015024239 A1 | 2/2015 |
| WO | WO-2015024247 A1 | 2/2015 |
| WO | WO-2015026081 A1 | 2/2015 |
| WO | WO-2015027383 A1 | 3/2015 |
| WO | WO2015027435 A1 | 3/2015 |
| WO | WO-2015027435 A1 | 3/2015 |
| WO | WO-2015027436 A1 | 3/2015 |
| WO | WO-2015027470 A1 | 3/2015 |
| WO | WO2015028815 | 3/2015 |
| WO | WO-2015028815 A1 | 3/2015 |
| WO | WO-2015032050 A1 | 3/2015 |
| WO | WO-2015032055 A1 | 3/2015 |
| WO | WO-2015032078 A1 | 3/2015 |
| WO | WO-2015032093 A1 | 3/2015 |
| WO | WO-2015035510 A1 | 3/2015 |
| WO | WO-2015035547 A1 | 3/2015 |
| WO | WO-2015035557 A1 | 3/2015 |
| WO | WO-2015035587 A1 | 3/2015 |
| WO | WO-2015035623 A1 | 3/2015 |
| WO | WO-2015035689 A1 | 3/2015 |
| WO | WO-2015037925 A1 | 3/2015 |
| WO | WO-2015039275 A1 | 3/2015 |
| WO | WO-2015039280 A1 | 3/2015 |
| WO | WO-2015039332 A1 | 3/2015 |
| WO | WO-2015042790 A1 | 4/2015 |
| WO | WO-2015042811 A1 | 4/2015 |
| WO | WO-2015042848 A1 | 4/2015 |
| WO | WO-2015042943 A1 | 4/2015 |
| WO | WO-2015051509 A1 | 4/2015 |
| WO | WO-2015051538 A1 | 4/2015 |
| WO | WO-2015052513 A2 | 4/2015 |
| WO | WO-2015054815 A1 | 4/2015 |
| WO | WO-2015054862 A1 | 4/2015 |
| WO | WO-2015054961 A1 | 4/2015 |
| WO | WO-2015055314 A1 | 4/2015 |
| WO | WO-2015058340 A1 | 4/2015 |
| WO | WO-2015058341 A1 | 4/2015 |
| WO | WO-2015058367 A1 | 4/2015 |
| WO | WO-2015058387 A1 | 4/2015 |
| WO | WO-2015062041 A1 | 5/2015 |
| WO | WO-2015066136 A1 | 5/2015 |
| WO | WO-2015066927 A1 | 5/2015 |
| WO | WO-2015070398 A1 | 5/2015 |
| WO | WO-2015070405 A1 | 5/2015 |
| WO | WO-2015071703 A1 | 5/2015 |
| WO | WO-2015073564 A1 | 5/2015 |
| WO | WO-2015073975 A1 | 5/2015 |
| WO | WO-2015074187 A1 | 5/2015 |
| WO | WO-2015074265 A1 | 5/2015 |
| WO | WO-2015074308 A1 | 5/2015 |
| WO | WO-2015077645 A1 | 5/2015 |
| WO | WO-2015077998 A1 | 6/2015 |
| WO | WO-2015077999 A1 | 6/2015 |
| WO | WO-2015078010 A1 | 6/2015 |
| WO | WO-2015078147 A1 | 6/2015 |
| WO | WO-2015079197 A1 | 6/2015 |
| WO | WO-2015089711 A1 | 6/2015 |
| WO | WO-2015091346 A2 | 6/2015 |
| WO | WO-2015/100361 A1 | 7/2015 |
| WO | WO-2015013327 A3 | 7/2015 |
| WO | WO-2015106434 A1 | 7/2015 |
| WO | WO-2015106440 A1 | 7/2015 |
| WO | WO-2015107551 A2 | 7/2015 |
| WO | WO-2015107552 A1 | 7/2015 |
| WO | WO-2015109476 A1 | 7/2015 |
| WO | WO-2015109532 A1 | 7/2015 |
| WO | WO-2015109540 A1 | 7/2015 |
| WO | WO-2015109616 A1 | 7/2015 |
| WO | WO-2015109618 A1 | 7/2015 |
| WO | WO-2015114325 A1 | 8/2015 |
| WO | WO-2015117285 A1 | 8/2015 |
| WO | WO-2015120588 A1 | 8/2015 |
| WO | WO-2015120591 A1 | 8/2015 |
| WO | WO-2015120623 A1 | 8/2015 |
| WO | WO-2015123831 A1 | 8/2015 |
| WO | WO-2015127609 A1 | 9/2015 |
| WO | WO-2015128599 A1 | 9/2015 |
| WO | WO-2015137815 A1 | 9/2015 |
| WO | WO-2015140312 A1 | 9/2015 |
| WO | WO-2015140336 A1 | 9/2015 |
| WO | WO-2015140768 A2 | 9/2015 |
| WO | WO-2015143637 A1 | 10/2015 |
| WO | WO-2015143648 A1 | 10/2015 |
| WO | WO-2015143749 A1 | 10/2015 |
| WO | WO-2015143765 A1 | 10/2015 |
| WO | WO-2015144057 A1 | 10/2015 |
| WO | WO-2015144328 A1 | 10/2015 |
| WO | WO-2015149311 A1 | 10/2015 |
| WO | WO-2015149330 A1 | 10/2015 |
| WO | WO-2015149332 A1 | 10/2015 |
| WO | WO-2015149338 A1 | 10/2015 |
| WO | WO-2015149368 A1 | 10/2015 |
| WO | WO-2015149403 A1 | 10/2015 |
| WO | WO-2015149406 A1 | 10/2015 |
| WO | WO-2015150068 A1 | 10/2015 |

(56) References Cited

FOREIGN PATENT DOCUMENTS

| | | |
|---|---|---|
| WO | WO-2015154309 A1 | 10/2015 |
| WO | WO-2015154619 A1 | 10/2015 |
| WO | WO-2015157891 A1 | 10/2015 |
| WO | WO-2015157893 A1 | 10/2015 |
| WO | WO-2015157900 A1 | 10/2015 |
| WO | WO-2015157901 A1 | 10/2015 |
| WO | WO-2015157928 A1 | 10/2015 |
| WO | WO-2015158522 A1 | 10/2015 |
| WO | WO-2015158548 A1 | 10/2015 |
| WO | WO-2015161406 A1 | 10/2015 |
| WO | WO-2015161407 A1 | 10/2015 |
| WO | WO-2015161485 A1 | 10/2015 |
| WO | WO-2015161486 A1 | 10/2015 |
| WO | WO-2015161491 A1 | 10/2015 |
| WO | WO-2015161514 A1 | 10/2015 |
| WO | WO-2015161553 A1 | 10/2015 |
| WO | WO-2015161555 A1 | 10/2015 |
| WO | WO-2015161557 A1 | 10/2015 |
| WO | WO-2015068044 A3 | 11/2015 |
| WO | WO-2015165067 A1 | 11/2015 |
| WO | WO-2015165081 A1 | 11/2015 |
| WO | WO-2015165083 A1 | 11/2015 |
| WO | WO-2015165086 A1 | 11/2015 |
| WO | WO-2015165105 A1 | 11/2015 |
| WO | WO-2015165146 A1 | 11/2015 |
| WO | WO-2015165747 A1 | 11/2015 |
| WO | WO-2015168827 A1 | 11/2015 |
| WO | WO-2015168828 A1 | 11/2015 |
| WO | WO-2015168853 A1 | 11/2015 |
| WO | WO-2015168904 A1 | 11/2015 |
| WO | WO-2015168912 A1 | 11/2015 |
| WO | WO-2015172224 A1 | 11/2015 |
| WO | WO-2015172331 A1 | 11/2015 |
| WO | WO-2015172361 A1 | 11/2015 |
| WO | WO-2015172368 A1 | 11/2015 |
| WO | WO-2015172382 A1 | 11/2015 |
| WO | WO-2015172383 A1 | 11/2015 |
| WO | WO-2015172384 A1 | 11/2015 |
| WO | WO-2015172387 A1 | 11/2015 |
| WO | WO-2015172388 A1 | 11/2015 |
| WO | WO-2015172389 A1 | 11/2015 |
| WO | WO-2015172390 A1 | 11/2015 |
| WO | WO-2015172606 A1 | 11/2015 |
| WO | WO-2015174657 A1 | 11/2015 |
| WO | WO-2015174708 A1 | 11/2015 |
| WO | WO-2015175979 A1 | 11/2015 |
| WO | WO-2015176210 A1 | 11/2015 |
| WO | WO-2015176230 A1 | 11/2015 |
| WO | WO-2015176300 A1 | 11/2015 |
| WO | WO-2015176580 A1 | 11/2015 |
| WO | WO-2015180027 A1 | 12/2015 |
| WO | WO-2015180061 A1 | 12/2015 |
| WO | WO-2015180062 A1 | 12/2015 |
| WO | WO-2015180071 A1 | 12/2015 |
| WO | WO-2015180088 A1 | 12/2015 |
| WO | WO-2015180089 A1 | 12/2015 |
| WO | WO-2015180145 A1 | 12/2015 |
| WO | WO-2015184580 A1 | 12/2015 |
| WO | WO-2015184590 A1 | 12/2015 |
| WO | WO-2015184620 A1 | 12/2015 |
| WO | WO-2015184747 A1 | 12/2015 |
| WO | WO-2015186000 A2 | 12/2015 |
| WO | WO-2015188295 A1 | 12/2015 |
| WO | WO-2015188296 A1 | 12/2015 |
| WO | WO-2015189613 A1 | 12/2015 |
| WO | WO-2015190810 A1 | 12/2015 |
| WO | WO-2015192301 A1 | 12/2015 |
| WO | WO-2015192326 A1 | 12/2015 |
| WO | WO-2015192336 A1 | 12/2015 |
| WO | WO-2015192337 A1 | 12/2015 |
| WO | WO-2015192377 A1 | 12/2015 |
| WO | WO-2015193456 A1 | 12/2015 |
| WO | WO-2015196331 A1 | 12/2015 |
| WO | WO-2015196332 A1 | 12/2015 |
| WO | WO-2015196357 A1 | 12/2015 |
| WO | WO-2015196367 A1 | 12/2015 |
| WO | WO-2015196395 A1 | 12/2015 |
| WO | WO-2015196463 A1 | 12/2015 |
| WO | WO-2015148649 A3 | 1/2016 |
| WO | WO-2016000113 A1 | 1/2016 |
| WO | WO-2016000130 A1 | 1/2016 |
| WO | WO-2016000135 A1 | 1/2016 |
| WO | WO-2016000136 A1 | 1/2016 |
| WO | WO-2016000139 A1 | 1/2016 |
| WO | WO-2016000206 A1 | 1/2016 |
| WO | WO-2016000207 A1 | 1/2016 |
| WO | WO-2016000214 A1 | 1/2016 |
| WO | WO-2016000232 A1 | 1/2016 |
| WO | WO-2016000233 A1 | 1/2016 |
| WO | WO-2016000305 A1 | 1/2016 |
| WO | WO-2016008067 A1 | 1/2016 |
| WO | WO-2016008096 A1 | 1/2016 |
| WO | WO-2016008217 A1 | 1/2016 |
| WO | WO-2016011573 A1 | 1/2016 |
| WO | WO-2016012769 A1 | 1/2016 |
| WO | WO-2016015196 A1 | 2/2016 |
| WO | WO-2016015245 A1 | 2/2016 |
| WO | WO-2016015246 A1 | 2/2016 |
| WO | WO-2016015247 A1 | 2/2016 |
| WO | WO-2016015264 A1 | 2/2016 |
| WO | WO-2016015712 A1 | 2/2016 |
| WO | WO-2016019508 A1 | 2/2016 |
| WO | WO-2016019550 A1 | 2/2016 |
| WO | WO-2016019573 A1 | 2/2016 |
| WO | WO-2016020675 A1 | 2/2016 |
| WO | WO-2016023173 A1 | 2/2016 |
| WO | WO-2016023176 A1 | 2/2016 |
| WO | WO-2016023177 A1 | 2/2016 |
| WO | WO-2016023181 A1 | 2/2016 |
| WO | WO-2016023182 A1 | 2/2016 |
| WO | WO-2016023183 A1 | 2/2016 |
| WO | WO-2016023212 A1 | 2/2016 |
| WO | WO-2016023651 A1 | 2/2016 |
| WO | WO-2016023824 A1 | 2/2016 |
| WO | WO-2016023965 A1 | 2/2016 |
| WO | WO-2016026104 A1 | 2/2016 |
| WO | WO-2016026105 A1 | 2/2016 |
| WO | WO-2016026156 A1 | 2/2016 |
| WO | WO-2016026811 A1 | 2/2016 |
| WO | WO-2016028544 A1 | 2/2016 |
| WO | WO-2016029344 A1 | 3/2016 |
| WO | WO-2016029382 A1 | 3/2016 |
| WO | WO-2016029386 A1 | 3/2016 |
| WO | WO-2016029389 A1 | 3/2016 |
| WO | WO-2016029429 A1 | 3/2016 |
| WO | WO-2016029464 A1 | 3/2016 |
| WO | WO-2016029468 A1 | 3/2016 |
| WO | WO-2016029470 A1 | 3/2016 |
| WO | WO-2016029473 A1 | 3/2016 |
| WO | WO-2016029567 A1 | 3/2016 |
| WO | WO-2016030661 A1 | 3/2016 |
| WO | WO-2016033721 A1 | 3/2016 |
| WO | WO-2016033734 A1 | 3/2016 |
| WO | WO-2016033783 A1 | 3/2016 |
| WO | WO-2016033817 A1 | 3/2016 |
| WO | WO-2016034100 A1 | 3/2016 |
| WO | WO-2016038029 A1 | 3/2016 |
| WO | WO-2016040575 A1 | 3/2016 |
| WO | WO-2016041114 A1 | 3/2016 |
| WO | WO-2016041140 A1 | 3/2016 |
| WO | WO-2016041141 A1 | 3/2016 |
| WO | WO-2016041207 A1 | 3/2016 |
| WO | WO-2016041209 A1 | 3/2016 |
| WO | WO-2016045058 A1 | 3/2016 |
| WO | WO-2016046116 A1 | 3/2016 |
| WO | WO-2015192834 A3 | 4/2016 |
| WO | WO-2016049822 A1 | 4/2016 |
| WO | WO-2016049823 A1 | 4/2016 |
| WO | WO-2016049855 A1 | 4/2016 |
| WO | WO-2016049863 A1 | 4/2016 |
| WO | WO-2016050246 A1 | 4/2016 |
| WO | WO-2016050247 A1 | 4/2016 |
| WO | WO-2016054793 A1 | 4/2016 |
| WO | WO-2016055653 A1 | 4/2016 |

(56) References Cited

FOREIGN PATENT DOCUMENTS

| | | |
|---|---|---|
| WO | WO-2016058139 A1 | 4/2016 |
| WO | WO-2016058187 A1 | 4/2016 |
| WO | WO-2016058189 A1 | 4/2016 |
| WO | WO2016059000 A1 | 4/2016 |
| WO | WO-2016059000 A1 | 4/2016 |
| WO | WO-2016060576 A1 | 4/2016 |
| WO | WO-2016061729 A1 | 4/2016 |
| WO | WO-2016061730 A1 | 4/2016 |
| WO | WO-2016061822 A1 | 4/2016 |
| WO | WO-2016061859 A1 | 4/2016 |
| WO | WO-2016062168 A1 | 4/2016 |
| WO | WO-2016062777 A1 | 4/2016 |
| WO | WO-2016063775 A1 | 4/2016 |
| WO | WO-2016065520 A1 | 5/2016 |
| WO | WO-2016065521 A1 | 5/2016 |
| WO | WO-2016065532 A1 | 5/2016 |
| WO | WO-2016065533 A1 | 5/2016 |
| WO | WO-2016065596 A1 | 5/2016 |
| WO | WO-2016065598 A1 | 5/2016 |
| WO | WO-2016065599 A1 | 5/2016 |
| WO | WO-2016065605 A1 | 5/2016 |
| WO | WO-2016065606 A1 | 5/2016 |
| WO | WO-2016065607 A1 | 5/2016 |
| WO | WO-2016070553 A1 | 5/2016 |
| WO | WO-2016071027 A1 | 5/2016 |
| WO | WO-2016071705 A1 | 5/2016 |
| WO | WO-2016071706 A1 | 5/2016 |
| WO | WO-2016074228 A1 | 5/2016 |
| WO | WO-2016074229 A1 | 5/2016 |
| WO | WO-2016074230 A1 | 5/2016 |
| WO | WO-2016074234 A1 | 5/2016 |
| WO | WO-2016074237 A1 | 5/2016 |
| WO | WO-2016076178 A1 | 5/2016 |
| WO | WO-2016079001 A1 | 5/2016 |
| WO | WO-2016079151 A1 | 5/2016 |
| WO | WO-2016079152 A1 | 5/2016 |
| WO | WO-2016079155 A1 | 5/2016 |
| WO | WO-2016079468 A1 | 5/2016 |
| WO | WO-2016079533 A1 | 5/2016 |
| WO | WO-2016079729 A1 | 5/2016 |
| WO | WO-2016058992 A3 | 6/2016 |
| WO | WO-2016059003 A3 | 6/2016 |
| WO | WO-2016082074 A1 | 6/2016 |
| WO | WO-2016082103 A1 | 6/2016 |
| WO | WO-2016082116 A1 | 6/2016 |
| WO | WO-2016082136 A1 | 6/2016 |
| WO | WO-2016082158 A1 | 6/2016 |
| WO | WO-2016082179 A1 | 6/2016 |
| WO | WO-2016082180 A1 | 6/2016 |
| WO | WO-2016082183 A1 | 6/2016 |
| WO | WO-2016082217 A1 | 6/2016 |
| WO | WO-2016082232 A1 | 6/2016 |
| WO | WO-2016082479 A1 | 6/2016 |
| WO | WO-2016086382 A1 | 6/2016 |
| WO | WO-2016090426 A1 | 6/2016 |
| WO | WO-2016090531 A1 | 6/2016 |
| WO | WO-2016090533 A1 | 6/2016 |
| WO | WO-2016090593 A1 | 6/2016 |
| WO | WO-2016090601 A1 | 6/2016 |
| WO | WO-2016090602 A1 | 6/2016 |
| WO | WO-2016090962 A1 | 6/2016 |
| WO | WO-2016092259 A1 | 6/2016 |
| WO | WO-2016092261 A1 | 6/2016 |
| WO | WO-2016095101 A1 | 6/2016 |
| WO | WO-2016095206 A1 | 6/2016 |
| WO | WO-2016095220 A1 | 6/2016 |
| WO | WO-2016095234 A1 | 6/2016 |
| WO | WO-2016095297 A1 | 6/2016 |
| WO | WO-2016096337 A1 | 6/2016 |
| WO | WO-2016096482 A1 | 6/2016 |
| WO | WO-2016096497 A1 | 6/2016 |
| WO | WO-2016096733 A1 | 6/2016 |
| WO | WO-2016096762 A1 | 6/2016 |
| WO | WO-2016099045 A1 | 6/2016 |
| WO | WO-2016099276 A1 | 6/2016 |
| WO | WO-2016101141 A1 | 6/2016 |
| WO | WO-2016101142 A1 | 6/2016 |
| WO | WO-2016101143 A1 | 6/2016 |
| WO | WO-2016101144 A1 | 6/2016 |
| WO | WO-2016101150 A1 | 6/2016 |
| WO | WO-2016101183 A1 | 6/2016 |
| WO | WO-2016101200 A1 | 6/2016 |
| WO | WO-2016101202 A1 | 6/2016 |
| WO | WO-2016101203 A1 | 6/2016 |
| WO | WO-2016101248 A1 | 6/2016 |
| WO | WO-2016103202 A1 | 6/2016 |
| WO | WO-2016105191 A1 | 6/2016 |
| WO | WO-2016036236 A3 | 7/2016 |
| WO | WO-2016106476 A1 | 7/2016 |
| WO | WO-2016106483 A1 | 7/2016 |
| WO | WO-2016106493 A1 | 7/2016 |
| WO | WO-2016106495 A1 | 7/2016 |
| WO | WO-2016106499 A1 | 7/2016 |
| WO | WO-2016106500 A1 | 7/2016 |
| WO | WO-2016106512 A1 | 7/2016 |
| WO | WO-2016108693 A1 | 7/2016 |
| WO | WO-2016108694 A1 | 7/2016 |
| WO | WO-2016109929 A1 | 7/2016 |
| WO | WO-2016109930 A1 | 7/2016 |
| WO | WO-2016109931 A1 | 7/2016 |
| WO | WO-2016109932 A1 | 7/2016 |
| WO | WO-2016109933 A1 | 7/2016 |
| WO | WO-2016109942 A1 | 7/2016 |
| WO | WO-2016109964 A1 | 7/2016 |
| WO | WO-2016109965 A1 | 7/2016 |
| WO | WO-2016110522 A1 | 7/2016 |
| WO | WO-2016112491 A1 | 7/2016 |
| WO | WO-2016112493 A1 | 7/2016 |
| WO | WO-2016112533 A1 | 7/2016 |
| WO | WO-2016112534 A1 | 7/2016 |
| WO | WO-2016112541 A1 | 7/2016 |
| WO | WO-2016112542 A1 | 7/2016 |
| WO | WO-2016112561 A1 | 7/2016 |
| WO | WO-2016112579 A1 | 7/2016 |
| WO | WO-2016115689 A1 | 7/2016 |
| WO | WO-2016115691 A1 | 7/2016 |
| WO | WO-2016115701 A1 | 7/2016 |
| WO | WO-2016115715 A1 | 7/2016 |
| WO | WO-2016116754 A1 | 7/2016 |
| WO | WO-2016116755 A1 | 7/2016 |
| WO | WO-2016118005 A1 | 7/2016 |
| WO | WO-2016119098 A1 | 8/2016 |
| WO | WO-2016119099 A1 | 8/2016 |
| WO | WO-2016119101 A1 | 8/2016 |
| WO | WO-2016119119 A1 | 8/2016 |
| WO | WO-2016119121 A1 | 8/2016 |
| WO | WO-2016119144 A1 | 8/2016 |
| WO | WO-2016119145 A1 | 8/2016 |
| WO | WO-2016119163 A1 | 8/2016 |
| WO | WO-2016119167 A1 | 8/2016 |
| WO | WO-2016119170 A1 | 8/2016 |
| WO | WO-2016119225 A1 | 8/2016 |
| WO | WO-2016119248 A1 | 8/2016 |
| WO | WO-2016119273 A1 | 8/2016 |
| WO | WO-2016119496 A1 | 8/2016 |
| WO | WO-2016122417 A1 | 8/2016 |
| WO | WO-2016123763 A1 | 8/2016 |
| WO | WO-2016123764 A1 | 8/2016 |
| WO | WO-2016123770 A1 | 8/2016 |
| WO | WO-2016123779 A1 | 8/2016 |
| WO | WO-2016123780 A1 | 8/2016 |
| WO | WO-2016123781 A1 | 8/2016 |
| WO | WO-2016124017 A1 | 8/2016 |
| WO | WO-2016124019 A1 | 8/2016 |
| WO | WO-2016124695 A1 | 8/2016 |
| WO | WO-2016124740 A1 | 8/2016 |
| WO | WO-2016124741 A1 | 8/2016 |
| WO | WO-2016127287 A1 | 8/2016 |
| WO | WO-2016127293 A1 | 8/2016 |
| WO | WO-2016127327 A1 | 8/2016 |
| WO | WO-2016127360 A1 | 8/2016 |
| WO | WO-2016127361 A1 | 8/2016 |
| WO | WO-2016127389 A1 | 8/2016 |
| WO | WO-2016127390 A1 | 8/2016 |

(56) References Cited

FOREIGN PATENT DOCUMENTS

| | | |
|---|---|---|
| WO | WO-2016127396 A1 | 8/2016 |
| WO | WO-2016127397 A1 | 8/2016 |
| WO | WO-2016127401 A1 | 8/2016 |
| WO | WO-2016127406 A1 | 8/2016 |
| WO | WO-2016127468 A1 | 8/2016 |
| WO | WO-2016127839 A1 | 8/2016 |
| WO | WO-2016128562 A1 | 8/2016 |
| WO | WO-2016131755 A1 | 8/2016 |
| WO | WO-2016132026 A1 | 8/2016 |
| WO | WO-2016134544 A1 | 9/2016 |
| WO | WO-2016135503 A1 | 9/2016 |
| WO | WO-2016138608 A1 | 9/2016 |
| WO | WO-2016138665 A1 | 9/2016 |
| WO | WO-2016138689 A1 | 9/2016 |
| WO | WO-2016141508 A1 | 9/2016 |
| WO | WO-2016141555 A1 | 9/2016 |
| WO | WO-2016141556 A1 | 9/2016 |
| WO | WO-2016141581 A1 | 9/2016 |
| WO | WO-2016141592 A1 | 9/2016 |
| WO | WO-2016141593 A1 | 9/2016 |
| WO | WO-2016145611 A | 9/2016 |
| WO | WO-2016145612 A1 | 9/2016 |
| WO | WO-2016145613 A1 | 9/2016 |
| WO | WO-2016145634 A1 | 9/2016 |
| WO | WO-2016145656 A1 | 9/2016 |
| WO | WO-2016145663 A1 | 9/2016 |
| WO | WO-2016149896 A1 | 9/2016 |
| WO | WO-2016149932 A1 | 9/2016 |
| WO | WO-2016149942 A1 | 9/2016 |
| WO | WO-2016150019 A1 | 9/2016 |
| WO | WO-2016150979 A1 | 9/2016 |
| WO | WO-201 6155105 A1 | 10/2016 |
| WO | WO-201 6155316 A1 | 10/2016 |
| WO | WO-2016154792 A1 | 10/2016 |
| WO | WO-2016154797 A1 | 10/2016 |
| WO | WO-2016154798 A1 | 10/2016 |
| WO | WO-2016154815 A1 | 10/2016 |
| WO | WO-2016154895 A1 | 10/2016 |
| WO | WO-2016154896 A1 | 10/2016 |
| WO | WO-2016154897 A1 | 10/2016 |
| WO | WO-2016154900 A1 | 10/2016 |
| WO | WO-2016154994 A1 | 10/2016 |
| WO | WO-2016155003 A1 | 10/2016 |
| WO | WO-2016155103 A1 | 10/2016 |
| WO | WO-2016155104 A1 | 10/2016 |
| WO | WO-2016156103 A1 | 10/2016 |
| WO | WO-2016156217 A1 | 10/2016 |
| WO | WO-2016156413 A1 | 10/2016 |
| WO | WO-2016161554 A1 | 10/2016 |
| WO | WO-2016161673 A1 | 10/2016 |
| WO | WO-2016162446 A1 | 10/2016 |
| WO | WO-2016162492 A1 | 10/2016 |
| WO | WO-2016165055 A1 | 10/2016 |
| WO | WO-2016165057 A1 | 10/2016 |
| WO | WO-2016165063 A1 | 10/2016 |
| WO | WO-2016165125 A1 | 10/2016 |
| WO | WO-2016166049 A1 | 10/2016 |
| WO | WO-2016166456 A1 | 10/2016 |
| WO | WO-2016166661 A1 | 10/2016 |
| WO | WO-2016166670 A1 | 10/2016 |
| WO | WO-2016168986 A1 | 10/2016 |
| WO | WO-2016169019 A1 | 10/2016 |
| WO | WO-2016169052 A1 | 10/2016 |
| WO | WO-2016169063 A1 | 10/2016 |
| WO | WO-2016169669 A1 | 10/2016 |
| WO | WO-2016169796 A1 | 10/2016 |
| WO | WO-2016169797 A1 | 10/2016 |
| WO | WO-2016172802 A1 | 11/2016 |
| WO | WO-2016172821 A1 | 11/2016 |
| WO | WO-2016172843 A1 | 11/2016 |
| WO | WO-2016172847 A1 | 11/2016 |
| WO | WO-2016172867 A1 | 11/2016 |
| WO | WO-2016172898 A1 | 11/2016 |
| WO | WO-2016172907 A1 | 11/2016 |
| WO | WO-2016172908 A1 | 11/2016 |
| WO | WO-2016172909 A1 | 11/2016 |
| WO | WO-2016172954 A1 | 11/2016 |
| WO | WO-2016174179 A1 | 11/2016 |
| WO | WO-2016176800 A1 | 11/2016 |
| WO | WO-2016177604 A1 | 11/2016 |
| WO | WO-2016179356 A1 | 11/2016 |
| WO | WO-2016179664 A1 | 11/2016 |
| WO | WO-2016179776 A1 | 11/2016 |
| WO | WO-2016179828 A1 | 11/2016 |
| WO | WO-2016183724 A1 | 11/2016 |
| WO | WO-2016184247 A1 | 11/2016 |
| WO | WO-2016184824 A1 | 11/2016 |
| WO | WO-2016171997 A3 | 12/2016 |
| WO | WO-2016187803 A1 | 12/2016 |
| WO | WO-2016187943 A1 | 12/2016 |
| WO | WO-2016188140 A1 | 12/2016 |
| WO | WO-2016188141 A1 | 12/2016 |
| WO | WO-2016188142 A1 | 12/2016 |
| WO | WO-2016188967 A1 | 12/2016 |
| WO | WO-2016189086 A1 | 12/2016 |
| WO | WO-2016191946 A1 | 12/2016 |
| WO | WO-2016193336 A1 | 12/2016 |
| WO | WO-2016193365 A1 | 12/2016 |
| WO | WO-2016193743 A1 | 12/2016 |
| WO | WO-2016197485 A1 | 12/2016 |
| WO | WO-2016197658 A1 | 12/2016 |
| WO | WO-2016198417 A1 | 12/2016 |
| WO | WO-2016198459 A1 | 12/2016 |
| WO | WO-2016198879 A1 | 12/2016 |
| WO | WO-2016199062 A1 | 12/2016 |
| WO | WO-2016199065 A1 | 12/2016 |
| WO | WO-2016199066 A1 | 12/2016 |
| WO | WO-2016200252 A1 | 12/2016 |
| WO | WO-2016200253 A1 | 12/2016 |
| WO | WO-2016200255 A1 | 12/2016 |
| WO | WO-2016200259 A1 | 12/2016 |
| WO | WO-2016200382 A1 | 12/2016 |
| WO | WO-2016201602 A1 | 12/2016 |
| WO | WO-2016201606 A1 | 12/2016 |
| WO | WO-2016201911 A1 | 12/2016 |
| WO | WO-2016202028 A1 | 12/2016 |
| WO | WO-2016202033 A1 | 12/2016 |
| WO | WO-2016202301 A1 | 12/2016 |
| WO | WO-2016202302 A1 | 12/2016 |
| WO | WO-2016202303 A1 | 12/2016 |
| WO | WO-2016202304 A1 | 12/2016 |
| WO | WO-2016207357 A1 | 12/2016 |
| WO | WO-2016208757 A1 | 12/2016 |
| WO | WO-2016208760 A1 | 12/2016 |
| WO | WO-2016210242 A1 | 12/2016 |
| WO | WO-2016193705 A3 | 1/2017 |
| WO | WO-2017000239 A1 | 1/2017 |
| WO | WO-2017001270 A1 | 1/2017 |
| WO | WO-2017001817 A1 | 1/2017 |
| WO | WO-2017001818 A1 | 1/2017 |
| WO | WO-2017001819 A1 | 1/2017 |
| WO | WO-2017001820 A1 | 1/2017 |
| WO | WO-2017005835 A1 | 1/2017 |
| WO | WO-2017007252 A1 | 1/2017 |
| WO | WO-2017008616 A1 | 1/2017 |
| WO | WO-2017009002 A1 | 1/2017 |
| WO | WO-2017011419 A1 | 1/2017 |
| WO | WO-2017012099 A1 | 1/2017 |
| WO | WO-2017012105 A1 | 1/2017 |
| WO | WO-2017012257 A1 | 1/2017 |
| WO | WO-2017012335 A1 | 1/2017 |
| WO | WO-2016172921 A8 | 2/2017 |
| WO | WO-2016178098 A3 | 2/2017 |
| WO | WO-2017015791 A1 | 2/2017 |
| WO | WO-2017015794 A1 | 2/2017 |
| WO | WO-2017015832 A1 | 2/2017 |
| WO | WO-2017015859 A1 | 2/2017 |
| WO | WO-2017016323 A1 | 2/2017 |
| WO | WO-2017017970 A1 | 2/2017 |
| WO | WO-2017020220 A1 | 2/2017 |
| WO | WO-2017020221 A1 | 2/2017 |
| WO | WO-2017020275 A1 | 2/2017 |
| WO | WO-2017020290 A1 | 2/2017 |
| WO | WO-2017023589 A1 | 2/2017 |

(56) References Cited

FOREIGN PATENT DOCUMENTS

| | | |
|---|---|---|
| WO | WO-2017024477 A1 | 2/2017 |
| WO | WO-2017024478 A1 | 2/2017 |
| WO | WO-2017024799 A1 | 2/2017 |
| WO | WO-2017024926 A1 | 2/2017 |
| WO | WO-2017025383 A1 | 2/2017 |
| WO | WO-2017028167 A1 | 2/2017 |
| WO | WO-2017028295 A1 | 2/2017 |
| WO | WO-2017029268 A1 | 2/2017 |
| WO | WO-2017029269 A1 | 2/2017 |
| WO | WO-2017029270 A1 | 2/2017 |
| WO | WO-2017021536 A3 | 3/2017 |
| WO | WO-2017031662 A1 | 3/2017 |
| WO | WO-2017031678 A1 | 3/2017 |
| WO | WO-2017031681 A1 | 3/2017 |
| WO | WO-2017033007 A1 | 3/2017 |
| WO | WO-2017033021 A1 | 3/2017 |
| WO | WO-2017033132 A1 | 3/2017 |
| WO | WO-2017035720 A1 | 3/2017 |
| WO | WO-2017036818 A1 | 3/2017 |
| WO | WO-2017036819 A1 | 3/2017 |
| WO | WO-2017036828 A1 | 3/2017 |
| WO | WO-2017036829 A1 | 3/2017 |
| WO | WO-2017036865 A1 | 3/2017 |
| WO | WO-2017036879 A1 | 3/2017 |
| WO | WO-2017041251 A1 | 3/2017 |
| WO | WO-2017042081 A1 | 3/2017 |
| WO | WO-2017045132 A1 | 3/2017 |
| WO | WO-2017045897 A1 | 3/2017 |
| WO | WO-2017045898 A1 | 3/2017 |
| WO | WO-2017045899 A1 | 3/2017 |
| WO | WO-2017046247 A1 | 3/2017 |
| WO | WO-2017046334 A1 | 3/2017 |
| WO | WO-2017046363 A1 | 3/2017 |
| WO | WO-2017046566 A1 | 3/2017 |
| WO | WO-2017049653 A1 | 3/2017 |
| WO | WO-2017049654 A1 | 3/2017 |
| WO | WO-2017051150 A1 | 3/2017 |
| WO | WO-2017051174 A1 | 3/2017 |
| WO | WO-2017051348 A1 | 3/2017 |
| WO | WO-2017051349 A1 | 3/2017 |
| WO | WO-2017046593 A3 | 4/2017 |
| WO | WO-2017054424 A1 | 4/2017 |
| WO | WO-2017054627 A1 | 4/2017 |
| WO | WO-2017054634 A1 | 4/2017 |
| WO | WO-2017055564 A1 | 4/2017 |
| WO | WO-2017055584 A1 | 4/2017 |
| WO | WO-2017055793 A1 | 4/2017 |
| WO | WO-2017055795 A1 | 4/2017 |
| WO | WO-2017055799 A1 | 4/2017 |
| WO | WO-2017055801 A1 | 4/2017 |
| WO | WO-2017055802 A1 | 4/2017 |
| WO | WO-2017055803 A1 | 4/2017 |
| WO | WO-2017055866 A1 | 4/2017 |
| WO | WO-2017056103 A1 | 4/2017 |
| WO | WO-2017057286 A1 | 4/2017 |
| WO | WO-2017059571 A1 | 4/2017 |
| WO | WO-2017060279 A1 | 4/2017 |
| WO | WO-2017063256 A1 | 4/2017 |
| WO | WO-2017063535 A1 | 4/2017 |
| WO | WO-2017064051 A1 | 4/2017 |
| WO | WO-2017064322 A1 | 4/2017 |
| WO | WO-2017064323 A1 | 4/2017 |
| WO | WO-2017064324 A1 | 4/2017 |
| WO | WO-2017064487 A1 | 4/2017 |
| WO | WO-2017066938 A1 | 4/2017 |
| WO | WO-2017066955 A1 | 4/2017 |
| WO | WO-2017067066 A1 | 4/2017 |
| WO | WO-2017067326 A1 | 4/2017 |
| WO | WO-2017068098 A1 | 4/2017 |
| WO | WO-2017068099 A1 | 4/2017 |
| WO | WO-2017068100 A1 | 4/2017 |
| WO | WO-2016096745 A9 | 5/2017 |
| WO | WO-2016173568 A3 | 5/2017 |
| WO | WO-2016198026 A3 | 5/2017 |
| WO | WO-2017051350 A3 | 5/2017 |
| WO | WO-2017070871 A1 | 5/2017 |
| WO | WO-2017071297 A1 | 5/2017 |
| WO | WO-2017071298 A1 | 5/2017 |
| WO | WO-2017072239 A1 | 5/2017 |
| WO | WO-2017072277 A1 | 5/2017 |
| WO | WO-2017072284 A1 | 5/2017 |
| WO | WO-2017075753 A1 | 5/2017 |
| WO | WO-2017075759 A1 | 5/2017 |
| WO | WO-2017075827 A1 | 5/2017 |
| WO | WO-2017075883 A1 | 5/2017 |
| WO | WO-2017075975 A1 | 5/2017 |
| WO | WO-2017076247 A1 | 5/2017 |
| WO | WO-2017076590 A1 | 5/2017 |
| WO | WO-2017081480 A1 | 5/2017 |
| WO | WO-2017082728 A1 | 5/2017 |
| WO | WO-2017084107 A1 | 5/2017 |
| WO | WO-2017084488 A1 | 5/2017 |
| WO | WO-2017084489 A1 | 5/2017 |
| WO | WO-2017084818 A1 | 5/2017 |
| WO | WO-2017084848 A1 | 5/2017 |
| WO | WO-2017084849 A1 | 5/2017 |
| WO | WO-2017084920 A2 | 5/2017 |
| WO | WO-2017085240 A1 | 5/2017 |
| WO | WO-2017085242 A1 | 5/2017 |
| WO | WO-2017081176 A3 | 6/2017 |
| WO | WO-2017088660 A1 | 6/2017 |
| WO | WO-2017089931 A1 | 6/2017 |
| WO | WO-2017091926 A1 | 6/2017 |
| WO | WO-2017092144 A1 | 6/2017 |
| WO | WO-2017093452 A1 | 6/2017 |
| WO | WO-2017093535 A1 | 6/2017 |
| WO | WO-2017096512 A1 | 6/2017 |
| WO | WO-2017096971 A1 | 6/2017 |
| WO | WO-2017096988 A1 | 6/2017 |
| WO | WO-2017097172 A1 | 6/2017 |
| WO | WO-2017097173 A1 | 6/2017 |
| WO | WO-2017097821 A1 | 6/2017 |
| WO | WO-2017101030 A1 | 6/2017 |
| WO | WO-2017101058 A1 | 6/2017 |
| WO | WO-2017101705 A1 | 6/2017 |
| WO | WO-2017102633 A1 | 6/2017 |
| WO | WO-2017102686 A1 | 6/2017 |
| WO | WO-2017102969 A1 | 6/2017 |
| WO | WO-2017107546 A1 | 6/2017 |
| WO | WO-2017108268 A1 | 6/2017 |
| WO | WO-2017108392 A1 | 6/2017 |
| WO | WO-2017108394 A1 | 6/2017 |
| WO | WO-2017108429 A1 | 6/2017 |
| WO | WO-2017109448 A2 | 6/2017 |
| WO | WO-2017109868 A1 | 6/2017 |
| WO | WO-2017110713 A1 | 6/2017 |
| WO | WO-2017036426 A3 | 7/2017 |
| WO | WO-2017113106 A1 | 7/2017 |
| WO | WO-2017113513 A1 | 7/2017 |
| WO | WO-2017113845 A1 | 7/2017 |
| WO | WO-2017114389 A1 | 7/2017 |
| WO | WO-2017117725 A1 | 7/2017 |
| WO | WO-2017117742 A1 | 7/2017 |
| WO | WO-2017118135 A1 | 7/2017 |
| WO | WO-2017118138 A1 | 7/2017 |
| WO | WO-2017118347 A1 | 7/2017 |
| WO | WO-2017121156 A1 | 7/2017 |
| WO | WO-2017121253 A1 | 7/2017 |
| WO | WO-2017121296 A1 | 7/2017 |
| WO | WO-2017121546 A1 | 7/2017 |
| WO | WO-2017121979 A1 | 7/2017 |
| WO | WO-2017122196 A1 | 7/2017 |
| WO | WO-2017124419 A1 | 7/2017 |
| WO | WO-2017124662 A1 | 7/2017 |
| WO | WO-2017124957 A1 | 7/2017 |
| WO | WO-2017128038 A1 | 8/2017 |
| WO | WO-2017130138 A1 | 8/2017 |
| WO | WO-2017133056 A1 | 8/2017 |
| WO | WO-2017137138 A1 | 8/2017 |
| WO | WO-2017137554 A1 | 8/2017 |
| WO | WO-2017139595 A1 | 8/2017 |
| WO | WO-2017139662 A1 | 8/2017 |
| WO | WO-2017139963 A1 | 8/2017 |
| WO | WO-2017141017 A1 | 8/2017 |

(56) References Cited

FOREIGN PATENT DOCUMENTS

| | | |
|---|---|---|
| WO | WO-2017141018 A1 | 8/2017 |
| WO | WO-2017141358 A1 | 8/2017 |
| WO | WO-2017143494 A1 | 8/2017 |
| WO | WO-2017143495 A1 | 8/2017 |
| WO | WO-2017143515 A1 | 8/2017 |
| WO | WO-2017143865 A1 | 8/2017 |
| WO | WO-2017143953 A1 | 8/2017 |
| WO | WO-2017144400 A1 | 8/2017 |
| WO | WO-2017144861 A1 | 8/2017 |
| WO | WO-2017149288 A1 | 9/2017 |
| WO | WO-2017152481 A1 | 9/2017 |
| WO | WO-2017153051 A1 | 9/2017 |
| WO | WO-2017153270 A1 | 9/2017 |
| WO | WO-2017156694 A1 | 9/2017 |
| WO | WO-2017156695 A1 | 9/2017 |
| WO | WO-2017156696 A1 | 9/2017 |
| WO | WO-2017156733 A1 | 9/2017 |
| WO | WO-2017156743 A1 | 9/2017 |
| WO | WO-2017161715 A1 | 9/2017 |
| WO | WO-2017161725 A1 | 9/2017 |
| WO | WO-2017163044 A1 | 9/2017 |
| WO | WO-2017163045 A1 | 9/2017 |
| WO | WO-2017163046 A1 | 9/2017 |
| WO | WO-2017163047 A1 | 9/2017 |
| WO | WO-2017163050 A1 | 9/2017 |
| WO | WO-2017163051 A1 | 9/2017 |
| WO | WO-2017163052 A1 | 9/2017 |
| WO | WO-2017164474 A1 | 9/2017 |
| WO | WO-2017166263 A1 | 10/2017 |
| WO | WO-2017166334 A1 | 10/2017 |
| WO | WO-2017167169 A1 | 10/2017 |
| WO | WO-2017167513 A1 | 10/2017 |
| WO | WO-2017173669 A1 | 10/2017 |
| WO | WO-2017173947 A1 | 10/2017 |
| WO | WO-2017173951 A1 | 10/2017 |
| WO | WO-2017174754 A1 | 10/2017 |
| WO | WO-2017175166 A1 | 10/2017 |
| WO | WO-2017176111 A1 | 10/2017 |
| WO | WO-2017176113 A1 | 10/2017 |
| WO | WO-2017177897 A1 | 10/2017 |

OTHER PUBLICATIONS

Pierce, D. *This Might Just Be the First Great E-Cig.* {online} Wired, Published on Apr. 21, 2015. Available at: https://www.wired.com/2015/04/pax-juul-ecig/?mbid=social_twitter.
The Verge. *Startup behind the Lambo of vaporizers just launched an intelligent e-cigarette.* [online], published on Apr. 21, 2015. Available at: https://www.theverge.com/2015/4/21/8458629/pax-labs-e-cigarette-juul.
"Commission Regulation (EC) No. 1275/2008," Official Journal of the European Union, Dec. 17, 2008.
"Guideline Accompanying Commission Regulation (EC) No. 1275/2008," Official Journal of the European Union, Oct. 2009.
"Lighter." Merriam-Webster Online Dictionary. 2009. Merriam-Webster Online. Jun. 8, 2009 [http://www.merriam-webster.com/dictionary/lighter].
AMB. Manual:TranX160/Rev. 10-06. published 2004-2006.
Baker et al., "The pyrolysis of tobacco ingredients," J. Anal. Appl. Pyrolysis, vol. 71, pp. 223-311 (2004).
Bombick, et al. Chemical and biological studies of a new cigarette that primarily heats tobacco. Part 2. In vitro toxicology of mainstream smoke condensate. Food and Chemical Toxicology. 1997;36:183-190.
Bombick, et al. Chemical and biological studies of a new cigarette that primarily heats tobacco. Part 3. In vitro toxicity of whole smoke. Food and Chemical Toxicology. 1998; 36:191-197.
Borgerding, et al. Chemical and biological studies of a new cigarette that primarily heats tobacco. Part 1. Chemical composition of mainstream smoke. Food and Chemical Toxicology. 1997;36:169-182.

Breland, Alison, et al. "Electronic cigarettes: what are they and what do they do?." Annals of the New York Academy of Sciences 1394.1 (2017): 5-30.
Brown, Christopher J., et al., "Electronic cigarettes: product characterisation and design considerations." Tobacco control 23.suppl 2 (2014): ii4-ii10.
Bullen, et al., "Effect of an electronic nicotine delivery device (e cigarette) on desire to smoke and withdrawal, user preferences and nicotine delivery: randomized cross-over trial," Tobacco Control, 19(2), pp. 98-103. Apr. 2010.
Burch, et al., "Effect of pH on nicotine absorption and side effects produced by areosolized nicotine," Journal of Aerosol Medicine: Deposition, Clearance, and Effects in the Lung, 6(1), pp. 45-52. 1993.
Capponnetto, et al., "Successful smoking cessation with cigarettes in smokers with a documented history of recurring relapses: a case series," Journal of Medical Case Reports; 5(1), 6 pages. 2011.
Davis & Nielsen, "Marketing, Processing and Storage: Green Leaf Threshing and Redrying Tobacco," Tobacco Production, Chemistry and Technology, (1999) Section 10B, pp. 330-333, Bill Ward, Expert Leaf Tobacco Company, Wilson, North Carolina, USA.
E-Cigarette Forum; pg-gv-peg (discussion/posting); retrieved from the Internet: https://e-cigarette-forum.com/forum/threads/pg-vg-peg.177551; 7 pgs.; Apr. 8, 2011.
ECF; Any interest in determining nicotine—by DVAP; (https://www.e-cigarette-forum.com/forum/threads/any-interest-in-determin- ing-nicotine-by-dvap.35922/); blog posts dated: 2009; 8 pgs.; print/retrieval date: Jul. 31, 2014.
Electronic Vaporization Device/ Gizmodo Pax 2 Vaporizer/ Gizmodo; retrieved from http://gizmodo.com/pax-2-vaporizer-reviews-its-like-smoking-in-the-future-1718310779; posted Jul. 23, 2015, retrieved Oct. 17, 2016.
Farsalinos, et al., "Electronic cigarettes do not damage the heart," European Society of Cardiology, 4 pages, (http://www.escardio.org/The-ESC/Press-Office/Press-releases/Electronic-cigarettes-do-not-damage-the-heart). Aug. 25, 2012.
Farsalinos, Konstantinos E., et al. "Protocol proposal for, and evaluation of, consistency in nicotine delivery from the liquid to the aerosol of electronic cigarettes atomizers: regulatory implications." Addiction 111.6 (2016): 1069-1076.
Farsalinos, Konstantinos E., et al. *Analytical Assessment of e-Cigarettes: From Contents to Chemical and Particle Exposure Profiles.* pp. 1-35. Elsevier, 2016.
FC Vaporizer Review Forum; Pax Vaporizer by Ploom; retrieved from : http://fuckcombustion.com/threads/pax-vaporizer-by-ploom.6223/; pp. 2 & 11 (2 pgs.); retrieval date: Nov. 16, 2015.
Flouris, et al., "Acute impact of active and passive electronic cigarette smoking on serum cotinine and lung function," Inhal. Toxicol., 25(2), pp. 91-101. Feb. 2013.
Food & Drug Administration; Warning letter to The Compounding Pharmacy, retrieved Oct. 10, 2014 from http://www.fda.gov/ICECI/EnforcementActions/WarningLetters/2002/ucm144843.htm, 3 pages. Apr. 9, 2002.
Geiss, Otmar, Ivana Bianchi, and Josefa Barrero-Moreno. "Correlation of volatile carbonyl yields emitted by e-cigarettes with the temperature of the heating coil and the perceived sensorial quality of the generated vapours." *International journal of hygiene and environmental health* 219.3 (2016): 268-277.
Gillman, I. G., et al. "Effect of variable power levels on the yield of total aerosol mass and formation of aldehydes in e-cigarette aerosols." *Regulatory Toxicology and Pharmacology* 75 (2016): 58-65.
Giorgio, Agostino. "E-Cig Digital Design for the Smoke Control Optimization." *International Journal of Applied Engineering Research* 11.8 (2016): 6018-6023.
Goniewicz, et al., "Nicotine levels in electronic cigarettes," Nicotine Tobacco Research, 15(1), pp. 158-166, Jan. 2013.
Gregory, Andrew, "E-cigarettes to go on prescription under move to class them as medicines," Mirror, Jun. 12, 2013. http://www.mirror.co.uk/news/uk-news/e-cigarettes-go-prescription-under-move-1949018.
Grotenhermen, et al., Developing science-based per se limits for driving under the influence of cannabis (DUIC): findings and

(56) References Cited

OTHER PUBLICATIONS recommendations by an expert panel; retreived Feb. 9, 2017 from (http://www.canorml.org/healthfacts/DUICreport.2005.pdf); Sep. 2005.
Harvest Vapor, American Blend Tobacco (product info), retrieved from the internet (http://harvestvapor.com/), 2 pages. Oct. 10, 2014.
Hurt, et al., "Treating tobacco dependence in a medical setting," CA: A Cancer Journal for Clinicians, 59(5), pp. 314-326. Sep. 2009.
Ijoy. "Who we are." *IJOY Diamond PD270 Kit*, Date Accessed Feb. 20, 2018. www.ijoycig.com/product/item-473.html.
Inchem; Benzoic Acid; JECFA Evaluation Summary; retrieved Oct. 10, 2014 from http://www.inchem.org/documents/jecfa/feceval/jec_184.htm, 2 pages. May 28, 2005.
Inchem; Levulinic Acid; JECFA Evaluation Summary; retrieved Oct. 10, 2014 from http://www.inchem.org/documents/jecfa/feceval/jec_1266.htm, 2 pages. Mar. 10, 2003.
Inchem; Pyruvic Acid; JECFA Evaluation Summary; retrieved Oct. 10, 2014 from http://www.inchem.org/documents/jecfa/feceval/jec_2072.htm, 2 pages. Jan. 29, 2003.
Inchem; Sorbic Acid; JECFA Evaluation Summary; retrieved Oct. 10, 2014 from http://www.inchem.org/documents/jecfa/feceval/jec_2181.htm, 2 pages. May 29, 2005.
Ingebrethsen et al., "Electronic Cigarette aerosol particle size distribution measurements", Inhalation Toxicology, 2012; 24 (14): 976-984.
*Kanger K1 Stabilized Wood DNA 75 Box Mod—KangerTech*. Date Accessed Feb. 20, 2018. https://kangeronline.com/products/kanger-k1-stabilized-wood-dna-75-box-mod.
Kuo et al. Applications of Turbulent and Multiphase Combustion, Appendix D: Particle Size—U.S. Sieve Size and Tyler Screen Mesh Equivalents, 2012, p. 541-543.
Marshall, John R., Shahram Lotfipour, and Bharath Chakravarthy. "Growing Trend of Alternative Tobacco Use Among the Nation's Youth: A New Generation of Addicts." *Western Journal of Emergency Medicine* 17.2 (2016): 139.
McCann et al., "Detection of carcinogens as mutagens in the *Salmonella*/microsome test: Assay of 300 chemicals: discussion." Proct. Nat. Acad. Sci, USA, Mar. 1976, vol. 73 (3), 950-954.
Mylaps, "Rechargeable Transponder Battery Status and Charging Instructions," Sep. 9, 2010.
Nicoli et al., Mammalian tumor xenografts induce neovascularization in Zebrafish embryos. Cancer Research, 67:2927-2931 (2007).
PAX Labs, Inc.; Juul product information ©2016; retrieved from https://www.juulvapor.com/shop-juul/; 6 pgs.; retrieved Mar. 9, 2016.
Perfetti, "Structural study of nicotine salts," Beitrage Zur Tabakforschung International, Contributions to Tobacco Research, 12(2), pp. 43-54. Jun. 1983.
Polosa, Riccardo, et al. "Effect of an electronic nicotine delivery device (e-Cigarette) on smoking reduction and cessation: a prospective 6-month pilot study." BMC public health 11.1 (2011): 786.
Poynton, Simon, et al. "A novel hybrid tobacco product that delivers a tobacco flavour note with vapour aerosol (part 1): Product operation and preliminary aerosol chemistry assessment." Food and Chemical Toxicology (2017).
Poynton, Simon, et al. "A novel hybrid tobacco product that delivers a tobacco flavour note with vapour aerosol (Part 1): product operation and preliminary aerosol chemistry assessment." *Food and Chemical Toxicology* 106 (2017): 522-532.
Seeman, et al., "The form of nicotine in tobacco. Thermal transfer of nicotine and nicotine acid salts to nicotine in the gas phase," J Aric Food Chem, 47(12), pp. 5133-5145. Dec. 1999.
Smok. *ProColor—SMOK® Innovation keeps changing the vaping experience!*, Date Accessed Feb. 20, 2018. www.smoktech.com/kit/procolor.
SRNT Subcommittee on Biochemical Verification, "Biochemical verification of tobacco use and cessation," Nicotine & Tobacco Research 4, pp. 149-159, 2002.
Tarantola, Andrew. "The Pax 2 vaporizer makes its predecessor look half-Baked." Engadget, Jul. 14, 2016, www.engadget.com/2015/04/20/pax-2-vaporizer-review/. Accessed Sep. 5, 2017.
Torikai et al., "Effects of temperature, atmosphere and pH on the generation of smoke compounds during tobacco pyrolysis," Food and Chemical Toxicology 42 (2004) 1409-1417.
Vansickel, et al. "A clinical laboratory model for evaluating the acute effects of electronic cigarettes: Nicotine delivery profile and cardiovascular and subjective effects," Cancer Epidemiology Biomarkers Prevention, 19(9), pp. 1945-1953. Jul. 20, 2010.
Vansickel, et al., "Electronic cigarettes: effective nicotine delivery after acute administration," Nicotine & Tobacco Research, 15(1), pp. 267-270. Jan. 2013.
VapeWorld; Original PAX Vaporizers for Portable and Home Use; retrieved from: https://www.vapeworld.com/pax-vaporizer-by-ploom?gclid=CPCi1PKojskCFU06gQodPr; 9 pgs.; retrieved Nov. 13, 2015.
Vaporesso (Shenzhen Smoore Technology Limited). "Target Pro Vape Mod." *Vape Batteries & Mods | Target Pro Vape Mod | Vaporesso*, Date Accessed Feb. 20, 2018. www.vaporesso.com/vape-batteries-and-mods/target-pro-vape-mod.
Vaporesso (Shenzhen Smoore Technology Limited). "Tarot Pro Vape Mod." *Vape Batteries & Mods | Tarot Pro Vape Mod | Vaporeso*, Date Accessed Feb. 20, 2018. www.vaporesso.com/vape-batteries-and-mods/tarot-pro-vape-mod.
Wells. "Glycerin as a Constituent of Cosmetics and Toilet Preparations." Journal of the Society of Cosmetic Chemists, 1958; 9(1): 19-25.
Williams, Monique, and Prue Talbot. "Variability among electronic cigarettes in the pressure drop, airflow rate, and aerosol production." Nicotine & Tobacco Research 13.12 (2011).
Youtube, "Pax2 Unboxing," retrieved from www.youtube.com/watch?v=Vjccs8co3YY, posted Apr. 20, 2015.
YouTube; Firefly Vaporizor Review w/ Usage Tips by the Vape Critic; retrieved from the internet (http://www.youtube.com/watch?v=1J38N0AV7wl); published Dec. 10, 2013; download/print date: Feb. 18, 2015.
Youtube; Pax by Ploom Vaporizer Review; posted Aug. 14, 2013, retrieved Sep. 8, 2016, https://www.youtube.com/watch?v=Jm06zW3-cxQ.
Zhang, et al., "In vitro partical size distributions in electronic and conventional cigarette aerosols suggest comparable deposition patterns," Nicotine Tobacci Research, 15(2), pp. 501-508. Feb. 2013.
U.S. Appl. No. 15/813,084, filed Nov. 14, 2017, US 2018-0064174.
U.S. Appl. No. 15/820,361, filed Nov. 21, 2017, US 2018-0070648.
U.S. Appl. No. 16/032,009, filed Jul. 10, 2018, US 2018-0317557.
U.S. Appl. No. 16/404,693, filed May 6, 2019, US 2019-0256231.
U.S. Appl. No. 16/864,007, filed Apr. 30, 2020.
U.S. Appl. No. 16/080,296, filed Feb. 27, 2017, US 2019-0069599.
"2011 New E-Cigarette GS-360With 1.2ml Clearomizer(Id:5861467) Product Details—View 2011 New E-Cigarette GS-360With 1.2ml Clearomizer from Green Sound High-Tech Co.Ltd—EC21." EC21 Global B2B Marketplace—Connecting Global Buyers with Manufacturers Suppliers Exporters Worldwide (2011) wo1138.en.ec21.com/2011_New_E-Cigarette_GS-360_With-5366965_5861467.html.
"Electronic Cigarette Refillable Cartridge GS-PUSHHold 1.5ml(Id:5722612) Product Details—View Electronic Cigarette Refillable Cartridge GS-PUSHHold 1.5ml from Green Sound High-Tech Co.Ltd—EC21" EC21 Global B2B Marketplace—Connecting Global Buyers with Manufacturers Suppliers Exporters Worldwide (2011) wo1138.en.ec21.com/Electronic_Cigarette_Refillable_Cartridge_GS-5366965_5722612.html.
"Esteam and J-Series Owner's Manual." Allbrands.com, 2002, www.allbrands.com/misc_files/pdfs/JiffySteamerOwnersManual.pdf.
"Hacking the Vuse E-Cig to Fully Use Cartridges and Allow Refills." Hacking the Vuse E-Cig to Fully Use Cartridges and Allow Refills, Oct. 16, 2015, se.azinstall.net/2015/10/hacking-vuse-e-cig-puff-counter.html?m=1".
"Lenmar CB0104 Battery for Panasonic Cordless Phones." Amazon, Amazon, first reviewed Jan. 5, 2011, www.amazon.com/Lenmar-CB0104-Battery-Panasonic-Cordless/dp/B000BS6Q78/.
"New Tank E-Cigarette:innokin 510T." From China Manufacturer, Manufactory, Factory and Supplier on ECVV.com, Nov. 15, 2011, www.ecvv.com/product/3118191.html.
"Terminal and Splices Selection Guide." TE.com, TE, 2013, www.te.com/commerce/DocumentDelivery/DDEController?Action=srchrtrv

(56) References Cited

OTHER PUBLICATIONS

&DocNm=2-1773700-5TerminalAndSplicesSelection&DocType=DS&DocLang=English&s_cid=1046.
"Uniden BT-990 Cordless Phone Battery Ni-CD, 3.6 Volt, 800 MAh—Ultra Hi-Capacity—Replacement for Uniden BP-990, Toshiba, GE TL96550, TL96556, Panasonic HHR-P505 Rechargeable Batteries." Amazon, Amazon, first reviewed on Feb. 8, 2017, www.amazon.com/Uniden-BT-990-Cordless-Phone-Battery/dp/B01HDV75YW.
513official4. "Glade Plug-Ins Scented Oils 2001." YouTube, YouTube, Jun. 29, 2011, www.youtube.com/watch?v=zW9acp4NOK8.
CannabisReviewTV™, "Official: Cloud Vape Pen Review #CRTV420." YouTube, YouTube, Apr. 17, 2013, www.youtube.com/watch?v=oujMMZ6l_tA&has_verified=1.
Chinabuye. "Innokin ITaste VV Tank Starter Kit Electronic Cigarette with Clearomizer." YouTube, YouTube, Jul. 23, 2013, www.youtube.com/watch?v=mz414d8MU20.
Cloud pen vaporizer unboxing review by vaporizer blog // VaporizerBlog.com, https://www.youtube.com/watch?v=ixHMkXoWKNg.
Cutlerylover. "Eletronic Cigarette (Vaping) Review : Halo G6 Basic Starter Kit." YouTube, YouTube, Oct. 10, 2012, www.youtube.com/watch?v=kUprxsQUPCU.
Darth Vapor Reviews. "Halo Cigs: Triton Starter Kit Review." YouTube, YouTube, Aug. 11, 2013, www.youtube.com/watch?v=KkVzsGsDDMY.
El Mono Vapeador. "EVic Joyetech—Revision." YouTube YouTube Dec. 12, 2012 www.youtube.com/watch?v=WNLVfgwb4Gs.
Following the Vapor Trail, https://www.nytimes.com/2013/12/19/fashion/for-vaporizers-new-technology-and-product-design.html.
Frakes, Dan. "Lightning: the IPhone's New Connector." Macworld, Macworld, Sep. 13, 2012, www.macworld.com/article/1168555/what-apples-new-lightning-connector-means-for-you.html.
Glory Vapes. "Glory Vapes TV: Kanger S1 Cubica Series Starter Kit Unboxing." YouTube, YouTube, Aug. 8, 2013, www.youtube.com/watch?v=NQjvJ6YhdbA.
Infocentre101. "Jiffy Steamer . . . No. 1 Seller." YouTube, YouTube, Dec. 31, 2011, www.youtube.com/watch?v=9ge8phdU6WY.
IWand Rectangular Pen Shape Design Flat Short Mouth Holder 1.0ML Tank Atomizer LED Display 800mAh Rechargeable E-Cigarette Set—Colorful, https://www.gearbest.com/electronic-cigarettes/pp_15466.html.
Joye eGo-Tank System XXL 1000mAh Starter Kit, https://www.myvaporstore.com/eGo-Tank-System-XXL-1000mAh-Starter-Kit-p/ego-t-xxlkit.htm.
Marino, Michelle. "Review—Glade PlugIns Scented Oil Fragrancers." YouTube, YouTube, Feb. 18, 2013, www.youtube.com/watch?v=lzEpGdwKSA4.
Prater, Bill. "Crown Seven Hydro Imperial Menthol Review." YouTube, YouTube, Jan. 12, 2013, www.youtube.com/watch?v=YT-ycf6mEa0.
Purity Home Fragrance—How to refill your plug in air freshener. wmv, https://www.youtube.com/watch?v=OreNgPBUwaY&t=66s.
Rose Plastic. Rose Plastic: Innovations in Plastic Packaging, www.rose-plastic./2030.0.html?&L=4p?id=2337id=2345iel25% worldwide unique plastic packaging with remarkable diversity, retrieved Mar. 17, 2019.
Ruyanchina. "RUYAN—The New Way to Smoke(English) E-Cigarette-Blog.com." YouTube, YouTube, Jun. 9, 2007, www.youtube.com/watch?v=ia2997x_kog.
Smith, Chris. "Next USB Connector Will Finally Be Reversible, like Apple's Lightning Plug." BGR, Dec. 5, 2013, bgr.com/2013/12/05/reversible-usb-connector-apple-lightning/.
SourDieselManCO. "O.pen Vape Pen Vaporizer Hybrid and Indica 250mg Cartridges." YouTube, YouTube, Apr. 8, 2013, www.youtube.com/watch?v=5jWTQVQbEw.
TechVitaminsTV. "E-Cigarettes: How It Works (Blu Premium E-Cig Social Kit Review) Must See!!" YouTube, YouTube, Mar. 14, 2012, www.youtube.com/watch?v=mFAYxw6csjg.
VapeandBake. "NJOY Electronic Cigarette Review." YouTube, YouTube, Apr. 9, 2013, www.youtube.com/watch?v=qUynQFK_Xpo.
Vaporizers Reviewed. "AtmosRX Optimus 510 Vaporizer Review." YouTube, YouTube, Oct. 10, 2013, www.youtube.com/watch?v=wsyQncG8FB8.
VapXtream. "The Elips By LSK." YouTube, YouTube, Jan. 13, 2013, www.youtube.com/watch?v=PTfJlsrfqWI.
Electronic Vaporization Device | JUUL Vapor, Available from Internet, https://www.juulvapor.com/shop-juul/.
EnsembleIQ "Vuse Product Reel" Youtube Jun. 6, 2013 https://www.youtube.com/watch?v=Igo_bBY8tNM.
Maiocco Roberto. "Modello IWand." YouTube YouTube Dec. 28, 2012 www.youtube.com/watch?v=_brQOLDqHX0.
Press Release by R.J. Reynolds https://www.reynoldsamerican.com/about-us/press-releases/Press-Release-Details-/2013/RJ-Reynolds-Vapor-Company-bringing-VUSE-Digital-Vapor-Cigarette-to-Colorado-/default.aspx Jun. 6, 2013.
Uptoyou Fromeme. "Elips Ego SOLE Electronic Cigarette Kit Patent Elipse Flat Upgrade F6 Section with Atomizer CE4." YouTube YouTube Sep. 12, 2013 www.youtube.com/watch?v=cnPcqDzFm0Q.
Uptoyou Fromeme. "F8 iWand Penstyle Adjustable Voltage Itaste VV Power Display Electronic Cigarette." YouTube Sep. 25, 2013. www.youtube.com/watch?v=5nqtHWJvWWo.
Vaporizers Reviewed. "MicroG Pen Vaporizer Review." YouTube YouTube Nov. 6, 2013 www.youtube.com/watch?v=pLhtL8vosrs.
Wholesale Consumer electronics. "Elips Ego SOLE Electronic Cigarette Kit Patent E-Cigarette E-Cig Elipse Flat Upgrade F6 Section." YouTube YouTube Sep. 13, 2013 www.youtube.com/watch?v=iCeE-O1scDg.
U.S. Appl. No. 14/581,666, filed Dec. 23, 2014, U.S. Pat. No. 10,058,124.
U.S. Appl. No. 15/257,748, filed Sep. 6, 2016, U.S. Pat. No. 10,159,282.
U.S. Appl. No. 15/257,760, filed Sep. 6, 2016, U.S. Pat. No. 10,076,139.
U.S. Appl. No. 15/257,768, filed Sep. 6, 2016, US 2016-0366947.
U.S. Appl. No. 15/379,898, filed Dec. 15, 2016, U.S. Pat. No. 10,058,129.
U.S. Appl. No. 15/813,084, filed Nov. 14, 2017, U.S. Pat. No. 10,701,975.
U.S. Appl. No. 15/813,089, filed Nov 14, 2017, U.S. Pat. No. 10,058,130.
U.S. Appl. No. 15/815,641, filed Nov. 16, 2017, U.S. Pat. No. 10,045,567.
U.S. Appl. No. 15/813,096, filed Nov. 14, 2017, U.S. Pat. No. 10,117,465.
U.S. Appl. No. 15/820,361, filed Nov. 21, 2017, U.S. Pat. No. 10,912,331.
U.S. Appl. No. 15/815,645, filed Nov. 16, 2017, U.S. Pat. No. 10,117,466.
U.S. Appl. No. 15/815,643, filed Nov. 16, 2017, U.S. Pat. No. 10,201,190.
U.S. Appl. No. 15/820,354, filed Nov. 21, 2017, U.S. Pat. No. 10,264,823.
U.S. Appl. No. 15/815,666, filed Nov. 16, 2017, U.S. Pat. No. 10,104,915.
U.S. Appl. No. 15/820,370, filed Nov. 21, 2017, U.S. Pat. No. 10,070,669.
U.S. Appl. No. 15/832,743, filed Dec. 5, 2017, U.S. Pat. No. 10,667,560.
U.S. Appl. No. 15/832,749, filed Dec. 5, 2017, U.S. Pat. No. 10,045,568.
U.S. Appl. No. 15/832,731, filed Dec. 5, 2017, US 2018-0092406.
U.S. Appl. No. 15/833,873, filed Dec. 6, 2017, U.S. Pat. No. 10,111,470.
U.S. Appl. No. 16/032,009, filed Jul. 10, 2018, U.S. Pat. No. 10,709,173.
U.S. Appl. No. 16/114,201, filed Aug. 27, 2018, US 2019-0000148.
U.S. Appl. No. 16/114,204, filed Aug. 27, 2018, US 2019-0008212.
U.S. Appl. No. 16/114,206, filed Aug. 27, 2018, US 2018-0360129.
U.S. Appl. No. 16/114,207, filed Aug. 27, 2018, US 2018-0360130.

(56) References Cited

OTHER PUBLICATIONS

U.S. Appl. No. 15/430,284, filed Feb. 10, 2017, U.S. Pat. No. 10,279,934.
U.S. Appl. No. 16/404,693, filed May 6, 2019, U.S. Pat. No. 10,865,001.
U.S. Appl. No. 15/430,317, filed Feb. 10, 2017, U.S. Pat. No. 10,130,123.
U.S. Appl. No. 16/077,731, filed Feb. 10, 2017, US 2019-0104767.
U.S. Appl. No. 15/430,357, filed Feb. 10, 2017, U.S. Pat. No. 10,638,792.
U.S. Appl. No. 16/864,007, filed Apr. 30, 2020, US 2020-0260785.
U.S. Appl. No. 15/053,927, filed Feb. 25, 2016, U.S. Pat. No. 9,549,573.
U.S. Appl. No. 16/080,296, filed Feb. 27, 2017, U.S. Pat. No. 10,912,333.
U.S. Appl. No. 17/154,982, filed Jan. 20, 2021.
U.S. Appl. No. 17/197,955, filed Mar. 10, 2021.
Costello et al., "Hermeticity testing of MEMS" published Oct. 2013.
Diniz et al., "Digital Signal Processing: System Analysis and Design", published Sep. 2010.
How to Measure Resistance—Hioki, https://www.hioki.com/en/learning/methods/resistancemeasurement-methods.html/, Jun. 15, 2021.
Low Level Measurements Handbook—7th Edition Precision DC Current, Voltage, and Resistance Measurements.
Resistance thermometer, https://en.wikipedia.org/wiki/Resistance_thermometer, Jun. 15, 2021.
Room temperature, https://en.wikipedia.org/wiki/Room_ temperature, Jun. 15, 2021.
Sha et al., "Optimal Design of Switching Power Supply", published Sep. 2015.
Tony R. Kuphaldt, Lessons in Electric Circuits, vol. 1 DC, 2006, especially section 12.6 'Temperature coefficient of resistance'.
https://en.wikipedia.org/w/index.php?title-Diode_bridge&oldid=583794015. edited Nov. 29, 2013, retrieved from the internet on Jul. 21, 2021.
JaSz_z, "Review Innokin iTaste VV—v2 (English)", YouTube (Jun. 8, 2012), https://www.youtube.com/watch?v=ejiWtKu6HVM.
Hidy, G.M. and Brock, J.R., 1970. Dynamics of Aerocolloidal Systems, Pergamon Press Inc. (excerpt of Chapter 9).
Itamar Lourenço (Vaper), "Innokin iTaste VV (v2) Review [PT]", YouTube (Jun. 27, 2012), https://www.youtube.com/watch?v=iDrGGREj608.
VUSE Device (Jun. 6, 2013).

\* cited by examiner

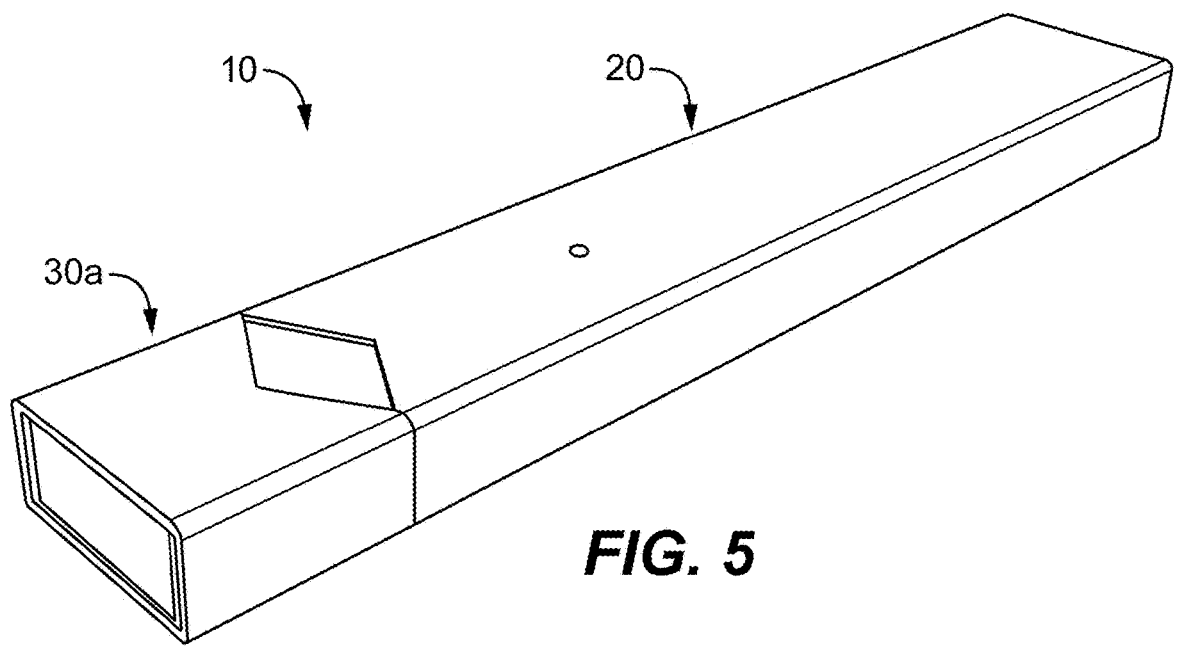
FIG. 5
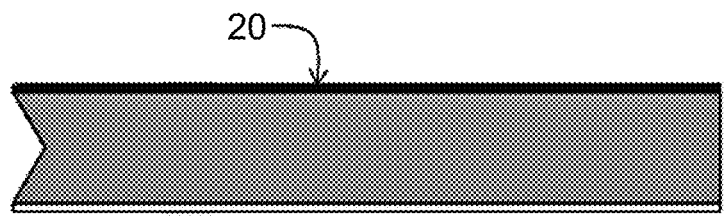
FIG. 6A
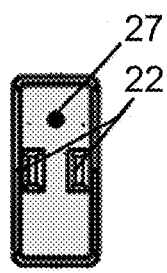
FIG. 6C
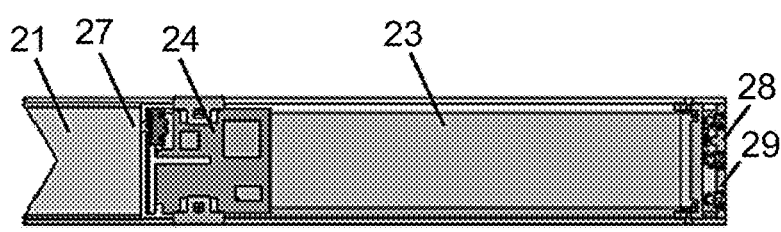
FIG. 6B
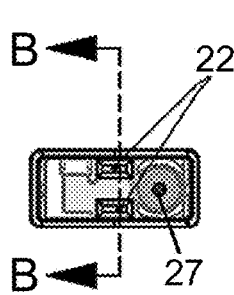
FIG. 6D
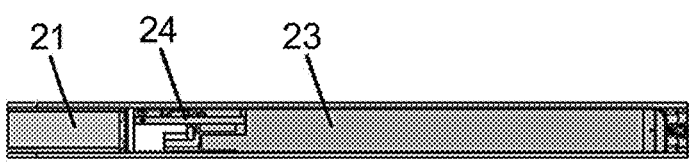
Section B-B

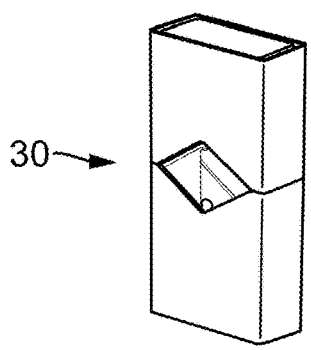
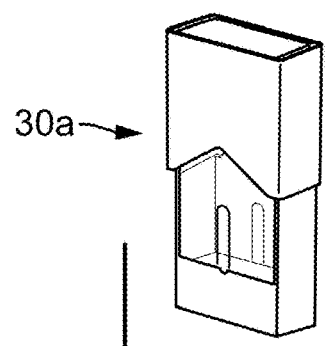
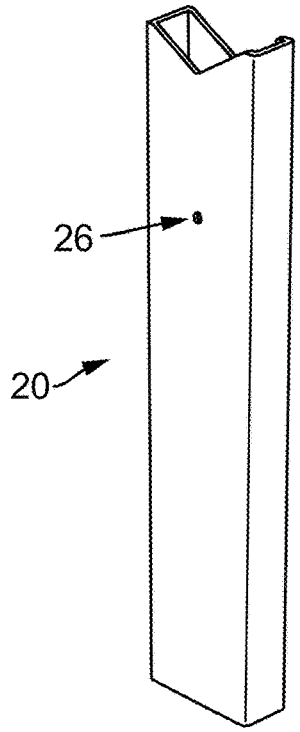
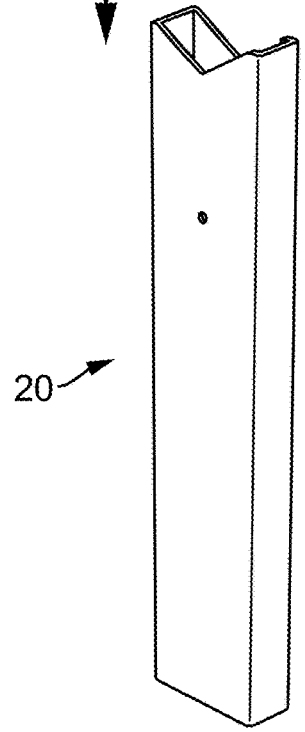
FIG. 11  FIG. 12
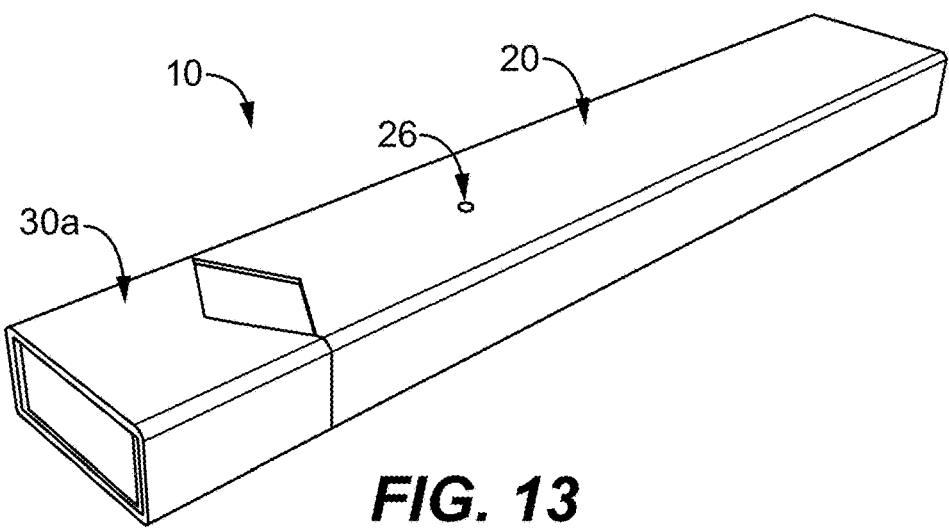
FIG. 13

VAPORIZATION DEVICE SYSTEMS AND METHODS

CROSS REFERENCE TO RELATED APPLICATIONS

This application is a continuation of U.S. patent application Ser. No. 14/581,666, filed Dec. 23, 2014 and entitled "VAPORIZATION DEVICE SYSTEMS AND METHODS", which claims priority to U.S. Provisional Patent Application Ser. No. 61/920,225, filed Dec. 23, 2013, U.S. Provisional Patent Application Ser. No. 61/936,593, filed Feb. 6, 2014, and U.S. Provisional Patent Application Ser. No. 61/937,755, filed Feb. 10, 2014, the disclosures of which are incorporated herein by reference in their entirety.

BACKGROUND OF THE INVENTION

The present invention is directed to improvements in electronic inhalable aerosol devices, or electronic vaping devices, particularly to electronic aerosol devices which utilize a vaporizable material that is vaporized to create an aerosol vapor capable of delivering an active ingredient to a user.

SUMMARY OF THE INVENTION

In some aspects of the invention, the device comprises an inhalable aerosol comprising: an oven comprising an oven chamber and a heater for heating a vapor forming medium in the oven chamber to generate a vapor; a condenser comprising a condensation chamber in which at least a fraction of the vapor condenses to form the inhalable aerosol; an air inlet that originates a first airflow path that includes the oven chamber; and an aeration vent that originates a second airflow path that allows air from the aeration vent to join the first airflow path prior to or within the condensation chamber and downstream from the oven chamber thereby forming a joined path, wherein the joined path is configured to deliver the inhalable aerosol formed in the condensation chamber to a user.

In some aspects of the invention the oven is within a body of the device. The device may further comprise a mouthpiece, wherein the mouthpiece comprises at least one of the air inlet, the aeration vent, and the condenser. The mouthpiece may be separable from the oven. The mouthpiece may be integral to a body of the device, wherein the body comprises the oven. The device may further comprise a body that comprises the oven, the condenser, the air inlet, and the aeration vent. The mouthpiece may be separable from the body.

In some aspects of the invention, the oven chamber may comprise an oven chamber inlet and an oven chamber outlet, and the oven further comprises a first valve at the oven chamber inlet, and a second valve at the oven chamber outlet. The aeration vent may comprise a third valve. The first valve, or said second valve may be chosen from the group of a check valve, a clack valve, a non-return valve, and a one-way valve. The third valve may be chosen from the group of a check valve, a clack valve, a non-return valve, and a one-way valve. The first or second valve may be mechanically actuated. The first or second valve may be electronically actuated. The first valve or second valve may be manually actuated. The third valve may be mechanically actuated. The third valve may be mechanically actuated. The third valve may be electronically actuated. The third valve may be manually actuated.

In another aspect of the invention, the device may further comprise a body that comprises at least one of: a power source, a printed circuit board, a switch, and a temperature regulator. The device may further comprise a temperature regulator in communication with a temperature sensor. The temperature sensor may be the heater. The power source may be rechargeable. The power source may be removable. The oven may further comprise an access lid. The vapor forming medium may comprise tobacco. The vapor forming medium may comprise a botanical. The vapor forming medium may be heated in the oven chamber wherein the vapor forming medium may comprise a humectant to produce the vapor, wherein the vapor comprises a gas phase humectant. The vapor may be mixed in the condensation chamber with air from the aeration vent to produce the inhalable aerosol comprising particle diameters of average size of about 1 micron. The vapor forming medium may be heated in the oven chamber, wherein the vapor is mixed in the condensation chamber with air from the aeration vent to produce the inhalable aerosol comprising particle diameters of average size of less than or equal to 0.9 micron. The vapor forming medium may be heated in the oven chamber, wherein the vapor is mixed in the condensation chamber with air from the aeration vent to produce the inhalable aerosol comprising particle diameters of average size of less than or equal to 0.8 micron. The vapor forming medium may be heated in the oven chamber, wherein the vapor is mixed in the condensation chamber with air from the aeration vent to produce the inhalable aerosol comprising particle diameters of average size of less than or equal to 0.7 micron. The vapor forming medium may be heated in the oven chamber, wherein the vapor is mixed in the condensation chamber with air from the aeration vent to produce the inhalable aerosol comprising particle diameters of average size of less than or equal to 0.6 micron. The vapor forming medium may be heated in the oven chamber, wherein the vapor is mixed in the condensation chamber with air from the aeration vent to produce the inhalable aerosol comprising particle diameters of average size of less than or equal to 0.5 micron.

In some aspects of the invention, the humectant may comprise glycerol as a vapor-forming medium. The humectant may comprise vegetable glycerol. The humectant may comprise propylene glycol. The humectant may comprise a ratio of vegetable glycerol to propylene glycol. The ratio may be about 100:0 vegetable glycerol to propylene glycol. The ratio may be about 90:10 vegetable glycerol to propylene glycol. The ratio may be about 80:20 vegetable glycerol to propylene glycol. The ratio may be about 70:30 vegetable glycerol to propylene glycol. The ratio may be about 60:40 vegetable glycerol to propylene glycol. The ratio may be about 50:50 vegetable glycerol to propylene glycol. The humectant may comprise a flavorant. The vapor forming medium may be heated to its pyrolytic temperature. The vapor forming medium may heated to 200° C. at most. The vapor forming medium may be heated to 160° C. at most. The inhalable aerosol may be cooled to a temperature of about 50°-70° C. at most, before exiting the aerosol outlet of the mouthpiece.

In an aspect of the invention, the method comprises A method for generating an inhalable aerosol, the method comprising: providing an inhalable aerosol generating device wherein the device comprises: an oven comprising an oven chamber and a heater for heating a vapor forming medium in the oven chamber and for forming a vapor therein; a condenser comprising a condensation chamber in which the vapor forms the inhalable aerosol; an air inlet that originates a first airflow path that includes the oven chamber; and an aeration vent that originates a second airflow path that allows air from the aeration vent to join the first airflow path prior to or within the condensation chamber and downstream from the oven chamber thereby forming a joined path, wherein the joined path is configured to deliver the inhalable aerosol formed in the condensation chamber to a user.

In some aspects of the invention the oven is within a body of the device. The device may further comprise a mouthpiece, wherein the mouthpiece comprises at least one of the air inlet, the aeration vent, and the condenser. The mouthpiece may be separable from the oven. The mouthpiece may be integral to a body of the device, wherein the body comprises the oven. The method may further comprise a body that comprises the oven, the condenser, the air inlet, and the aeration vent. The mouthpiece may be separable from the body.

In some aspects of the invention, the oven chamber may comprise an oven chamber inlet and an oven chamber outlet, and the oven further comprises a first valve at the oven chamber inlet, and a second valve at the oven chamber outlet.

The vapor forming medium may comprise tobacco. The vapor forming medium may comprise a botanical. The vapor forming medium may be heated in the oven chamber wherein the vapor forming medium may comprise a humectant to produce the vapor, wherein the vapor comprises a gas phase humectant. The vapor may comprise particle diameters of average mass of about 1 micron. The vapor may comprise particle diameters of average mass of about 0.9 micron. The vapor may comprise particle diameters of average mass of about 0.8 micron. The vapor may comprise particle diameters of average mass of about 0.7 micron. The vapor may comprise particle diameters of average mass of about 0.6 micron. The vapor may comprise particle diameters of average mass of about 0.5 micron.

In some aspects of the invention, the humectant may comprise glycerol as a vapor-forming medium. The humectant may comprise vegetable glycerol. The humectant may comprise propylene glycol. The humectant may comprise a ratio of vegetable glycerol to propylene glycol. The ratio may be about 100:0 vegetable glycerol to propylene glycol. The ratio may be about 90:10 vegetable glycerol to propylene glycol. The ratio may be about 80:20 vegetable glycerol to propylene glycol. The ratio may be about 70:30 vegetable glycerol to propylene glycol. The ratio may be about 60:40 vegetable glycerol to propylene glycol. The ratio may be about 50:50 vegetable glycerol to propylene glycol. The humectant may comprise a flavorant. The vapor forming medium may be heated to its pyrolytic temperature. The vapor forming medium may heated to 200° C. at most. The vapor forming medium may be heated to 160° C. at most. The inhalable aerosol may be cooled to a temperature of about 50°-70° C. at most, before exiting the aerosol outlet of the mouthpiece.

In an aspect of the invention, the device may be user serviceable. The device may not be user serviceable.

In an aspect of the invention, a method for generating an inhalable aerosol, the method comprising: providing a vaporization device, wherein said device produces a vapor comprising particle diameters of average mass of about 1 micron or less, wherein said vapor is formed by heating a vapor forming medium in an oven chamber to a first temperature below the pyrolytic temperature of said vapor forming medium, and cooling said vapor in a condensation chamber to a second temperature below the first temperature, before exiting an aerosol outlet of said device.

In an aspect of the invention, a method of manufacturing a device for generating an inhalable aerosol comprising: providing said device comprising a mouthpiece comprising an aerosol outlet at a first end of the device; an oven comprising an oven chamber and a heater for heating a vapor forming medium in the oven chamber and for forming a vapor therein, a condenser comprising a condensation chamber in which the vapor forms the inhalable aerosol, an air inlet that originates a first airflow path that includes the oven chamber and then the condensation chamber, an aeration vent that originates a second airflow path that joins the first airflow path prior to or within the condensation chamber after the vapor is formed in the oven chamber, wherein the joined first airflow path and second airflow path are configured to deliver the inhalable aerosol formed in the condensation chamber through the aerosol outlet of the mouthpiece to a user.

The method may further comprise providing the device comprising a power source or battery, a printed circuit board, a temperature regulator or operational switches.

In an aspect of the invention a device for generating an inhalable aerosol may comprise a mouthpiece comprising an aerosol outlet at a first end of the device and an air inlet that originates a first airflow path; an oven comprising an oven chamber that is in the first airflow path and includes the oven chamber and a heater for heating a vapor forming medium in the oven chamber and for forming a vapor therein; a condenser comprising a condensation chamber in which the vapor forms the inhalable aerosol; and an aeration vent that originates a second airflow path that allows air from the aeration vent to join the first airflow path prior to or within the condensation chamber and downstream from the oven chamber thereby forming a joined path, wherein the joined path is configured to deliver the inhalable aerosol formed in the condensation chamber through the aerosol outlet of the mouthpiece to a user.

In another aspect of the invention a device for generating an inhalable aerosol may comprise: a mouthpiece comprising an aerosol outlet at a first end of the device, an air inlet that originates a first airflow path, and an aeration vent that originates a second airflow path that allows air from the aeration vent to join the first airflow path; an oven comprising an oven chamber that is in the first airflow path and includes the oven chamber and a heater for heating a vapor forming medium in the oven chamber and for forming a vapor therein; and a condenser comprising a condensation chamber in which the vapor forms the inhalable aerosol and wherein air from the aeration vent joins the first airflow path prior to or within the condensation chamber and downstream from the oven chamber thereby forming a joined path, wherein the joined path is configured to deliver the inhalable aerosol through the aerosol outlet of the mouthpiece to a user.

In another aspect of the invention, a device for generating an inhalable aerosol may comprise: a device body comprising a cartridge receptacle; a cartridge comprising: a fluid storage compartment, and a channel integral to an exterior surface of the cartridge, and an air inlet passage formed by the channel and an internal surface of the cartridge receptacle when the cartridge is inserted into the cartridge receptacle; wherein the channel forms a first side of the air inlet passage, and an internal surface of the cartridge receptacle forms a second side of the air inlet passage.

In another aspect of the invention, a device for generating an inhalable aerosol may comprise: a device body comprising a cartridge receptacle; a cartridge comprising: a fluid storage compartment, and a channel integral to an exterior surface of the cartridge, and an air inlet passage formed by the channel and an internal surface of the cartridge receptacle when the cartridge is inserted into the cartridge receptacle; wherein the channel forms a first side of the air inlet passage, and an internal surface of the cartridge receptacle forms a second side of the air inlet passage.

In some aspects of the invention the channel may comprise at least one of a groove, a trough, a depression, a dent, a furrow, a trench, a crease, and a gutter. The integral channel may comprise walls that are either recessed into the surface or protrude from the surface where it is formed. The internal side walls of the channel may form additional sides of the air inlet passage. The cartridge may further comprise a second air passage in fluid communication with the air inlet passage to the fluid storage compartment, wherein the second air passage is formed through the material of the cartridge. The cartridge may further comprise a heater. The heater may be attached to a first end of the cartridge.

In an aspect of the invention the heater may comprise a heater chamber, a first pair of heater contacts, a fluid wick, and a resistive heating element in contact with the wick, wherein the first pair of heater contacts comprise thin plates affixed about the sides of the heater chamber, and wherein the fluid wick and resistive heating element are suspended therebetween. The first pair of heater contacts may further comprise a formed shape that comprises a tab having a flexible spring value that extends out of the heater to couple to complete a circuit with the device body. The first pair of heater contacts may be a heat sink that absorbs and dissipates excessive heat produced by the resistive heating element. The first pair of heater contacts may contact a heat shield that protects the heater chamber from excessive heat produced by the resistive heating element. The first pair of heater contacts may be press-fit to an attachment feature on the exterior wall of the first end of the cartridge. The heater may enclose a first end of the cartridge and a first end of the fluid storage compartment. The heater may comprise a first condensation chamber. The heater may comprise more than one first condensation chamber. The first condensation chamber may be formed along an exterior wall of the cartridge. The cartridge may further comprise a mouthpiece. The mouthpiece may be attached to a second end of the cartridge. The mouthpiece may comprise a second condensation chamber. The mouthpiece may comprise more than one second condensation chamber. The second condensation chamber may be formed along an exterior wall of the cartridge.

In an aspect of the invention the cartridge may comprise a first condensation chamber and a second condensation chamber. The first condensation chamber and the second condensation chamber may be in fluid communication. The mouthpiece may comprise an aerosol outlet in fluid communication with the second condensation chamber. The mouthpiece may comprise more than one aerosol outlet in fluid communication with more than one the second condensation chamber. The mouthpiece may enclose a second end of the cartridge and a second end of the fluid storage compartment.

In an aspect of the invention, the device may comprise an airflow path comprising an air inlet passage, a second air passage, a heater chamber, a first condensation chamber, a second condensation chamber, and an aerosol outlet. The airflow path may comprise more than one air inlet passage, a heater chamber, more than one first condensation chamber, more than one second condensation chamber, more than one second condensation chamber, and more than one aerosol outlet. The heater may be in fluid communication with the fluid storage compartment. The fluid storage compartment may be capable of retaining condensed aerosol fluid. The condensed aerosol fluid may comprise a nicotine formulation. The condensed aerosol fluid may comprise a humectant. The humectant may comprise propylene glycol. The humectant may comprise vegetable glycerin.

In an aspect of the invention the cartridge may be detachable. In an aspect of the invention the cartridge may be receptacle and the detachable cartridge form a separable coupling. The separable coupling may comprise a friction assembly, a snap-fit assembly or a magnetic assembly. The cartridge may comprise a fluid storage compartment, a heater affixed to a first end with a snap-fit coupling, and a mouthpiece affixed to a second end with a snap-fit coupling.

In an aspect of the invention, a device for generating an inhalable aerosol may comprise: a device body comprising a cartridge receptacle for receiving a cartridge; wherein an interior surface of the cartridge receptacle forms a first side of an air inlet passage when a cartridge comprising a channel integral to an exterior surface is inserted into the cartridge receptacle, and wherein the channel forms a second side of the air inlet passage.

In an aspect of the invention, a device for generating an inhalable aerosol may comprise: a device body comprising a cartridge receptacle for receiving a cartridge; wherein the cartridge receptacle comprises a channel integral to an interior surface and forms a first side of an air inlet passage when a cartridge is inserted into the cartridge receptacle, and wherein an exterior surface of the cartridge forms a second side of the air inlet passage.

In an aspect of the invention, A cartridge for a device for generating an inhalable aerosol comprising: a fluid storage compartment; a channel integral to an exterior surface, wherein the channel forms a first side of an air inlet passage; and wherein an internal surface of a cartridge receptacle in the device forms a second side of the air inlet passage when the cartridge is inserted into the cartridge receptacle.

In an aspect of the invention, a cartridge for a device for generating an inhalable aerosol may comprise: a fluid storage compartment, wherein an exterior surface of the cartridge forms a first side of an air inlet channel when inserted into a device body comprising a cartridge receptacle, and wherein the cartridge receptacle further comprises a channel integral to an interior surface, and wherein the channel forms a second side of the air inlet passage.

The cartridge may further comprise a second air passage in fluid communication with the channel, wherein the second air passage is formed through the material of the cartridge from an exterior surface of the cartridge to the fluid storage compartment.

The cartridge may comprise at least one of: a groove, a trough, a depression, a dent, a furrow, a trench, a crease, and a gutter. The integral channel may comprise walls that are either recessed into the surface or protrude from the surface where it is formed. The internal side walls of the channel may form additional sides of the air inlet passage.

In another aspect of the invention, a device for generating an inhalable aerosol may comprise: a cartridge comprising; a fluid storage compartment; a heater affixed to a first end comprising; a first heater contact, a resistive heating element affixed to the first heater contact; a device body comprising; a cartridge receptacle for receiving the cartridge; a second heater contact adapted to receive the first heater contact and to complete a circuit; a power source connected to the second heater contact; a printed circuit board (PCB) connected to the power source and the second heater contact; wherein the PCB is configured to detect the absence of fluid based on the measured resistance of the resistive heating element, and turn off the device.

The printed circuit board (PCB) may comprise a microcontroller; switches; circuitry comprising a reference resister; and an algorithm comprising logic for control parameters; wherein the microcontroller cycles the switches at fixed intervals to measure the resistance of the resistive heating element relative to the reference resistor, and applies the algorithm control parameters to control the temperature of the resistive heating element.

The micro-controller may instruct the device to turn itself off when the resistance exceeds the control parameter threshold indicating that the resistive heating element is dry.

In another aspect of the invention, a cartridge for a device for generating an inhalable aerosol may comprise: a fluid storage compartment; a heater affixed to a first end comprising: a heater chamber, a first pair of heater contacts, a fluid wick, and a resistive heating element in contact with the wick; wherein the first pair of heater contacts comprise thin plates affixed about the sides of the heater chamber, and wherein the fluid wick and resistive heating element are suspended therebetween.

The first pair of heater contacts may further comprise: a formed shape that comprises a tab having a flexible spring value that extends out of the heater to complete a circuit with the device body. The heater contacts may be configured to mate with a second pair of heater contacts in a cartridge receptacle of the device body to complete a circuit. The first pair of heater contacts may also be a heat sink that absorbs and dissipates excessive heat produced by the resistive heating element. The first pair of heater contacts may be a heat shield that protect the heater chamber from excessive heat produced by the resistive heating element.

In another aspect of the invention, a cartridge for a device for generating an inhalable aerosol may comprise: a heater comprising; a heater chamber, a pair of thin plate heater contacts therein, a fluid wick positioned between the heater contacts, and a resistive heating element in contact with the wick; wherein the heater contacts each comprise a fixation site wherein the resistive heating element is tensioned therebetween.

In another aspect of the invention, a cartridge for a device for generating an inhalable aerosol may comprise a heater, wherein the heater is attached to a first end of the cartridge.

The heater may enclose a first end of the cartridge and a first end of the fluid storage compartment. The heater may comprise more than one first condensation chamber. The heater may comprise a first condensation chamber. The condensation chamber may be formed along an exterior wall of the cartridge.

In another aspect of the invention, a cartridge for a device for generating an inhalable aerosol may comprise a fluid storage compartment; and a mouthpiece, wherein the mouthpiece is attached to a second end of the cartridge.

The mouthpiece may enclose a second end of the cartridge and a second end of the fluid storage compartment. The mouthpiece may comprise a second condensation chamber. The mouthpiece may comprise more than one second condensation chamber. The second condensation chamber may be formed along an exterior wall of the cartridge.

In an aspect of the invention, a cartridge for a device for generating an inhalable aerosol may comprise: a fluid storage compartment; a heater affixed to a first end; and a mouthpiece affixed to a second end; wherein the heater comprises a first condensation chamber and the mouthpiece comprises a second condensation chamber.

The heater may comprise more than one first condensation chamber and the mouthpiece comprises more than one second condensation chamber. The first condensation chamber and the second condensation chamber may be in fluid communication. The mouthpiece may comprise an aerosol outlet in fluid communication with the second condensation chamber. The mouthpiece may comprise two to more aerosol outlets. The cartridge may meet ISO recycling standards. The cartridge may meet ISO recycling standards for plastic waste.

In an aspect of the invention, a device for generating an inhalable aerosol may comprise: a device body comprising a cartridge receptacle; and a detachable cartridge; wherein the cartridge receptacle and the detachable cartridge form a separable coupling, wherein the separable coupling comprises a friction assembly, a snap-fit assembly or a magnetic assembly.

In an aspect of the invention, a method of fabricating a device for generating an inhalable aerosol may comprise: providing a device body comprising a cartridge receptacle; and providing a detachable cartridge; wherein the cartridge receptacle and the detachable cartridge form a separable coupling comprising a friction assembly, a snap-fit assembly or a magnetic assembly.

In an aspect of the invention, a method of fabricating a cartridge for a device for generating an inhalable aerosol may comprise: providing a fluid storage compartment; affixing a heater to a first end with a snap-fit coupling; and affixing a mouthpiece to a second end with a snap-fit coupling.

In an aspect of the invention, A cartridge for a device for generating an inhalable aerosol with an airflow path comprising: a channel comprising a portion of an air inlet passage; a second air passage in fluid communication with the channel; a heater chamber in fluid communication with the second air passage; a first condensation chamber in fluid communication with the heater chamber; a second condensation chamber in fluid communication with the first condensation chamber; and an aerosol outlet in fluid communication with second condensation chamber.

In an aspect of the invention, a cartridge for a device for generating an inhalable aerosol may comprise: a fluid storage compartment; a heater affixed to a first end; and a mouthpiece affixed to a second end; wherein said mouthpiece comprises two or more aerosol outlets.

In an aspect of the invention, a system for providing power to an electronic device for generating an inhalable vapor, the system may comprise; a rechargeable power storage device housed within the electronic device for generating an inhalable vapor; two or more pins that are accessible from an exterior surface of the electronic device for generating an inhalable vapor, wherein the charging pins are in electrical communication with the rechargeable power storage device; a charging cradle comprising two or more charging contacts configured to provided power to the rechargeable storage device, wherein the device charging pins are reversible such that the device is charged in the charging cradle for charging with a first charging pin on the device in contact a first charging contact on the charging cradle and a second charging pin on the device in contact with second charging contact on the charging cradle and with the first charging pin on the device in contact with second charging contact on the charging cradle and the second charging pin on the device in contact with the first charging contact on the charging cradle.

The charging pins may be visible on an exterior housing of the device. The user may permanently disable the device by opening the housing. The user may permanently destroy the device by opening the housing.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 5 is an illustrative isometric view of an assembled inhalable aerosol device.

FIGS. 6A-6D are illustrative arrangements and section views of the device body and sub-components.

FIGS. 11-13 represent an illustrative assembly sequence for assembling the main components of the device.

DETAILED DESCRIPTION OF THE INVENTION

Figure 1:
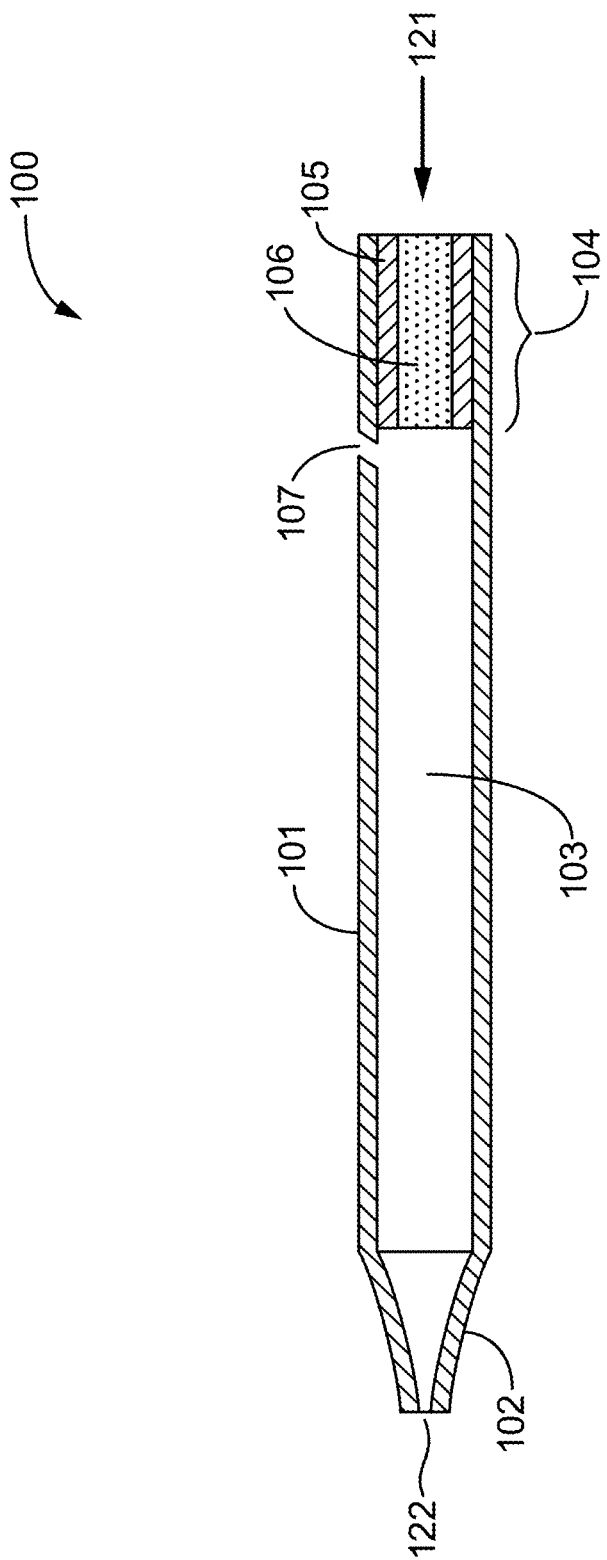
FIG. 1 is an illustrative cross-sectional view of an exemplary vaporization device.

Provided herein are systems and methods for generating a vapor from a material. The vapor may be delivered for inhalation by a user. The material may be a solid, liquid, powder, solution, paste, gel, or any a material with any other physical consistency. The vapor may be delivered to the user for inhalation by a vaporization device. The vaporization device may be a handheld vaporization device. The vaporization device may be held in one hand by the user.

The vaporization device may comprise one or more heating elements the heating element may be a resistive heating element. The heating element may heat the material such that the temperature of the material increases. Vapor may be generated as a result of heating the material. Energy may be required to operate the heating element, the energy may be derived from a battery in electrical communication with the heating element. Alternatively a chemical reaction (e.g., combustion or other exothermic reaction) may provide energy to the heating element.

One or more aspects of the vaporization device may be designed and/or controlled in order to deliver a vapor with one or more specified properties to the user. For example, aspects of the vaporization device that may be designed and/or controlled to deliver the vapor with specified properties may comprise the heating temperature, heating mechanism, device air inlets, internal volume of the device, and/or composition of the material.

In some cases, a vaporization device may have an "atomizer" or "cartomizer" configured to heat an aerosol forming solution (e.g., vaporizable material). The aerosol forming solution may comprise glycerin and/or propylene glycol. The vaporizable material may be heated to a sufficient temperature such that it may vaporize.

An atomizer may be a device or system configured to generate an aerosol. The atomizer may comprise a small heating element configured to heat and/or vaporize at least a portion of the vaporizable material and a wicking material that may draw a liquid vaporizable material in to the atomizer. The wicking material may comprise silica fibers, cotton, ceramic, hemp, stainless steel mesh, and/or rope cables. The wicking material may be configured to draw the liquid vaporizable material in to the atomizer without a pump or other mechanical moving part. A resistance wire may be wrapped around the wicking material and then connected to a positive and negative pole of a current source (e.g., energy source). The resistance wire may be a coil. When the resistance wire is activated the resistance wire (or coil) may have a temperature increase as a result of the current flowing through the resistive wire to generate heat. The heat may be transferred to at least a portion of the vaporizable material through conductive, convective, and/or radiative heat transfer such that at least a portion of the vaporizable material vaporizes.

Alternatively or in addition to the atomizer, the vaporization device may comprise a "cartomizer" to generate an aerosol from the vaporizable material for inhalation by the user. The cartomizer may comprise a cartridge and an atomizer. The cartomizer may comprise a heating element surrounded by a liquid-soaked poly-foam that acts as holder for the vaporizable material (e.g., the liquid). The cartomizer may be reusable, rebuildable, refillable, and/or disposable. The cartomizer may be used with a tank for extra storage of a vaporizable material.

Air may be drawn into the vaporization device to carry the vaporized aerosol away from the heating element, where it then cools and condenses to form liquid particles suspended in air, which may then be drawn out of the mouthpiece by the user.

The vaporization of at least a portion of the vaporizable material may occur at a lower temperatures in the vaporization device compared to temperatures required to generate an inhalable vapor in a cigarette. A cigarette may be a device in which a smokable material is burned to generate an inhalable vapor. The lower temperature of the vaporization device may result in less decomposition and/or reaction of the vaporized material, and therefore produce an aerosol with many fewer chemical components compared to a cigarette. In some cases, the vaporization device may generate an aerosol with fewer chemical components that may be harmful to human health compared to a cigarette. Additionally, the vaporization device aerosol particles may undergo nearly complete evaporation in the heating process, the nearly complete evaporation may yield an average particle size (e.g., diameter) value that may be smaller than the average particle size in tobacco or botanical based effluent.

A vaporization device may be a device configured to extract for inhalation one or more active ingredients of plant material, tobacco, and/or a botanical, or other herbs or blends. A vaporization device may be used with pure chemicals and/or humectants that may or may not be mixed with plant material. Vaporization may be alternative to burning (smoking) that may avoid the inhalation of many irritating and/or toxic carcinogenic by-products which may result from the pyrolytic process of burning tobacco or botanical products above 300° C. The vaporization device may operate at a temperature at or below 300° C.

A vaporizer (e.g., vaporization device) may not have an atomizer or cartomizer. Instead the device may comprise an oven. The oven may be at least partially closed. The oven may have a closable opening. The oven may be wrapped with a heating element, alternatively the heating element may be in thermal communication with the oven through another mechanism. A vaporizable material may be placed directly in the oven or in a cartridge fitted in the oven. The heating element in thermal communication with the oven may heat a vaporizable material mass in order to create a gas phase vapor. The heating element may heat the vaporizable material through conductive, convective, and/or radiative heat transfer. The vapor may be released to a vaporization chamber where the gas phase vapor may condense, forming an aerosol cloud having typical liquid vapor particles with particles having a diameter of average mass of approximately 1 micron or greater. In some cases the diameter of average mass may be approximately 0.1-1 micron.

A used herein, the term "vapor" may generally refer to a substance in the gas phase at a temperature lower than its critical point. The vapor may be condensed to a liquid or to a solid by increasing its pressure without reducing the temperature.

As used herein, the term "aerosol" may generally refer to a colloid of fine solid particles or liquid droplets in air or another gas. Examples of aerosols may include clouds, haze, and smoke, including the smoke from tobacco or botanical products. The liquid or solid particles in an aerosol may have varying diameters of average mass that may range from monodisperse aerosols, producible in the laboratory, and containing particles of uniform size; to polydisperse colloidal systems, exhibiting a range of particle sizes. As the sizes of these particles become larger, they have a greater settling speed which causes them to settle out of the aerosol faster, making the appearance of the aerosol less dense and to shorten the time in which the aerosol will linger in air. Interestingly, an aerosol with smaller particles will appear thicker or denser because it has more particles. Particle number has a much bigger impact on light scattering than particle size (at least for the considered ranges of particle size), thus allowing for a vapor cloud with many more smaller particles to appear denser than a cloud having fewer, but larger particle sizes.

As used herein the term "humectant" may generally refer to as a substance that is used to keep things moist. A humectant may attract and retain moisture in the air by absorption, allowing the water to be used by other substances. Humectants are also commonly used in many tobaccos or botanicals and electronic vaporization products to keep products moist and as vapor-forming medium. Examples include propylene glycol, sugar polyols such as glycerol, glycerin, and honey.

Rapid Aeration

In some cases, the vaporization device may be configured to deliver an aerosol with a high particle density. The particle density of the aerosol may refer to the number of the aerosol droplets relative to the volume of air (or other dry gas) between the aerosol droplets. A dense aerosol may easily be visible to a user. In some cases the user may inhale the aerosol and at least a fraction of the aerosol particles may impinge on the lungs and/or mouth of the user. The user may exhale residual aerosol after inhaling the aerosol. When the aerosol is dense the residual aerosol may have sufficient particle density such that the exhaled aerosol is visible to the user. In some cases, a user may prefer the visual effect and/or mouth feel of a dense aerosol.

A vaporization device may comprise a vaporizable material. The vaporizable material may be contained in a cartridge or the vaporizable material may be loosely placed in one or more cavities the vaporization device. A heating element may be provided in the device to elevate the temperature of the vaporizable material such that at least a portion of the vaporizable material forms a vapor. The heating element may heat the vaporizable material by convective heat transfer, conductive heat transfer, and/or radiative heat transfer. The heating element may heat the cartridge and/or the cavity in which the vaporizable material is stored.

Vapor formed upon heating the vaporizable material may be delivered to the user. The vapor may be transported through the device from a first position in the device to a second position in the device. In some cases, the first position may be a location where at least a portion of the vapor was generated, for example, the cartridge or cavity or an area adjacent to the cartridge or cavity. The second position may be a mouthpiece. The user may suck on the mouthpiece to inhale the vapor.

At least a fraction of the vapor may condense after the vapor is generated and before the vapor is inhaled by the user. The vapor may condense in a condensation chamber. The condensation chamber may be a portion of the device that the vapor passes through before delivery to the user. In some cases, the device may include at least one aeration vent, placed in the condensation chamber of the vaporization device. The aeration vent may be configured to introduce ambient air (or other gas) into the vaporization chamber. The air introduced into the vaporization chamber may have a temperature lower than the temperature of a gas and/or gas/vapor mixture in the condensation chamber. Introduction of the relatively lower temperature gas into the vaporization chamber may provide rapid cooling of the heated gas vapor mixture that was generated by heating the vaporizable material. Rapid cooling of the gas vapor mixture may generate a dense aerosol comprising a high concentration of liquid droplets having a smaller diameter and/or smaller average mass compared to an aerosol that is not rapidly cooled prior to inhalation by the user.

An aerosol with a high concentration of liquid droplets having a smaller diameter and/or smaller average mass compared to an aerosol that is not rapidly cooled prior to inhalation by the user may be formed in a two-step process. The first step may occur in the oven chamber where the vaporizable material (e.g., tobacco and/or botanical and humectant blend) may be heated to an elevated temperature. At the elevated temperature, evaporation may happen faster than at room temperature and the oven chamber may fill with the vapor phase of the humectants. The humectant may continue to evaporate until the partial pressure of the humectant is equal to the saturation pressure. At this point, the gas is said to have a saturation ratio of 1 ($S=P_{partial}/P_{sat}$).

In the second step, the gas (e.g., vapor and air) may exit the oven and enter a condenser or condensation chamber and begin to cool. As the gas phase vapor cools, the saturation pressure may decrease. As the saturation pressure decreases, the saturation ratio may increase and the vapor may begin to condense, forming droplets. In some devices, with the absence of added cooling aeration, the cooling may be relatively slower such that high saturation pressures may not be reached, and the droplets that form in the devices without added cooling aeration may be relatively larger and fewer in numbers. When cooler air is introduced, a temperature gradient may be formed between the cooler air and the relatively warmer gas in the device. Mixing between the cooler air and the relatively warmer gas in a confined space inside of the vaporization device may lead to rapid cooling. The rapid cooling may generate high saturation ratios, small particles, and high concentrations of smaller particles, forming a thicker, denser vapor cloud compared to particles generated in a device without the aeration vents.

For the purpose of this disclosure, when referring to ratios of humectants such as vegetable glycerol or propylene glycol, "about" means a variation of 5%, 10%, 20% or 25% depending on the embodiment.

For the purpose of this disclosure, when referring to a diameter of average mass in particle sizes, "about" means a variation of 5%, 10%, 20% or 25% depending on the embodiment.

A vaporization device configured to rapidly cool a vapor may comprise: a mouthpiece comprising an aerosol outlet at a first end of the device; an oven comprising an oven chamber and a heater for heating a vapor forming medium in the oven chamber and for forming a vapor therein; a condenser comprising a condensation chamber in which the vapor forms the inhalable aerosol; an air inlet that originates a first airflow path that includes the oven chamber and then the condensation chamber, an aeration vent that originates a second airflow path that joins the first airflow path prior to or within the condensation chamber after the vapor is formed in the oven chamber, wherein the joined first airflow path and second airflow path are configured to deliver the inhalable aerosol formed in the condensation chamber through the aerosol outlet of the mouthpiece to a user.

In some embodiments, the oven is within a body of the device. The oven chamber may comprise an oven chamber inlet and an oven chamber outlet. The oven may further comprise a first valve at the oven chamber inlet, and a second valve at the oven chamber outlet.

The oven may be contained within a device housing. In some cases the body of the device may comprise the aeration vent and/or the condenser. The body of the device may comprise one or more air inlets. The body of the device may comprise a housing that holds and/or at least partially contains one or more elements of the device.

The mouthpiece may be connected to the body. The mouthpiece may be connected to the oven. The mouthpiece may be connected to a housing that at least partially encloses the oven. In some cases, the mouthpiece may be separable from the oven, the body, and/or the housing that at least partially encloses the oven. The mouthpiece may comprise at least one of the air inlet, the aeration vent, and the condenser. The mouthpiece may be integral to the body of the device. The body of the device may comprise the oven.

In some cases, the one or more aeration vents may comprise a valve. The valve may regulate a flow rate of air entering the device through the aeration vent. The valve may be controlled through a mechanical and/or electrical control system.

A vaporization device configured to rapidly cool a vapor may comprise: a body, a mouthpiece, an aerosol outlet, a condenser with a condensation chamber, a heater, an oven with an oven chamber, a primary airflow inlet, and at least one aeration vent provided in the body, downstream of the oven, and upstream of the mouthpiece.

FIG. 1 shows an example of a vaporization device configured to rapidly cool a vapor. The device 100, may comprise a body 101. The body may house and/or integrate with one or more components of the device. The body may house and/or integrate with a mouthpiece 102. The mouthpiece 102 may have an aerosol outlet 122. A user may inhale the generated aerosol through the aerosol outlet 122 on the mouthpiece 102. The body may house and/or integrate with an oven region 104. The oven region 104 may comprise an oven chamber where vapor forming medium 106 may be placed. The vapor forming medium may include tobacco and/or botanicals, with or without a secondary humectant. In some cases the vapor forming medium may be contained in a removable and/or refillable cartridge.

Air may be drawn into the device through a primary air inlet 121. The primary air inlet 121 may be on an end of the device 100 opposite the mouthpiece 102. Alternatively, the primary air inlet 121 may be adjacent to the mouthpiece 102. In some cases, a pressure drop sufficient to pull air into the device through the primary air inlet 121 may be due to a user puffing on the mouthpiece 102.

The vapor forming medium (e.g., vaporizable material) may be heated in the oven chamber by a heater 105, to generate elevated temperature gas phases (vapor) of the tobacco or botanical and humectant/vapor forming components. The heater 105 may transfer heat to the vapor forming medium through conductive, convective, and/or radiative heat transfer. The generated vapor may be drawn out of the oven region and into the condensation chamber 103a, of the condenser 103 where the vapors may begin to cool and condense into micro-particles or droplets suspended in air, thus creating the initial formation of an aerosol, before being drawn out of the mouthpiece through the aerosol outlet 122.

In some cases, relatively cooler air may be introduced into the condensation chamber 103a, through an aeration vent 107 such that the vapor condenses more rapidly compared to a vapor in a device without the aeration vent 107. Rapidly cooling the vapor may create a denser aerosol cloud having particles with a diameter of average mass of less than or equal to about 1 micron, and depending on the mixture ratio of the vapor-forming humectant, particles with a diameter of average mass of less than or equal to about 0.5 micron In another aspect, the present invention provides a device for generating an inhalable aerosol said device comprising a body with a mouthpiece at one end, an attached body at the other end comprising a condensation chamber, a heater, an oven, wherein the oven comprises a first valve in the airflow path at the primary airflow inlet of the oven chamber, and a second valve at the outlet end of the oven chamber, and at least one aeration vent provided in the body, downstream of the oven, and upstream of the mouthpiece.

Figure 2:
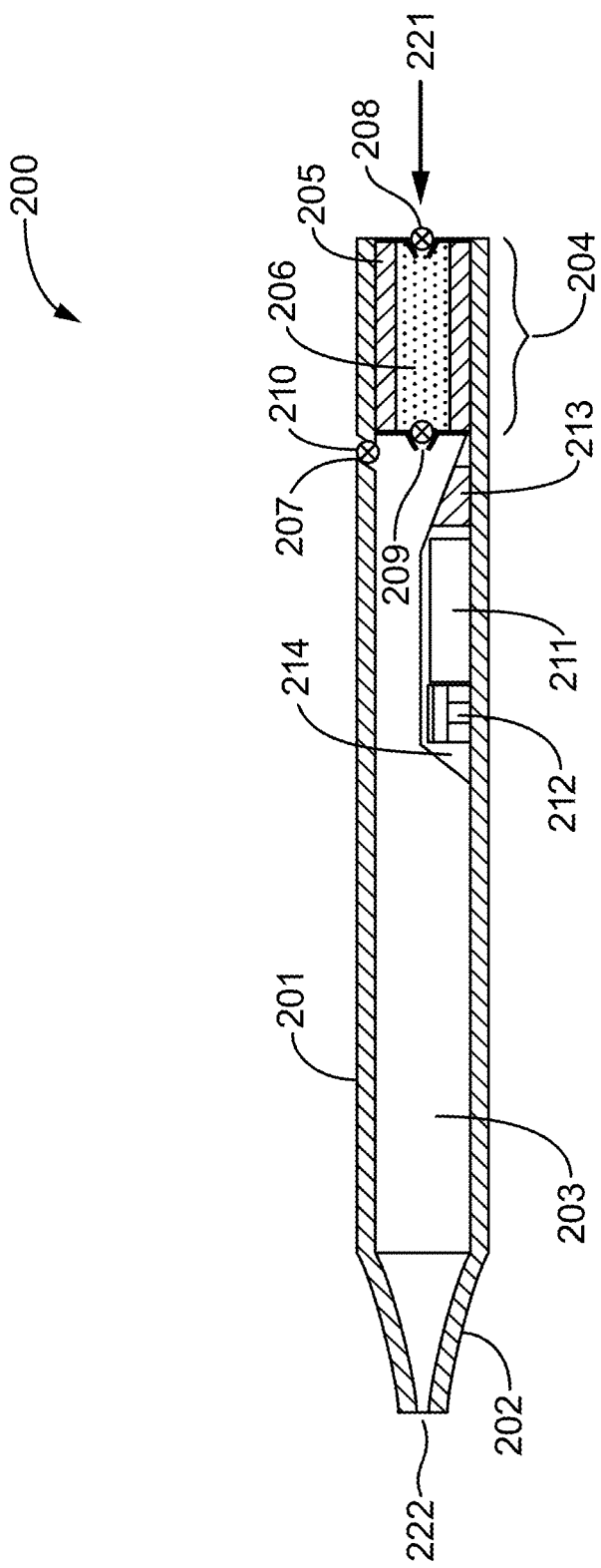
FIG. 2 is an illustrative cross-sectional view of an exemplary vaporization device with various electronic features and valves.

FIG. 2 shows a diagram of an alternative embodiment of the vaporization device 200. The vaporization device may have a body 201. The body 201 may integrate with and/or contain one or more components of the device. The body may integrate with or be connected to a mouthpiece 202

The body may comprise an oven region 204, with an oven chamber 204a having a first constricting valve 208 in the primary air inlet of the oven chamber and a second constricting valve 209 at the oven chamber outlet. The oven chamber 204a may be sealed with a tobacco or botanical and/or humectant/vapor forming medium 206 therein. The seal may be an air tight and/or liquid tight seal. The heater may be provided to the oven chamber with a heater 205. The heater 205 may be in thermal communication with the oven, for example the heater may be surrounding the oven chamber during the vaporization process. Heater may contact the oven. The heater may be wrapped around the oven. Before inhalation and before air is drawn in through a primary air inlet 221, pressure may build in the sealed oven chamber as heat is continually added. The pressure may build due to a phase change of the vaporizable material. Elevated temperature gas phases (vapor) of the tobacco or botanical and humectant/vapor forming components may be achieved by continually adding heat to the oven. This heated pressurization process may generate even higher saturation ratios when the valves 208, 209 are opened during inhalation. The higher saturation ratios may cause relatively higher particle concentrations of gas phase humectant in the resultant aerosol. When the vapor is drawn out of the oven region and into the condensation chamber 203a of the condenser 203, for example by inhalation by the user, the gas phase humectant vapors may be exposed to additional air through an aeration vent 207, and the vapors may begin to cool and condense into droplets suspended in air. As described previously the aerosol may be drawn through the mouthpiece 222 by the user. This condensation process may be further refined by adding an additional valve 210, to the aeration vent 207 to further control the air-vapor mixture process.

FIG. 2 also illustrates an exemplary embodiment of the additional components which would be found in a vaporizing device, including a power source or battery 211, a printed circuit board 212, a temperature regulator 213, and operational switches (not shown), housed within an internal electronics housing 214, to isolate them from the damaging effects of the moisture in the vapor and/or aerosol. The additional components may be found in a vaporizing device that may or may not comprise an aeration vent as described above.

In some embodiments of the vaporization device, components of the device are user serviceable, such as the power source or battery. These components may be replaceable or rechargeable.

In yet another aspect, the invention provides a device for generating an inhalable aerosol said device comprising a first body, a mouthpiece having an aerosol outlet, a condensation chamber within a condenser and an airflow inlet and channel, an attached second body, comprising a heater and oven with an oven chamber, wherein said airflow channel is upstream of the oven and the mouthpiece outlet to provide airflow through the device, across the oven, and into the condensation chamber where an auxiliary aeration vent is provided.

Figure 3:
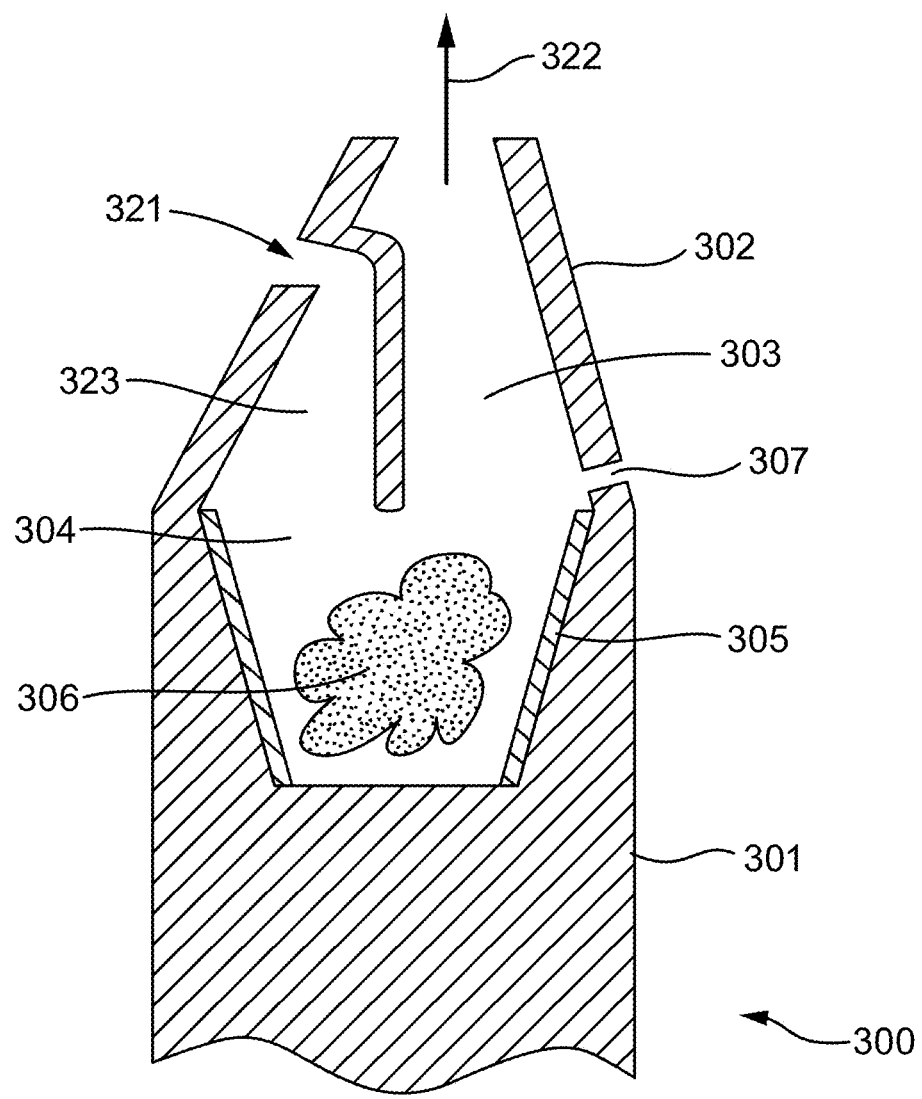
FIG. 3 is an illustrative sectional view of another exemplary vaporization device comprising a condensation chamber, air inlet and aeration vent in the mouthpiece.

FIG. 3 shows a section view of a vaporization device 300. The device 300 may comprise a body 301. The body may be connected to or integral with a mouthpiece 302 at one end. The mouthpiece may comprise a condensation chamber 303a within a condenser section 303 and an airflow inlet 321 and air channel 323. The device body may comprise a proximally located oven 304 comprising an oven chamber 304a. The oven chamber may be in the body of the device. A vapor forming medium 306 (e.g., vaporizable material) comprising tobacco or botanical and humectant vapor forming medium may be placed in the oven. The vapor forming medium may be in direct contact with an air channel 323 from the mouthpiece. The tobacco or botanical may be heated by heater 305 surrounding the oven chamber, to generate elevated temperature gas phases (vapor) of the tobacco or botanical and humectant/vapor forming components and air drawn in through a primary air inlet 321, across the oven, and into the condensation chamber 303a of the condenser region 303 due to a user puffing on the mouthpiece. Once in the condensation chamber where the gas phase humectant vapors begin to cool and condense into droplets suspended in air, additional air is allowed to enter through aeration vent 307, thus, once again creating a denser aerosol cloud having particles with a diameter of average mass of less than a typical vaporization device without an added aeration vent, before being drawn out of the mouthpiece through the aerosol outlet 322.

In some aspects of the invention, the device comprises a mouthpiece comprising an aerosol outlet at a first end of the device and an air inlet that originates a first airflow path; an oven comprising an oven chamber that is in the first airflow path and includes the oven chamber and a heater for heating a vapor forming medium in the oven chamber and for forming a vapor therein, a condenser comprising a condensation chamber in which the vapor forms the inhalable aerosol, an aeration vent that originates a second airflow path that allows air from the aeration vent to join the first airflow path prior to or within the condensation chamber and downstream from the oven chamber thereby forming a joined path, wherein the joined path is configured to deliver the inhalable aerosol formed in the condensation chamber through the aerosol outlet of the mouthpiece to a user.

In some aspects of the invention, the device may comprise a mouthpiece comprising an aerosol outlet at a first end of the device, an air inlet that originates a first airflow path, and an aeration vent that originates a second airflow path that allows air from the aeration vent to join the first airflow path; an oven comprising an oven chamber that is in the first airflow path and includes the oven chamber and a heater for heating a vapor forming medium in the oven chamber and for forming a vapor therein, a condenser comprising a condensation chamber in which the vapor forms the inhalable aerosol and wherein air from the aeration vent joins the first airflow path prior to or within the condensation chamber and downstream from the oven chamber thereby forming a joined path, wherein the joined path is configured to deliver the inhalable aerosol through the aerosol outlet of the mouthpiece to a user, as illustrated in exemplary FIG. 3.

In some aspects of the invention, the device may comprise a body with one or more separable components. For example, the mouthpiece may be separably attached to the body comprising the condensation chamber, a heater, and an oven, as illustrated in exemplary FIG. 1 or 2.

In some aspects of the invention, the device may comprise a body with one or more separable components. For example, the mouthpiece may be separably attached to the body. The mouthpiece may comprise the condensation chamber, and may be attached to or immediately adjacent to the oven and which is separable from the body comprising a heater, and the oven, as illustrated in exemplary FIG. 3.

In other aspects of the invention, the at least one aeration vent may be located in the condensation chamber of the condenser, as illustrated in exemplary FIG. 1, 2, or 3. The at least one aeration vent may comprise a third valve in the airflow path of the at least one aeration vent, as illustrated in exemplary FIG. 2. The first, second and third valve is a check valve, a clack valve, a non-return valve, or a one-way valve. In any of the preceding aspects of the invention, the first, second or third valve may be mechanically actuated, electronically actuated or manually actuated. One skilled in the art will recognize after reading this disclosure that this device may be modified in a way such that any one, or each of these openings or vents could be configured to have a different combination or variation of mechanisms as described to control airflow, pressure and temperature of the vapor created and aerosol being generated by these device configurations, including a manually operated opening or vent with or without a valve.

In some embodiments of the invention, the device may further comprise at least one of: a power source, a printed circuit board, a switch, and a temperature regulator. Alternately, one skilled in the art would recognize that each configuration previously described will also accommodate said power source (battery), switch, printed circuit board, or temperature regulator as appropriate, in the body.

In some embodiments of the invention, the device may be disposable when the supply of pre-packaged aerosol-forming media is exhausted. Alternatively, the device may be rechargeable such that the battery may be rechargeable or replaceable, and/or the aerosol-forming media may be refilled, by the user/operator of the device. Still further, in other embodiments of the invention, the device may be rechargeable such that the battery may be rechargeable or replaceable, and/or the operator may also add or refill a tobacco or botanical component, in addition to a refillable or replaceable aerosol-forming media to the device.

As illustrated in FIG. 1, 2 or 3, in some embodiments of the invention, the vaporization device comprises tobacco or a botanical heated in said oven chamber, wherein said tobacco or botanical further comprises humectants to produce an aerosol comprising gas phase components of the humectant and tobacco or botanical. In some embodiments of the invention, the gas phase humectant and tobacco or botanical vapor produced by said heated aerosol forming media 106, 206, 306 is further mixed with air from a special aeration vent 107, 207, 307 after exiting the oven area 104, 204, 304 and entering a condensation chamber 103a, 203a, 303a to cool and condense said gas phase vapors to produce a far denser, thicker aerosol comprising more particles than would have otherwise been produced without the extra cooling air, with a diameter of average mass of less than or equal to about 1 micron.

In other embodiments of the invention, each aerosol configuration produced by mixing the gas phase vapors with the cool air may comprise a different range of particles, for example; with a diameter of average mass of less than or equal to about 0.9 micron; less than or equal to about 0.8 micron; less than or equal to about 0.7 micron; less than or equal to about 0.6 micron; and even an aerosol comprising particle diameters of average mass of less than or equal to about 0.5 micron.

The possible variations and ranges of aerosol density are great in that the possible number of combinations of temperature, pressure, tobacco or botanical choices and humectant selections are numerous. However, by excluding the tobacco or botanical choices and limiting the temperatures ranges and the humectant ratios to those described herein, the inventor has demonstrated that this device will produce a far denser, thicker aerosol comprising more particles than would have otherwise been produced without the extra cooling air, with a diameter of average mass of less than or equal to about 1 micron.

In some embodiments of the invention, the humectant comprises glycerol or vegetable glycerol as a vapor-forming medium.

In still other embodiments of the invention, the humectant comprises propylene glycol as a vapor-forming medium.

In preferred embodiments of the invention, the humectant may comprise a ratio of vegetable glycerol to propylene glycol as a vapor-forming medium. The ranges of said ratio may vary between a ratio of about 100:0 vegetable glycerol to propylene glycol and a ratio of about 50:50 vegetable glycerol to propylene glycol. The difference in preferred ratios within the above stated range may vary by as little as 1, for example, said ratio may be about 99:1 vegetable glycerol to propylene glycol. However, more commonly said ratios would vary in increments of about 5, for example, about 95:5 vegetable glycerol to propylene glycol; or about 85:15 vegetable glycerol to propylene glycol; or about 55:45 vegetable glycerol to propylene glycol.

In a preferred embodiment the ratio for the vapor forming medium will be between the ratios of about 80:20 vegetable glycerol to propylene glycol, and about 60:40 vegetable glycerol to propylene glycol.

In a most preferred embodiment, the ratio for the vapor forming medium will be about 70:30 vegetable glycerol to propylene glycol.

In any of the preferred embodiments, the humectant may further comprise flavoring products. These flavorings may include enhancers comprising cocoa solids, licorice, tobacco or botanical extracts, and various sugars, to name but a few.

In some embodiments of the invention, the tobacco or botanical is heated in the oven up to its pyrolytic temperature, which as noted previously is most commonly measured in the range of 300-1000° C.

In preferred embodiments, the tobacco or botanical is heated to about 300° C. at most. In other preferred embodiments, the tobacco or botanical is heated to about 200° C. at most. In still other preferred embodiments, the tobacco or botanical is heated to about 160° C. at most. It should be noted that in these lower temperature ranges (<300° C.), pyrolysis of tobacco or botanical does not typically occur, yet vapor formation of the tobacco or botanical components and flavoring products does occur. In addition, vapor formation of the components of the humectant, mixed at various ratios will also occur, resulting in nearly complete vaporization, depending on the temperature, since propylene glycol has a boiling point of about 180°-190° C. and vegetable glycerin will boil at approximately 280°-290° C.

In still other preferred embodiments, the aerosol produced by said heated tobacco or botanical and humectant is mixed with air provided through an aeration vent.

In still other preferred embodiments, the aerosol produced by said heated tobacco or botanical and humectant mixed with air, is cooled to a temperature of about 50°-70° C. at most, and even as low as 35° C. before exiting the mouthpiece, depending on the air temperature being mixed into the condensation chamber. In some embodiments, the temperature is cooled to about 35°-55° C. at most, and may have a fluctuating range of ± about 10° C. or more within the overall range of about 35°-70° C.

In yet another aspect, the invention provides a vaporization device for generating an inhalable aerosol comprising a unique oven configuration, wherein said oven comprises an access lid and an auxiliary aeration vent located within the airflow channel immediately downstream of the oven and before the aeration chamber. In this configuration, the user may directly access the oven by removing the access lid, providing the user with the ability to recharge the device with vaporization material.

In addition, having the added aeration vent in the airflow channel immediately after the oven and ahead of the vaporization chamber provides the user with added control over the amount of air entering the aeration chamber downstream and the cooling rate of the aerosol before it enters the aeration chamber.

Figure 4A:
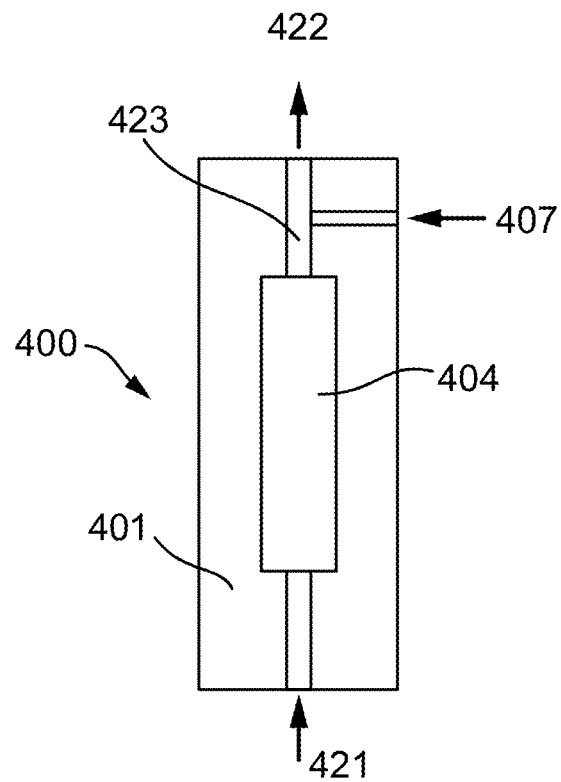
FIGS. 4A-4C is an illustrative example of an oven section of another exemplary vaporization device configuration with a access lid, comprising an oven having an air inlet, air outlet, and an additional aeration vent in the airflow pathway, after the oven.
Figure 4B:
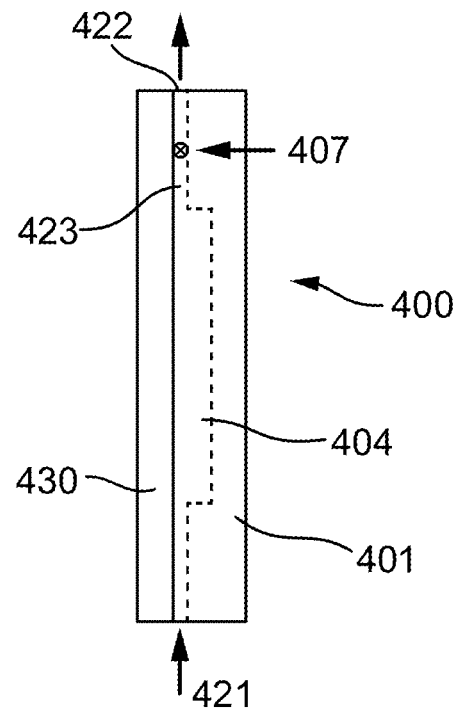
Figure 4C:
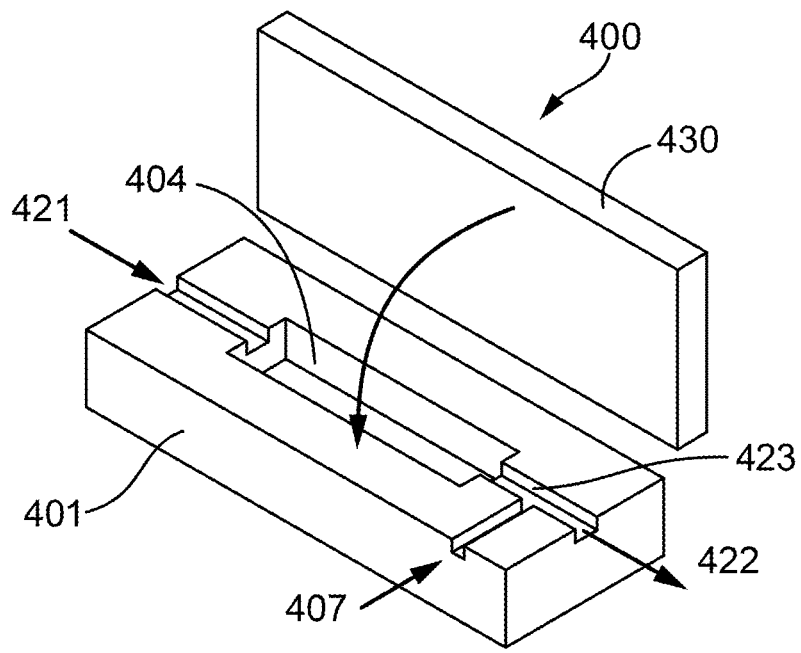

As noted in FIGS. 4A-4C, the device 400 may comprise a body 401, having an air inlet 421 allowing initial air for the heating process into the oven region 404. After heating the tobacco or botanical, and humectant (heater not shown), the gas phase humectant vapor generated may travel down the airflow channel 423, passing the added aeration vent 407 wherein the user may selectively increase airflow into the heated vapor. The user may selectively increase and/or decrease the airflow to the heated vapor by controlling a valve in communication with the aeration vent 407. In some cases, the device may not have an aeration vent. Airflow into the heated vapor through the aeration vent may decrease the vapor temperature before exiting the airflow channel at the outlet 422, and increase the condensation rate and vapor density by decreasing the diameter of the vapor particles within the aeration chamber (not shown), thus producing a thicker, denser vapor compared to the vapor generated by a device without the aeration vent. The user may also access the oven chamber 404a to recharge or reload the device 400, through an access lid 430 provided therein, making the device user serviceable. The access lid may be provided on a device with or without an aeration vent.

Provided herein is a method for generating an inhalable aerosol, the method comprising: providing an vaporization device, wherein said device produces a vapor comprising particle diameters of average mass of about 1 micron or less, wherein the vapor is formed by heating a vapor forming medium in an oven chamber of the device to a first temperature below the pyrolytic temperature of the vapor forming medium, and cooling the vapor in a condensation chamber to a temperature below the first temperature, before exiting an aerosol outlet of said device.

In some embodiments the vapor may be cooled by mixing relatively cooler air with the vapor in the condensation chamber during the condensation phase, after leaving the oven, where condensation of the gas phase humectants occurs more rapidly due to high saturation ratios being achieved at the moment of aeration, producing a higher concentration of smaller particles, with fewer by-products, in a denser aerosol, than would normally occur in a standard vaporization or aerosol generating device.

In some embodiments, formation of an inhalable aerosol is a two step process. The first step occurs in the oven where the tobacco or botanical and humectant blend is heated to an elevated temperature. At the elevated temperature, evaporation happens faster than at room temperature and the oven chamber fills with the vapor phase of the humectants. The humectant will continue to evaporate until the partial pressure of the humectant is equal to the saturation pressure. At this point, the gas is said to have a saturation ratio of 1 ($S=P_{partial}/P_{sat}$).

In the second step, the gas leaves the oven chamber, passes to a condensation chamber in a condenser and begins to cool. As the gas phase vapor cools, the saturation pressure also goes down, causing the saturation ratio to rise, and the vapor to condensate, forming droplets. When cooling air is introduced, the large temperature gradient between the two fluids mixing in a confined space leads to very rapid cooling, causing high saturation ratios, small particles, and higher concentrations of smaller particles, forming a thicker, denser vapor cloud.

Provided herein is a method for generating an inhalable aerosol comprising: a vaporization device having a body with a mouthpiece at one end, and an attached body at the other end comprising; a condenser with a condensation chamber, a heater, an oven with an oven chamber, and at least one aeration vent provided in the body, downstream of the oven, and upstream of the mouthpiece, wherein tobacco or botanical comprising a humectant is heated in said oven chamber to produce a vapor comprising gas phase humectants.

As previously described, a vaporization device having an auxiliary aeration vent located in the condensation chamber capable of supplying cool air (relative to the heated gas components) to the gas phase vapors and tobacco or botanical components exiting the oven region, may be utilized to provide a method for generating a far denser, thicker aerosol comprising more particles than would have otherwise been produced without the extra cooling air, with a diameter of average mass of less than or equal to about 1 micron.

In another aspect, provided herein is a method for generating an inhalable aerosol comprising: a vaporization device, having a body with a mouthpiece at one end, and an attached body at the other end comprising: a condenser with a condensation chamber, a heater, an oven with an oven chamber, wherein said oven chamber further comprises a first valve in the airflow path at the inlet end of the oven chamber, and a second valve at the outlet end of the oven chamber; and at least one aeration vent provided in said body, downstream of the oven, and upstream of the mouthpiece wherein tobacco or botanical comprising a humectant is heated in said oven chamber to produce a vapor comprising gas phase humectants.

As illustrated in exemplary FIG. 2, by sealing the oven chamber 204a with a tobacco or botanical and humectant vapor forming medium 206 therein, and applying heat with the heater 205 during the vaporization process, before inhalation and air is drawn in through a primary air inlet 221, the pressure will build in the oven chamber as heat is continually added with an electronic heating circuit generated through the combination of the battery 211, printed circuit board 212, temperature regulator 213, and operator controlled switches (not shown), to generate even greater elevated temperature gas phase humectants (vapor) of the tobacco or botanical and humectant vapor forming components. This heated pressurization process generates even higher saturation ratios when the valves 208, 209 are opened during inhalation, which cause higher particle concentrations in the resultant aerosol, when the vapor is drawn out of the oven region and into the condensation chamber 203a, where they are again exposed to additional air through an aeration vent 207, and the vapors begin to cool and condense into droplets suspended in air, as described previously before the aerosol is withdrawn through the mouthpiece 222. The inventor also notes that this condensation process may be further refined by adding an additional valve 210, to the aeration vent 207 to further control the air-vapor mixture process.

In some embodiments of any one of the inventive methods, the first, second and/or third valve is a one-way valve, a check valve, a clack valve, or a non-return valve. The first, second and/or third valve may be mechanically actuated. The first, second and/or third valve may be electronically actuated. The first, second and/or third valve may be automatically actuated. The first, second and/or third valve may be manually actuated either directly by a user or indirectly in response to an input command from a user to a control system that actuates the first, second and/or third valve.

In other aspects of the inventive methods, said device further comprises at least one of: a power source, a printed circuit board, or a temperature regulator.

In any of the preceding aspects of the inventive method, one skilled in the art will recognize after reading this disclosure that this method may be modified in a way such that any one, or each of these openings or vents could be configured to have a different combination or variation of mechanisms or electronics as described to control airflow, pressure and temperature of the vapor created and aerosol being generated by these device configurations, including a manually operated opening or vent with or without a valve.

The possible variations and ranges of aerosol density are great in that the possible number of temperature, pressure, tobacco or botanical choices and humectant selections and combinations are numerous. However, by excluding the tobacco or botanical choices and limiting the temperatures to within the ranges and the humectant ratios described herein, the inventor has demonstrated a method for generating a far denser, thicker aerosol comprising more particles than would have otherwise been produced without the extra cooling air, with a diameter of average mass of less than or equal to 1 micron.

In some embodiments of the inventive methods, the humectant comprises a ratio of vegetable glycerol to propylene glycol as a vapor-forming medium. The ranges of said ratio will vary between a ratio of about 100:0 vegetable glycerol to propylene glycol and a ratio of about 50:50 vegetable glycerol to propylene glycol. The difference in preferred ratios within the above stated range may vary by as little as 1, for example, said ratio may be about 99:1 vegetable glycerol to propylene glycol. However, more commonly said ratios would vary in increments of 5, for example, about 95:5 vegetable glycerol to propylene glycol; or about 85:15 vegetable glycerol to propylene glycol; or about 55:45 vegetable glycerol to propylene glycol.

Because vegetable glycerol is less volatile than propylene glycol, it will recondense in greater proportions. A humectant with higher concentrations of glycerol will generate a thicker aerosol. The addition of propylene glycol will lead to an aerosol with a reduced concentration of condensed phase particles and an increased concentration of vapor phase effluent. This vapor phase effluent is often perceived as a tickle or harshness in the throat when the aerosol is inhaled. To some consumers, varying degrees of this sensation may be desirable. The ratio of vegetable glycerol to propylene glycol may be manipulated to balance aerosol thickness with the right amount of "throat tickle."

In a preferred embodiment of the method, the ratio for the vapor forming medium will be between the ratios of about 80:20 vegetable glycerol to propylene glycol, and about 60:40 vegetable glycerol to propylene glycol.

In a most preferred embodiment of the method, the ratio for the vapor forming medium will be about 70:30 vegetable glycerol to propylene glycol. On will envision that there will be blends with varying ratios for consumers with varying preferences.

In any of the preferred embodiments of the method, the humectant further comprises flavoring products. These flavorings include enhancers such as cocoa solids, licorice, tobacco or botanical extracts, and various sugars, to name a few.

In some embodiments of the method, the tobacco or botanical is heated to its pyrolytic temperature.

In preferred embodiments of the method, the tobacco or botanical is heated to about 300° C. at most.

In other preferred embodiments of the method, the tobacco or botanical is heated to about 200° C. at most. In still other embodiments of the method, the tobacco or botanical is heated to about 160° C. at most.

As noted previously, at these lower temperatures, (<300° C.), pyrolysis of tobacco or botanical does not typically occur, yet vapor formation of the tobacco or botanical components and flavoring products does occur. As may be inferred from the data supplied by Baker et al., an aerosol produced at these temperatures is also substantially free from Hoffman analytes or at least 70% less Hoffman analytes than a common tobacco or botanical cigarette and scores significantly better on the Ames test than a substance generated by burning a common cigarette. In addition, vapor formation of the components of the humectant, mixed at various ratios will also occur, resulting in nearly complete vaporization, depending on the temperature, since propylene glycol has a boiling point of about 180°-190° C. and vegetable glycerin will boil at approximately 280°-290° C.

In any one of the preceding methods, said inhalable aerosol produced by tobacco or a botanical comprising a humectant and heated in said oven produces an aerosol comprising gas phase humectants is further mixed with air provided through an aeration vent.

In any one of the preceding methods, said aerosol produced by said heated tobacco or botanical and humectant mixed with air, is cooled to a temperature of about 50°-70° C., and even as low as 35° C., before exiting the mouthpiece. In some embodiments, the temperature is cooled to about 35°-55° C. at most, and may have a fluctuating range of ± about 10° C. or more within the overall range of about 35°-70° C.

In some embodiments of the method, the vapor comprising gas phase humectant may be mixed with air to produce an aerosol comprising particle diameters of average mass of less than or equal to about 1 micron.

In other embodiments of the method, each aerosol configuration produced by mixing the gas phase vapors with the cool air may comprise a different range of particles, for example; with a diameter of average mass of less than or equal to about 0.9 micron; less than or equal to about 0.8 micron; less than or equal to about 0.7 micron; less than or equal to about 0.6 micron; and even an aerosol comprising particle diameters of average mass of less than or equal to about 0.5 micron.

Cartridge Design and Vapor Generation from Material in Cartridge

In some cases, a vaporization device may be configured to generate an inhalable aerosol. A device may be a self-contained vaporization device. The device may comprise an elongated body which functions to complement aspects of a separable and recyclable cartridge with air inlet channels, air passages, multiple condensation chambers, flexible heater contacts, and multiple aerosol outlets. Additionally, the cartridge may be configured for ease of manufacture and assembly.

Provided herein is a vaporization device for generating an inhalable aerosol. The device may comprise a device body, a separable cartridge assembly further comprising a heater, at least one condensation chamber, and a mouthpiece. The device provides for compact assembly and disassembly of components with detachable couplings; overheat shut-off protection for the resistive heating element; an air inlet passage (an enclosed channel) formed by the assembly of the device body and a separable cartridge; at least one condensation chamber within the separable cartridge assembly; heater contacts; and one or more refillable, reusable, and/or recyclable components.

Figure 7A:
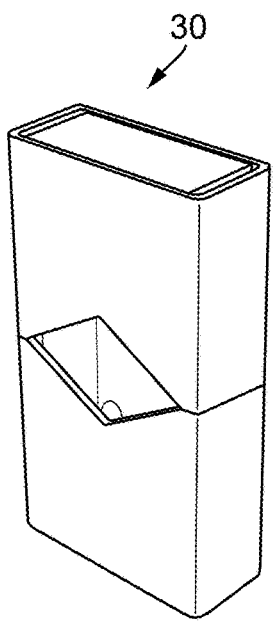
FIG. 7A is an illustrative isometric view of an assembled cartridge.

Provided herein is a device for generating an inhalable aerosol comprising: a device body comprising a cartridge receptacle; a cartridge comprising: a storage compartment, and a channel integral to an exterior surface of the cartridge, and an air inlet passage formed by the channel and an internal surface of the cartridge receptacle when the cartridge is inserted into the cartridge receptacle. The cartridge may be formed from a metal, plastic, ceramic, and/or composite material. The storage compartment may hold a vaporizable material. FIG. 7A shows an example of a cartridge 30 for use in the device. The vaporizable material may be a liquid at or near room temperature. In some cases the vaporizable material may be a liquid below room temperature. The channel may form a first side of the air inlet passage, and an internal surface of the cartridge receptacle may form a second side of the air inlet passage, as illustrated in various non-limiting aspects of FIGS. 5-6D, 7C, 8A, 8B, and 10A Provided herein is a device for generating an inhalable aerosol. The device may comprise a body that houses, contains, and or integrates with one or more components of the device. The device body may comprise a cartridge receptacle. The cartridge receptacle may comprise a channel integral to an interior surface of the cartridge receptacle; and an air inlet passage formed by the channel and an external surface of the cartridge when the cartridge is inserted into the cartridge receptacle. A cartridge may be fitted and/or inserted into the cartridge receptacle. The cartridge may have a fluid storage compartment. The channel may form a first side of the air inlet passage, and an external surface of the cartridge forms a second side of the air inlet passage. The channel may comprise at least one of: a groove; a trough; a track; a depression; a dent; a furrow; a trench; a crease; and a gutter. The integral channel may comprise walls that are either recessed into the surface or protrude from the surface where it is formed. The internal side walls of the channel may form additional sides of the air inlet passage. The channel may have a round, oval, square, rectangular, or other shaped cross section. The channel may have a closed cross section. The channel may be about 0.1 cm, 0.5 cm, 1 cm, 2 cm, or 5 cm wide. The channel may be about 0.1 mm, 0.5 mm, 1 mm, 2 mm, or 5 mm deep. The channel may be about 0.1 cm, 0.5 cm, 1 cm, 2 cm, or 5 cm long. There may be at least 1 channel.

In some embodiments, the cartridge may further comprise a second air passage in fluid communication with the air inlet passage to the fluid storage compartment, wherein the second air passage is formed through the material of the cartridge.

FIGS. 5-7C show various views of a compact electronic device assembly 10 for generating an inhalable aerosol. The compact electronic device 10 may comprise a device body 20 with a cartridge receptacle 21 for receiving a cartridge 30. The device body may have a square or rectangular cross section. Alternatively, the cross section of the body may be any other regular or irregular shape. The cartridge receptacle may be shaped to receive an opened cartridge 30a or "pod". The cartridge may be opened when a protective cap is removed from a surface of the cartridge. In some cases, the cartridge may be opened when a hole or opening is formed on a surface of the cartridge. The pod 30a may be inserted into an open end of the cartridge receptacle 21 so that an exposed first heater contact tips 33a on the heater contacts 33 of the pod make contact with the second heater contacts 22 of the device body, thus forming the device assembly 10.

Figure 14:
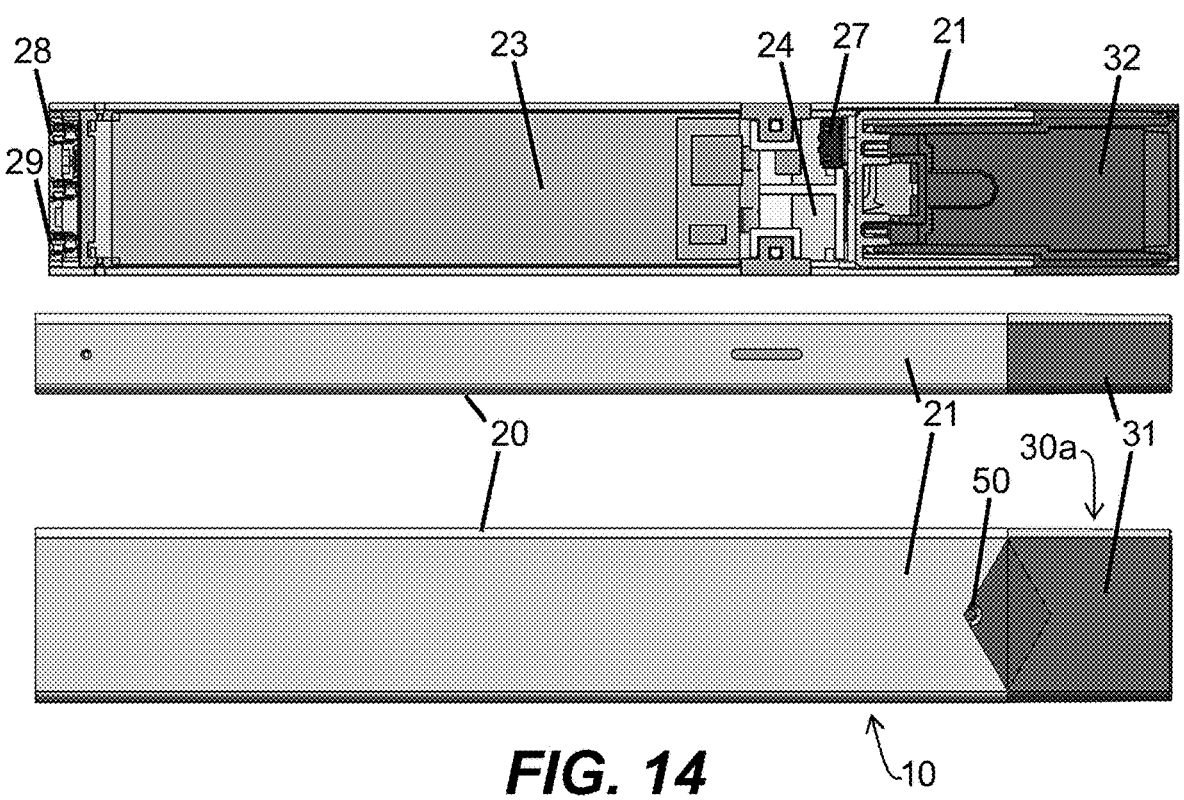
FIG. 14 illustrates front, side and section views of the assembled inhalable aerosol device.

Referring to FIG. 14, it is apparent in the plan view that when the pod 30a is inserted into the notched body of the cartridge receptacle 21, the channel air inlet 50 is left exposed. The size of the channel air inlet 50 may be varied by altering the configuration of the notch in the cartridge receptacle 21.

The device body may further comprise a rechargeable battery, a printed circuit board (PCB) 24 containing a microcontroller with the operating logic and software instructions for the device, a pressure switch 27 for sensing the user's puffing action to activate the heater circuit, an indicator light 26, charging contacts (not shown), and an optional charging magnet or magnetic contact (not shown). The cartridge may further comprise a heater 36. The heater may be powered by the rechargeable battery. The temperature of the heater may be controlled by the microcontroller. The heater may be attached to a first end of the cartridge.

In some embodiments, the heater may comprise a heater chamber 37, a first pair of heater contacts 33, 33', a fluid wick 34, and a resistive heating element 35 in contact with the wick. The first pair of heater contacts may comprise thin plates affixed about the sides of the heater chamber. The fluid wick and resistive heating element may be suspended between the heater contacts.

In some embodiments, there may be two or more resistive heating elements 35, 35' and two or more wicks 34, 34'. In some of the embodiments, the heater contact 33 may comprise: a flat plate; a male contact; a female receptacle, or both; a flexible contact and/or copper alloy or another electrically conductive material. The first pair of heater contacts may further comprise a formed shape that may comprise a tab (e.g., flange) having a flexible spring value that extends out of the heater to complete a circuit with the device body. The first pair of heater contact may be a heat sink that absorb and dissipate excessive heat produced by the resistive heating element. Alternatively, the first pair of heater contacts may be a heat shield that protects the heater chamber from excessive heat produced by the resistive heating element. The first pair of heater contacts may be press-fit to an attachment feature on the exterior wall of the first end of the cartridge. The heater may enclose a first end of the cartridge and a first end of the fluid storage compartment.

Figure 7B:
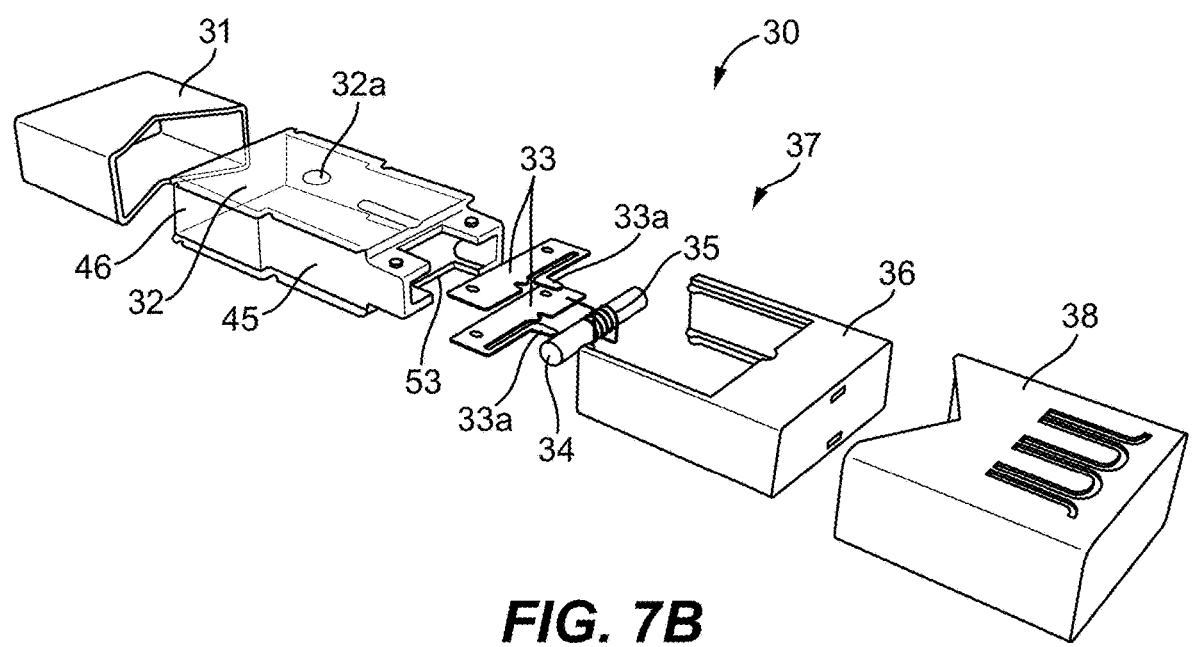
FIG. 7B is an illustrative exploded isometric view of a cartridge assembly
Figure 7C:
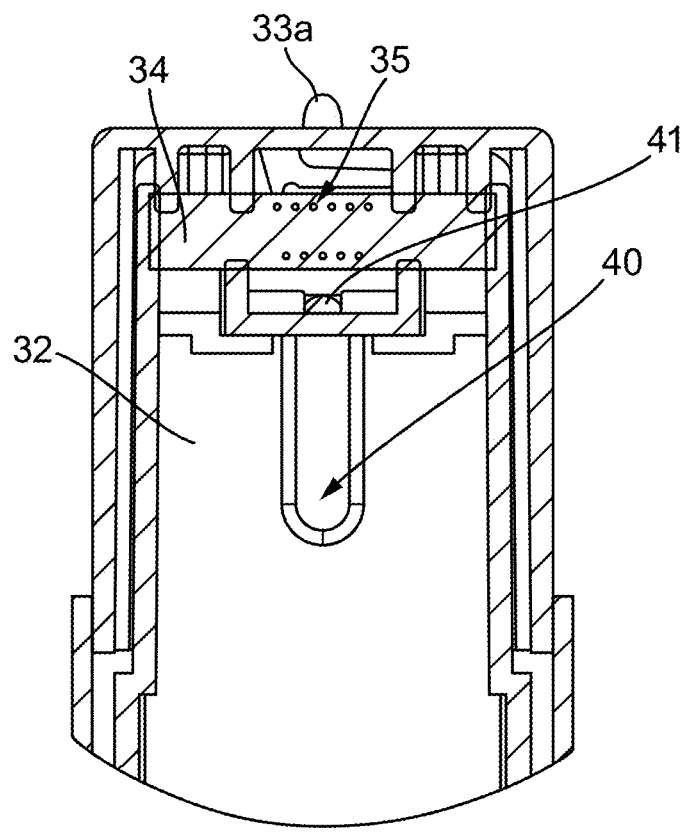
FIG. 7C is a side section view of FIG. 3A illustrating the inlet channel, inlet hole and relative placement of the wick, resistive heating element, and heater contacts, and the heater chamber inside of the heater.

As illustrated in the exploded assembly of FIG. 7B, a heater enclosure may comprises two or more heater contacts 33, each comprising a flat plate which may be machined or stamped from a copper alloy or similar electrically conductive material. The flexibility of the tip is provided by the cut-away clearance feature 33b created below the male contact point tip 33a which capitalizes on the inherent spring capacity of the metal sheet or plate material. Another advantage and improvement of this type of contact is the reduced space requirement, simplified construction of a spring contact point (versus a pogo pin) and the easy of assembly. The heater may comprise a first condensation chamber. The heater may comprise more one or more additional condensation chambers in addition to the first condensation chamber. The first condensation chamber may be formed along an exterior wall of the cartridge.

In some cases, the cartridge (e.g., pod) is configured for ease of manufacturing and assembly. The cartridge may comprise an enclosure. The enclosure may be a tank. The tank may comprise an interior fluid storage compartment 32. The interior fluid storage compartment 32 which is open at one or both ends and comprises raised rails on the side edges 45b and 46b. The cartridge may be formed from plastic, metal, composite, and/or a ceramic material. The cartridge may be rigid or flexible.

The tank may further comprise a set of first heater contact plates 33 formed from copper alloy or another electrically conductive material, having a thin cut-out 33b below the contact tips 33a (to create a flexible tab) which are affixed to the sides of the first end of the tank and straddle the open-sided end 53 of the tank. The plates may affix to pins, or posts as shown in FIG. 7B or 5, or may be attached by other common means such as compression beneath the enclosure 36. A fluid wick 34 having a resistive heating element 35 wrapped around it, is placed between the first heater contact plates 33, and attached thereto. A heater 36, comprising raised internal edges on the internal end (not shown), a thin mixing zone (not shown), and primary condensation channel covers 45a that slide over the rails 45b on the sides of the tank on the first half of the tank, creating a primary condensation channel/chamber 45. In addition, a small male snap feature 39b located at the end of the channel cover is configured fall into a female snap feature 39a, located mid-body on the side of the tank, creating a snap-fit assembly.

As will be further clarified below, the combination of the open-sided end 53, the protruding tips 33a of the contact plates 33, the fluid wick 34 having a resistive heating element 35, enclosed in the open end of the fluid storage tank, under the heater 36, with a thin mixing zone therein, creates a efficient heater system. In addition, the primary condensation channel covers 45a which slide over the rails 45b on the sides of the tank create an integrated, easily assembled, primary condensation chamber 45, all within the heater at the first end of the cartridge 30 or pod 30a.

Figure 9:
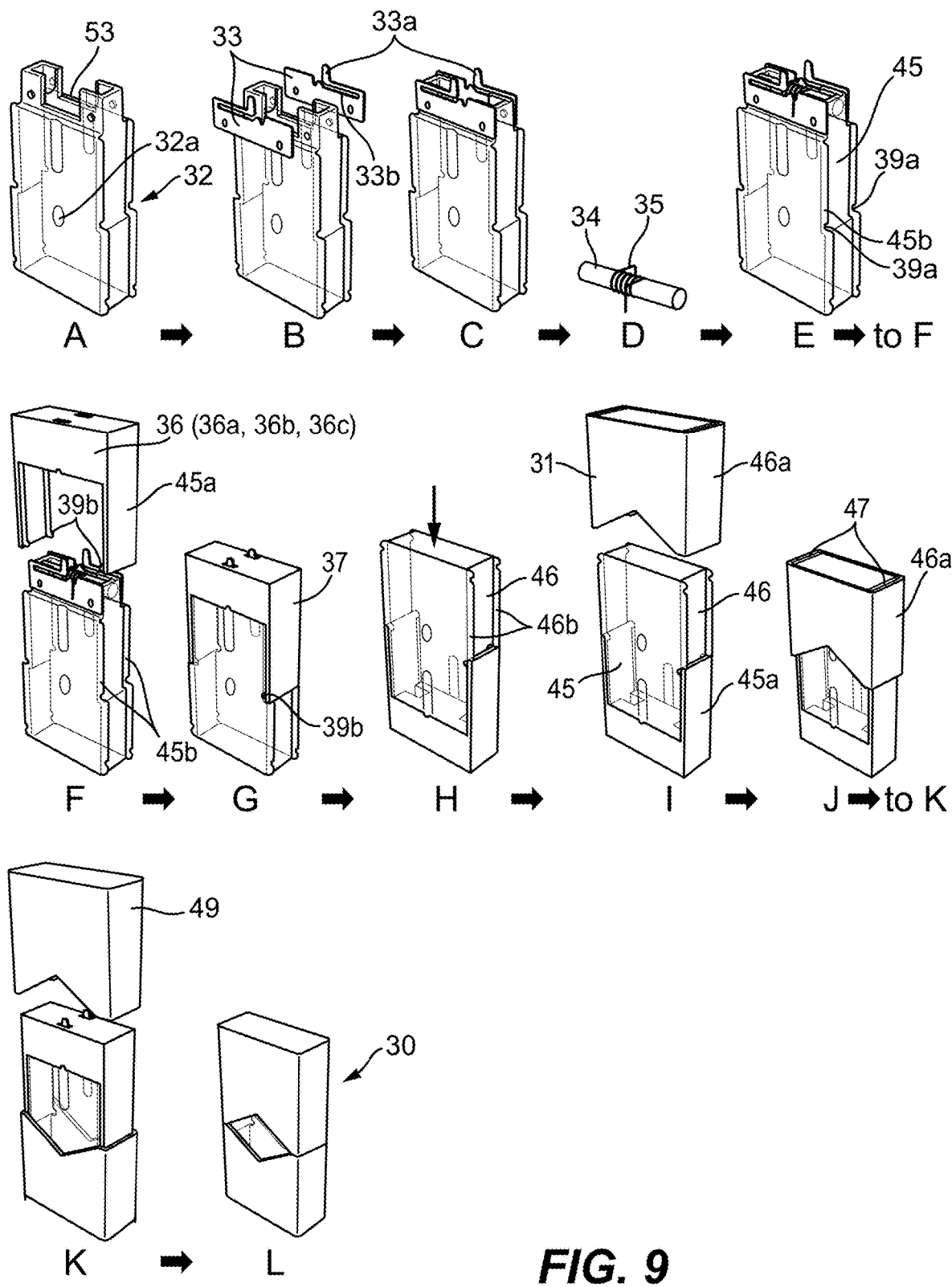
FIG. 9 is an illustrative sequence of the assembly method for the cartridge.

In some embodiments of the device, as illustrated in FIG. 9, the heater may encloses at least a first end of the cartridge. The enclosed first end of the cartridge may include the heater and the interior fluid storage compartment. In some embodiments, the heater further comprises at least one first condensation chamber 45.

FIG. 9 shows diagramed steps that mat be performed to assemble a cartomizer and/or mouthpiece. In A-B the fluid storage compartment 32a may be oriented such that the heater inlet 53 faces upward. The heater contacts 33 may be inserted into the fluid storage compartment. Flexible tabs 33a may be inserted into the heater contacts 33. In a step D the resistive heating element 35 may be wound on to the wick 34. In step E the wick 34 and heater 35 may be placed on the fluid storage compartment. One or more free ends of the heater may sit outside the heater contacts. The one or more free ends may be soldered in place, rested in a groove, or snapped into a fitted location. At least a fraction of the one or more free ends may be in communication with the heater contacts 33. In a step F the heater enclosure 36 may be snapped in place. The heater enclosure 36 may be fitted on the fluid storage compartment. Step G shows the heater enclosure 36 is in place on the fluid storage compartment. In step H the fluid storage compartment can be flipped over. In step I the mouthpiece 31 can be fitted on the fluid storage compartment. Step J shows the mouthpiece 31 in place on the fluid storage compartment. In step K an end 49 can be fitted on the fluid storage compartment opposite the mouthpiece. Step L shows a fully assembled cartridge 30. FIG. 7B shows an exploded view of the assembled cartridge 30.

Depending on the size of the heater and/or heater chamber, the heater may have more than one wick 34 and resistive heating element 35.

In some embodiments, the first pair of heater contacts 33 further comprises a formed shape that comprises a tab 33a having a flexible spring value that extends out of the heater. In some embodiments, the cartridge 30 comprises heater contacts 33 which are inserted into the cartridge receptacle 21 of the device body 20 wherein, the flexible tabs 33a insert into a second pair of heater contacts 22 to complete a circuit with the device body. The first pair of heater contacts 33 may be a heat sink that absorbs and dissipates excessive heat produced by the resistive heating element 35. The first pair of heater contacts 33 may be a heat shield that protects the heater chamber from excessive heat produced by the resistive heating element 35. The first pair of heater contacts may be press-fit to an attachment feature on the exterior wall of the first end of the cartridge. The heater 36 may enclose a first end of the cartridge and a first end of the fluid storage compartment 32a. The heater may comprise a first condensation chamber 45. The heater may comprise at least one additional condensation chamber 45, 45',45", etc. The first condensation chamber may be formed along an exterior wall of the cartridge.

In still other embodiments of the device, the cartridge may further comprise a mouthpiece 31, wherein the mouthpiece comprises at least one aerosol outlet channel/secondary condensation chamber 46; and at least one aerosol outlet 47. The mouthpiece may be attached to a second end of the cartridge. The second end of the cartridge with the mouthpiece may be exposed when the cartridge is inserted in the device. The mouthpiece may comprise more than one second condensation chamber 46, 46',46", etc. The second condensation chamber is formed along an exterior wall of the cartridge.

The mouthpiece 31 may enclose the second end of the cartridge and interior fluid storage compartment. The partially assembled (e.g., mouthpiece removed) unit may be inverted and filled with a vaporizable fluid through the opposite, remaining (second) open end. Once filled, a snap-on mouthpiece 31 that also closes and seals the second end of the tank is inserted over the end. It also comprises raised internal edges (not shown), and aerosol outlet channel covers 46a that may slide over the rails 46b located on the sides of the second half of the tank, creating aerosol outlet channels/secondary condensation chambers 46. The aerosol outlet channels/secondary condensation chambers 46 slide over the end of primary condensation chamber 45, at a transition area 57, to create a junction for the vapor leaving the primary chamber and proceed out through the aerosol outlets 47, at the end of the aerosol outlet channels 46 and user-end of the mouthpiece 31.

The cartridge may comprise a first condensation chamber and a second condensation chamber 45, 46. The cartridge may comprise more than one first condensation chamber and more than one second condensation chamber 45, 46, 45',46', etc.

In some embodiments of the device, a first condensation chamber 45 may be formed along the outside of the cartridge fluid storage compartment 31. In some embodiments of the device an aerosol outlet 47 exists at the end of aerosol outlet chamber 46. In some embodiments of the device, a first and second condensation chamber 45, 46 may be formed along the outside of one side of the cartridge fluid storage compartment 31. In some embodiments the second condensation chamber may be an aerosol outlet chamber. In some embodiments another pair of first and/or second condensation chambers 45',46' is formed along the outside of the cartridge fluid storage compartment 31 on another side of the device. In some embodiments another aerosol outlet 47' will also exist at the end of the second pair of condensation chambers 45',46'.

Figure 10A:
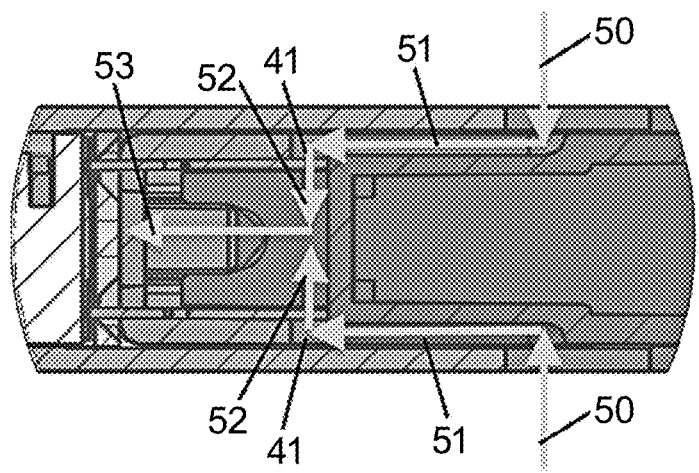
FIGS. 10A-10C are illustrative sequences showing the airflow/vapor path for the cartridge.
Figure 10B:
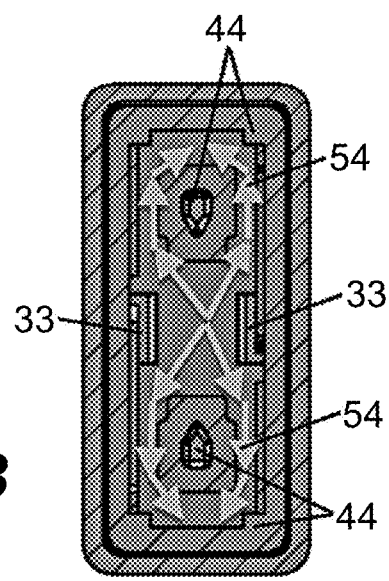
Figure 10C:
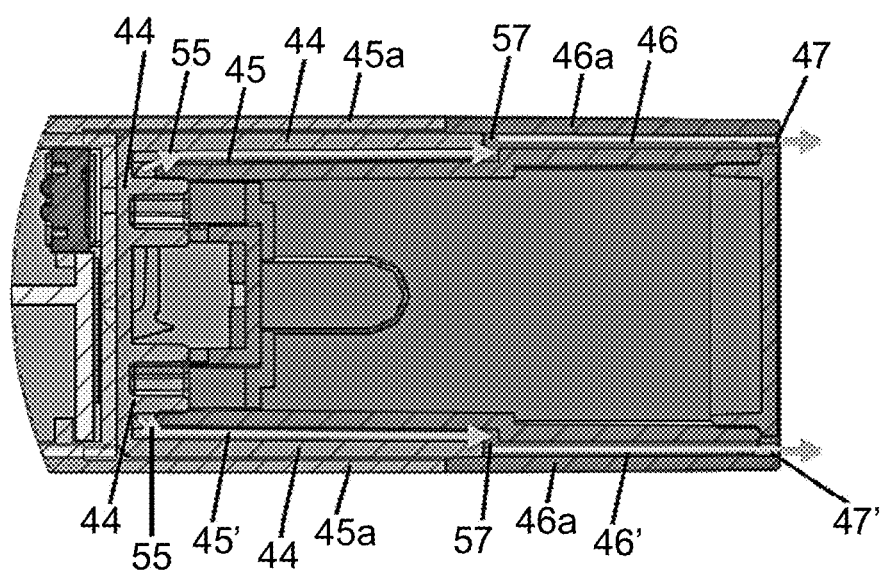

In any one of the embodiments, the first condensation chamber and the second condensation chamber may be in fluid communication as illustrated in FIG. 10C.

In some embodiments, the mouthpiece may comprise an aerosol outlet 47 in fluid communication with the second condensation chamber 46. The mouthpiece may comprise more than one aerosol outlet 47, 47' in fluid communication with more than one the second condensation chamber 46, 46'. The mouthpiece may enclose a second end of the cartridge and a second end of the fluid storage compartment.

In each of the embodiments described herein, the cartridge may comprise an airflow path comprising: an air inlet passage; a heater; at least a first condensation chamber; an aerosol outlet chamber, and an outlet port. In some of the embodiments described herein, the cartridge comprises an airflow path comprising: an air inlet passage; a heater; a first condensation chamber; a secondary condensation chamber; and an outlet port.

In still other embodiments described herein the cartridge may comprise an airflow path comprising at least one air inlet passage; a heater; at least one first condensation chamber; at least one secondary condensation chamber; and at least one outlet port.

Figure 8A:
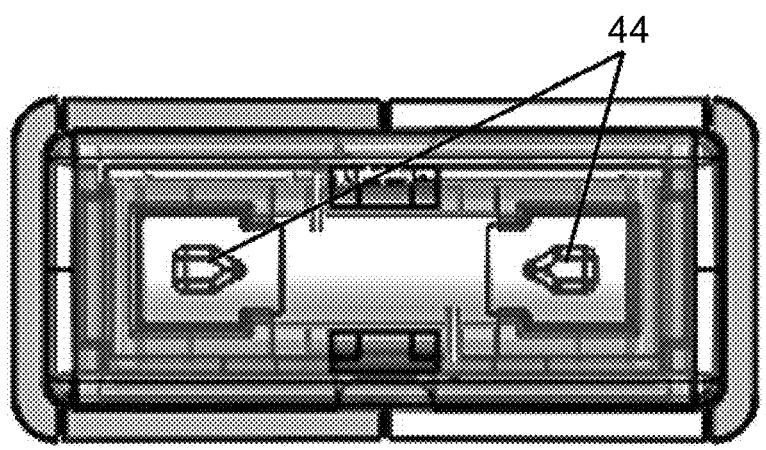
FIG. 8A is an illustrative end section view of an exemplary cartridge inside the heater.
Figure 8B:
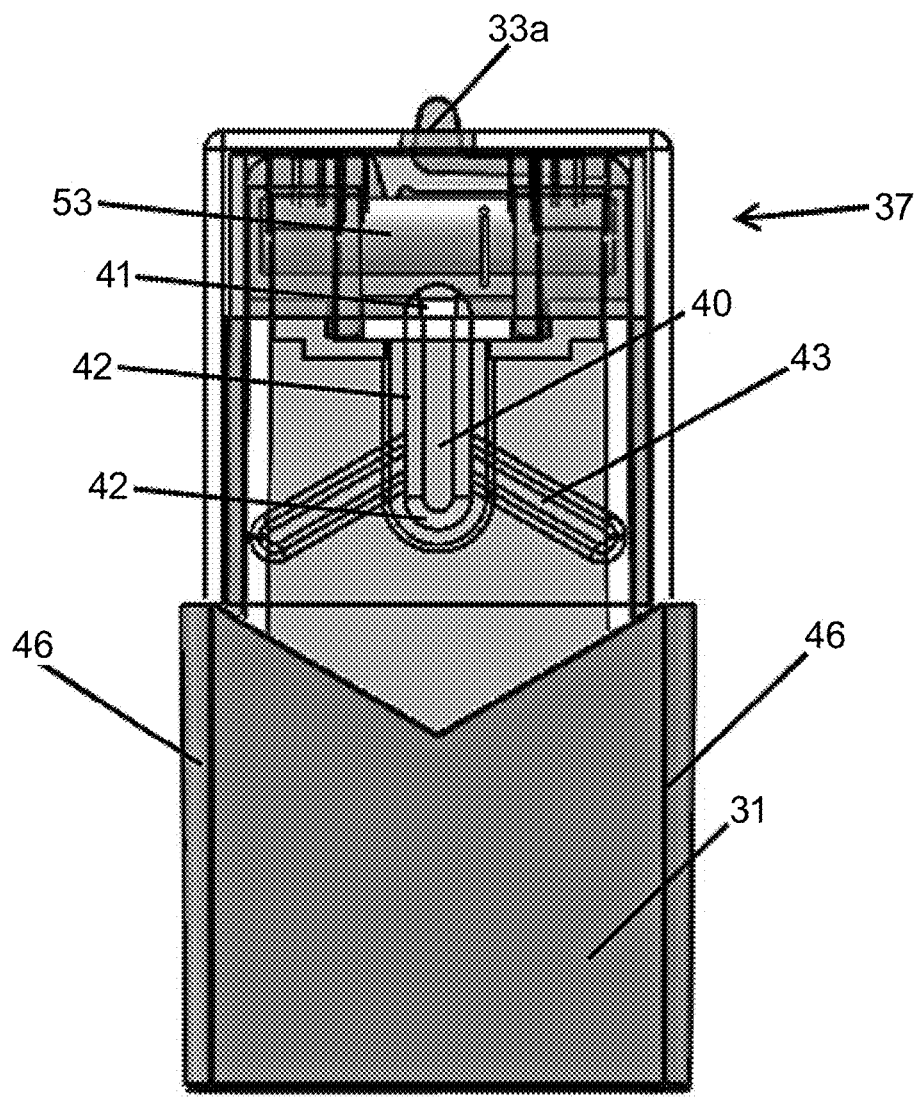
FIG. 8B is an illustrative side view of the cartridge with the cap removed and heater shown in shadow/outline.

As illustrated in FIGS. 10A-10C, an airflow path is created when the user draws on the mouthpiece 31 to create a suction (e.g., a puff), which essentially pulls air through the channel air inlet opening 50, through the air inlet passage 51, and into the heater chamber 37 through the second air passage (tank air inlet hole) 41 at the tank air inlet 52, then into the heater inlet 53. At this point, the pressure sensor has sensed the user's puff, and activated the circuit to the resistive heating element 35, which in turn, begins to generate vapor from the vapor fluid (e-juice). As air enters the heater inlet 53, it begins to mix and circulate in a narrow chamber above and around the wick 34 and between the heater contacts 33, generating heat, and dense, concentrated vapor as it mixes in the flow path 54 created by the sealing structure obstacles 44. FIG. 8A shows a detailed view of the sealing structure obstacles 44. Ultimately the vapor may be drawn, out of the heater along an airpath 55 near the shoulder of the heater and into the primary condensation chamber 45 where the vapor expands and begins to cool. As the expanding vapor moves along the airflow path, it makes a transition from the primary condensation chamber 45 through a transition area 57, creating a junction for the vapor leaving the primary chamber, and entering the second vapor chamber 46, and proceeds out through the aerosol outlets 47, at the end of the mouthpiece 31 to the user.

As illustrated in FIGS. 10A-10C, the device may have a dual set of air inlet passages 50-53, dual first condensation chambers 55/45, dual second condensation chambers and aeration channels 57/46, and/or dual aerosol outlet vents 47.

Alternatively, the device may have an airflow path comprising: an air inlet passage 50, 51; a second air passage 41; a heater chamber 37; a first condensation chamber 45; a second condensation chamber 46; and/or an aerosol outlet 47.

In some cases, the devise may have an airflow path comprising: more than one air inlet passage; more than one second air passage; a heater chamber; more than one first condensation chamber; more than one second condensation chamber; and more than one aerosol outlet as clearly illustrated in FIGS. 10A-10C.

In any one of the embodiments described herein, the heater 36 may be in fluid communication with the internal fluid storage compartment 32a.

In each of the embodiments described herein, the fluid storage compartment 32 is in fluid communication with the heater chamber 37, wherein the fluid storage compartment is capable of retaining condensed aerosol fluid, as illustrated in FIGS. 10A, 10C and 14.

In some embodiments of the device, the condensed aerosol fluid may comprise a nicotine formulation. In some embodiments, the condensed aerosol fluid may comprise a humectant. In some embodiments, the humectant may comprise propylene glycol. In some embodiments, the humectant may comprise vegetable glycerin.

In some cases, the cartridge may be detachable from the device body. In some embodiments, the cartridge receptacle and the detachable cartridge may form a separable coupling. In some embodiments the separable coupling may comprise a friction assembly. As illustrated in FIGS. 11-14, the device may have a press-fit (friction) assembly between the cartridge pod 30a and the device receptacle. Additionally, a dent/friction capture such as 43 may be utilized to capture the pod 30a to the device receptacle or to hold a protective cap 38 on the pod, as further illustrated in FIG. 8B.

In other embodiments, the separable coupling may comprise a snap-fit or snap-lock assembly. In still other embodiments the separable coupling may comprise a magnetic assembly.

In any one of the embodiments described herein, the cartridge components may comprise a snap-fit or snap-lock assembly, as illustrated in FIG. 5. In any one of the embodiments, the cartridge components may be reusable, refillable, and/or recyclable. The design of these cartridge components lend themselves to the use of such recyclable plastic materials as polypropylene, for the majority of components.

In some embodiments of the device 10, the cartridge 30 may comprise: a fluid storage compartment 32; a heater 36 affixed to a first end with a snap-fit coupling 39a, 39b; and a mouthpiece 31 affixed to a second end with a snap-fit coupling 39c, 39d (not shown—but similar to 39a and 39b). The heater 36 may be in fluid communication with the fluid storage compartment 32. The fluid storage compartment may be capable of retaining condensed aerosol fluid. The condensed aerosol fluid may comprise a nicotine formulation. The condensed aerosol fluid may comprise a humectant. The humectant may comprise propylene glycol and/or vegetable glycerin.

Provided herein is a device for generating an inhalable aerosol comprising: a device body 20 comprising a cartridge receptacle 21 for receiving a cartridge 30; wherein an interior surface of the cartridge receptacle forms a first side of an air inlet passage 51 when a cartridge comprising a channel integral 40 to an exterior surface is inserted into the cartridge receptacle 21, and wherein the channel forms a second side of the air inlet passage 51.

Provided herein is a device for generating an inhalable aerosol comprising: a device body 20 comprising a cartridge receptacle 21 for receiving a cartridge 30; wherein the cartridge receptacle comprises a channel integral to an interior surface and forms a first side of an air inlet passage when a cartridge is inserted into the cartridge receptacle, and wherein an exterior surface of the cartridge forms a second side of the air inlet passage 51.

Provided herein is a cartridge 30 for a device for generating an inhalable aerosol 10 comprising: a fluid storage compartment 32; a channel integral 40 to an exterior surface, wherein the channel forms a first side of an air inlet passage 51; and wherein an internal surface of a cartridge receptacle 21 in the device forms a second side of the air inlet passage 51 when the cartridge is inserted into the cartridge receptacle.

Provided herein is a cartridge 30 for a device for generating an inhalable aerosol 10 comprising a fluid storage compartment 32, wherein an exterior surface of the cartridge forms a first side of an air inlet channel 51 when inserted into a device body 10 comprising a cartridge receptacle 21, and wherein the cartridge receptacle further comprises a channel integral to an interior surface, and wherein the channel forms a second side of the air inlet passage 51.

In some embodiments, the cartridge further comprises a second air passage 41 in fluid communication with the channel 40, wherein the second air passage 41 is formed through the material of the cartridge 32 from an exterior surface of the cartridge to the internal fluid storage compartment 32a.

In some embodiments of the device body cartridge receptacle 21 or the cartridge 30, the integral channel 40 comprises at least one of: a groove; a trough; a depression; a dent; a furrow; a trench; a crease; and a gutter.

In some embodiments of the device body cartridge receptacle 21 or the cartridge 30, the integral channel 40 comprises walls that are either recessed into the surface or protrude from the surface where it is formed.

In some embodiments of the device body cartridge receptacle 21 or the cartridge 30, the internal side walls of the channel 40 form additional sides of the air inlet passage 51.

Provided herein is a device for generating an inhalable aerosol comprising: a cartridge comprising; a fluid storage compartment; a heater affixed to a first end comprising; a first heater contact, a resistive heating element affixed to the first heater contact; a device body comprising; a cartridge receptacle for receiving the cartridge; a second heater contact adapted to receive the first heater contact and to complete a circuit; a power source connected to the second heater contact; a printed circuit board (PCB) connected to the power source and the second heater contact; wherein the PCB is configured to detect the absence of fluid based on the measured resistance of the resistive heating element, and turn off the device.

Figure 15:
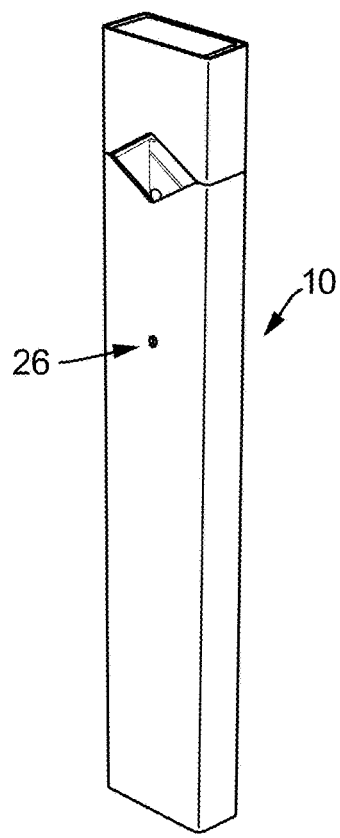
FIG. 15 is an illustrative view of an activated, assembled inhalable aerosol device.

Referring now to FIGS. 13, 14, and 15, in some embodiments, the device body further comprises at least one: second heater contact 22 (best shown in FIG. 6C detail); a battery 23; a printed circuit board 24; a pressure sensor 27; and an indicator light 26.

In some embodiments, the printed circuit board (PCB) further comprises: a microcontroller; switches; circuitry comprising a reference resister; and an algorithm comprising logic for control parameters; wherein the microcontroller cycles the switches at fixed intervals to measure the resistance of the resistive heating element relative to the reference resistor, and applies the algorithm control parameters to control the temperature of the resistive heating element.

Figure 17A:
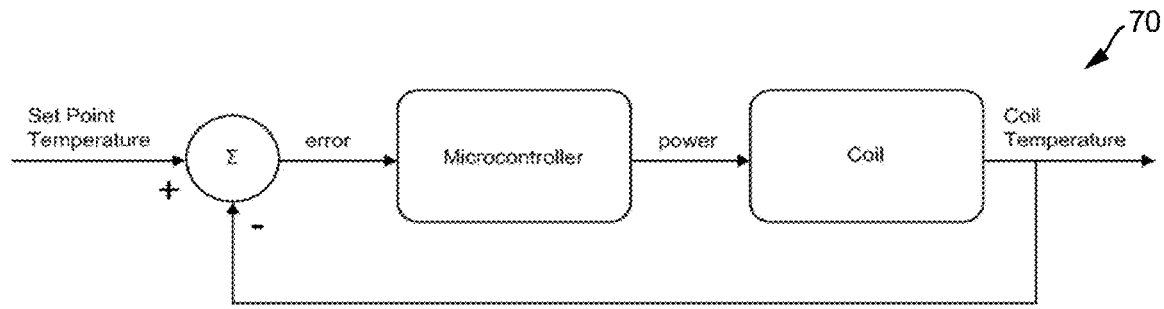
FIG. 17A-17B are representative illustrations of a proportional-integral-derivative controller (PID) block diagram and circuit diagram representing the essential components in a device to control coil temperature.

As illustrated in the basic block diagram of FIG. 17A, the device utilizes a proportional-integral-derivative controller or PID control law. A PID controller calculates an "error" value as the difference between a measured process variable and a desired setpoint. When PID control is enabled, power to the coil is monitored to determine whether or not acceptable vaporization is occurring. With a given airflow over the coil, more power will be required to hold the coil at a given temperature if the device is producing vapor (heat is removed from the coil to form vapor). If power required to keep the coil at the set temperature drops below a threshold, the device indicates that it cannot currently produce vapor. Under normal operating conditions, this indicates that there is not enough liquid in the wick for normal vaporization to occur.

In some embodiments, the micro-controller instructs the device to turn itself off when the resistance exceeds the control parameter threshold indicating that the resistive heating element is dry.

In still other embodiments, the printed circuit board further comprises logic capable of detecting the presence of condensed aerosol fluid in the fluid storage compartment and is capable of turning off power to the heating contact(s) when the condensed aerosol fluid is not detected. When the microcontroller is running the PID temperature control algorithm 70, the difference between a set point and the coil temperature (error) is used to control power to the coil so that the coil quickly reaches the set point temperature, [between 200° C. and 400° C.]. When the over-temperature algorithm is used, power is constant until the coil reaches an over-temperature threshold, [between 200° C. and 400° C.]; (FIG. 17A applies: set point temperature is over-temperature threshold; constant power until error reaches 0).

Figure 17B:
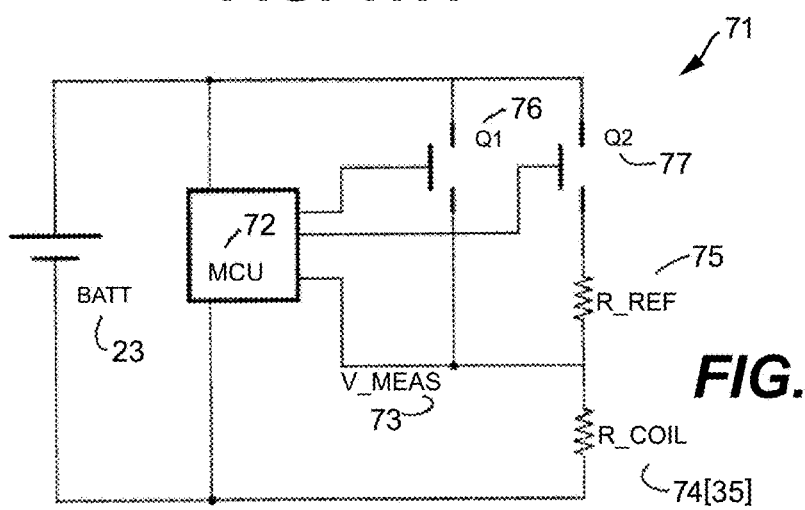

The essential components of the device used to control the resistive heating element coil temperature are further illustrated in the circuit diagram of FIG. 17B. Wherein, BATT 23 is the battery; MCU 72 is the microcontroller; Q1 (76) and Q2 (77) are P-channel MOSFETs (switches); R_COIL 74 is the resistance of the coil. R_REF 75 is a fixed reference resistor used to measure R_COIL 74 through a voltage divider 73.

The battery powers the microcontroller. The microcontroller turns on Q2 for 1 ms every 100 ms so that the voltage between R_REF and R_COIL (a voltage divider) may be measured by the MCU at V_MEAS. When Q2 is off, the control law controls Q1 with PWM (pulse width modulation) to power the coil (battery discharges through Q1 and R_COIL when Q1 is on).

In some embodiments of the device, the device body further comprises at least one: second heater contact; a power switch; a pressure sensor; and an indicator light.

In some embodiments of the device body, the second heater contact 22 may comprise: a female receptacle; or a male contact, or both, a flexible contact; or copper alloy or another electrically conductive material.

In some embodiments of the device body, the battery supplies power to the second heater contact, pressure sensor, indicator light and the printed circuit board. In some embodiments, the battery is rechargeable. In some embodiments, the indicator light 26 indicates the status of the device and/or the battery or both.

In some embodiments of the device, the first heater contact and the second heater contact complete a circuit that allows current to flow through the heating contacts when the device body and detachable cartridge are assembled, which may be controlled by an on/off switch. Alternatively, the device can be turned on an off by a puff sensor. The puff sensor may comprise a capacitive membrane. The capacitive membrane may be similar to a capacitive membrane used in a microphone.

Figure 16A:
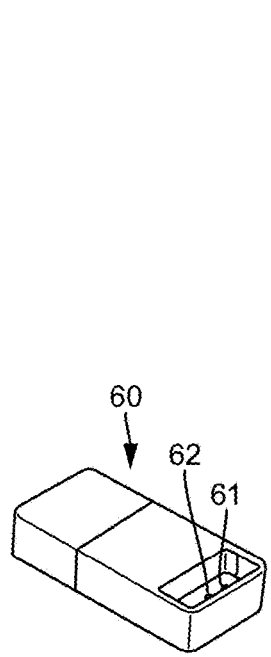
FIG. 16A-16C are representative illustrations of a charging device for the aerosol device and the application of the charger with the device.
Figure 16B:
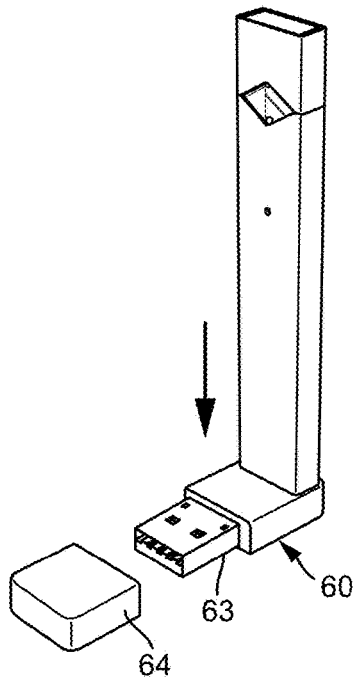
Figure 16C:
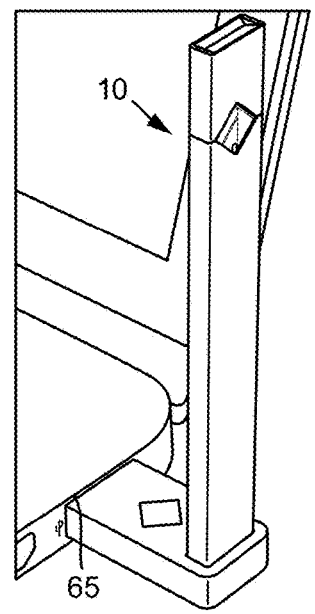

In some embodiments of the device, there is also an auxiliary charging unit for recharging the battery 23 in the device body. As illustrated in FIGS. 16A-16C, the charging unit 60, may comprise a USB device with a plug for a power source 63 and protective cap 64, with a cradle 61 for capturing the device body 20 (with or without the cartridge installed). The cradle may further comprise either a magnet or a magnetic contact 62 to securely hold the device body in place during charging. As illustrated in FIG. 6B, the device body further comprises a mating charging contact 28 and a magnet or magnetic contact 29 for the auxiliary charging unit. FIG. 16C is an illustrative example of the device 20 being charged in a power source 65 (laptop computer or tablet).

In some cases the microcontroller on the PCB may be configured to monitor the temperature of the heater such that the vaporizable material is heated to a prescribed temperature. The prescribed temperature may be an input provided by the user. A temperature sensor may be in communication with the microcontroller to provide an input temperature to the microcontroller for temperature regulation. A temperature sensor may be a thermistor, thermocouple, thermometer, or any other temperature sensors. In some cases, the heating element may simultaneously perform as both a heater and a temperature sensor. The heating element may differ from a thermistor by having a resistance with a relatively lower dependence on temperature. The heating element may comprise a resistance temperature detector.

The resistance of the heating element may be an input to the microcontroller. In some cases, the resistance may be determined by the microcontroller based on a measurement from a circuit with a resistor with at least one known resistance, for example, a Wheatstone bridge. Alternatively, the resistance of the heating element may be measured with a resistive voltage divider in contact with the heating element and a resistor with a known and substantially constant resistance. The measurement of the resistance of the heating element may be amplified by an amplifier. The amplifier may be a standard op amp or instrumentation amplifier. The amplified signal may be substantially free of noise. In some cases, a charge time for a voltage divider between the heating element and a capacitor may be determined to calculate the resistance of the heating element. In some cases, the microcontroller must deactivate the heating element during resistance measurements. The resistance of the heating element may be directly proportional to the temperature of the heating element such that the temperature may be directly determine from the resistance measurement. Determining the temperature directly from the heating element resistance measurement rather than from an additional temperature sensor may generate a more accurate measurement because unknown contact thermal resistance between the temperature sensor and the heating element is eliminated. Additionally, the temperature measurement may be determined directly and therefore faster and without a time lag associated with attaining equilibrium between the heating element and a temperature sensor in contact with the heating element.

Provided herein is a device for generating an inhalable aerosol comprising: a cartridge comprising a first heater contact; a device body comprising; a cartridge receptacle for receiving the cartridge; a second heater contact adapted to receive the first heater contact and to complete a circuit; a power source connected to the second heater contact; a printed circuit board (PCB) connected to the power source and the second heater contact; and a single button interface; wherein the PCB is configured with circuitry and an algorithm comprising logic for a child safety feature.

In some embodiments, the algorithm requires a code provided by the user to activate the device. In some embodiments; the code is entered by the user with the single button interface. In still further embodiments the single button interface is the also the power switch.

Provided herein is a cartridge 30 for a device 10 for generating an inhalable aerosol comprising: a fluid storage compartment 32; a heater 36 affixed to a first end comprising: a heater chamber 37, a first pair of heater contacts 33, a fluid wick 34, and a resistive heating element 35 in contact with the wick; wherein the first pair of heater contacts 33 comprise thin plates affixed about the sides of the heater chamber 37, and wherein the fluid wick 34 and resistive heating element 35 are suspended therebetween.

Depending on the size of the heater or heater chamber, the heater may have more than one wick 34, 34' and resistive heating element 35, 35'.

In some embodiments, the first pair of heater contacts further comprise a formed shape that comprises a tab 33a having a flexible spring value that extends out of the heater 36 to complete a circuit with the device body 20.

In some embodiments, the heater contacts 33 are configured to mate with a second pair of heater contacts 22 in a cartridge receptacle 21 of the device body 20 to complete a circuit.

In some embodiments, the first pair of heater contacts is also a heat sink that absorbs and dissipates excessive heat produced by the resistive heating element.

In some embodiments, the first pair of heater contacts is a heat shield that protects the heater chamber from excessive heat produced by the resistive heating element.

Provided herein is a cartridge 30 for a device for generating an inhalable aerosol 10 comprising: a heater 36 comprising; a heater chamber 37, a pair of thin plate heater contacts 33 therein, a fluid wick 34 positioned between the heater contacts 33, and a resistive heating element 35 in contact with the wick; wherein the heater contacts 33 each comprise a fixation site 33c wherein the resistive heating element 35 is tensioned therebetween.

As will be obvious to one skilled in the art after reviewing the assembly method illustrated in FIG. 9, the heater contacts 33 simply snap or rest on locator pins on either side of the air inlet 53 on the first end of the cartridge interior fluid storage compartment, creating a spacious vaporization chamber containing the at least one wick 34 and at least one heating element 35.

Provided herein is a cartridge 30 for a device for generating an inhalable aerosol 10 comprising a heater 36 attached to a first end of the cartridge.

In some embodiments, the heater encloses a first end of the cartridge and a first end of the fluid storage compartment 32, 32a.

In some embodiments, the heater comprises a first condensation chamber 45.

In some embodiments, the heater comprises more than one first condensation chamber 45, 45'.

In some embodiments, the condensation chamber is formed along an exterior wall of the cartridge 45b.

As noted previously, and described in FIGS. 10A, 10B and 10C, the airflow path through the heater and heater chamber generates vapor within the heater circulating airpath 54, which then exits through the heater exits 55 into a first (primary) condensation chamber 45, which is formed by components of the tank body comprising the primary condensation channel/chamber rails 45b, the primary condensation channel cover 45a, (the outer side wall of the heater enclosure).

Provided herein is a cartridge 30 for a device for generating an inhalable aerosol 10 comprising a fluid storage compartment 32 and a mouthpiece 31, wherein the mouthpiece is attached to a second end of the cartridge and further comprises at least one aerosol outlet 47.

In some embodiments, the mouthpiece 31 encloses a second end of the cartridge 30 and a second end of the fluid storage compartment 32, 32a.

Additionally, as clearly illustrated in FIG. 10C in some embodiments the mouthpiece also contains a second condensation chamber 46 prior to the aerosol outlet 47, which is formed by components of the tank body 32 comprising the secondary condensation channel/chamber rails 46b, the second condensation channel cover 46a, (the outer side wall of the mouthpiece). Still further, the mouthpiece may contain yet another aerosol outlet 47' and another (second) condensation chamber 46' prior to the aerosol outlet, on another side of the cartridge.

In other embodiments, the mouthpiece comprises more than one second condensation chamber 46, 46'.

In some preferred embodiments, the second condensation chamber is formed along an exterior wall of the cartridge 46b.

In each of the embodiments described herein, the cartridge 30 comprises an airflow path comprising: an air inlet channel and passage 40, 41, 42; a heater chamber 37; at least a first condensation chamber 45; and an outlet port 47. In some of the embodiments described herein, the cartridge 30 comprises an airflow path comprising: an air inlet channel and passage 40, 41, 42; a heater chamber 37; a first condensation chamber 45; a second condensation chamber 46; and an outlet port 47.

In still other embodiments described herein the cartridge 30 may comprise an airflow path comprising at least one air inlet channel and passage 40, 41, 42; a heater chamber 37; at least one first condensation chamber 45; at least one second condensation chamber 46; and at least one outlet port 47.

In each of the embodiments described herein, the fluid storage compartment 32 is in fluid communication with the heater 36, wherein the fluid storage compartment is capable of retaining condensed aerosol fluid.

In some embodiments of the device, the condensed aerosol fluid comprises a nicotine formulation. In some embodiments, the condensed aerosol fluid comprises a humectant. In some embodiments, the humectant comprises propylene glycol. In some embodiments, the humectant comprises vegetable glycerin.

Provided herein is a cartridge 30 for a device for generating an inhalable aerosol 10 comprising: a fluid storage compartment 32; a heater 36 affixed to a first end; and a mouthpiece 31 affixed to a second end; wherein the heater comprises a first condensation chamber 45 and the mouthpiece comprises a second condensation chamber 46.

In some embodiments, the heater comprises more than one first condensation chamber 45, 45' and the mouthpiece comprises more than one second condensation chamber 46, 46'.

In some embodiments, the first condensation chamber and the second condensation chamber are in fluid communication. As illustrated in FIG. 10C, the first and second condensation chambers have a common transition area 57, 57', for fluid communication.

In some embodiments, the mouthpiece comprises an aerosol outlet 47 in fluid communication with the second condensation chamber 46.

In some embodiments, the mouthpiece comprises two or more aerosol outlets 47, 47'.

In some embodiments, the mouthpiece comprises two or more aerosol outlets 47, 47' in fluid communication with the two or more second condensation chambers 46, 46'.

In any one of the embodiments, the cartridge meets ISO recycling standards.

In any one of the embodiments, the cartridge meets ISO recycling standards for plastic waste.

And in still other embodiments, the plastic components of the cartridge are composed of polylactic acid (PLA), wherein the PLA components are compostable and or degradable.

Provided herein is a device for generating an inhalable aerosol 10 comprising a device body 20 comprising a cartridge receptacle 21; and a detachable cartridge 30; wherein the cartridge receptacle and the detachable cartridge form a separable coupling, and wherein the separable coupling comprises a friction assembly, a snap-fit assembly or a magnetic assembly.

In other embodiments of the device, the cartridge is a detachable assembly. In any one of the embodiments described herein, the cartridge components may comprise a snap-lock assembly such as illustrated by snap features 39a and 39b. In any one of the embodiments, the cartridge components are recyclable.

Provided herein is a method of fabricating a device for generating an inhalable aerosol comprising: providing a device body comprising a cartridge receptacle; and providing a detachable cartridge; wherein the cartridge receptacle and the detachable cartridge form a separable coupling comprising a friction assembly, a snap-fit assembly or a magnetic assembly when the cartridge is inserted into the cartridge receptacle.

Provided herein is a method of making a device 10 for generating an inhalable aerosol comprising: providing a device body 20 with a cartridge receptacle 21 comprising one or more interior coupling surfaces 21a, 21b, 21c . . . ; and further providing a cartridge 30 comprising: one or more exterior coupling surfaces 36a, 36b, 36c, . . . , a second end and a first end; a tank 32 comprising an interior fluid storage compartment 32a; at least one channel 40 on at least one exterior coupling surface, wherein the at least one channel forms one side of at least one air inlet passage 51, and wherein at least one interior wall of the cartridge receptacle forms at least one side one side of at least one air inlet passage 51 when the detachable cartridge is inserted into the cartridge receptacle.

FIG. 9 provides an illustrative example of a method of assembling such a device.

In some embodiments of the method, the cartridge 30 is assembled with a [protective] removable end cap 38 to protect the exposed heater contact tabs 33a protruding from the heater 36.

Provided herein is a method of fabricating a cartridge for a device for generating an inhalable aerosol comprising: providing a fluid storage compartment; affixing a heater to a first end with a snap-fit coupling; and affixing a mouthpiece to a second end with a snap-fit coupling.

Provided herein is a cartridge 30 for a device for generating an inhalable aerosol 10 with an airflow path comprising: a channel 50 comprising a portion of an air inlet passage 51; a second air passage 41 in fluid communication with the channel; a heater chamber 37 in fluid communication with the second air passage; a first condensation chamber 45 in fluid communication with the heater chamber; a second condensation chamber 46 in fluid communication with the first condensation chamber; and an aerosol outlet 47 in fluid communication with second condensation chamber.

Provided herein is a device 10 for generating an inhalable aerosol adapted to receive a removable cartridge 30, wherein the cartridge comprises a fluid storage compartment [or tank] 32; an air inlet 41; a heater 36, a [protective] removable end cap 38, and a mouthpiece 31.

Charging

In some cases, the vaporization device may comprise a power source. The power source may be configured to provide power to a control system, one or more heating elements, one or more sensors, one or more lights, one or more indicators, and/or any other system on the electronic cigarette that requires a power source. The power source may be an energy storage device. The power source may be a battery or a capacitor. In some cases, the power source may be a rechargeable battery.

The battery may be contained within a housing of the device. In some cases the battery may be removed from the housing for charging. Alternatively, the battery may remain in the housing while the battery is being charged. Two or more charge contact may be provided on an exterior surface of the device housing. The two or more charge contacts may be in electrical communication with the battery such that the battery may be charged by applying a charging source to the two or more charge contacts without removing the battery from the housing.

Figure 18:
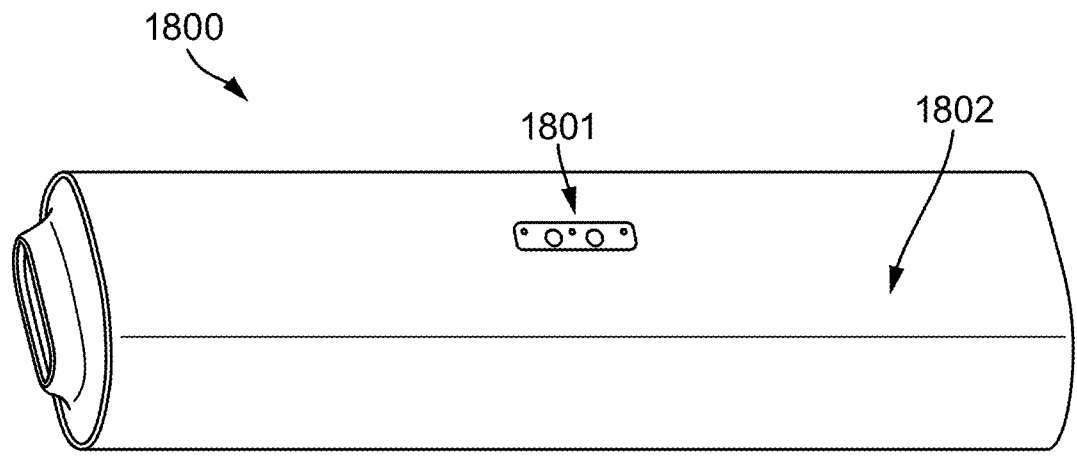
FIG. 18 is a device with charging contacts visible from an exterior housing of the device.

FIG. 18 shows a device 1800 with charge contacts 1801. The charge contacts 1801 may be accessible from an exterior surface of a device housing 1802. The charge contacts 1801 may be in electrical communication with an energy storage device (e.g., battery) inside of the device housing 1802. In some cases, the device housing may not comprise an opening through which the user may access components in the device housing. The user may not be able to remove the battery and/or other energy storage device from the housing. In order to open the device housing a user must destroy or permanently disengage the charge contacts. In some cases, the device may fail to function after a user breaks open the housing.

Figure 19:
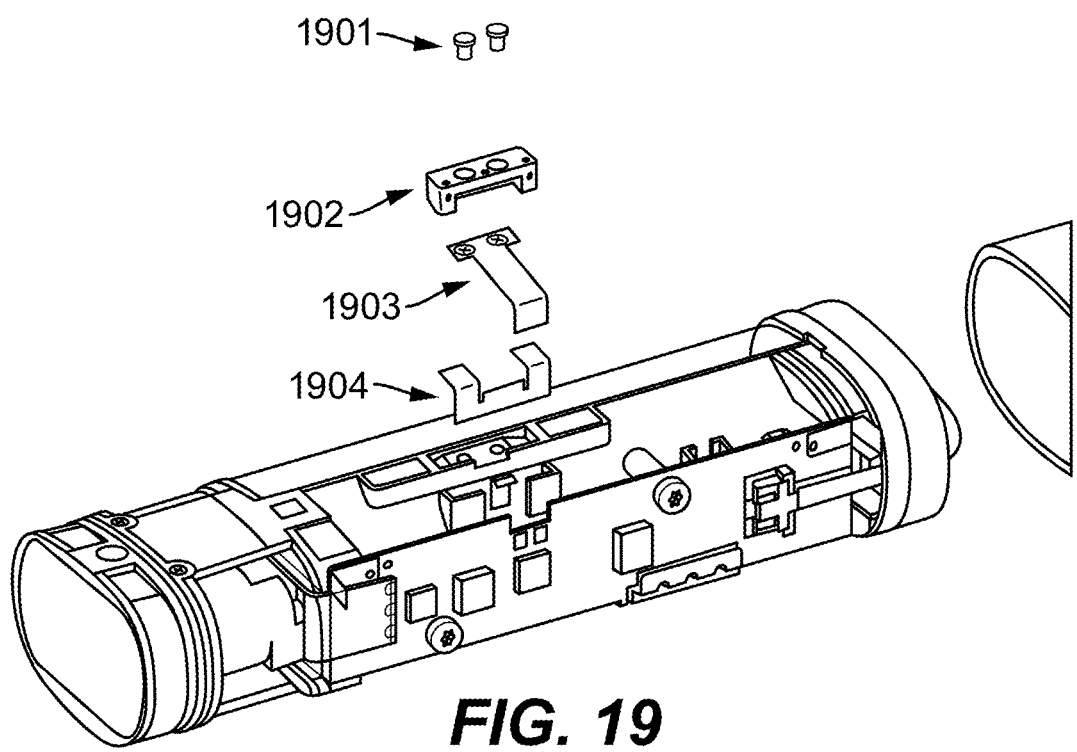
FIG. 19 is an exploded view of a charging assembly of a device.

FIG. 19 shows an exploded view of a charging assembly 1900 in an electronic vaporization device. The housing (not shown) has been removed from the exploded view in FIG. 19. The charge contact pins 1901 may be visible on the exterior of the housing. The charge contact pins 1901 may be in electrical communication with a power storage device of the electronic vaporization device. When the device is connected to a power source (e.g., during charging of the device) the charging pins may facilitate electrical communication between the power storage device inside of the electronic vaporization device and the power source outside of the housing of the vaporization device. The charge contact pins 1901 may be held in place by a retaining bezel 1902. The charge contact pins 1901 may be in electrical communication with a charger flex 1903. The charging pins may contact the charger flex such that a need for soldering of the charger pins to an electrical connection to be in electrical communication with the power source may be eliminated. The charger flex may be soldered to a printed circuit board (PCB). The charger flex may be in electrical communication with the power storage device through the PCB. The charger flex may be held in place by a bent spring retainer 1904.

Figure 20:
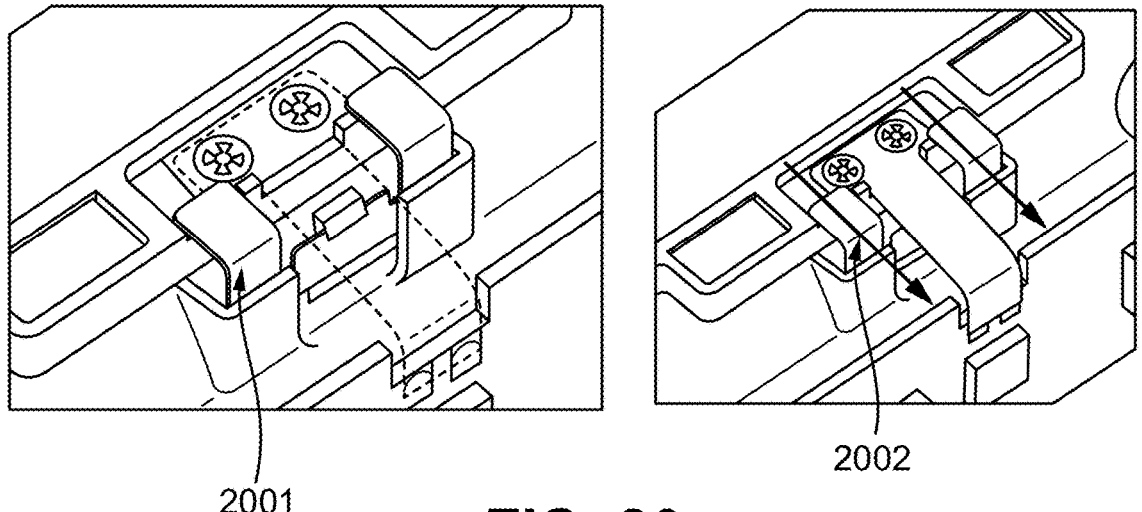
FIG. 20 is a detailed view of a charging assembly of a device.

FIG. 20 shows the bent spring retainer in an initial position 2001 and a deflected position 2002. The bent spring retainer may hold the retaining bezel in a fixed location. The bent spring retainer may deflect only in one direction when the charging assembly is enclosed in the housing of the electronic vaporization device.

Figure 21:
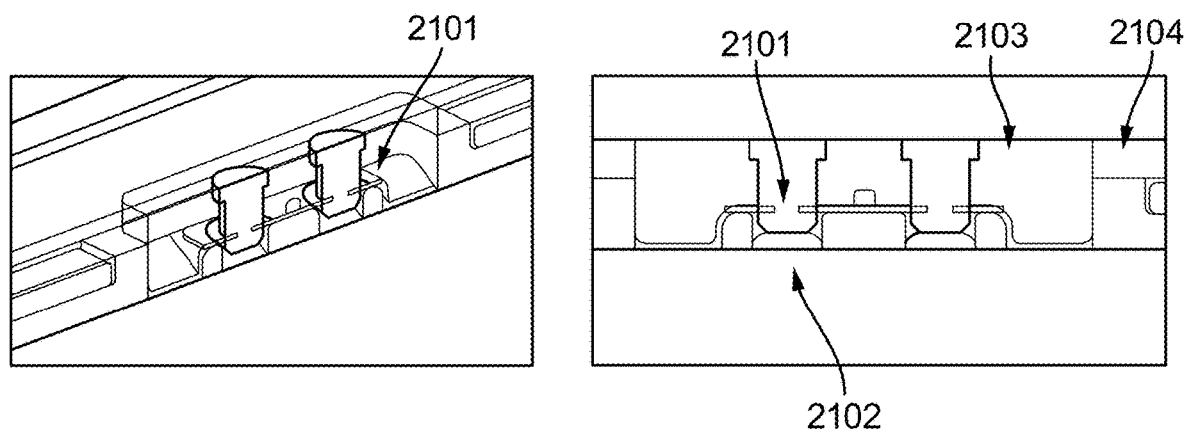
FIG. 21 is a detailed view of charging pins in a charging assembly of a device.

FIG. 21 shows a location of the charger pins 2101 when the electronic vaporization device is fully assembled with the charging pins 2101 contact the charging flex 2102. When the device is fully assembled at least a portion of the retaining bezel may be fitted in an indentation 2103 on the inside of the housing 2104. In some cases, disassembling the electronic vaporization device may destroy the bezel such that the device cannot be reassembled after disassembly.

Figure 22:
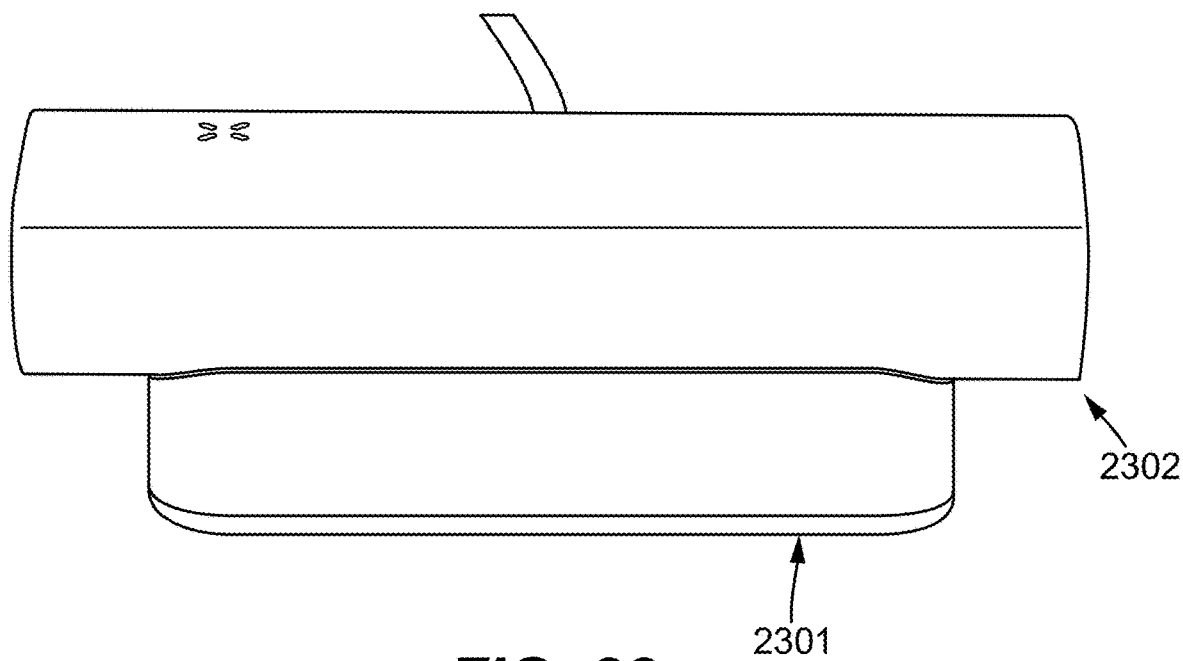
FIG. 22 is a device in a charging cradle.

A user may place the electronic smoking device in a charging cradle. The charging cradle may be a holder with charging contact configured to mate or couple with the charging pins on the electronic smoking device to provide charge to the energy storage device in the electronic vaporization device from a power source (e.g., wall outlet, generator, and/or external power storage device). FIG. 22 shows a device 2302 in a charging cradle 2301. The charging cable may be connected to a wall outlet, USB, or any other power source. The charging pins (not shown) on the device 2302 may be connected to charging contacts (not shown) on the charging cradle 2301. The device may be configured such that when the device is placed in the cradle for charging a first charging pin on the device may contact a first charging contact on the charging cradle and a second charging pin on the device may contact a second charging contact on the charging cradle or the first charging pin on the device may contact a second charging contact on the charging cradle and the second charging pin on the device may contact the first charging contact on the charging cradle. The charging pins on the device and the charging contacts on the cradle may be in contact in any orientation. The charging pins on the device and the charging contacts on the cradle may be agnostic as to whether they are current inlets or outlets. Each of the charging pins on the device and the charging contacts on the cradle may be negative or positive. The charging pins on the device may be reversible.

Figure 23:
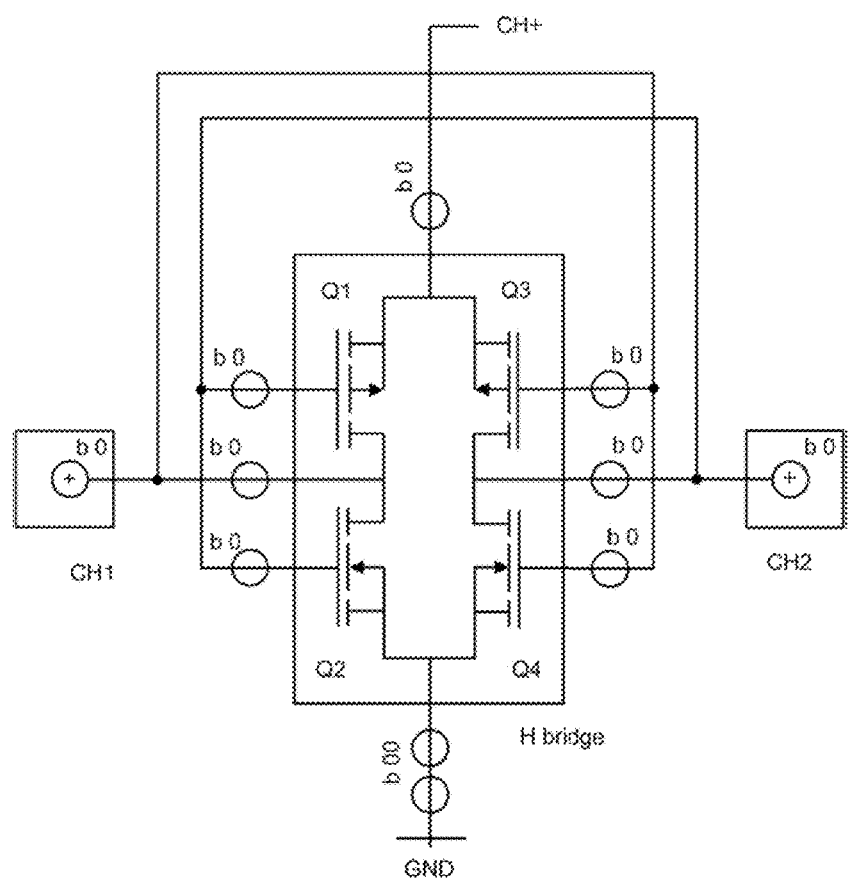
FIG. 23 is a circuit provided on a PCB configured to permit a device to comprise reversible charging contacts.

FIG. 23 shows a circuit 2400 that may permit the charging pins on the device to be reversible. The circuit 2400 may be provided on a PCB in electrical communication with the charging pins. The circuit 2400 may comprise a metaloxide-semiconductor field-effect transistor (MOSFET) H bridge. The MOSFET H bridge may rectify a change in voltage across the charging pins when the charging pins are reversed from a first configuration where in a first configuration the device is placed in the cradle for charging with the first charging pin on the device in contact with the first charging contact on the charging cradle to a second charging pin on the device in contact with the second charging contact on the charging cradle to a second configuration where the first charging pin on the device is in contact with the second charging contact on the charging cradle and the second charging pin on the device is in contact with the first charging contact on the charging cradle. The MOSFET H bridge may rectify the change in voltage with an efficient current path.

As shown in FIG. 23 the MOSFET H bridge may comprise two or more n-channel MOSFETs and two or more p-channel MOSFETs. The n-channel and p-channel MOSFETs may be arranged in an H bridge. Sources of p-channels MOSFETs (Q1 and Q3) may be in electrical communication. Similarly, sources of n-channel FETs (Q2 and Q4) may be in electrical communication. Drains of pairs of n and p MOSFETs (Q1 with Q2 and Q3 with Q4) may be in electrical communication. TA common drain from one n and p pair may be in electrical communication with one or more gates of the other n and p pair and/or vice versa. Charge contacts (CH1 and CH2) may be in electrical communication to common drains separately. A common source of the n MOSFETs may be in electrical communication to PCB ground (GND). The common source of the p MOSFETs may be in electrical communication with the PCB's charge controller input voltage (CH+). When CH1 voltage is greater than CH2 voltage by the MOSFET gate threshold voltages, Q1 and Q4 may be "on," connecting CH1 to CH+ and CH2 to GND. When CH2 voltage is greater than CH1 voltage by the FET gate threshold voltages, Q2 and Q3 may be "on," connecting CH1 to GND and CH2 to CH+. For example, whether there is 9V or −9V across CH1 to CH2, CH+ will be 9V above GND. Alternatively, a diode bridge could be used, however the MOSFET bridge may be more efficient compared to the diode bridge.

In some cases the charging cradle may be configured to be a smart charger. The smart charger may put the battery of the device in series with a USB input to charge the device at a higher current compared to a typical charging current. In some cases, the device may charge at a rate up to about 2 amps (A), 4 A, 5 A, 6 A, 7 A, 10 A, or 15 A. In some cases, the smart charger may comprise a battery, power from the battery may be used to charge the device battery. When the battery in the smart charger has a charge below a predetermined threshold charge, the smart charger may simultaneously charge the battery in the smart charger and the battery in the device.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A device for generating an inhalable aerosol comprising:
   a cartridge having a proximal end and a distal end opposite the proximal end, the cartridge comprising a first electrical contact and a second electrical contact disposed proximate the distal end of the cartridge, the first electrical contact and the second electrical contact electrically isolated and disposed in a plane substantially parallel to the distal end of the cartridge;
   a body including a receptacle configured to insertably receive the cartridge through a proximal end of the body, the receptacle terminating in a proximal edge, a distal end of the body opposite the proximal end of the body along a longitudinal dimension of the body;
   a storage compartment configured to hold a vaporizable material;
   a heater disposed proximate to the distal end of the cartridge, the heater configured to heat the vaporizable material to generate a vapor;
   a separable mouthpiece disposed proximate to the proximal end of the cartridge and attached to the storage compartment, the separable mouthpiece comprising a condensation chamber, the condensation chamber in fluid communication with the heater, the separable mouthpiece further comprising an aerosol outlet in fluid communication with the condensation chamber;
   a first airflow path configured to deliver air towards the heater, the first airflow path comprising a first inlet near the proximal edge of the receptacle, a portion of the first airflow path situated between the distal end of the cartridge and the first inlet along the longitudinal dimension of the body when the cartridge is insertably received in the receptacle; and
   a second airflow path configured to deliver air towards the heater, the second airflow path comprising a second inlet near the proximal edge of the receptacle, a portion of the second airflow path situated between the distal end of the cartridge and the second inlet along the longitudinal dimension of the body when the cartridge is insertably received in the receptacle, wherein the cartridge and the receptacle are configured to form the first airflow path and the second airflow path between a plurality of exterior surfaces of the cartridge and a plurality of internal surfaces of the receptacle when the cartridge is insertably received in the receptacle.

2. The device of claim 1, wherein the cartridge further comprises a protrusion extending from an exterior surface of the plurality of exterior surfaces of the cartridge, wherein the protrusion is configured to define at least a portion of the first airflow path when the cartridge is insertably received in the receptacle, and wherein at least part of the protrusion is configured to be disposed within the receptacle when the cartridge is inserted into the body.

3. The device of claim 1, wherein the receptacle is disposed at the proximal end, wherein the body longitudinal dimension extends from the proximal end to the distal end, and wherein a first body transverse dimension and a second body transverse dimension extend substantially perpendicular to the body longitudinal dimension, the body having a greater dimension along the first body transverse dimension than along the second body transverse dimension.

4. The device of claim 1, wherein the condensation chamber is configured to allow at least a fraction of the vapor to condense therein to form the inhalable aerosol.

5. The device of claim 1, wherein the body comprises at least one of: a power source, a printed circuit board, a switch, and a temperature regulator.

6. The device of claim 1, further comprising:
a microcontroller configured to measure a resistance of the heater, wherein a temperature is determined from the resistance measurement of the heater.

7. The device of claim 1, wherein the receptacle comprises a third electrical contact and a fourth electrical contact configured to couple with the first electrical contact and the second electrical contact of the cartridge.

8. The device of claim 1, wherein the cartridge has a longitudinal dimension extending from the proximal end of the cartridge to the distal end of the cartridge, and wherein an exterior surface of the plurality of exterior surfaces of the cartridge and an internal surface of the plurality of internal surfaces of the receptacle are configured to be substantially parallel to the longitudinal dimension when the receptacle insertably receives and couples to the cartridge.

9. The device of claim 1, further comprising a wick, the wick comprising at least one of: a silica material, a cotton material, a ceramic material, a hemp material, or a stainless steel material.

10. A device for generating an inhalable aerosol comprising:
a cartridge;
a body including a receptacle configured to insertably receive the cartridge through a proximal end of the body, the receptacle terminating in a proximal edge a distal end of the body opposite the proximal end of the body along a longitudinal dimension of the body;
a storage compartment configured to hold a vaporizable material;
a heater for heating the vaporizable material to generate a vapor;
a separable mouthpiece disposed over part of the storage compartment and comprising a condensation chamber, the condensation chamber in fluid communication with the heater, the separable mouthpiece further comprising an aerosol outlet in fluid communication with the condensation chamber;
a first airflow path configured to deliver air towards the heater, the first airflow path comprising a first inlet near the proximal edge of the receptacle, a portion of the first airflow path situated between a distal end of the cartridge and the first inlet along the longitudinal dimension of the body when the cartridge is insertably received in the receptacle; and
a second airflow path configured to deliver air towards the heater, the second airflow path comprising a second inlet near the proximal edge of the receptacle, a portion of the second airflow path situated between the distal end of the cartridge and the second inlet along the longitudinal dimension of the body when the cartridge is insertably received in the receptacle, wherein the cartridge and the receptacle are configured to form the first airflow path and the second airflow path between exterior surfaces of the cartridge and internal surfaces of the receptacle when the cartridge is insertably received in the receptacle,
wherein the cartridge comprises a first electrical contact and a second electrical contact proximate the distal end of the cartridge, the separable mouthpiece disposed at a proximal end of the cartridge opposite the distal end, wherein the first electrical contact and the second electrical contact are electrically isolated and disposed in a plane substantially parallel to the distal end of the cartridge.

11. The device of claim 10, wherein the receptacle comprises a third electrical contact and a fourth electrical contact disposed in a second plane, the second plane substantially parallel to the distal end of the cartridge when the cartridge is received within the receptacle.

12. A device for generating an inhalable aerosol comprising:
a cartridge comprising a first electrical contact and a second electrical contact disposed proximate an insertion end of the cartridge, the first electrical contact and the second electrical contact electrically isolated and disposed in a plane substantially parallel to the insertion end of the cartridge;
a body including a receptacle configured to insertably receive the insertion end of the cartridge through a proximal end of the body, the receptacle terminating in a proximal edge, a distal end of the body opposite the proximal end of the body along a longitudinal dimension of the body;
a heater for heating a vaporizable material to generate a vapor;
a mouthpiece comprising a condensation chambers configured to allow at least a fraction of the vapor to condense therein, the condensation chamber in fluid communication with the heater, the mouthpiece further comprising an aerosol outlet in fluid communication with the condensation chamber;
a first airflow path configured to deliver air towards the heater, the first airflow path comprising a first inlet near the proximal edge of the receptacle, a portion of the first airflow path situated between the distal end of the cartridge and the first inlet along the longitudinal dimension of the body when the cartridge is insertably received in the receptacle; and
a second airflow path configured to deliver air towards the heater, the second airflow path comprising a second inlet near the proximal edge of the receptacle, a portion of the second airflow path situated between the distal end of the cartridge and the second inlet along the longitudinal dimension of the body when the cartridge is insertably received in the receptacle, wherein the cartridge and the receptacle are configured to form the first airflow path and the second airflow path between exterior surfaces of the cartridge and internal surfaces of the receptacle when the cartridge is insertably received in the receptacle,
wherein the cartridge comprises a storage compartment, wherein the mouthpiece is attached to the storage compartment by a snap-fit coupling.

13. The device of claim 12, wherein the storage compartment comprises the vaporizable material, and wherein the vaporizable material comprises a nicotine formulation.

14. The device of claim 12, wherein the storage compartment comprises four exterior walls of the cartridge between a distal end and a proximal end.

15. The device of claim 14, wherein the mouthpiece forms a cavity, wherein a first portion of the storage compartment is disposed inside of the cavity and a second portion of the storage compartment is disposed outside of the cavity, at least part of the second portion configured for insertion into the receptacle.

16. The device of claim 15, wherein the mouthpiece comprises a first coupling feature and a second coupling feature, wherein the storage compartment comprises a third coupling feature and a fourth coupling feature on opposite exterior surfaces of the storage compartment, wherein the first coupling feature is configured to couple with one of the third coupling feature and the fourth coupling feature, and wherein the second coupling feature is configured to couple with the other of the third coupling feature and the fourth coupling feature.

17. The device of claim 16, wherein the third coupling feature comprises a first raised rail, and wherein the fourth coupling feature comprises a second raised rail.

18. The device of claim 15, wherein the mouthpiece is opaque, and wherein the second portion of the storage compartment comprises a surface configured so that the vaporizable material is visible through the surface.

19. The device of claim 18, wherein the receptacle is configured so that the second portion of the storage compartment is visible when the cartridge is coupled to the receptacle.

20. A device for generating an inhalable aerosol comprising:
   a cartridge having a proximal end and a distal end opposite the proximal end, the cartridge comprising a first electrical contact and a second electrical contact disposed proximate the distal end of the cartridge, the first electrical contact and the second electrical contact electrically isolated and disposed in a plane substantially parallel to the distal end of the cartridge;
   a body including a receptacle configured to insertably receive the cartridge through a proximal end of the body, the receptacle terminating in a proximal edge, a distal end of the body opposite the proximal end of the body along a longitudinal dimension of the body;
   a storage compartment configured to hold a vaporizable material;
   a heater disposed proximate to the distal end for heating the vaporizable material to generate a vapor;
   a separable mouthpiece disposed proximate to the proximal end of the cartridge and attached to the storage compartment, the separable mouthpiece comprising a condensation chamber, the condensation chamber in fluid communication with the heater, the separable mouthpiece further comprising an aerosol outlet in fluid communication with the condensation chamber; and
   an airflow path configured to deliver air towards the heater, the airflow path comprising an inlet near the proximal edge of the receptacle, a portion of the airflow path situated between the distal end of the cartridge and the inlet along the longitudinal dimension of the body when the cartridge is insertably received in the receptacle, wherein the cartridge and the receptacle are configured to form the airflow path between an exterior surface of the cartridge and an internal surface of the receptacle when the cartridge is insertably received in the receptacle.

21. The device of claim 20, wherein the condensation chamber is configured to allow at least a fraction of the vapor to condense therein to form the inhalable aerosol.

* * * * *

UNITED STATES PATENT AND TRADEMARK OFFICE
CERTIFICATE OF CORRECTION

| | |
|---|---|
| PATENT NO. | : 11,752,283 B2 |
| APPLICATION NO. | : 15/832719 |
| DATED | : September 12, 2023 |
| INVENTOR(S) | : Ariel Atkins et al. |

It is certified that error appears in the above-identified patent and that said Letters Patent is hereby corrected as shown below:

In the Claims

At Column 39, Claim 10, Line number 30, please delete "edge a" and insert --edge, a--.

Signed and Sealed this
Twenty-first Day of May, 2024

Katherine Kelly Vidal
*Director of the United States Patent and Trademark Office*